United States Patent
Yamane

(10) Patent No.: US 8,512,231 B2
(45) Date of Patent: Aug. 20, 2013

(54) ELECTRONIC ENDOSCOPE INCLUDING LENS HOLDER AND OBJECTIVE MIRROR

(75) Inventor: Kenji Yamane, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 236 days.

(21) Appl. No.: 12/999,815

(22) PCT Filed: Jun. 15, 2009

(86) PCT No.: PCT/JP2009/060885
§ 371 (c)(1),
(2), (4) Date: Dec. 17, 2010

(87) PCT Pub. No.: WO2009/154174
PCT Pub. Date: Dec. 23, 2009

(65) Prior Publication Data
US 2011/0098530 A1    Apr. 28, 2011

(30) Foreign Application Priority Data

| Jun. 17, 2008 | (JP) | 2008-157991 |
| Jun. 17, 2008 | (JP) | 2008-157992 |
| Jun. 17, 2008 | (JP) | 2008-157993 |
| Jun. 17, 2008 | (JP) | 2008-157999 |
| Jun. 17, 2008 | (JP) | 2008-158000 |
| Jun. 17, 2008 | (JP) | 2008-158002 |
| Jun. 17, 2008 | (JP) | 2008-158004 |
| Jun. 17, 2008 | (JP) | 2008-158005 |
| Jun. 17, 2008 | (JP) | 2008-158006 |
| Jun. 17, 2008 | (JP) | 2008-158013 |

(51) Int. Cl.
*A61B 1/04* (2006.01)

(52) U.S. Cl.
USPC .............................. 600/170; 600/173

(58) Field of Classification Search
USPC ............ 600/183, 173, 174, 170, 137, 138, 600/130, 114, 167; 356/241, 241.3, 241.6; 385/119; 348/84, 85
See application file for complete search history.

(56) References Cited

U.S. PATENT DOCUMENTS 3,090,378 A * 5/1963 Sheldon et al. ............... 600/167
3,804,081 A * 4/1974 Kinoshita et al. ............. 600/167

(Continued)

FOREIGN PATENT DOCUMENTS

JP    3-191944 A    8/1991
JP    6-335450 A    12/1994

(Continued)

OTHER PUBLICATIONS

Partial translation of JP 2002-95632 (A).

(Continued)

*Primary Examiner* — John P Leubecker
(74) *Attorney, Agent, or Firm* — McGinn IP Law Group, PLLC

(57) ABSTRACT

An electronic endoscope includes a cylindrical transparent cover whose observation window in a cylindrical part is transparent, a body part that has a cylindrical part provided continuously to the cylindrical part of the transparent cover, a lens holder that revolves about a center axis of the transparent cover in an inside of the transparent cover and the body part and that moves in a direction of the center axis, an objective mirror that is provided in the lens holder and that reflects, toward the body part, light entering through an objective lens provided at a position facing the cylindrical part of the transparent cover, an imaging device that receives light reflected from the objective mirror and that converts the light into an electric signal, and a driving section provided inside the body part and that drives and revolves the lens holder.

8 Claims, 106 Drawing Sheets

(56) References Cited

U.S. PATENT DOCUMENTS

| | | | | |
|---|---|---|---|---|
| 4,633,304 A | * | 12/1986 | Nagasaki | 348/69 |
| 4,819,620 A | * | 4/1989 | Okutsu | 600/114 |
| 5,191,879 A | * | 3/1993 | Krauter | 600/109 |
| 5,879,289 A | * | 3/1999 | Yarush et al. | 600/179 |
| 5,976,076 A | * | 11/1999 | Kolff et al. | 600/166 |
| 6,134,003 A | | 10/2000 | Tearney et al. | |
| 6,478,730 B1 | * | 11/2002 | Bala et al. | 600/121 |
| 6,687,010 B1 | * | 2/2004 | Horii et al. | 356/479 |
| 6,887,196 B2 | | 5/2005 | Arai et al. | |
| 7,322,934 B2 | | 1/2008 | Miyake et al. | |
| 7,544,162 B2 | * | 6/2009 | Ohkubo | 600/173 |
| 7,627,208 B2 | * | 12/2009 | Kuroiwa | 385/31 |
| 2002/0103420 A1 | * | 8/2002 | Coleman et al. | 600/173 |
| 2002/0123664 A1 | * | 9/2002 | Mitsumori | 600/130 |
| 2003/0097044 A1 | * | 5/2003 | Rovegno | 600/170 |
| 2003/0191364 A1 | * | 10/2003 | Czarnek et al. | 600/111 |
| 2003/0191369 A1 | | 10/2003 | Arai et al. | |
| 2004/0097791 A1 | * | 5/2004 | Tokuda et al. | 600/173 |
| 2004/0181148 A1 | * | 9/2004 | Uchiyama et al. | 600/425 |
| 2004/0220478 A1 | * | 11/2004 | Wallace et al. | 600/476 |
| 2004/0249247 A1 | * | 12/2004 | Iddan | 600/170 |
| 2004/0267095 A1 | | 12/2004 | Miyake et al. | |
| 2006/0069314 A1 | | 3/2006 | Farr | |
| 2007/0060789 A1 | | 3/2007 | Uchimura et al. | |
| 2007/0191682 A1 | * | 8/2007 | Rolland et al. | 600/173 |
| 2008/0208006 A1 | | 8/2008 | Farr | |
| 2009/0292168 A1 | | 11/2009 | Farr | |
| 2009/0310230 A1 | | 12/2009 | Togino | |
| 2009/0318758 A1 | | 12/2009 | Farr | |
| 2010/0013910 A1 | | 1/2010 | Farr | |
| 2010/0198009 A1 | | 8/2010 | Farr | |
| 2010/0208054 A1 | | 8/2010 | Farr | |
| 2011/0028790 A1 | | 2/2011 | Farr | |

FOREIGN PATENT DOCUMENTS

| | | |
|---|---|---|
| JP | 9-192084 A | 7/1997 |
| JP | 9-327447 A | 12/1997 |
| JP | 10-248844 A | 9/1998 |
| JP | 11-6904 A | 1/1999 |
| JP | H11-056774 | 3/1999 |
| JP | 2002-95632 A | 4/2002 |
| JP | 2002-214127 A | 7/2002 |
| JP | 2003-93339 A | 4/2003 |
| JP | 2003-279862 A | 10/2003 |
| JP | 2005-013359 A | 1/2005 |
| JP | 2005-323889 A | 11/2005 |
| JP | 2006-235346 A | 9/2006 |
| JP | 2007-061296 A | 3/2007 |
| JP | 2008-040468 A | 2/2008 |
| JP | 2008-514304 T | 5/2008 |

OTHER PUBLICATIONS

Japanese Office Action dated Aug. 21, 2012 (JP 2008-157991) with English translation.
Japanese Office Action dated Aug. 21, 2012 (JP 2008-157993) with English translation.
Japanese Office Action dated Aug. 21, 2012 (JP 2008-158000) with English translation.
Japanese Office Action dated Aug. 21, 2012 (JP 2008-158002) with English translation.
Japanese Office Action dated Aug. 21, 2012 (JP 2008-158004) with English translation.
Japanese Office Action dated Aug. 21, 2012 (JP 2008-158005) with English translation.
Japanese Office Action dated Aug. 21, 2012 (JP 2008-158006) with English translation.
Japanese Office Action dated Sep. 11, 2012 (JP 2008-157992) with English translation.
Japanese Office Action dated Sep. 11, 2012 (JP 2008-157999) with English translation.
Japanese Office Action dated Sep. 11, 2012 (JP 2008-158013) with English translation.

* cited by examiner

FIG. 22

| No. 001 | No. 002 | No. 003 | No. 004 | No. 005 | No. 006 | No. 007 | No. 008 | No. 009 | No. 010 |
|---|---|---|---|---|---|---|---|---|---|
| No. 011 | No. 012 | No. 013 | No. 014 | No. 015 | No. 016 | No. 017 | No. 018 | No. 019 | No. 020 |
| No. 021 | No. 022 | No. 023 | No. 024 | No. 025 | No. 026 | No. 027 | No. 028 | No. 029 | No. 030 |
| No. 031 | No. 032 | No. 033 | No. 034 | No. 035 | No. 036 | No. 037 | No. 038 | No. 039 | No. 040 |
| No. 041 | No. 042 | No. 043 | No. 044 | No. 045 | No. 046 | No. 047 | No. 048 | No. 049 | No. 050 |
| No. 051 | No. 052 | | | | | | | | |

FIG. 28

| No. 001 | No. 002 | No. 003 | No. 004 | No. 005 | No. 006 | No. 007 | No. 008 | No. 009 | No. 010 |
|---|---|---|---|---|---|---|---|---|---|
| No. 011 | No. 012 | No. 013 | No. 014 | No. 015 | No. 016 | No. 017 | No. 018 | No. 019 | No. 020 |
| No. 021 | No. 022 | No. 023 | No. 024 | No. 025 | No. 026 | No. 027 | No. 028 | No. 029 | No. 030 |
| No. 031 | No. 032 | No. 033 | No. 034 | No. 035 | No. 036 | No. 037 | No. 038 | No. 039 | No. 040 |
| No. 041 | No. 042 | No. 043 | No. 044 | No. 045 | No. 046 | No. 047 | No. 048 | No. 049 | No. 050 |
| No. 051 | No. 052 | | | | | | | | |

FIG. 53

| No. 001 | No. 002 | No. 003 | No. 004 | No. 005 | No. 006 | No. 007 | No. 008 | No. 009 | No. 010 |
|---|---|---|---|---|---|---|---|---|---|
| No. 011 | No. 012 | No. 013 | No. 014 | No. 015 | No. 016 | No. 017 | No. 018 | No. 019 | No. 020 |
| No. 021 | No. 022 | No. 023 | No. 024 | No. 025 | No. 026 | No. 027 | No. 028 | No. 029 | No. 030 |
| No. 031 | No. 032 | No. 033 | No. 034 | No. 035 | No. 036 | No. 037 | No. 038 | No. 039 | No. 040 |
| No. 041 | No. 042 | No. 043 | No. 044 | No. 045 | No. 046 | No. 047 | No. 048 | No. 049 | No. 050 |
| No. 051 | No. 052 | | | | | | | | |

*FIG. 77*

| No. 001 | No. 002 | No. 003 | No. 004 | No. 005 | No. 006 | No. 007 | No. 008 | No. 009 | No. 010 |
|---------|---------|---------|---------|---------|---------|---------|---------|---------|---------|
| No. 011 | No. 012 | No. 013 | No. 014 | No. 015 | No. 016 | No. 017 | No. 018 | No. 019 | No. 020 |
| No. 021 | No. 022 | No. 023 | No. 024 | No. 025 | No. 026 | No. 027 | No. 028 | No. 029 | No. 030 |
| No. 031 | No. 032 | No. 033 | No. 034 | No. 035 | No. 036 | No. 037 | No. 038 | No. 039 | No. 040 |
| No. 041 | No. 042 | No. 043 | No. 044 | No. 045 | No. 046 | No. 047 | No. 048 | No. 049 | No. 050 |
| No. 051 | No. 052 |         |         |         |         |         |         |         |         |

FIG. 88

| No. 001 | No. 002 | No. 003 | No. 004 | No. 005 | No. 006 | No. 007 | No. 008 | No. 009 | No. 010 |
|---|---|---|---|---|---|---|---|---|---|
| No. 011 | No. 012 | No. 013 | No. 014 | No. 015 | No. 016 | No. 017 | No. 018 | No. 019 | No. 020 |
| No. 021 | No. 022 | No. 023 | No. 024 | No. 025 | No. 026 | No. 027 | No. 028 | No. 029 | No. 030 |
| No. 031 | No. 032 | No. 033 | No. 034 | No. 035 | No. 036 | No. 037 | No. 038 | No. 039 | No. 040 |
| No. 041 | No. 042 | No. 043 | No. 044 | No. 045 | No. 046 | No. 047 | No. 048 | No. 049 | No. 050 |
| No. 051 | No. 052 | | | | | | | | |

FIG. 97

| No. 001 | No. 002 | No. 003 | No. 004 | No. 005 | No. 006 | No. 007 | No. 008 | No. 009 | No. 010 |
|---|---|---|---|---|---|---|---|---|---|
| No. 011 | No. 012 | No. 013 | No. 014 | No. 015 | No. 016 | No. 017 | No. 018 | No. 019 | No. 020 |
| No. 021 | No. 022 | No. 023 | No. 024 | No. 025 | No. 026 | No. 027 | No. 028 | No. 029 | No. 030 |
| No. 031 | No. 032 | No. 033 | No. 034 | No. 035 | No. 036 | No. 037 | No. 038 | No. 039 | No. 040 |
| No. 041 | No. 042 | No. 043 | No. 044 | No. 045 | No. 046 | No. 047 | No. 048 | No. 049 | No. 050 |
| No. 051 | No. 052 | | | | | | | | |

ELECTRONIC ENDOSCOPE INCLUDING LENS HOLDER AND OBJECTIVE MIRROR

CROSS-REFERENCE TO RELATED APPLICATIONS

This application claims the benefit of Japanese Patent Application Nos. 2008-157991, 2008-157992, 2008-157993, 2008-157999, 2008-158000, 2008-158002, 2008-158004, 2008-158005, 2008-158006, and 2008-158013 filed on Jun. 17, 2008, the entire contents of which are hereby incorporated by reference, the same as if set forth at length, the entire of which are incorporated herein by reference.

TECHNICAL FIELD

The present invention relates to an electronic endoscope.

BACKGROUND ART

In an electronic endoscope described in Patent Document 1, an insert part of a small diameter is inserted into a hole or an abdominal cavity so that an objective lens attached at the tip of the insert part is directed to a diseased part or the like in the direction of insertion. Then, in this state, image information is acquired.

Further, in an electronic endoscope described in Patent Document 2, an objective lens is provided in a side surface of the tip part of an insert part. Thus, an image is acquired within the field of view extending sideward.

Further, in an electronic endoscope described in Patent Document 3, an omnidirectional light receiving unit is provided at the tip of an insert part so that an image covering the entire circumferential directions at the tip of the insert part is acquired using reflection by a convex mirror provided inside the omnidirectional light receiving unit.

Further, an electronic endoscope described in Patent Document 4 is of capsule type used for medical checkup of the alimentary canal in the medical field. This electronic endoscope has an imaging device in the inside, and hence continuously performs image pick-up of the inside of the alimentary canal in the course that the electronic endoscope is conveyed along the inside of the alimentary canal in association with peristaltic motion of the alimentary canal.

In many cases, the imaging device accommodated in the tip part of such an electronic endoscope has a smaller area and a smaller number of pixels than a solid-state imaging device used in a digital camera or the like. Thus, when a detailed image of a diseased part or the like is acquired, the image information obtained by each single image pick-up is limited to the image of a small view field region.

Thus, when detailed image information is to be acquired over a large region, the operator of the electronic endoscope need repeat image pick-up multiple times with adjusting the insertion position of the electronic endoscope by manual operation. Thus, attention need be paid to both of the operation of searching a diseased part or the like, that is, adjusting the insertion position, and the operation of image taking. Thus, skill has been necessary in such work.

Further, in the electronic endoscope in which an image over the entire circumference of the tip of the insert part is acquired using an omnidirectional light receiving unit, image information over the entire circumference region of the insertion position where image pick-up is performed is obtained at once. Nevertheless, the image pick-up region is restricted to a region of a narrow width at the insertion position. Thus, in order that entire circumferential image information should be acquired over a large region, image pick-up need be repeated in such a manner that the insertion position is adjusted at each time. This causes a possibility that information is missing at a junction part of images or that useless image pick-up is repeated.

Further, the electronic endoscope of capsule type is conveyed along the inside of an alimentary canal by peristaltic motion of the alimentary canal. Thus, the operation of moving the field of view is unnecessary. Nevertheless, such an electronic endoscope is not applicable to a hole or an abdominal cavity where peristaltic motion is absent.

CITATION LIST

Patent Literatures

Patent Document 1: Japanese Laid-Open Patent Publication No. H09-192084
Patent Document 2: Japanese Laid-Open Patent Publication No. H03-191944
Patent Document 3: Japanese Laid-Open Patent Publication No. 2003-279862
Patent Document 4: Japanese Laid-Open Patent Publication No. H09-327447

SUMMARY OF INVENTION

Technical Problem

An object of the present invention is to provide an electronic endoscope that has a new structure for realizing easy and accurate acquisition of detailed image information over a large region.

Solution to Problem (1) An electronic endoscope characterized in that an outer shell that is formed in a tube shape and whose peripheral wall is provided with a transparent window part extending in an axial dilation; a solid-state imaging device that is provided inside the outer shell; an objective optical system that includes an objective lens for focusing object light through the window part and that forms an image onto the solid-state imaging device; and a drive mechanism that causes at least the objective lens in the objective optical system to move along an axis of the outer shell.

(2) An electronic endoscope that is inserted into a subject and then acquires an image inside the subject, characterized in that: a lens holder that has a tube-shaped part; a wide-angle lens that is mounted on the lens holder and that is arranged on one-end side of the tube-shaped part in a state that an optical axis is aligned to a center axis of the tube-shaped part so that an observational field of view extends to a sideward region of the tube-shaped part; an imaging device that receives light acquired through the wide-angle lens and that converts the light into an electric signal; a transparent cover that covers one-end side of the tube-shaped part and at least whose part facing the observational field of view of the wide-angle lens has transparency; a tube-shaped body part that is connected to the transparent cover on the-other-end side of the tube-shaped part; and a driving section that is arranged inside the body part and that causes the lens holder to advance or retreat in the center axis direction.

(3) An electronic endoscope characterized in that: a cylindrical transparent cover at least whose observation window in a cylindrical part is transparent; a body part that has a cylindrical part provided continuously to the cylindrical part of the transparent cover; a lens holder that revolves about a center axis of the transparent cover in an inside of the transparent cover and the body part and that moves in a direction of the center axis; an objective mirror that is provided in the lens holder and that reflects, toward the body part, light entering through an objective lens provided at a position facing the cylindrical part of the transparent cover; an imaging device that receives light reflected from the objective mirror and that converts the light into an electric signal; and a driving section that is provided inside the body part and that drives and revolves the lens holder so as to drive the lens holder in the center axis direction.

Advantageous Effects of Invention

According to the present invention, detailed image information over a large region is acquired easily and accurately.

BRIEF DESCRIPTION OF THE DRAWINGS

FIG. 22 is a schematic diagram used for describing a view field region in an endoscope shown in FIG. 16.

FIG. 28 is a schematic diagram used for describing a view field region in an endoscope shown in FIG. 23.

FIG. 53 is a diagram showing a situation of movement of a field of view of image pick-up of an objective lens shown in FIG. 47.

FIG. 77 is a diagram showing a situation of movement of a field of view of image pick-up of an objective lens shown in FIG. 72.

FIG. 88 is a diagram illustrating movement of a field of view of image pick-up of an objective lens in a case that image pick-up steps are executed repeatedly.

FIG. 97 is a schematic diagram showing a situation of movement of a field of view of image pick-up of an electronic endoscope shown in FIG. 90.

DESCRIPTION OF EMBODIMENTS

Figure 1:
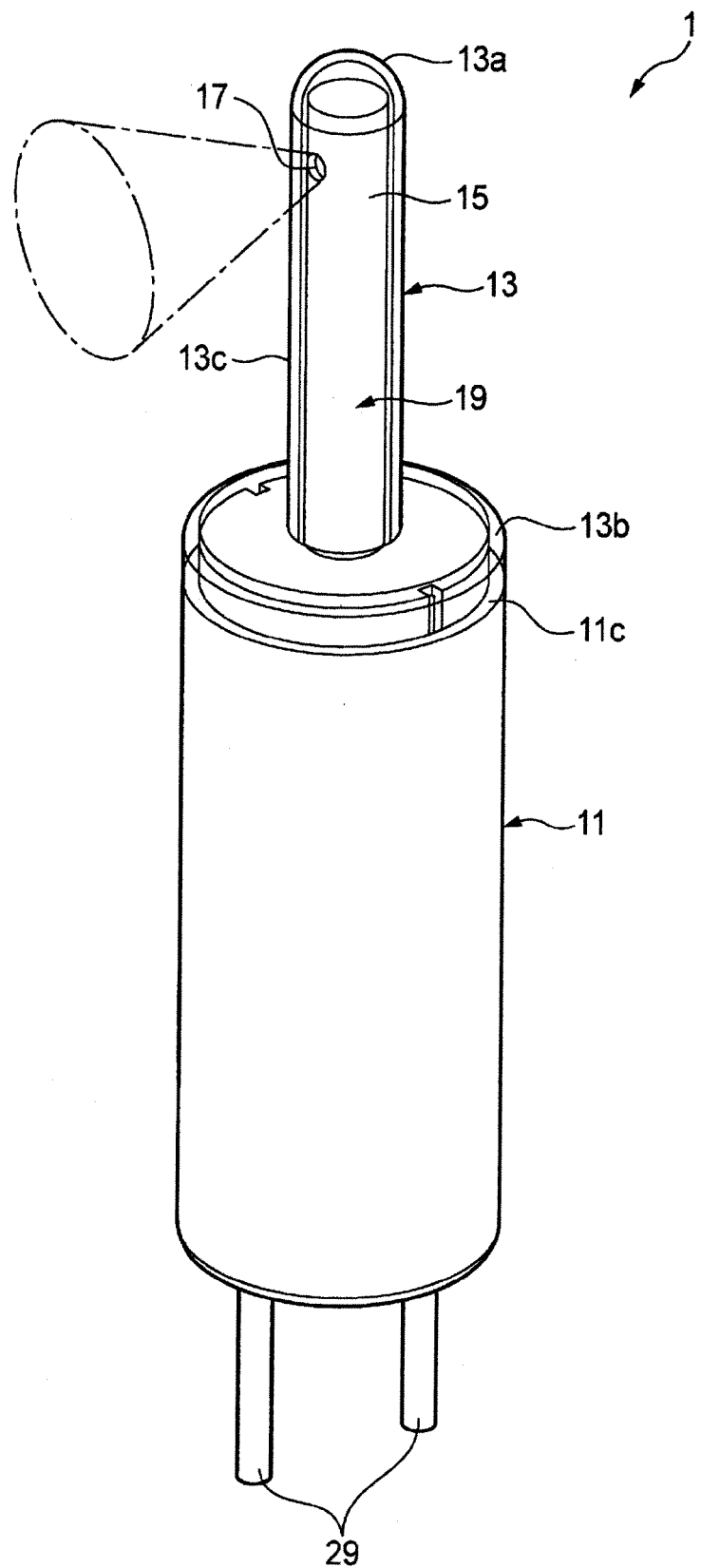
FIG. 1 is an external appearance perspective view of an example of an electronic endoscope used for describing an embodiment of the present invention.
Figure 2:
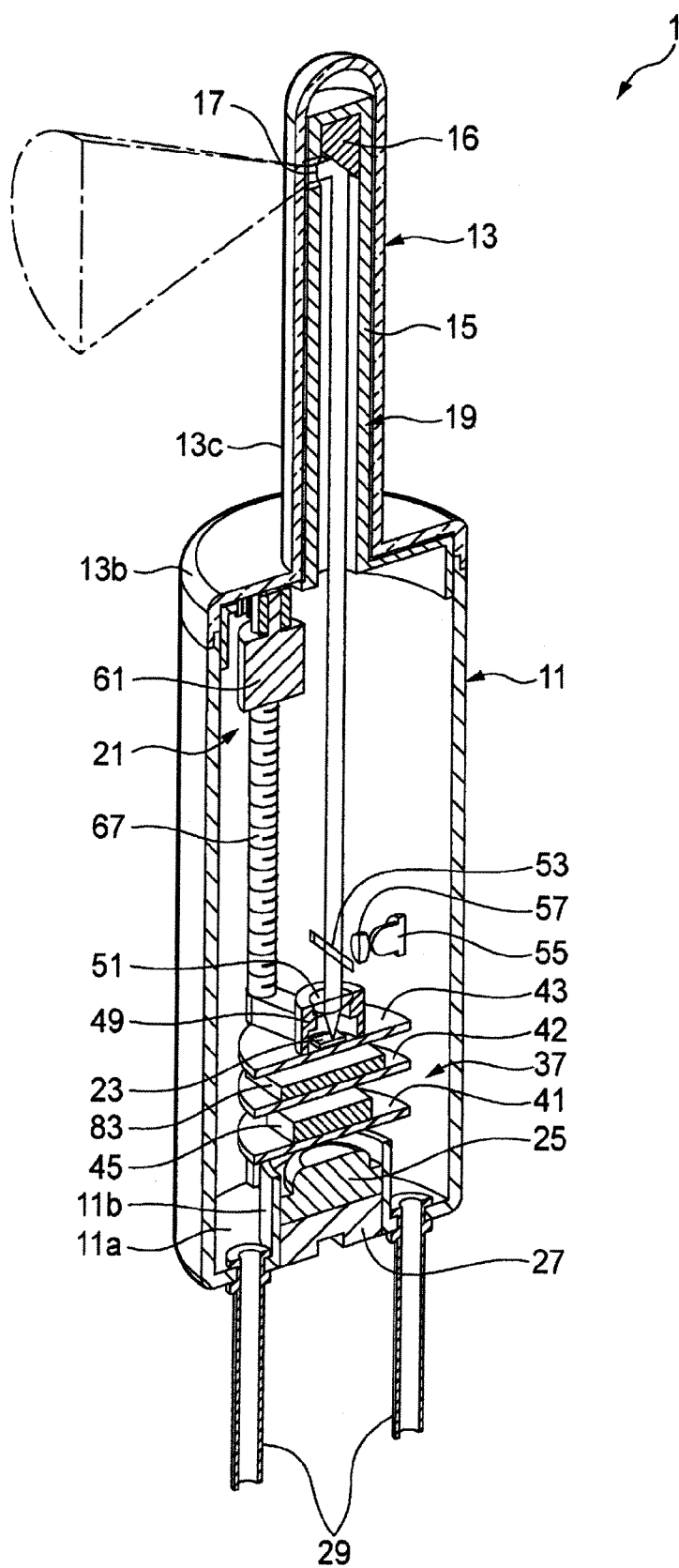
FIG. 2 is a longitudinal sectional view of an endoscope shown in FIG. 1.
Figure 3:
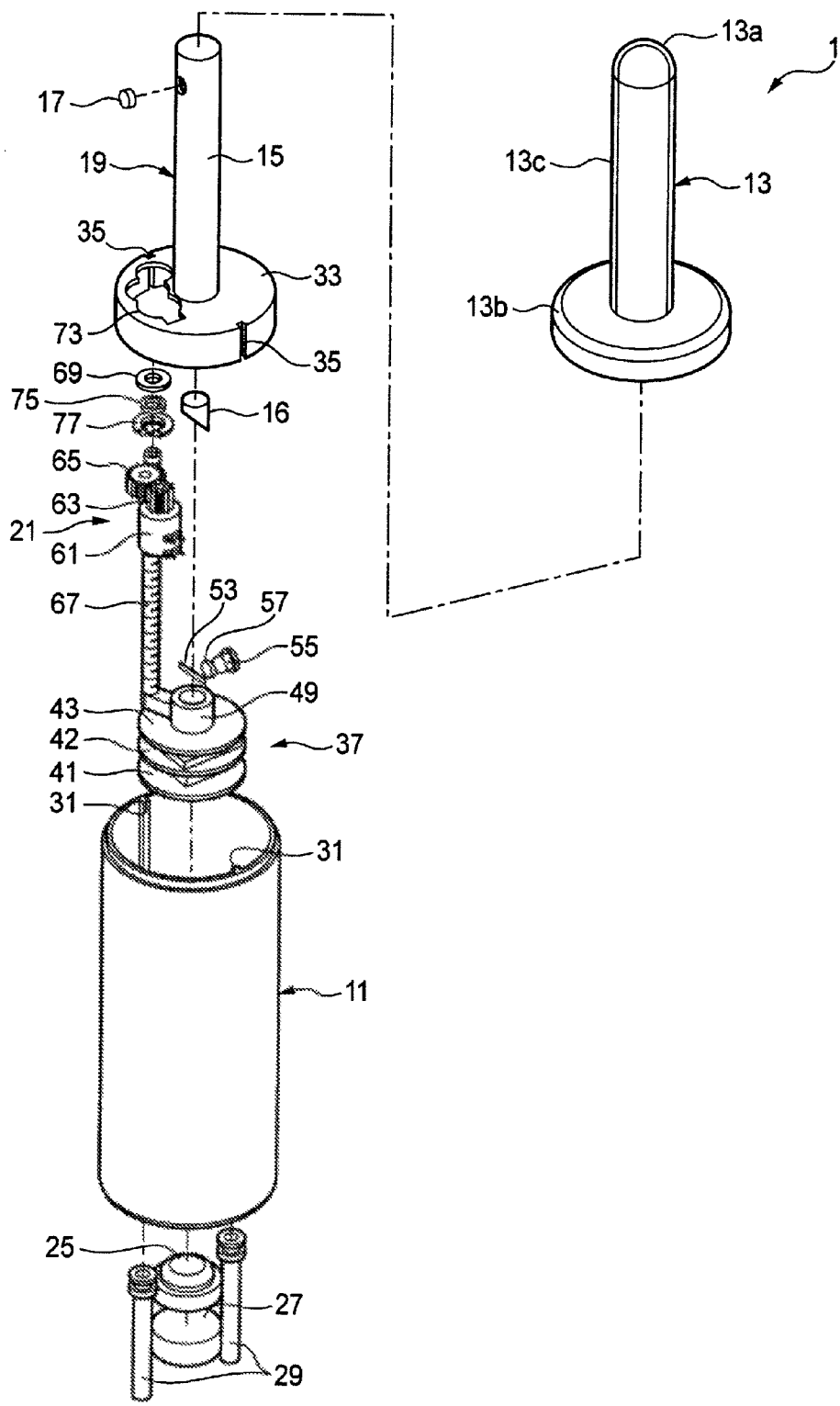
FIG. 3 is an exploded perspective view of an endoscope shown in FIG. 1.

An electronic endoscope 1 shown in FIGS. 1 to 3 has an outer shell constructed from a body part 11 and a transparent cover 13. Then, its inside is provided with: a lens holder 19 that holds an objective lens 17 for focusing object light through the transparent cover 13; a driving section 21 for moving the lens holder 19 inside the outer shell; and a solid-state imaging device 23 that receives the object light acquired through the objective lens 17 and then converts the light into an electric signal.

The body part 11 constituting a part of the outer shell is fabricated from resin material or the like having light shielding property and formed into a cylindrical shape whose one-end part 11a is closed and whose the other end part 11c is open. The closed end part (bottom part) 11a is provided with a tube-shaped battery accommodating part 11b. The battery accommodating part 11b is closed by a battery lid 27 after a power battery 25 is mounted.

That is, the electronic endoscope 1 is provided with the power battery 25 in the inside, and hence does not require other power supply from the outside. Thus, the electronic endoscope 1 need not be connected to a power supply cable, and hence permits easy handling.

Here, in the example shown in the figure, in the bottom part 11a, two pipes 29 protrude outward from the outer shell. For example, in a case that image data and an image map stored in a memory 83 described later are to be transferred to an external device, data transfer cables are inserted through and protected by the pipes 29. The pipes 29 may be fabricated from soft material, or alternatively may be fabricated from hard material so as to serve as a grip used for inserting or extracting the electronic endoscope 1 into or from a hole serving as a subject, or for rotating the electronic endoscope 1 during the use of the electronic endoscope 1.

The transparent cover 13 formed in a cylindrical shape whose one-end part 13b is open. In the transparent cover 13, the open end part 13b is aligned with the open end part 11c of the body part 11, and then fixed to the body part 11 by appropriate means such as bonding. Here, in the electronic endoscope 1, the shape of the body part 11 and the transparent cover 13 serving as an outer shell reed not be a cylinder and may be a tube of another kind.

The other end part (tip part) 13a of the transparent cover 13 is formed in a smooth hemispherical shape for permitting easy insertion into a hole serving as a subject. Then, the tip part 13a and the open end part 13b are connected by a cylindrical part 13c having the scare diameter as the tip part 13a. The tip part 13a and the cylindrical part 13c are formed in a smaller diameter than the open end part 13b. As such, since the hemispherically formed tip part 13a and the cylindrical part 13c are formed in a small diameter, easy insertion into a relatively narrow hole serving as a subject is achieved so that the range of application of the electronic endoscope 1 is expanded.

The transparent cover 13 having the above-mentioned configuration is fabricated from transparent resin material or the like by integral molding or the like. Alternatively, the hemispherically formed tip part 13a, the open end part 13b, and the cylindrical part 13c may be fabricated as separate members, and then may be joined to each other by appropriate means as such bonding. In this case, at least the cylindrical part 13c serving as a window part facing the inner peripheral surface of a hole serving as a subject is formed transparent. Here, in the present invention, the term "transparent" indicates that the material is transparent to light at a particular wavelength sensitive to the imaging device 23. That is, the material need not be transparent to visible light.

The lens holder 19 is formed from resin material or the like and has: a disk-shaped flange 33 fit into the body part 11; and a tube-shaped part 15 formed in a smaller diameter than the flange 33 and capable of entering the cylindrical part 13c of the transparent cover 13. In the flange 33, its outer diameter is formed somewhat smaller than the inner diameter of the body part 11. Thus, the flange 33 moves in the inside of the body part 11 along the center axis of the body part 11, that is, along the center axis of the outer shell, smoothly without chattering. Further, in the tube-shaped part 15, its outer diameter is formed somewhat smaller than the inner diameter of the cylindrical part 13c of the transparent cover 13. Thus, the tube-shaped part 15 moves in the inside of the cylindrical part 13c along the center axis of the outer shell smoothly without chattering.

In the flange 33 of the lens holder 19, engagement grooves 35 are formed in the outer peripheral surface. The inner peripheral surface of the body part 11 is provided with ribs 31 extending along the axis of the outer shell. Then, in the lens holder 19, the engagement grooves 35 of the flange 33 are engaged with the ribs 31 of the body part 11. Thus, movement of the lens holder 19 is guided in parallel to the center axis of the outer shell. That is, revolution about a feed screw 67 described later is stopped. Here, in the example shown in the figure, two engagement grooves 35 are provided at intervals in the circumferential direction. However, the number of such grooves need not be two.

In the tip part of the tube-shaped part 15, an objective mirror 16 is accommodated. The objective mirror 16 has a shape obtained by cutting a cylinder with an included plane intersecting the center axis at 45 degrees. Then, the inclined surface is fabricated in the form of a reflecting surface by formation of a reflection film or the like.

Further, in the tube-shaped part 15, an image pick-up hole is formed at a site radially facing the reflecting surface of the objective mirror 16. Then, the objective lens 17 is mounted inside the image pick-up hole. Then, object light is focused along the cylindrical part 13c of the transparent cover 13 by the objective lens 17 so as to travel to the objective mirror 16 in the form of a parallel light beam. Then, the object light is reflected by the reflecting surface of the objective mirror 16, and then travels along the center axis of the tube-shaped part 15 in parallel to the center axis of the outer shell with maintaining the form of a parallel light beam.

In the inside of the body part 11, an image pick-up drive unit part 37 is arranged at a position located on an extended line of the center axis of the tube-shaped part 15 of the lens holder 19. The image pick-up drive unit part 37 is fixed inside the body part 11 by a fixing member (not shown). The image pick-up drive unit part 37 has three base plates 41, 42, and 43.

Figure 4:
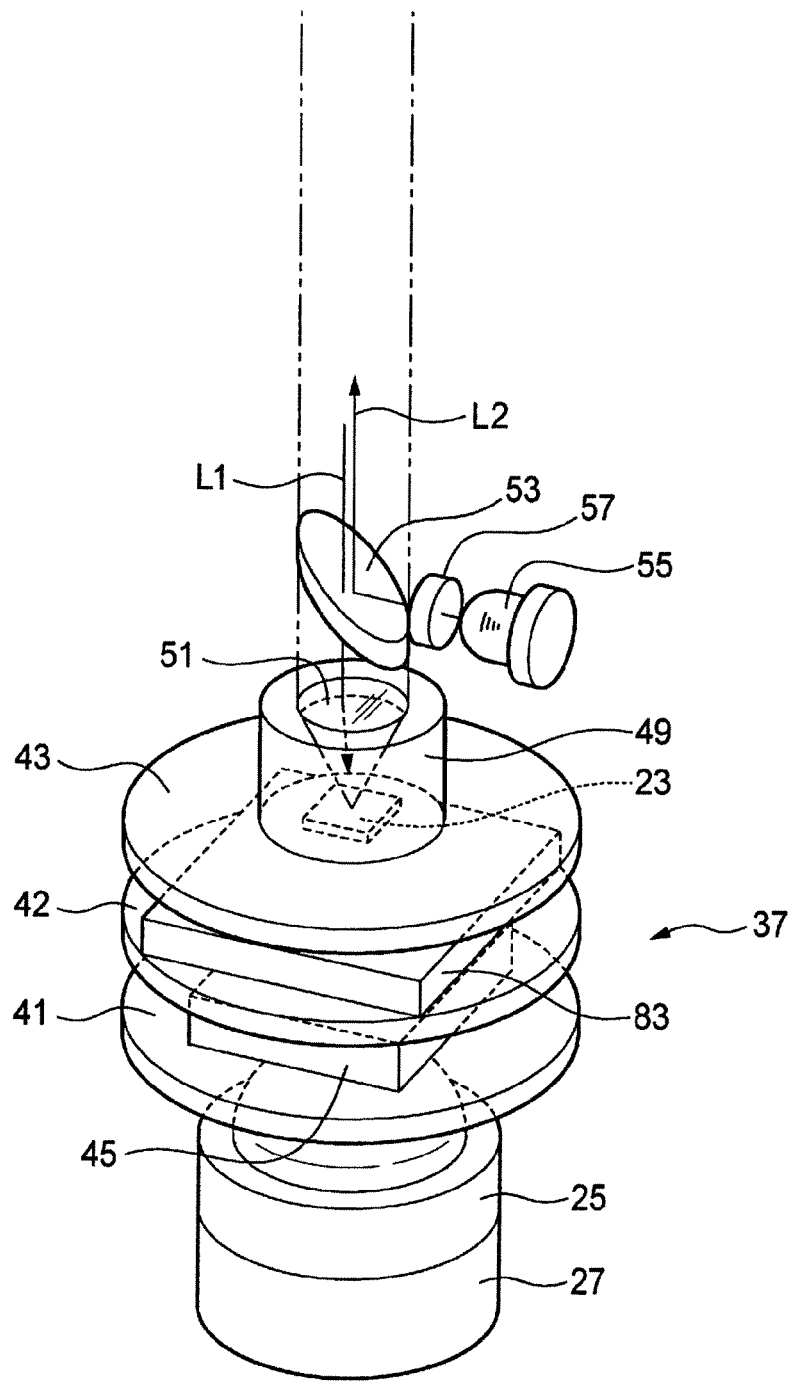
FIG. 4 is an enlarged perspective view of an image pick-up drive unit part that contains a solid-state imaging device in an endoscope shown in FIG. 1.

FIG. 4 shows the image pick-up drive unit part 37 in an enlarged view. The solid-state imaging device 23 is provided on a base plate 43 arranged most adjacent to the lens holder 19. The imaging device 23 may be a CCD type imaging device, a CMOS type imaging device, or the like. A memory 83 is mounted on a base plate 42 arranged under the base plate 43 (on the bottom part 11a side of the body part 11). The memory 83 stores image data and the like generated from image pick-up signals read out from the imaging device 23. Further, a control unit 45 is mounted on a base plate 41 arranged under the base plate 42. The control unit 45 performs, for example, read of image pick-up signals from the imaging device 23 and generation of image data on the basis of the read-out image pick-up signals.

The imaging device 23 is arranged on the base plate 43 at a position located on an extended line of the center axis of the tube-shaped part 15 of the lens holder 19. Then, a focusing lens 51 is arranged at a position located above the imaging device 23 and located on an extended line of the center axis of the tube-shaped part 15. The focusing lens 51 is held by a focusing lens holder 49 provided on the base plate 43 in a manner of surrounding the imaging device 23. The focusing lens 51 causes the object light L1 traveling in the form of a parallel light beam along the center axis of the tube-shaped part 15 to be focused on the light acceptance surface of the imaging device 23 so that image formation is achieved. That is, the objective lens 17, the objective mirror 16, and the focusing lens 51 constitute an objective optical system.

Further, a half mirror 53 is arranged on the optical path of the object light between the objective mirror 16 accommodated in the tube-shaped part 15 of the lens holder 19 and the focusing lens 51. The half mirror 53 allows transmission of at least a part of the object light traveling from the objective mirror 16 toward the focusing lens 51. Further, at a position located outside the optical path of the object light between the objective mirror 16 and the focusing lens 51 and that faces the half mirror 53, a light emitting diode (LED) 55 is provided that serves as a light source for illuminating the image-taking object. Light for illumination L2 projected from the LED 55 is brought into the form of a parallel light beam by an illumination lens 57 arranged between the LED 55 and the half mirror 53, and then enters the half mirror 53 so that at least a part of the light is reflected toward the objective mirror 16. Then, the light for illumination having entered the objective mirror 16 is reflected toward the objective lens 17, and then projected through the objective lens 17 and the transparent cover 13 onto the image-taking object. Here, the half mirror 53, the LED 55, and the illumination lens 57 are fixed inside the body part 11 individually by appropriate fixing members.

Here, the movement of the lens holder 19 is guided along the center axis of the outer shell by the above-mentioned engagement between the engagement grooves 35 of the flange 33 and the ribs 31 of the body part 11. Then, the lens holder 19 whose movement is guided along the center axis of the outer shell is allowed to move such that the objective lens 17 held in the tube-shaped part 15 moves between height h1 shown in FIG. 5A and height hn shown in FIG. 5B. In the following, the driving section 21 for moving the lens holder 19 is described in detail with reference to FIGS. 3, 6A, 6B, and 7.

Figure 7:
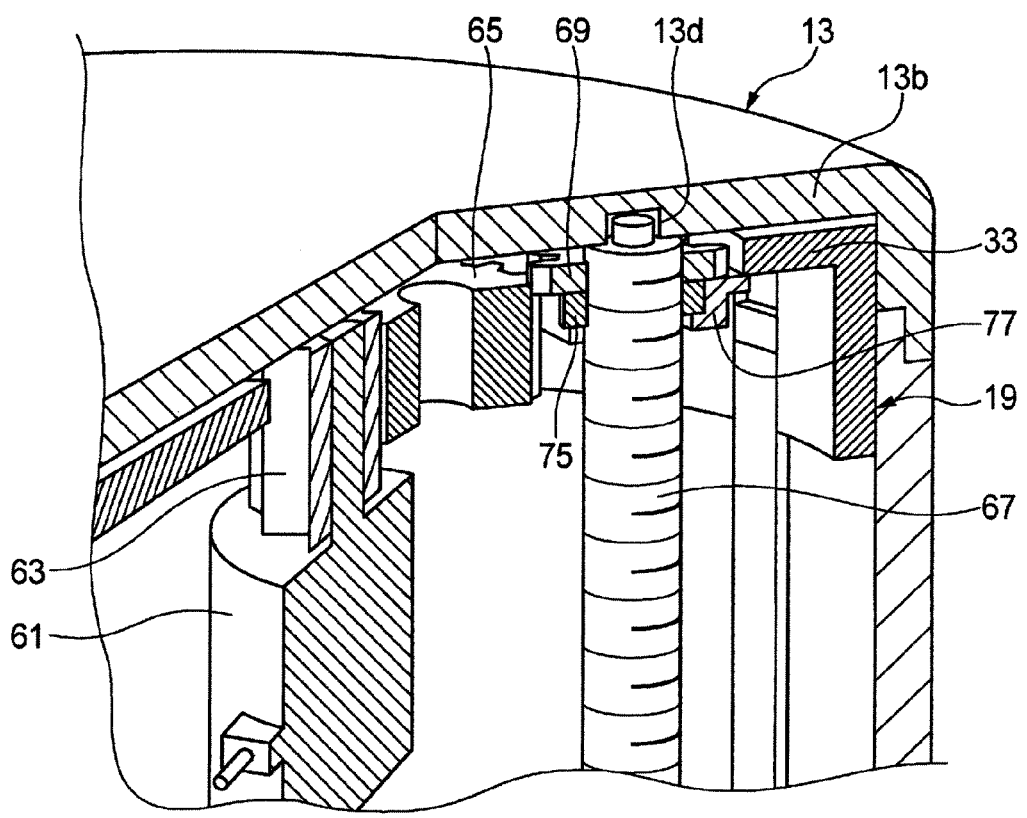
FIG. 7 is a partly sectional perspective view of a driving section shown in FIG. 6A.

The inside of the body part 11 is provided with: a feed screw 67 arranged in parallel to the center axis of the outer shell; and a stepping motor 61 serving as a source of power for driving and revolving the feed screw 67. A motor gear wheel 63 is integrally attached to the shaft of the stepping motor 61, and a gear wheel 69 is integrally attached to one-end part of the feed screw 67. Then, between the motor gear wheel 63 and the gear wheel 69, an idle gear wheel 65 is provided such as to engage with these gear wheels 63 and 69. The stepping motor 61 and the idle gear wheel 65 are fixed inside the body part 11 by appropriate fixing members. Further, as shown in FIG. 7, in the feed screw 67, its one-end part is inserted into a shaft hole 13d formed in the flange face of the open end part 13b of the transparent cover 13, while the other end part is supported by a support arm 71 provided in the side face of the focusing lens holder 49 of the image pick-up drive unit part 37, so that the feed screw 67 is revolvable about the center axis.

The revolution of the stepping motor 61 is transmitted through the motor gear wheel 63, the idle gear wheel 65, and the gear wheel 69 to the feed screw 67. Here, the idle gear wheel 65 has a larger number of gear teeth than the motor gear wheel 63. Thus, the revolution of the stepping motor 61 is slowed down and then transmitted to the idle gear wheel 65. Here, the employed source of power for driving and revolving the feed screw 67 is not limited to a stepping motor operated by pulse drive, and may be a motor of a diverse kind such as a servo motor provided with an encoder, or alternatively may be a power source of another type.

On the other hand, in the flange 33 of the lens holder 19, a through-hole 73 is formed that allows the stepping motor 61, the motor gear wheel 63, the idle gear wheel 65, the feed screw 67, the gear wheel 69, and the like to pass through. Then, in the lens holder 19, a feed nut 75 screwed onto the feed screw 67 is attached integrally by a nut holding piece 77. As described above, the lens holder 19 is guided such that movement in the up and down directions in the figure is permitted along the center axis of the outer shell and that revolution movement about the feed screw 67 is restricted. Thus, in association with revolution of the feed screw 67, the feed nut 75 screwed on the feed screw 67 and the lens holder 19 that holds the feed nut 75 move along the feed screw 67, that is, along the center axis of the outer shell.

Figure 6A:
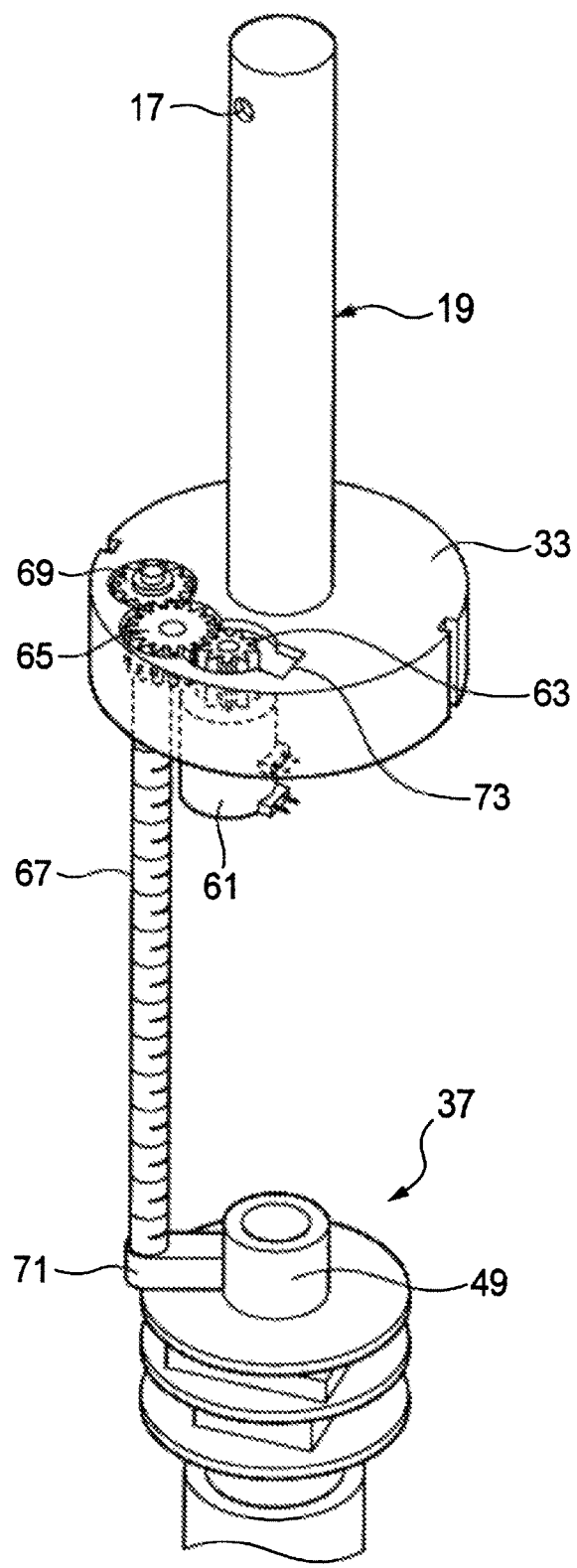
FIG. 6A is a perspective view used for describing a driving section for moving a lens holder for holding an objective lens in an endoscope shown in FIG. 1.
Figure 6B:
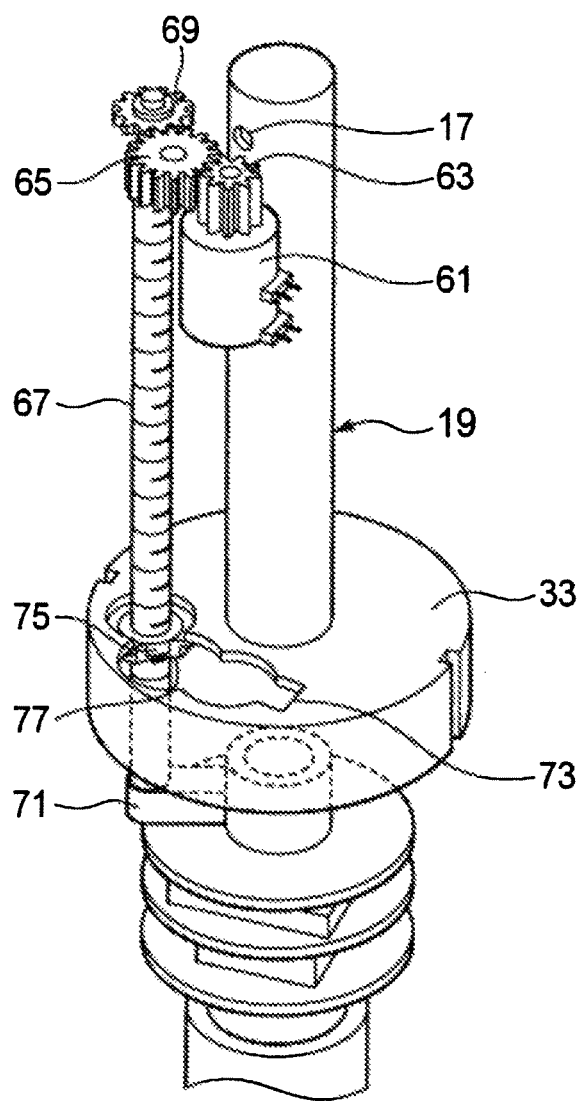
FIG. 6B is a perspective view used for describing a driving section for moving a lens holder for holding an objective lens in an endoscope shown in FIG. 1.

For example, in a situation that the lens holder 19 is located at a raised position shown in FIG. 6A, the stepping motor 61 is revolved in a predetermined direction so that the feed screw 67 is revolved via the motor gear wheel 63, the idle gear wheel 65, and the gear wheel 69. In association with the revolution of the feed screw 67, the feed nut 75 moves along the feed screw 67. By virtue of this, the lens holder 19 formed integrally with the feed nut 75 is lowered to the lowered position shown in FIG. 6B.

Figure 8:
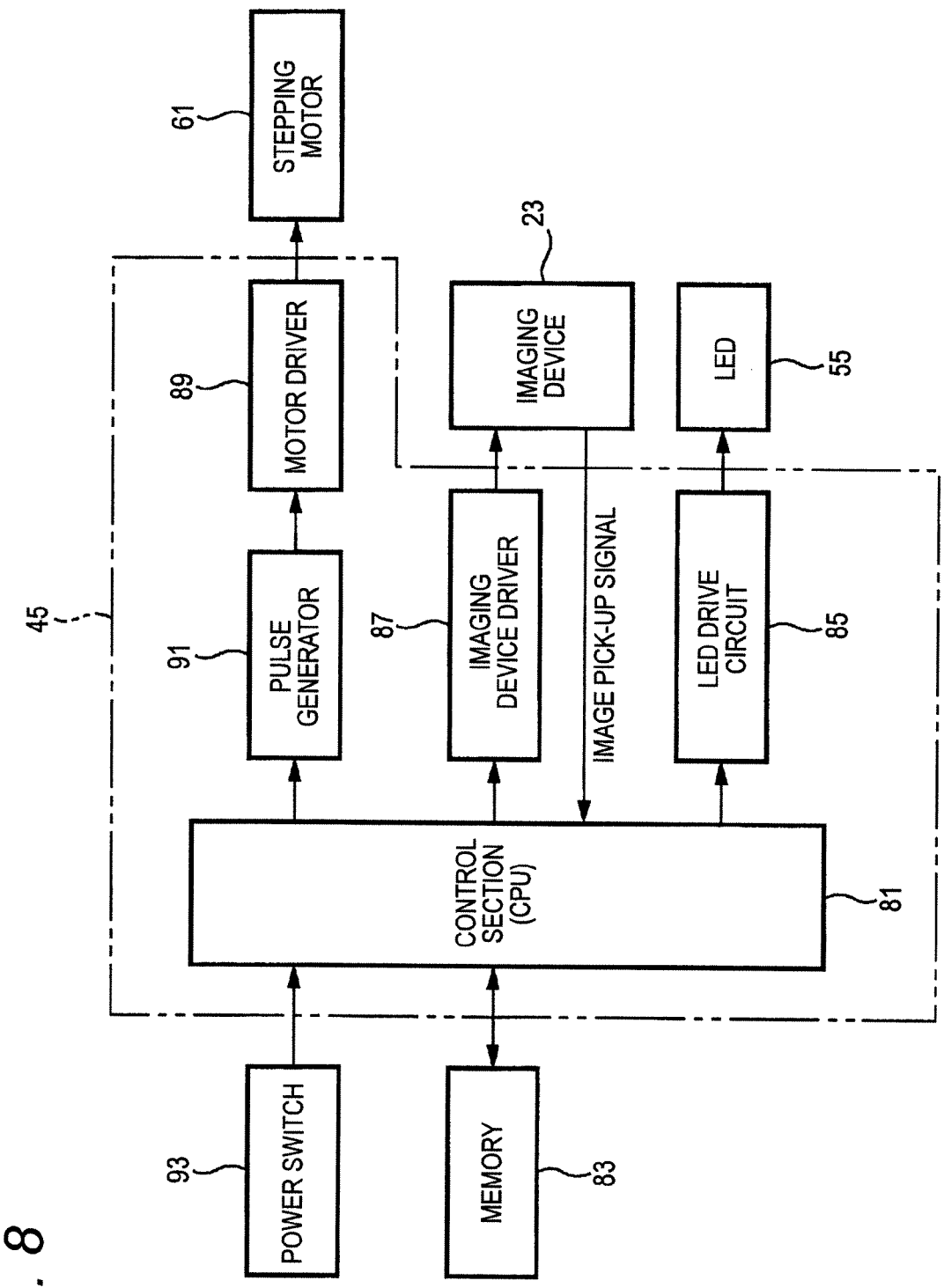
FIG. 8 is a functional block diagram showing an endoscope shown in FIG. 1.

FIG. 8 is a functional block diagram showing the image pick-up drive unit part 37. In the image pick-up drive unit part 37, the control unit 45 has: an LED drive circuit 85 for driving the LED 55; an imaging device driver 87 for driving the imaging device 23; a motor driver 89 for driving the stepping motor 61; a pulse generator 91 for providing driving pulses to the motor driver 89; and a control section 81 for controlling the operation of the LED drive circuit 85, the imaging device driver 87, and the pulse generator 91. Further, the memory 83 stores a control program for the control unit 45. Here, in addition to the storing of a control program, the memory 83 stores image data and serves also as a work memory. The control section 81 performs appropriate image processing onto image pick-up signals read from the imaging device 23, so as to generate image data, and then stores the generated image data into the memory 83. This configuration allows the electronic endoscope 1 in a stand alone mode to acquire save images of image-taking objects. This provides excellence in easy handling.

When the power switch 93 of the electronic endoscope 1 is closed, electric power from the power battery 25 is supplied through wiring (not shown) to the individual parts of the image pick-up drive unit part 37, so that image pick-up is performed. For example, the power switch 93 may be provided in the bottom part 11a of the body part 11, and may be opened or closed by manual operation. Alternatively, a switch terminal that follows magnetism may be built in the body part 11. Then, from the outside of the electronic endoscope 1, a magnet may be brought close or apart so that the switch terminal may be opened or closed.

Next, the operation of the electronic endoscope 1 is described below. When the power switch 93 is turned ON, electric power is supplied from the power battery 25 to the individual pmts. Then, light for illumination is projected from the LED 55 through the objective lens 17 and the cylindrical part 13c of the transparent cover 13 toward a side direction so that an image-taking object is illuminated.

Reflected light from the image-taking object is acquired into the electronic endoscope 1 through the cylindrical part 13c of the transparent cover 13 and the objective lens 17, so that an image is formed onto the light acceptance surface of the imaging device 23 by the focusing lens 51. Then, charge accumulated in the imaging device 23 as a result of photoelectric conversion is read as an image pick-up signal by the control section (CPU) 81 of the control unit 45. The control section 81 performs appropriate image processing onto the read-out image pick-up signal so as to generate image data, and then stores the generated image data into the memory 83.

Figure 9:
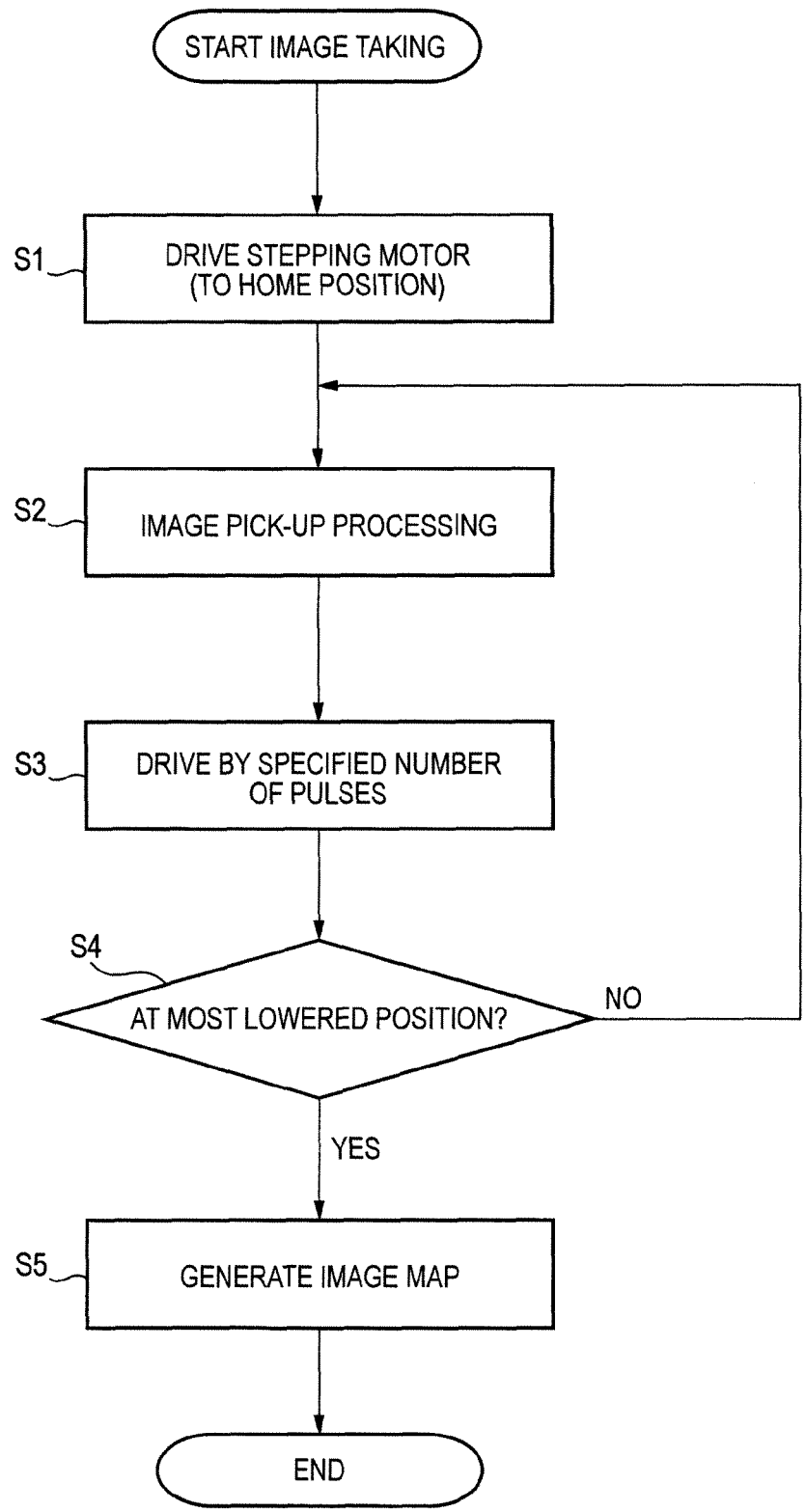
FIG. 9 is a control flow chart of an endoscope shown in FIG. 1.

FIG. 9 is a flow chart showing the processing procedure of a control program of the control unit 45 When the power switch 93 is turned ON, first, the stepping motor 61 is driven and revolved, so that the lens holder 19 goes along the center axis of the outer shell of the electronic endoscope 1 to a home position (step S1). Here, the home position indicates, for example, the position shown in FIG. 5A where the objective lens 17 is located on the tip side of the electronic endoscope 1. However, the definition is not limited to this. That is, the home position may be defined as the opposite position where the objective lens 17 is located on the pedestal side (the position shown in FIG. 5B).

After the lens holder 19 is set at the home position, image pick-up processing is performed (step S2). The image pick-up processing includes such processes that: the LED 55 is driven so as to emit light for illumination; object light is acquired through the objective lens 17 into the electronic endoscope 1 so that an image is formed onto the light acceptance surface of the imaging device 23; and on the basis of the image pick-up signal read from the imaging device 23, image data is generated and then stored into the memory 83.

Then the stepping motor 61 is driven by a specified number of pulses (step S3), so that the lens holder 19 is lowered by a predetermined distance. Until the lens holder 19 reaches the most lowered position (step S4), image pick-up processing is performed at each destination of the movement (step S2). When the lens holder 19 reaches the most lowered position, the lowering operation of the lens holder 19 and the image pick-up processing are terminated (step S4). Here, in the electronic endoscope 1, the plural pieces of image data stored in the memory 83 are combined into an image map as shown in FIG. 10 (step S5).

Figure 5A:
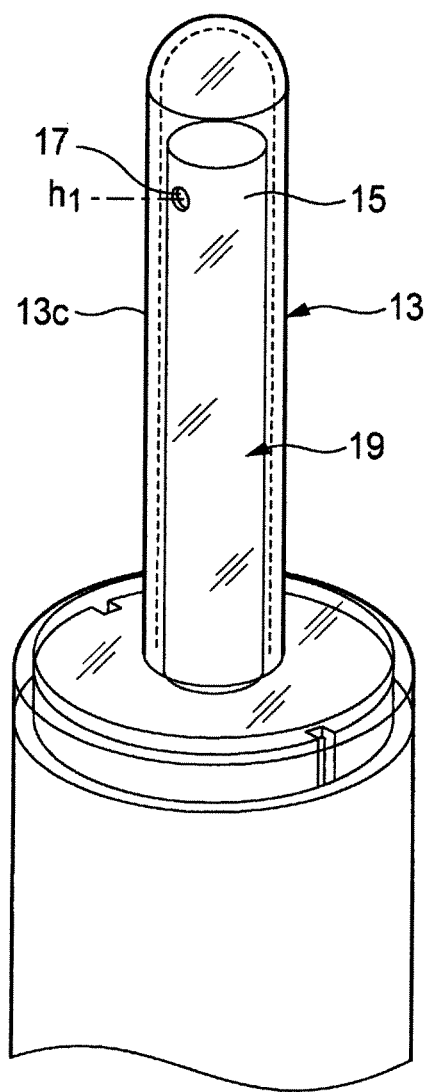
FIG. 5A is a perspective view used for describing operation of a lens holder for holding an objective lens in an endoscope shown in FIG. 1.
Figure 5B:
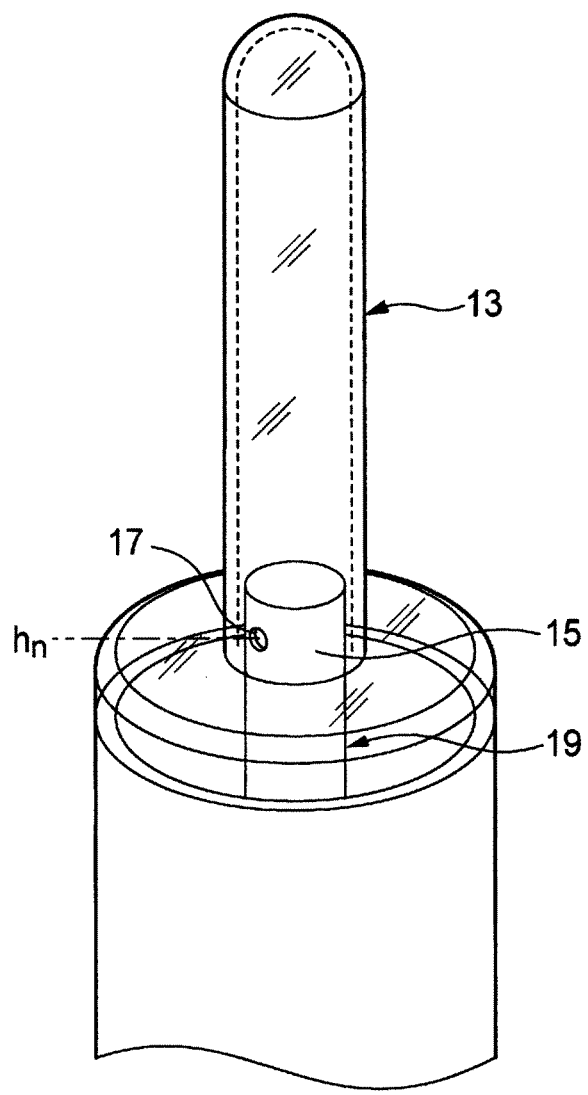
FIG. 5B is a perspective view used for describing operation of a lens holder for holding an objective lens in an endoscope shown in FIG. 1.
Figure 10:
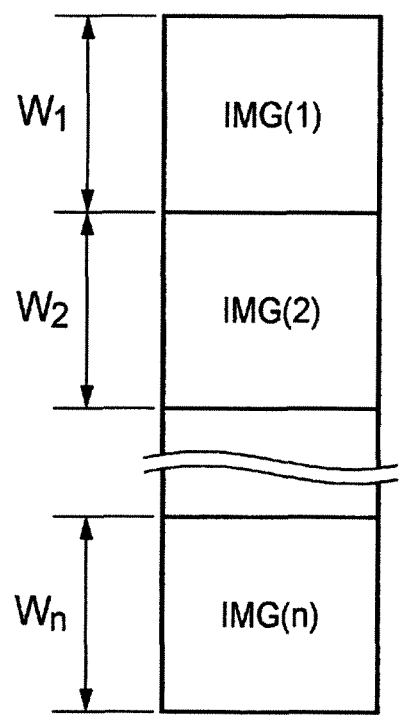
FIG. 10 is a schematic diagram showing an image map generated by an endoscope shown in FIG. 1.

In the image map shown in FIG. 10, the image data IMG(1) indicates image data acquired in the first occasion of image pick-up operation, which was taken over the view field region W1 in a situation that the objective lens 17 was located at height h1 shown in FIG. 5A. Further, the image data IMG(2) indicates image data acquired in the second occasion of image pick-up operation, which was taken over the view field region W2 in a situation that the objective lens 17 was lowered together with the lens holder 19 by a predetermined distance and thereby located at height h2.

As such, plural pieces of image data IMG(1) to IMG(n) each obtained at each position of the movement of the lens holder 19 are combined into a substantially single sheet of image data (image map) by linking the data pieces sequentially in the order of image pick-up in the moving direction of the lens holder 19. Here, for example, the number of pulses provided to the stepping motor 61 at step S3 may be adjusted appropriately, or alternatively the screw pitch of the feed screw 67 may be adjusted appropriately, such that a part of the view field region in the present occasion of image pick-up processing should overlap with the view field region in the preceding occasion of image pick-up processing. By virtue of this, images of the image-taking object are acquired without a missing part in the axial direction so that an image map without a gap is obtained.

When the above-mentioned image map has been generated, the image map is to be read from the memory 83 to the outside (see FIG. 8). This read may be performed by wireless, or alternatively through a cable in a configuration that a data transfer cable is inserted through the pipe 29 shown in FIG. 1 and connected to the image pick-up drive unit part 37. Alternatively, the memory 83 may be provided in a removable manner from the electronic endoscope 1. Then, the removed memory 83 may be read by a personal computer provided separately.

Further, the electronic endoscope 1 may transmit the image data to an external monitor, so that the image may be observed on line through the external monitor. In addition, operation instructions may be inputted from the outside. In this case, without performing image processing, the control section 81 transmits the image pick-up signal acquired from the imaging device 23, to an external video processor in an intact manner. Then, an object image obtained by image processing by the video processor is displayed on the external monitor. The communication between the external video processor, the external monitor, and the control section 81 may be of cable or wireless. In a case that the communication is of cable, an external power source becomes employable when a power source line is included in the wiring.

Further, as another example of the control program, a control program may be employed that, in addition to the control procedure shown in the flow chart of FIG. 9, allows the view field region of the objective lens 17 to be moved to an arbitrary position in accordance with an operation instruction from the outside. In this case, selective image pick-up of a desired site is achieved in accordance with the purpose of image pick-up, and hence more detailed observation of the site is allowed.

According to the electronic endoscope 1 described above, after being installed inside a hole, the objective lens 17 is moved in the axial direction by the driving section 21. In association with this, the field of view moves in the axial direction. This permits accurate acquisition of an image over a large region of the inner peripheral surface of the hole, without the necessity of a skill in the operation.

Figure 11:
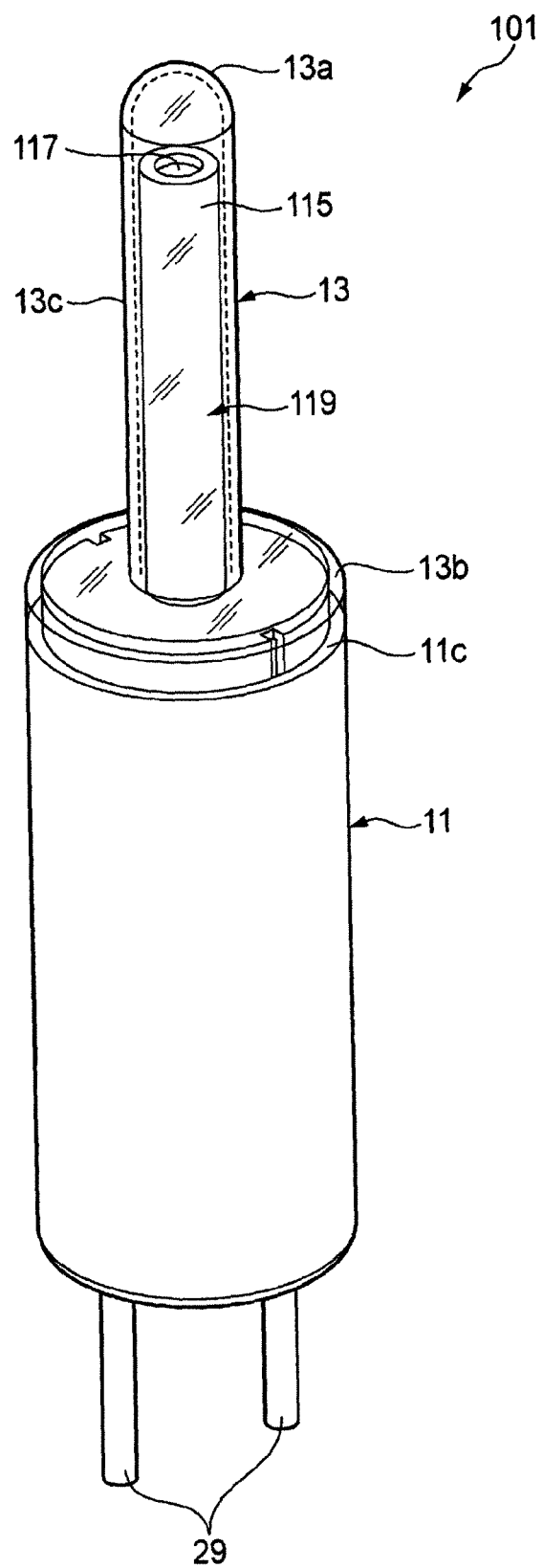
FIG. 11 is an external appearance perspective view of another example of an electronic endoscope used for describing an embodiment of the present invention.
Figure 12:
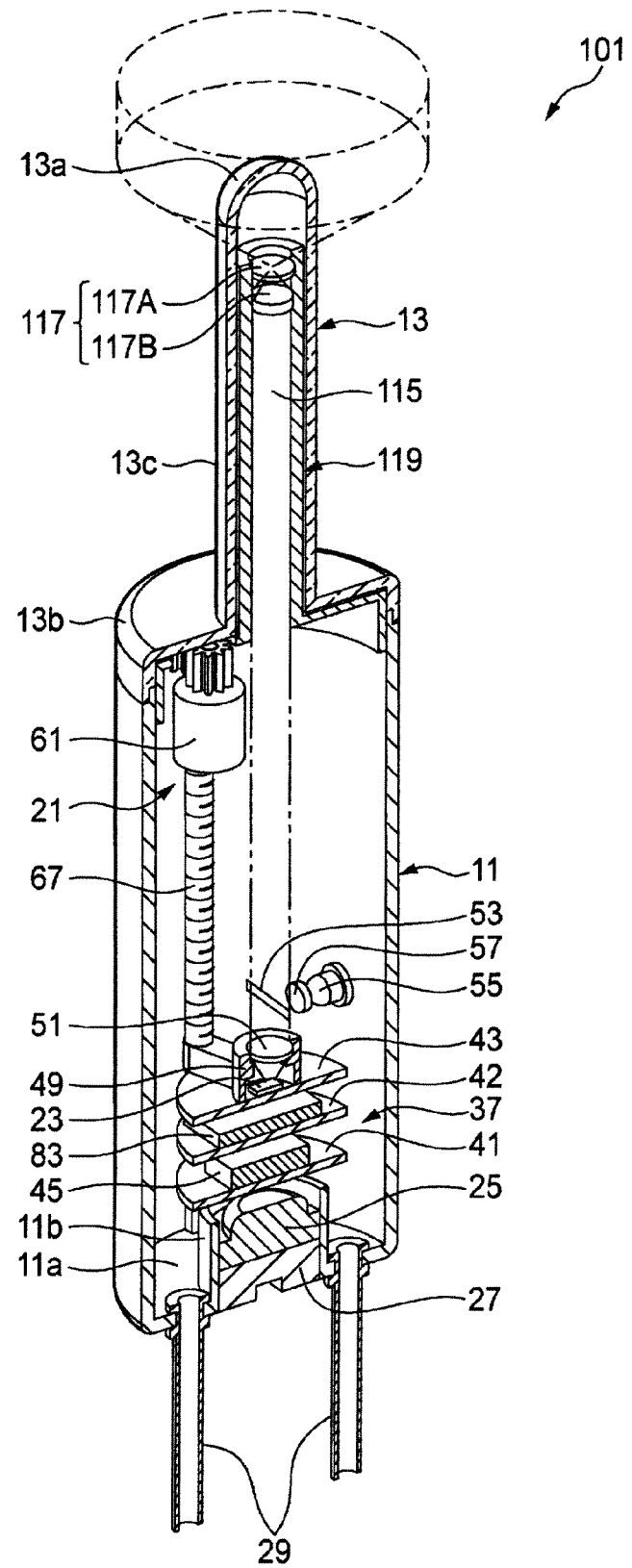
FIG. 12 is a longitudinal sectional view of an endoscope shown in FIG. 10.
Figure 13:
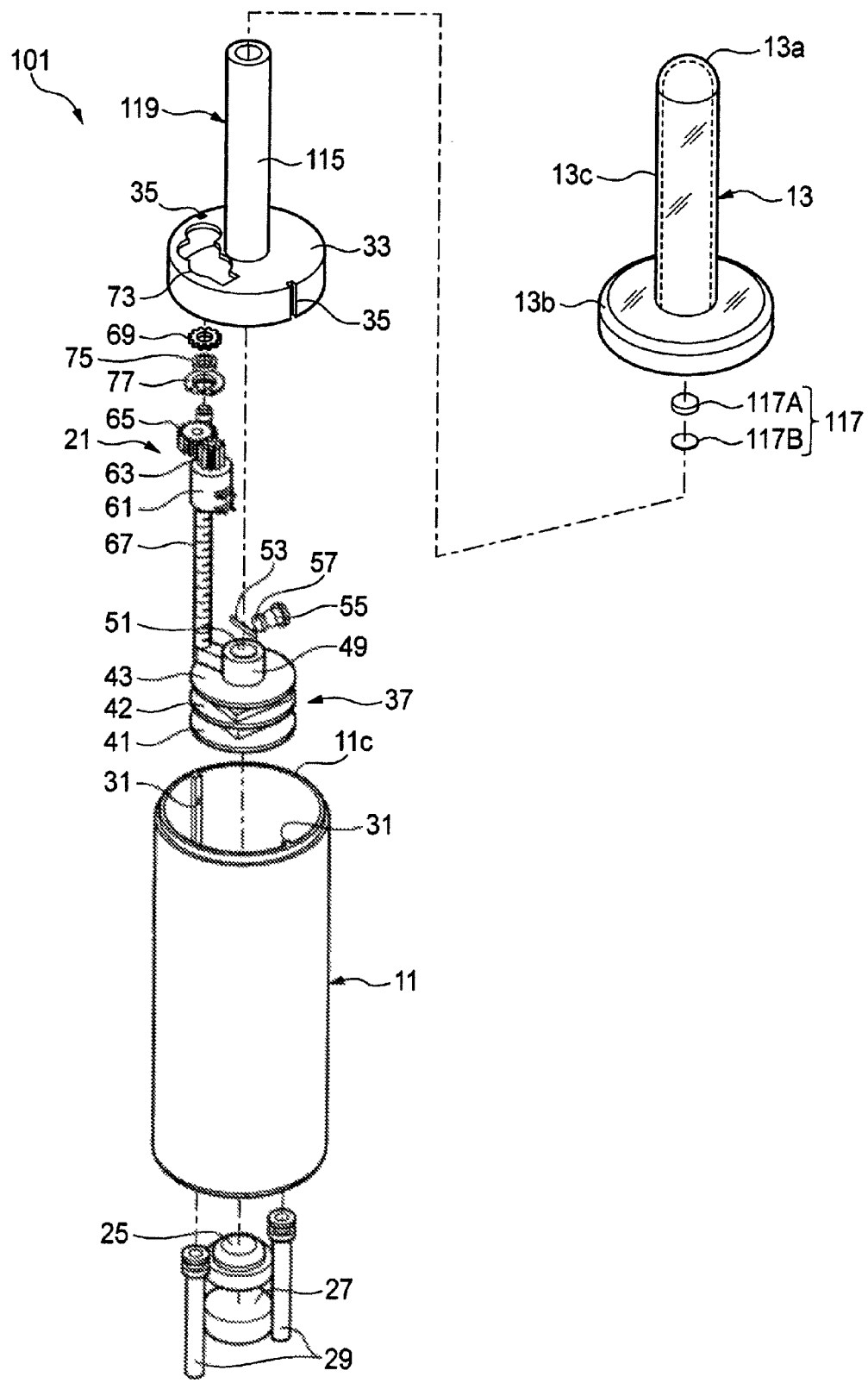
FIG. 13 is an exploded perspective view of an endoscope shown in FIG. 10.

An electronic endoscope 101 shown in FIGS. 11 to 13 has an outer shell constructed from a body part 11 and a transparent cover 13. Then, its inside is provided with: a lens holder 119 that holds an objective lens group 117 for focusing object light through the transparent cover 13; a driving section 21 for moving the lens holder 119 inside the outer shell; and a solid-state imaging device 23 that receives the object light acquired through the objective lens group 117 and then converts the light into an electric signal. Here, like members to those of the electronic endoscope 1 described above are designated by like numerals, and functionally common members are designated by appropriately corresponding numerals. Then, their description is omitted or simplified.

The lens holder 119 is formed from resin material or the like and has: a disk-shaped flange 33 fit into the body part 11; and a tube-shaped part 115 formed in a smaller diameter than the flange 33 and capable of entering the cylindrical part 13c of the transparent cover 13. The flange 33 moves in the inside of the body part 11 along the center axis of the body part 11, that is, along the center axis of the outer shell, smoothly without chattering. Further, the tube-shaped part 115 moves in the inside of the cylindrical part 13c along the center axis of the outer shell smoothly without chattering.

In the electronic endoscope 101, the objective lens group 117 held by the lens holder 119 includes a wide-angle lens and constructed from a wide-angle lens 117A and a lens 117B. Preferably the wide-angle lens 117A is composed of a fish-eye lens. In this case, a circular fish-eye lens is suitable for observation in the entire circumferential directions where the inclination angle (angle relative to the lens optical axis) is large. That is, the wide-angle lens of the present invention is a wide-angle lens having an observational field of view that permits observation in the entire side circumferential directions around the optical axis (the center axis of the tube-shaped part 115) of the objective lens group 117. Here, in addition to this configuration, the wide-angle lens 117A may be composed of a diagonal fish-eye lens, a common wide-angle lens, or the like. The objective lens group 117 is attached to the opening part on the tip side of the tube-shaped part 115 in a state that its lens optical axis agrees with the center axis of the tube-shaped part 115 of the lens holder 119.

Object light is focused along the cylindrical part 13c of the transparent cover 13 into the form of a parallel light beam by the objective lens group 117, and then travels along the center axis of the tube-shaped part 115 in parallel to the center axis of the outer shell. In the inside of the body part 11, the image pick-up drive unit part 37 is arranged at a position located on an extended line of the center axis of the tube-shaped part 115 of the lens holder 119. The image pick-up drive unit part 37 and the driving section 21 for moving the lens holder 119 are the same as those of the electronic endoscope 1 described above. Thus, their description is omitted.

Next, the operation of the electronic endoscope 101 is described below. With reference to FIG. 8, the power switch 93 is turned ON so that electric power is supplied from the power battery 25 to the individual parts. Then, light for illumination is projected from the LED 55 through the objective lens group 117 and the cylindrical part 13c of the transparent cover 13 toward a side direction so that an image-taking object is illuminated. Reflected light from the image-taking object is acquired into the electronic endoscope 1 through the cylindrical part 13c of the transparent cover 13 and the objective lens group 117, so that an image is formed onto the light acceptance surface of the imaging device 23 by the focusing lens 51.

Figure 14:
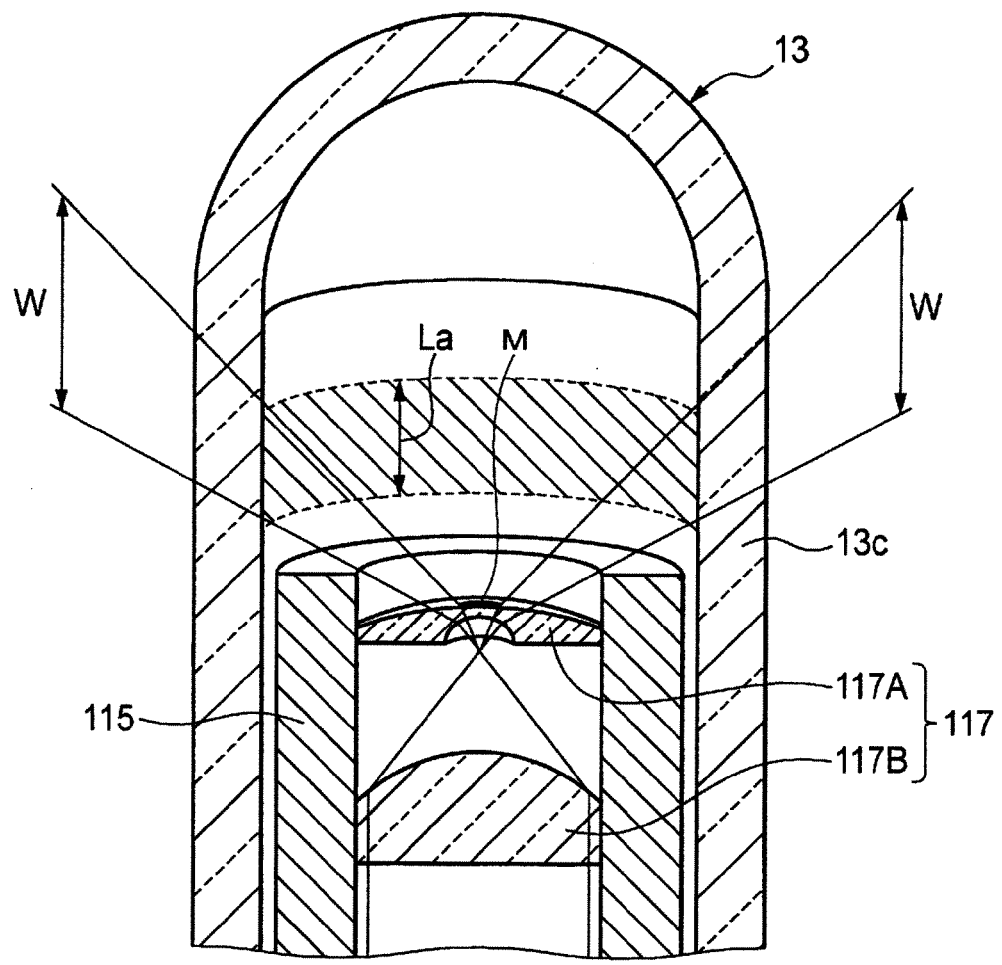
FIG. 14 is a sectional view used for describing a view field region in an endoscope shown in FIG. 10.

FIG. 14 shows the situation of the view field region W formed by the objective lens group 117. The light for illumination emitted from the wide-angle lens 117A is projected onto the region indicated as the view field region W. Among the reflected light from the image-taking object illuminated by the light for illumination, the part of light belonging to the view field region W is used in image formation and then acquired by the imaging device 23. Here, symbol M indicates a mask for limiting the view field region into W.

Then, charge accumulated in the imaging device 23 as a result of photoelectric conversion is read as an image pick-up signal by the control section (CPU) 81 of the control trait 45. The control section 81 performs appropriate image processing onto the read-out image pick-up signal so as to generate image data, and then stores the generated image data into the memory 83.

The control program for the electronic endoscope 101 is the same as that for the electronic endoscope 1 described above. Thus, with reference to FIG. 9, when the power switch 93 is turned ON, first, the stepping motor 61 is driven and revolved so that the lens holder 119 goes along the center axis of the outer shell of the electronic endoscope 1 to a home position (step S1). After the lens holder 119 is set at the home position, image pick-up processing is performed (step S2).

Then, the stepping motor 61 is driven by a specified number of pulses (step S3), so that the lens holder 119 is lowered by a predetermined distance. Here, the predetermined distance indicates a step distance by which the lens holder 119 is to be moved stepwise in order that the view field region W shown in FIG. 14 should cover stepwise the movable region of the lens holder 119. For example, the predetermined distance may be the height La of a part contained in the view field region W in the cylindrical part 13c of the transparent cover 13.

Until the lens holder 119 reaches the most lowered position (step S4), image pick-up processing is performed at each destination of the movement (step S2). When the lens holder 119 reaches the most lowered position, the lowering operation of the lens holder 119 and the image pick-up processing are terminated (step S4). Here, also in the electronic endoscope 101, the plural pieces of image data stored in the memory 83 are combined into an image map as shown in FIG. 15 (step S5).

Figure 15:
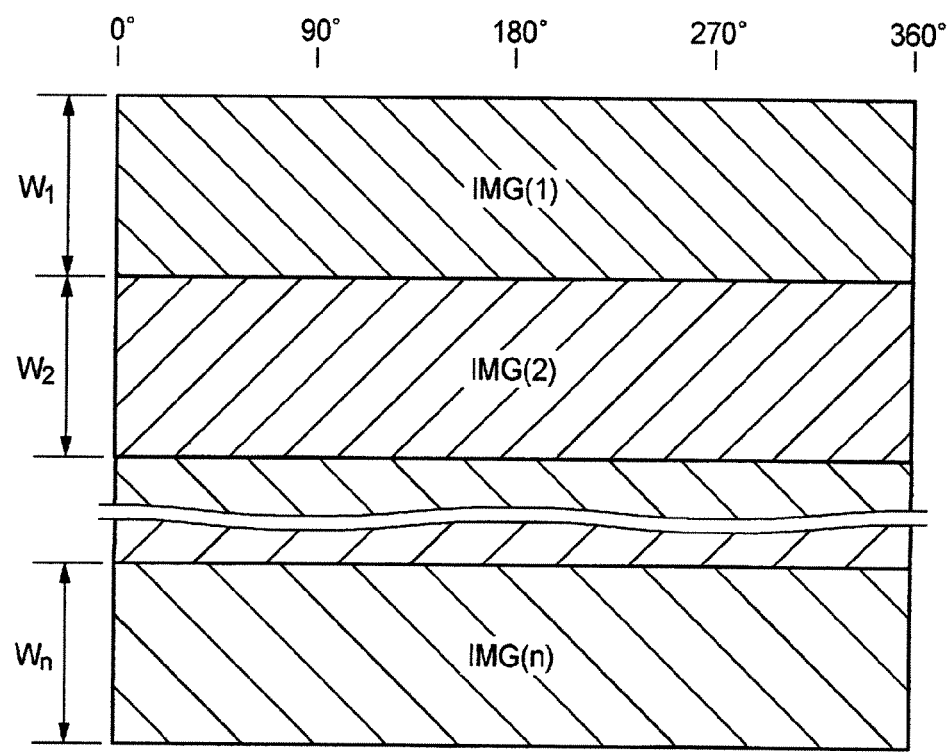
FIG. 15 is a schematic diagram showing an image map generated by an endoscope shown in FIG. 10.

In the image map shown in FIG. 15, the image data IMG(1) indicates image data that was acquired in the first occasion of image pick-up operation, which was taken over the view field region W1 ht the entire directions (circumferential angle from 0 degree to 360 degrees) in a situation that the objective lens group 117 is at height h1. Further, the image data IMG(2) indicates image data acquired in the second occasion of image pick-up operation, which was taken over the view field region W2 in the entire directions in a situation that the objective lens group 117 was lowered together with the lens holder 119 by a predetermined distance and thereby located at height h2. As such, plural pieces of image data IMG(1) to IMG(n) each obtained at each position of the movement of the lens holder 119 are combined into a substantially single sheet of image data (image map) by linking the data pieces sequentially in the order of image pick-up in the moving direction of the lens holder 119.

According to the electronic endoscope 101, the objective lens group 117 includes the wide-angle lens 117A. This permits image pick-up over a larger region in the circumferential direction in comparison with the case of the electronic endoscope 1. In particular, when a fish-eye lens is employed, image pick-up is achieved in the entire directions.

Figure 16:
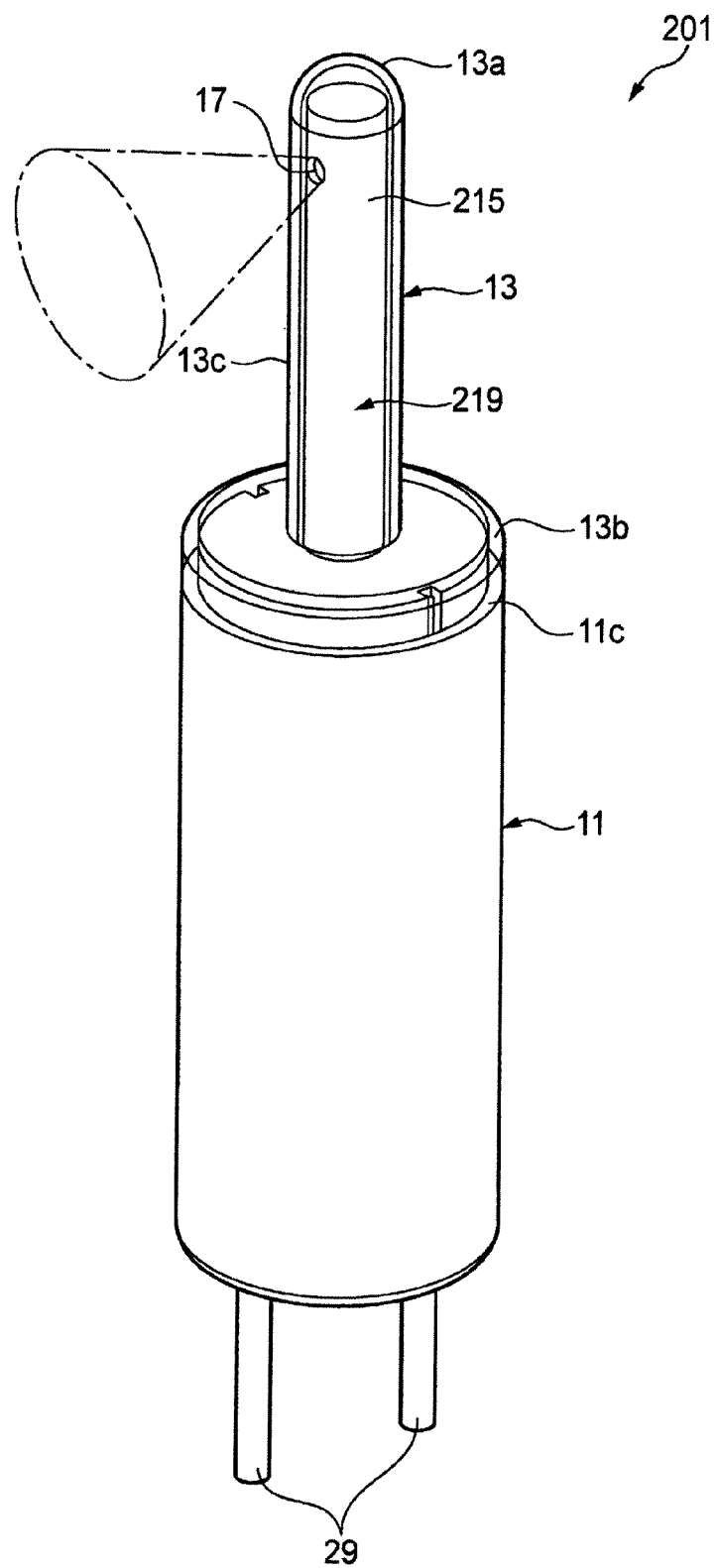
FIG. 16 is an external appearance perspective view of another example of an electronic endoscope used for describing an embodiment of the present invention.
Figure 17:
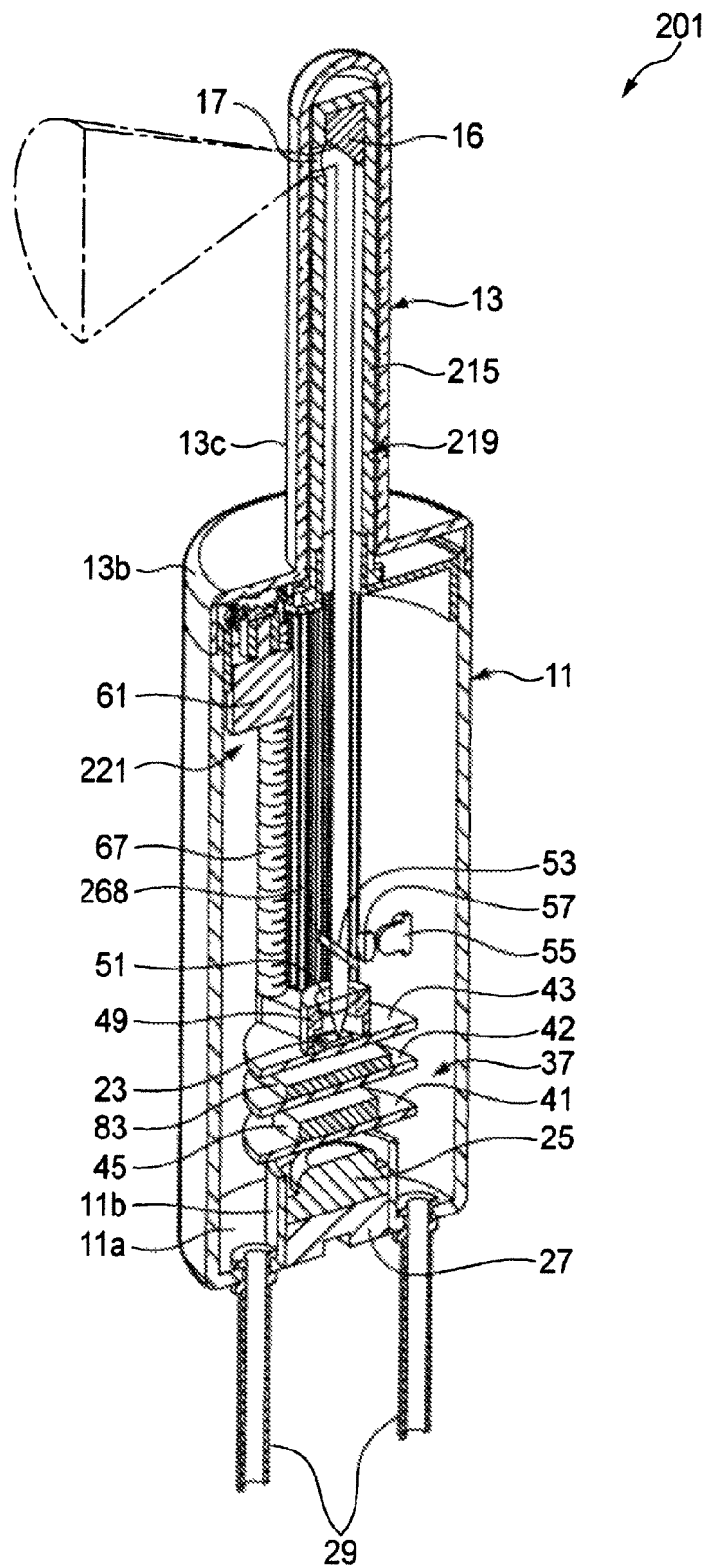
FIG. 17 is a longitudinal sectional view of an endoscope shown in FIG. 16.
Figure 18:
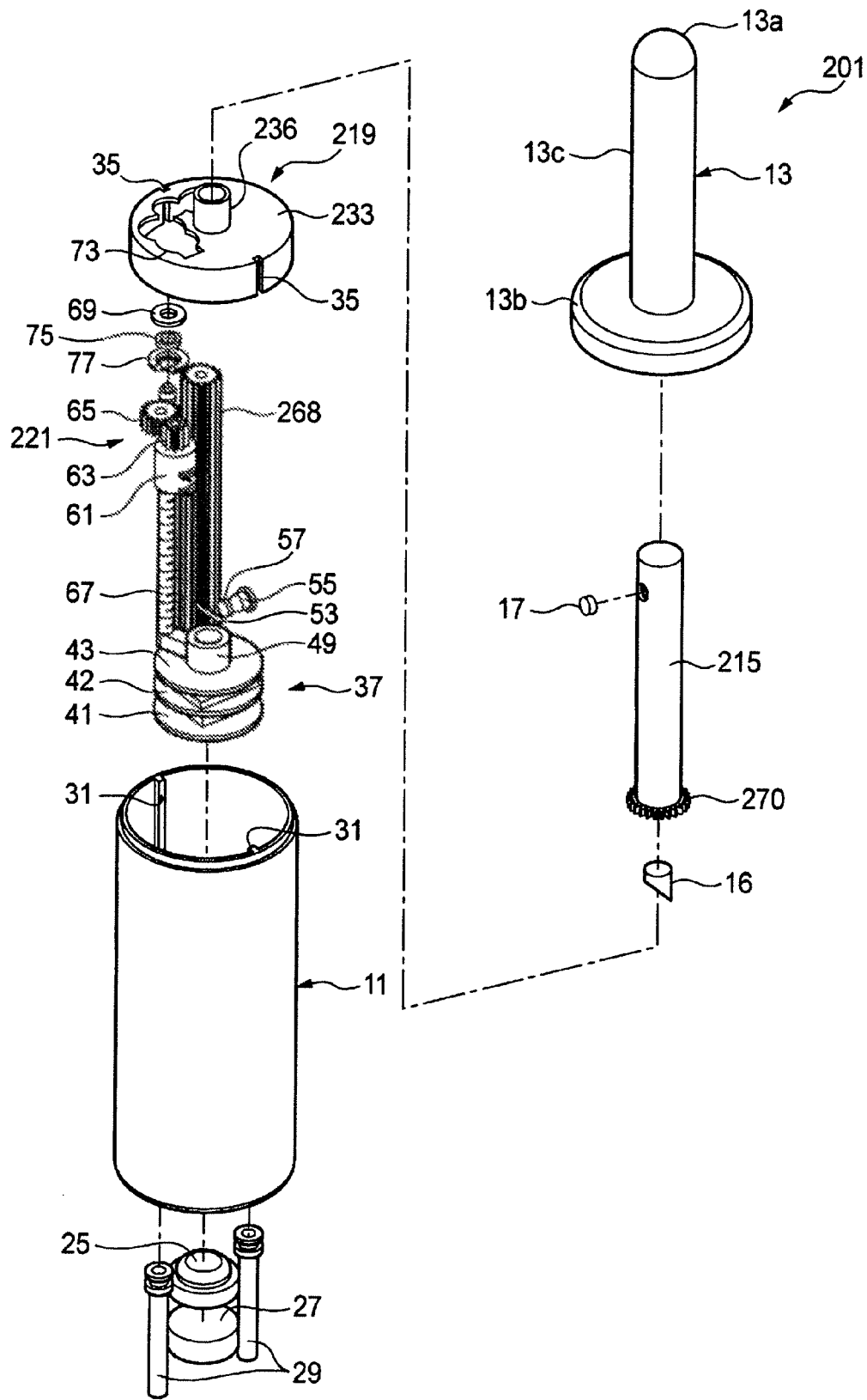
FIG. 18 is an exploded perspective view of an endoscope shown in FIG. 16.

An electronic endoscope 201 shown in FIGS. 16 to 18 has an outer shell constructed from a body part 11 and a transparent cover 13. Then, its inside is provided with: a lens holder 219 that holds an objective lens 17 for focusing object light through the transparent cover 13; a driving section 221 for moving the lens holder 219 in the axial direction inside the outer shell; and a solid-state imaging device 23 that receives the object light acquired through the objective lens 17 and then converts the light into an electric signal. Here, like members to those of the electronic endoscope 1 described above are designated by like numerals, and functionally common members are designated by appropriately corresponding numerals. Then, their description is omitted or simplified.

The lens holder 219 is formed from resin material or the like and has: a disk-shaped flange 233 fit into the body part 11; and a tube-shaped pot 215 formed in a smaller diameter than the flange 233 and capable of entering the cylindrical part 13c of the transparent cover 13. The flange 233 moves in the inside of the body part 11 along the center axis of the body part 11, that is, along the center axis of the outer shell, smoothly without chattering. Further, the tube-shaped part 215 moves in the inside of the cylindrical part 13c along the center axis of the outer shell smoothly without chattering.

The tube-shaped pan 215 and the flange 233 are formed separately from each other. Then, the tube-shaped part 215 is attached to the flange 233. In the center pan of the flange 233, a hollow cylindrical shaft 236 is provided in a protruding manner. The tube-shaped part 215 is attached to the flange 233 in a state that the pedestal part of the tube-shaped part 215 is fit outside the shaft 236. Thus, the tube-shaped part 215 is supported in a revolvable manner about the shaft 236.

In the flange 233 of the lens holder 219, engagement grooves 235 are formed in the outer peripheral surface. The inner peripheral surface of the body part 11 is provided with ribs 31 extending along the axis of the outer shell. Then, in the lens holder 219, the engagement grooves 235 of the flange 233 are engaged with the ribs 31 of the body part 11. Thus, movement of the lens holder 219 is guided in parallel to the center axis of the outer shell. That is, revolution about a feed screw 67 described later is stopped.

On the tip side of the tube-shaped part 215, an objective mirror 16 is accommodated. Further, in the tube-shaped part 215, an image pick-up hole is formed at a site radially facing the reflecting surface of the objective mirror 16. Then, the objective lens 17 is mounted inside the image pick-up hole. Then, object light is focused along the cylindrical part 13c of the transparent cover 13 by the objective lens 17 so as to travel to the objective mirror 16 in the form of a parallel light beam. Then, the object light is reflected by the reflecting surface of the objective mirror 16, and then travels along the center axis of the tube-shaped pan 215 in parallel to the center axis of the outer shell with maintaining the form of a parallel light beam.

In the inside of the body part 11, an image pick-up drive unit part 37 is arranged at a position located on an extended line of the center axis of the tube-shaped part 15 of the lens holder 19. The image pick-up drive unit part 37 is the same as that of the electronic endoscope 1 described above. Thus, description is omitted.

Figure 19:
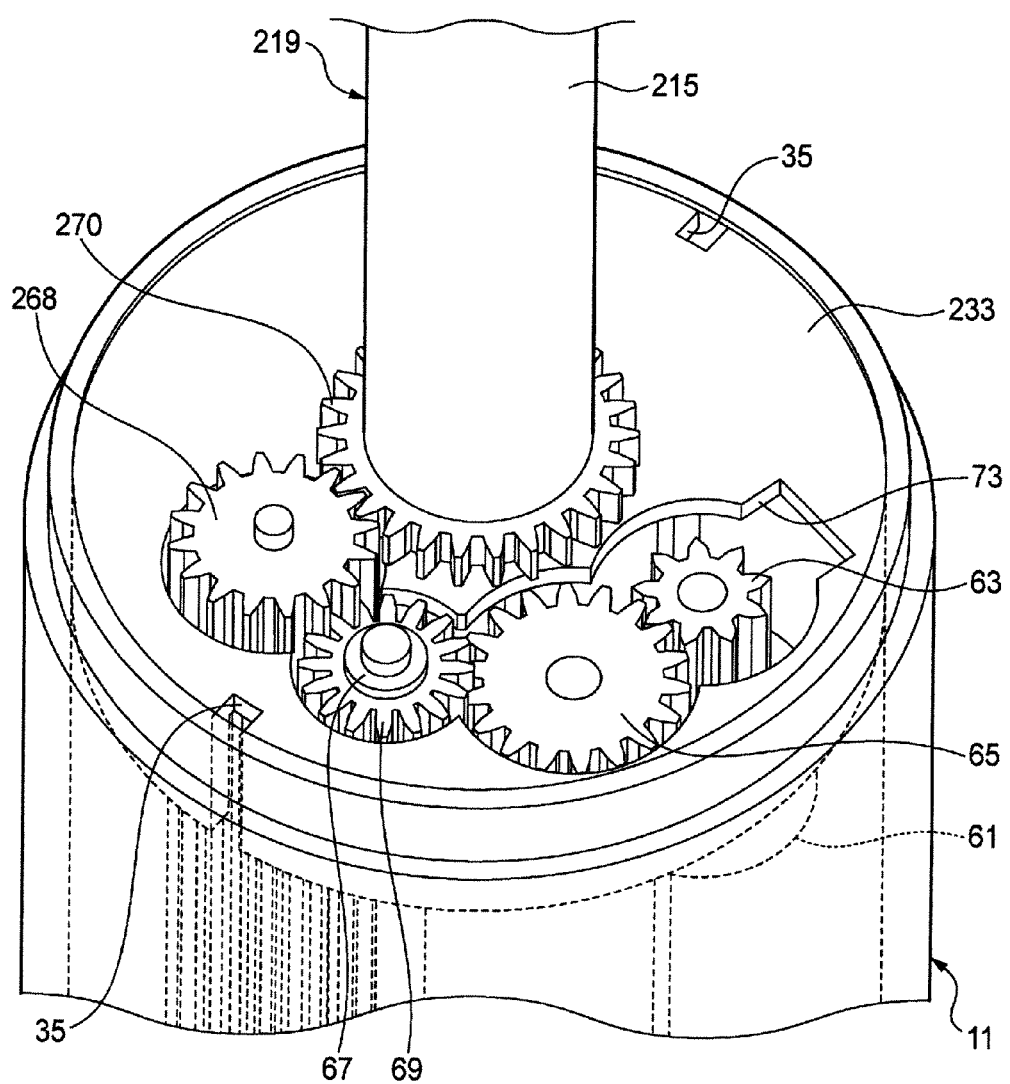
FIG. 19 is a perspective view used for describing a driving section for moving a lens holder for holding an objective lens in an endoscope shown in FIG. 16.

Here, the movement of the lens holder 219 is guided along the center axis of the outer shell by the above-mentioned engagement between the engagement grooves 235 of the flange 233 and the ribs 31 of the body part 11. The driving section 221 for moving the lens holder 219 along the center axis of the outer shell is described below in detail with reference to FIGS. 18 and 19.

The inside of the body part 11 is provided with: a feed screw 67 arranged in parallel to the center axis of the outer shell; and a stepping motor 61 serving as a source of power for driving and revolving the feed screw 67. A motor gear wheel 63 is attached to the shaft of the stepping motor 61, and a gear wheel 69 is attached to one-end part of the feed screw 67. Then, between the motor gear wheel 63 and the gear wheel 69, an idle gear wheel 65 is provided such as to engage with these gear wheels 63 and 69. The revolution of the stepping motor 61 is transmitted through the motor gear wheel 63, the idle gear wheel 65, and the gear wheel 69 to the feed screw 67.

On the other hand, in the flange 233 of the lens holder 219, a through-hole 73 is formed that allows the stepping motor 61, the motor gear wheel 63, the idle gear wheel 65, the feed screw 67, the gear wheel 69, and the like to pass through. Then, in the periphery of the through-hole 73 of the flange 233, a feed nut 75 screwed onto the feed screw 67 is attached by a nut holding piece 77. As described above, in the lens holder 219, movement is guided along the center axis of the outer shell, that is revolution about the feed screw 67 is stopped. Thus, in association with revolution of the feed screw 67, the feed nut 75 screwed on the feed screw 67 and the lens holder 219 that holds the feed nut 75 move along the feed screw 67, that is, along the center axis of the outer shell.

Further, in the driving section 221, a shaft 268 arranged in parallel to the feed screw 67 is provided. In the shaft 268, an external-tooth gear is formed in the outer peripheral surface and engages with the gear wheel 69 fixed to the feed screw 67, and hence revolves about the center axis together with the feed screw 67. Then, in the pedestal part of the tube-shaped part 215, a gear wheel 270 engaging with the shaft 268 is fixed by appropriateness means such as press fit and bonding. In accordance with the revolution of the feed screw 67, the gear wheel 270 of the tube-shaped part 215 moves in the axial direction together with the lens holder 219 and maintains the engagement with the shaft 268. Then, the tube-shaped part 215 is driven and revolved through the shaft 268 and the gear wheel 270.

Figure 20:
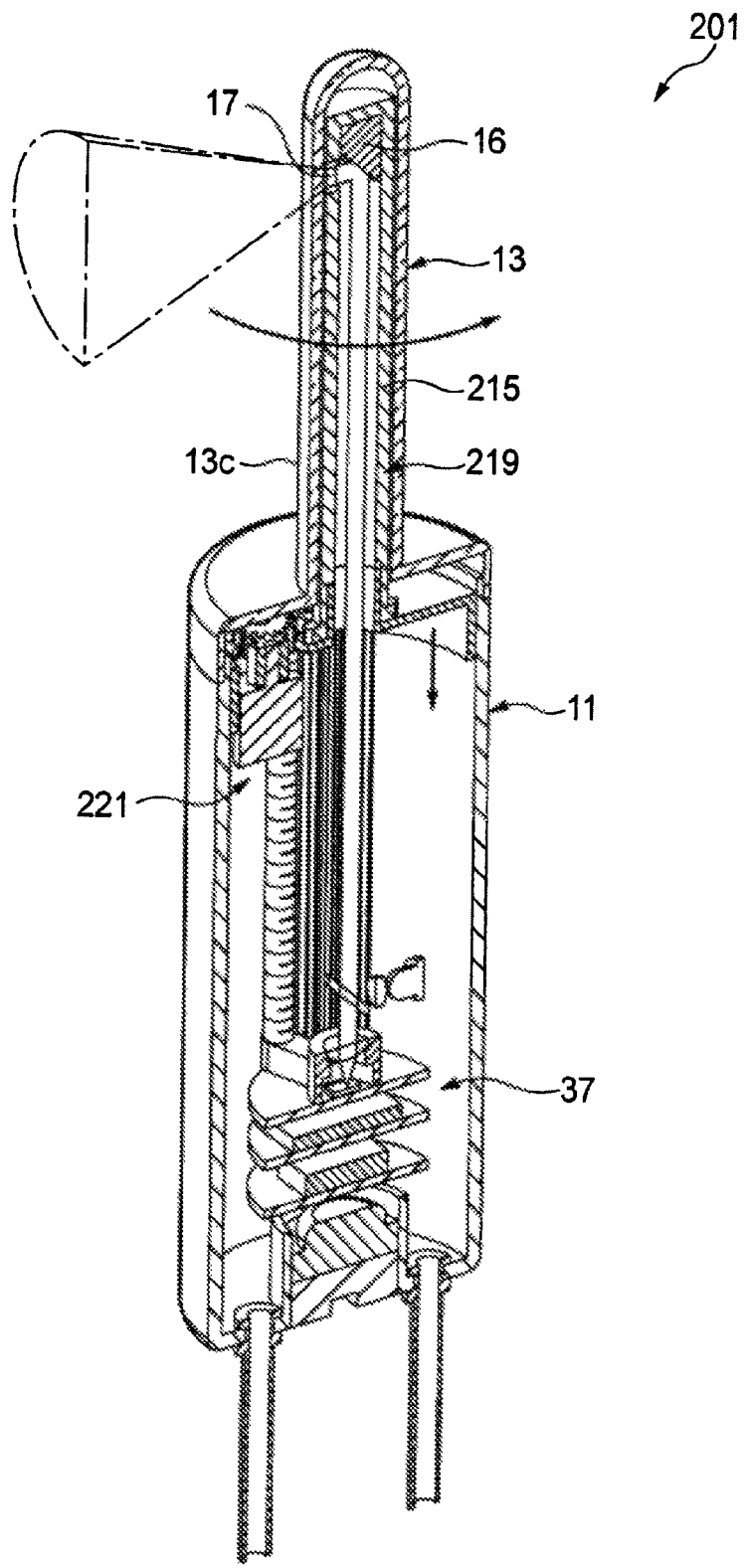
FIG. 20 is a longitudinal sectional view used for describing operation of a lens holder for holding an objective lens in an endoscope shown in FIG. 16.

For example, in a situation that the lens holder 219 is located at a raised position shown in FIG. 20, the stepping motor 61 is revolved in a predetermined direction so that the feed screw 67 is revolved via the motor gear wheel 63, the idle gear wheel 65, and the gear wheel 69. In association with the revolution of the feed screw 67, the feed nut 75 moves along the feed screw 67. As a result, the lens holder 219 is lowered.

Figure 21:
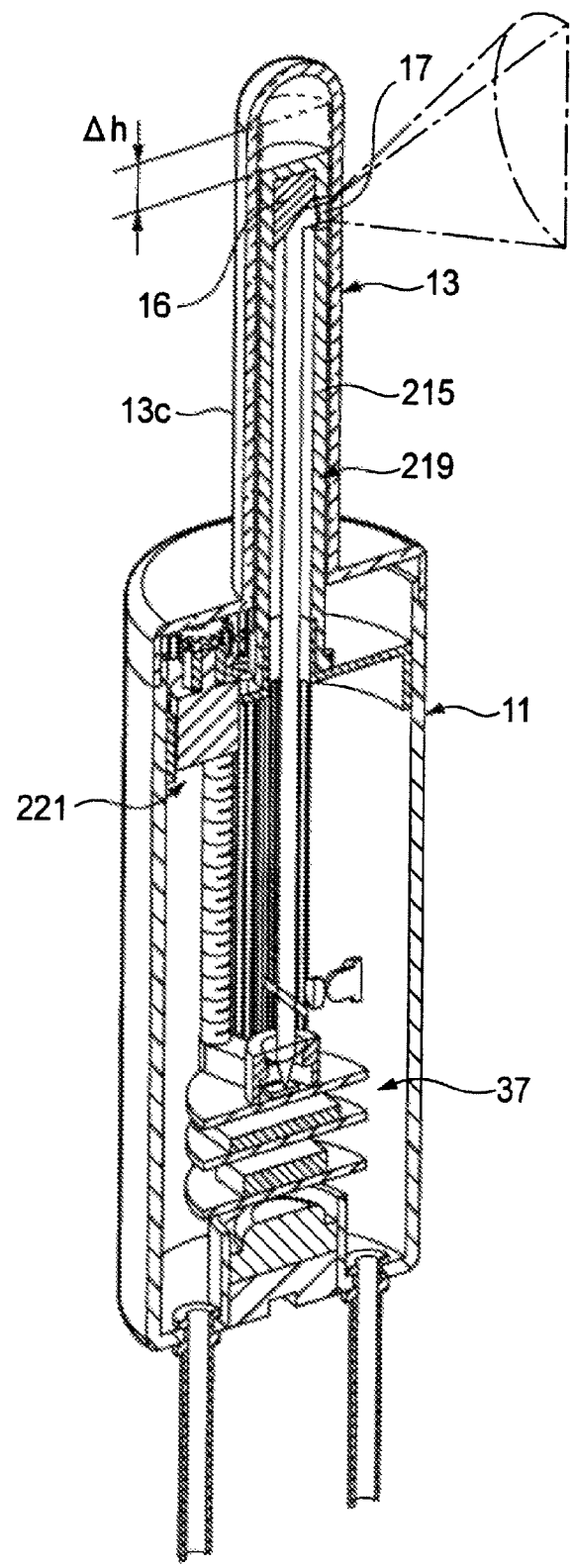
FIG. 21 is a longitudinal sectional view used for describing operation of a lens holder for holding an objective lens in an endoscope shown in FIG. 16.

Then, as shown in FIG. 21, during the course that the lens holder 219 is lowered by Δh, the tube-shaped part 215 is revolved via the shaft 268 and the gear wheel 270 by a predetermined angle. In accordance with the revolution of the tube-shaped part 215, the objective lens 17 is also revolved so that the field of view of image pick-up moves in the circumferential direction.

Next, the operation of the electronic endoscope 201 is described below. With reference to FIG. 8, the power switch 93 is turned ON so that electric power is supplied from the power battery 25 to the individual parts. Then, light for illumination is projected from the LED 55 through the objective lens 17 and the cylindrical part 13c of the transparent cover 13 toward a side direction so that an image-taking object is illuminated. Reflected light from the image-taking object is acquired into the electronic endoscope 201 through the cylindrical part 13c of the transparent cover 13 and the objective lens 17, so that an image is formed onto the light acceptance surface of the imaging device 23 by the focusing lens 51. Then, charge accumulated in the imaging device 23 as a result of photoelectric conversion is read as an image pick-up signal by the control section (CPU) 81 of the control unit 45. The control section 81 performs appropriate image processing onto the read-out image pick-up signal so as to generate image data, and then stores the generated image data into the memory 83.

The control program for the electronic endoscope 201 is the same as that for the electronic endoscope 1 described above. Thus, with reference to FIG. 9, when the power switch 93 is turned ON, first, the stepping motor 61 is driven and revolved so that the lens holder 219 goes along the center axis of the outer shell of the electronic endoscope 201 to a home position (step S1). After the lens holder 219 is set at the home position, image pick-up processing is performed (step S2). Then, the stepping motor 61 is driven by a specified number of pulses (step S3), so that the lens holder 219 is lowered by a predetermined distance. Until the lens holder 219 reaches the most lowered position (step S4), image pick-up processing is performed at each destination of the movement (step S2). When the lens holder 219 reaches the most lowered position, the lowering operation of the lens holder 219 and the image pick-up processing are terminated (step S4).

FIG. 22 is a diagram illustrating the movement of the field of view of image pick-up achieved when the above-mentioned steps S2 to S4 are executed repeatedly. In the first occasion of image pick-up processing performed at the home position, image pick-up is performed in the field of view "No. 001", and hence image data of the field of view "No. 001" is generated from the image pick-up signal read from the imaging device 23.

Once the image pick-up processing in the field of view "No. 001" is completed, the stepping motor 61 is driven at step S3 by a specified number of pulses so that the lens holder 219 is lowered and the tube-shaped part 215 is revolved. As a result, the next field of view "No. 002" is set up. Then, image pick-up is performed in the field of view "No. 002", and hence image data of the field of view "No. 002" is generated from the image pick-up signal read from the imaging device 23.

After that, image pick-up processing is repeated with moving the field of view like "No. 003"→"No. 004"→"No. 005".... When the tube-shaped part 215 has gone one around from the home position, the field of view of image pick-up is located at "No. 011" in FIG. 22. In case of having gone around twice, the field of view of image pick-up is located at "021" in FIG. 22.

Here, for example, the number of pulses provided to the stepping motor 61 at step S3 may be adjusted appropriately, or alternatively the screw pitch of the feed screw 67 may be adjusted appropriately, so that circumferentially adjacent fields of view of image pick-up may be positioned such that their left and right edge parts should be in contact with each other or overlapping somewhat with each other and axially adjacent fields of view of image pick-up may be positioned such that their upper and lower edge parts should be in contact with each other or overlapping somewhat with each other. According to this configuration, image taking of an object is achieved without a missing part in the axial and the circumferential directions. Thus, an image map without a gap is obtained.

According to the electronic endoscope 201, the objective lens 17 is moved in the axial and the circumferential directions by the driving section 221. Then, in accordance with this the field of view moves in the axial and the circumferential directions. By virtue of this, image pick-up is achieved in the entire directions without the necessity of a fish-eye lens like in the electronic endoscope 101.

Figure 23:
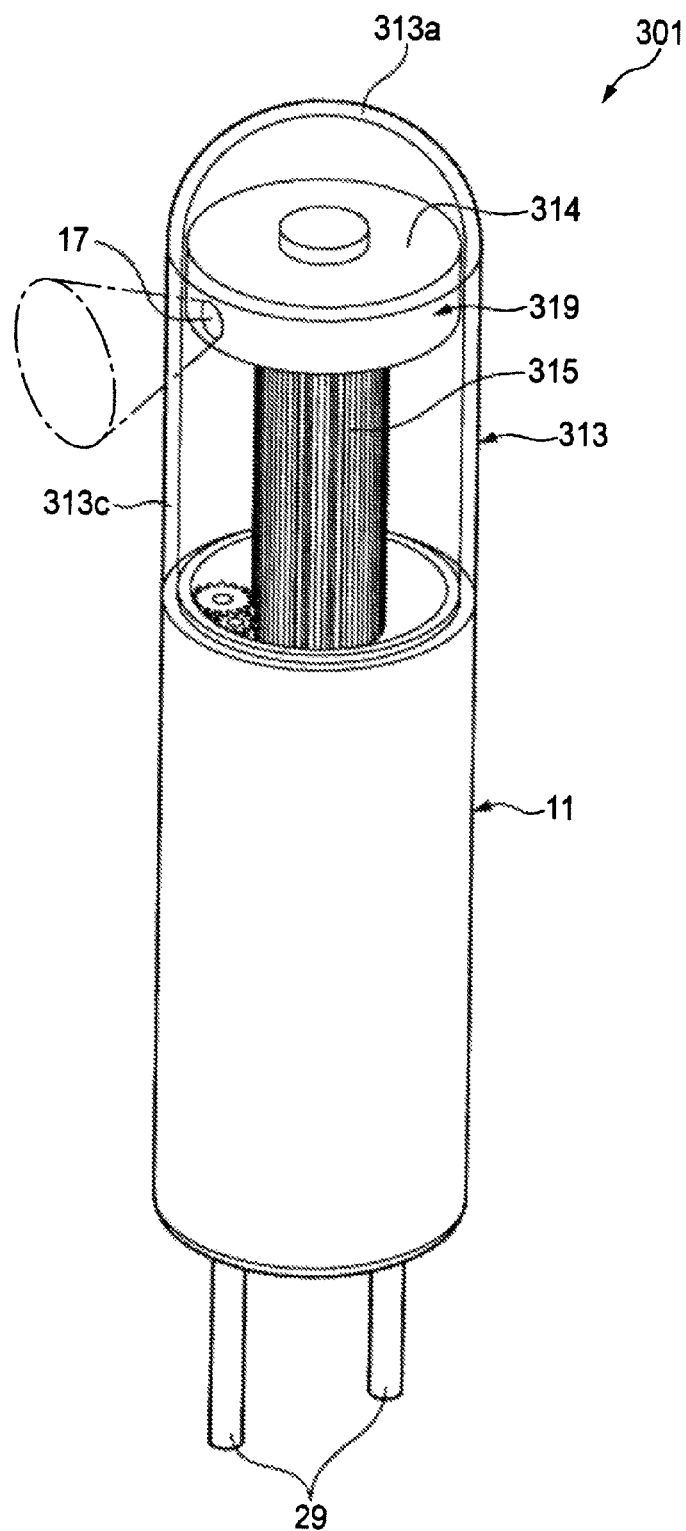
FIG. 23 is an external appearance perspective view of another example of an electronic endoscope used for describing an embodiment of the present invention.
Figure 24:
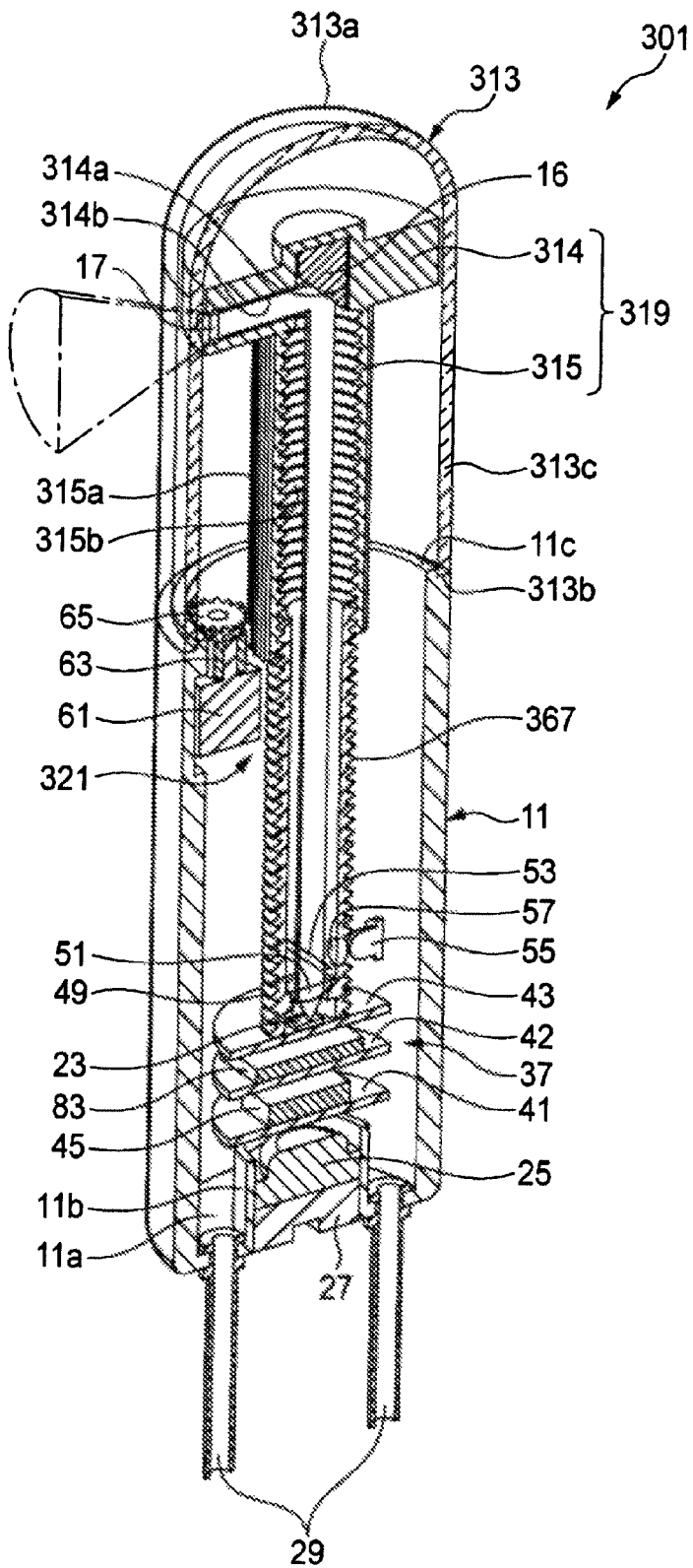
FIG. 24 is a longitudinal sectional view of an endoscope shown in FIG. 23.
Figure 25:
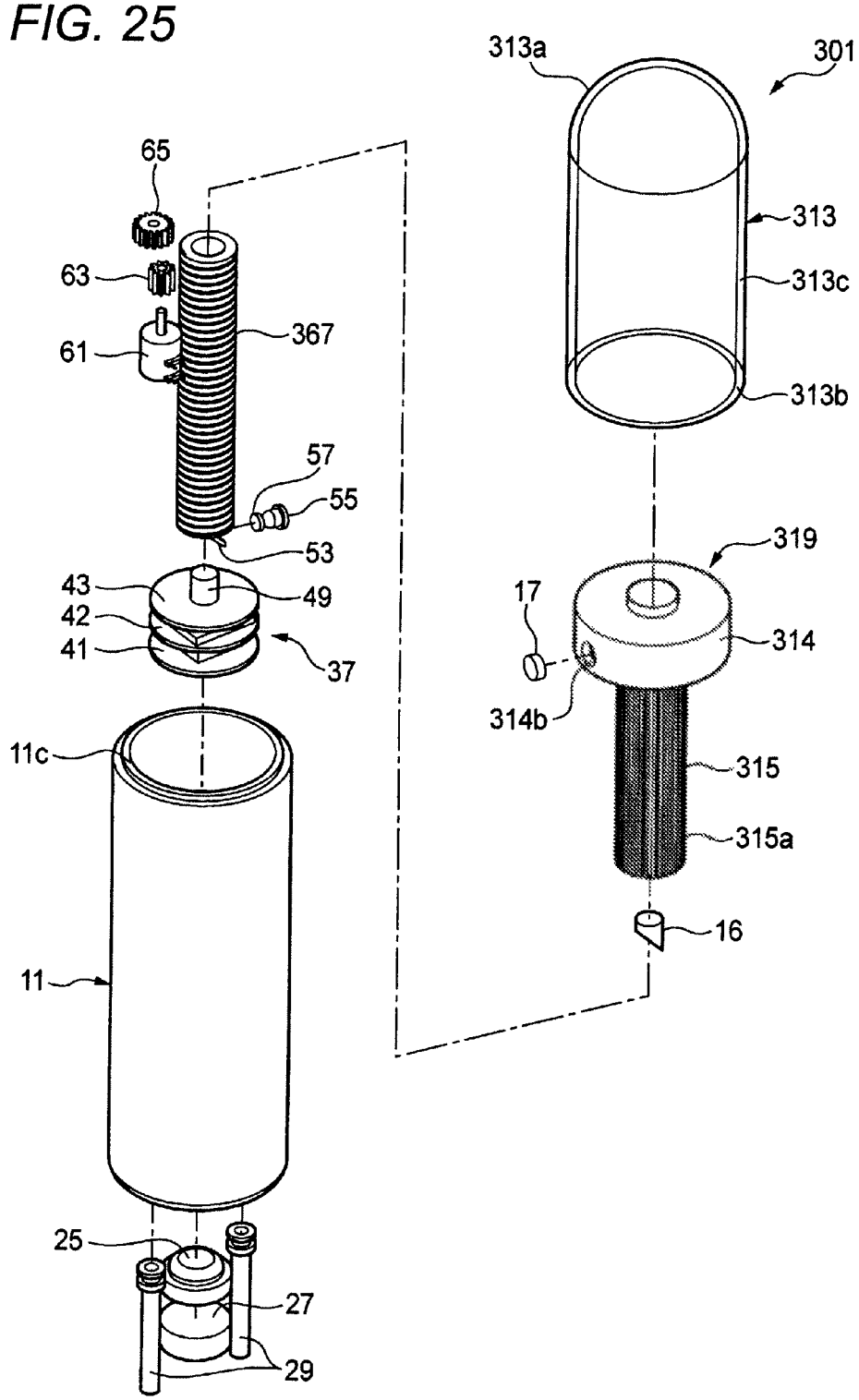
FIG. 25 is an exploded perspective view of an endoscope shown in FIG. 23.

An electronic endoscope 301 shown in FIGS. 23 to 25 has an outer shell constructed from a body part 11 and a transparent cover 313. Then, its inside is provided with: a lens holder 319 that holds an objective lens 17 for focusing object light through the transparent cover 313; a driving section 321 for moving the lens holder 319 inside the outer shell; and a solid-state imaging device 23 that receives the object light acquired through the objective lens 17 and then converts the light into an electric signal. Here, like members to those of the electronic endoscope 1 described above are designated by like numerals, and functionally common members are designated by appropriately corresponding numerals. Then, their description is omitted or simplified.

The transparent cover 313 formed in a cylindrical shape whose one-end part 313b is open. The transparent cover 313 is fixed to the body part 11 in a state that the open end part 313b is aligned with the open end part 11c of the body part 11. The other end part (tip pan) 313a of the transparent cover 313 is formed in a smooth hemispherical shape for permitting easy insertion into a hole serving as a subject. Then, the tip part 313a and the open end part 313b are connected by a cylindrical part 313c having the same diameter as the tip part 313a. In the electronic endoscope 301, the tip part 313a and the cylindrical part 313c are formed in the same diameter as the open end pan 313b.

The transparent cover 313 having the above-mentioned configuration may be fabricated, for example, by integral molding by using transparent resin material or the like. However, it is sufficient that at least the cylindrical part 313c serving as a window part facing the inner peripheral surface of a hole serving as a subject is formed transparent.

The lens holder 319 is formed from resin material or the like and has: an objective lens mount part 314 formed in an approximately disk shape; and a tube-shaped part 315 formed in a cylindrical shape having a smaller diameter than the objective lens mount pot 314. The tube-shaped part 315 is arranged such that its center axis agrees with the center axis of the transparent cover 313, that is, the center axis of the outer shell. The objective lens mount part 314 is provided at the tip of the tube-shaped part 315 coaxially to the tube-shaped part 315.

In the objective lens mount part 314, its outer diameter is formed somewhat smaller than the inner diameter of the cylindrical part 313c of the transparent cover 313. Thus, the objective lens mount part 314 is allowed to move in the inside of the transparent cover 313 smoothly without chattering along the center axis of the transparent cover 313, that is, the center axis of the outer shell.

In the outer peripheral surface of the tube-shaped part 315, an external-tooth gear 315a is formed. The gear teeth of the external-tooth gear 315a extend in parallel to the center axis of the tube-shaped part 315, and are formed at equal intervals in the circumferential direction. Further, in the inner peripheral surface of the tube-shaped part 315, a female screw 315b is formed that is screwed into a thread groove formed in the outer peripheral surface of the feed screw 367 described later.

In the objective lens mount part 314, a cylindrical hole 314a is formed that is continuous to the tip opening of the tube-shaped part 315 and extends in the axial direction of the tube-shaped part 315. Then, an objective mirror 16 is accommodated in the cylindrical hole 314a. Further, in the objective lens mount part 314, an image pick-up hole 314b is formed that extends in a radial direction and whose one end opens in the outer peripheral surface and whose the other end faces the reflecting surface of the objective mirror 16 in a radial direction and communicates with the cylindrical hole 314a. Then, an objective lens 17 is mounted in the opening part on the outer periphery side of the image pick-up hole 314b.

Object light is focused along the cylindrical part 313c of the transparent cover 313 by the objective lens 17 so as to travel to the objective mirror 16 in the form of a parallel light beam. Then, the object light is reflected by the reflecting surface of the objective mirror 16, and then travels along the center axis of the tube-shaped part 315, that is, along the center axis of the outer shell, with maintaining the form of a parallel light beam.

In the inside of the body part 11, an image pick-up drive unit part 37 is arranged at a position located on an extended line of the center axis of the tube-shaped part 315 of the lens holder 319. The image pick-up drive unit part 37 is the same as that of the electronic endoscope 1 described above. Thus, description is omitted.

On the base plate 43 of the image pick-up drive unit part 37, a feed screw 367 is attached coaxially to the tube-shaped part 315 of the lens holder 319. The feed screw 367 formed in a cylindrical shape, and accommodates the focusing lens holder 49 in the inside. Further, the feed screw 367 has a thread groove formed in the outer peripheral surface. Then, in such a manner that this thread groove is screwed into the female screw 315b of the inner peripheral surface of the tube-shaped part 315, the feed screw 367 is inserted into the tube-shaped part 315. The object light traveling along the center axis of the tube-shaped part 315 goes into the feed screw 367, then enters the focusing lens 51 held by the focusing lens holder 49, and then is focused onto the light acceptance surface of the imaging device 23 by the focusing lens 51 so that an image is formed.

Here, the LED 55 serving as a light source for illuminating the image-taking object is arranged outside the feed screw 367. The half mirror 53 for reflecting the light for illumination from the LED 55 toward the objective mirror 16 is arranged inside the feed screw 367 and is located in the middle of the optical path of the object light. The tube wall of the feed screw 367, which intervenes between the LED 55 and the half mirror 53, is provided with an attachment hole. Then, the illumination lens 57 is attached in the attachment hole. The light for illumination from the LED 55 is brought into the form of a parallel light beam by the illumination lens 57, and then enters the half mirror 53. Then, at least a part of the light is reflected toward the objective mirror 16. Then, the light for illumination having entered the objective mirror 16 is reflected toward the objective lens 17, and then projected through the objective lens 17 and the transparent cover 313 onto the image-taking object.

Here, in the lens holder 319 where its tube-shaped part 315 is screwed into the feed screw 367, movement is guided along the feed screw 367, that is, along the center axis of the outer shell. The driving section 321 for moving the lens holder 319 along the center axis of the outer shell is described below in detail with reference to FIG. 24.

A stepping motor 61 is fixed inside the body part 11. Further, an idle gear wheel 65 is provided that is located between and engaging with both of the motor gear wheel 63 of the stepping motor 61 and the external-tooth gear 315a formed in the tube-shaped part 315 of the lens holder 319. The revolution of the stepping motor 61 is transmitted through the motor gear wheel 63 and the idle gear wheel 65 to the lens holder 319.

In the lens holder 319, the tube-shaped part 315 is fit outside the feed screw 367. Thus, when revolution of the stepping motor 61 is transmitted, the lens holder 319 revolves about the feed screw 367. At the same time, the tube-shaped part 315 is screwed onto the feed screw 367 by means of the female screw 315b framed in the inner peripheral surface. Thus, in association with revolution about the feed screw 367, the lens holder 319 moves along the feed screw 367.

Figure 26:
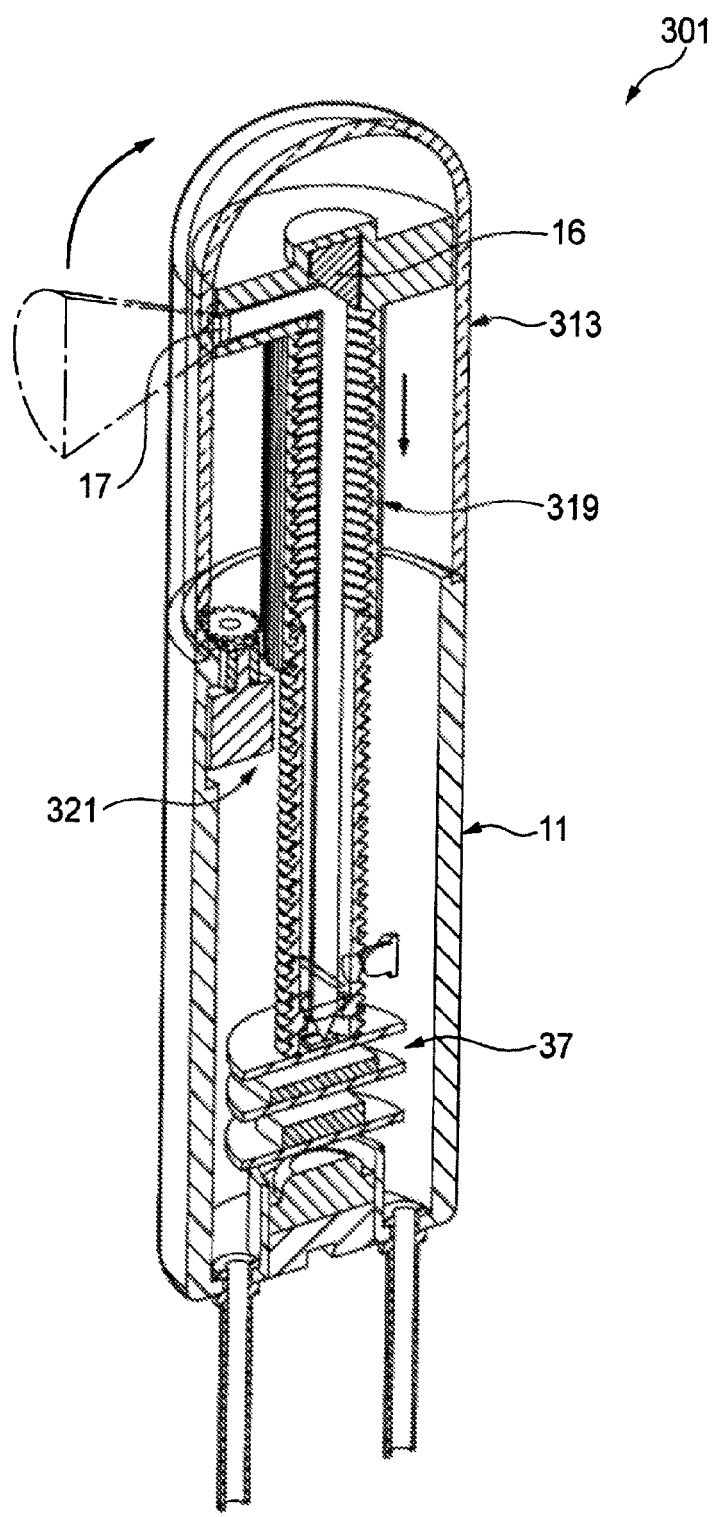
FIG. 26 is a longitudinal sectional view used for describing operation of a lens holder for holding an objective lens in an endoscope shown in FIG. 23.
Figure 27:
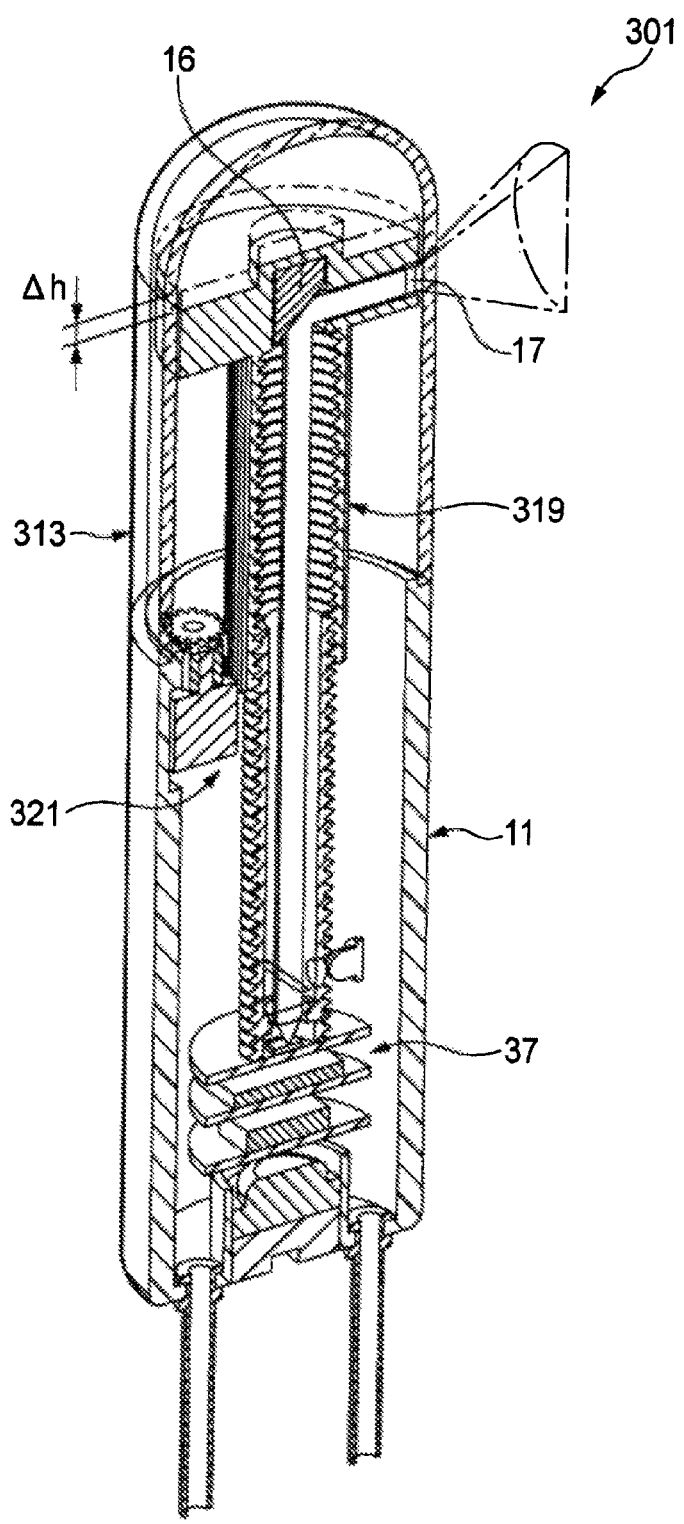
FIG. 27 is a longitudinal sectional view used for describing operation of a lens holder for holding an objective lens in an endoscope shown in FIG. 23.

For example, in a situation that the lens holder 319 is located at a raised position shown in FIG. 26, the stepping motor 61 is revolved in a predetermined direction so that the lens holder 319 is revolved via the motor gear wheel 63 and the idle gear wheel 65. As a result, as shown in FIG. 27, the lens holder 319 revolves about the feed screw 367 so as to go lower by Δh along the feed screw 367. In accordance with the revolution of the lens holder 319, the objective lens 17 is also revolved so that the field of view of image pick-up moves in the circumferential direction.

Next, the operation of the electronic endoscope 301 is described below.

With reference to FIG. 8, the power switch 93 is turned ON so that electric power is supplied from the power battery 25 to the individual parts. Then, light for illumination is projected from the LED 55 through the objective lens 17 and the cylindrical part 313c of the transparent cover 313 toward a side direction so that an image-taking object is illuminated. Reflected light from the image-taking object is acquired into the electronic endoscope 301 through the cylindrical part 313c of the transparent cover 313 and the objective lens 17, so that an image is formed onto the light acceptance surface of the imaging device 23 by the focusing lens 51. Then, charge accumulated in the imaging device 23 as a result of photoelectric conversion is read as an image pick-up signal by the control section (CPU) 81 of the control unit 45. The control section 81 performs appropriate image processing onto the read-out image pick-up signal so as to generate image data, and then stores the generated image data into the memory 83.

The control program for the electronic endoscope 301 is the same as that for the electronic endoscope 1 described above. Thus, with reference to FIG. 9, when the power switch 93 is turned ON, first, the stepping motor 61 is driven and revolved so that the lens holder 319 goes along the center axis of the outer shell of the electronic endoscope 301 to a home position (step S1). After the lens holder 319 is set at the home position, image pick-up processing is performed (step S2). Then, the stepping motor 61 is driven by a specified number of pulses (step S3), so that the lens holder 319 is lowered by a predetermined distance. Until the lens holder 319 reaches the most lowered position (step S4), image pick-up processing is performed at each destination of the movement (step S2). When the lens holder 319 reaches the most lowered position, the lowering operation of the lens holder 319 and the image pick-up processing are terminated (step S4).

FIG. 28 is a diagram illustrating the movement of the field of view of image pick-up achieved when the above-mentioned steps S2 to S4 are executed repeatedly. In the first occasion of image pick-up processing performed at the home position, image pick-up is performed in the field of view "No. 001", and hence image data of the field of view "No. 001" is generated from the image pick-up signal read from the imaging device 23.

Once the image pick-up processing in the field of view "No. 001" is completed, the stepping motor 61 is driven at step S3 by a specified number of pulses so that the lens holder 319 is lowered and revolved. As a result, the next field of view "No. 002" is set up. Then, image pick-up is performed in the field of view "No. 002", and hence image data of the field of view "No. 002" is generated from the image pick-up signal read from the imaging device 23.

After that, image pick-up processing is repeated with moving the field of view like "No. 003"→"No. 004"→"No. 005".... When the lens holder 319 has gone one around from the home position, the field of view of image pick-up is located at "No. 011" in FIG. 28. In case of having gone around twice, the field of view of image pick-up is located at "No. 021" in FIG. 28.

Here, for example, the number of pulses provided to the stepping motor 61 at step S3 may be adjusted appropriately, or alternatively the screw pitch of the feed screw 367 may be adjusted appropriately, so that circumferentially adjacent fields of view of image pick-up may be positioned such that their left and right edge parts should be in contact with each other or overlapping somewhat with each other and axially adjacent fields of view of image pick-up may be positioned such that their upper and lower edge parts should be in contact with each other or overlapping somewhat with each other. According to this configuration, image taking of an object is achieved without a missing part in the axial and the circumferential directions. Thus, an image map without a gap is obtained.

According to the electronic endoscope 301, the objective lens 17 is moved in the axial and the circumferential directions by the driving section 321. Then, in accordance with this, the field of view moves in the axial and the circumferential directions. By virtue of this, image pick-up is achieved in the entire directions without the necessity of a fish-eye lens like in the electronic endoscope 101 described above.

Figure 29:
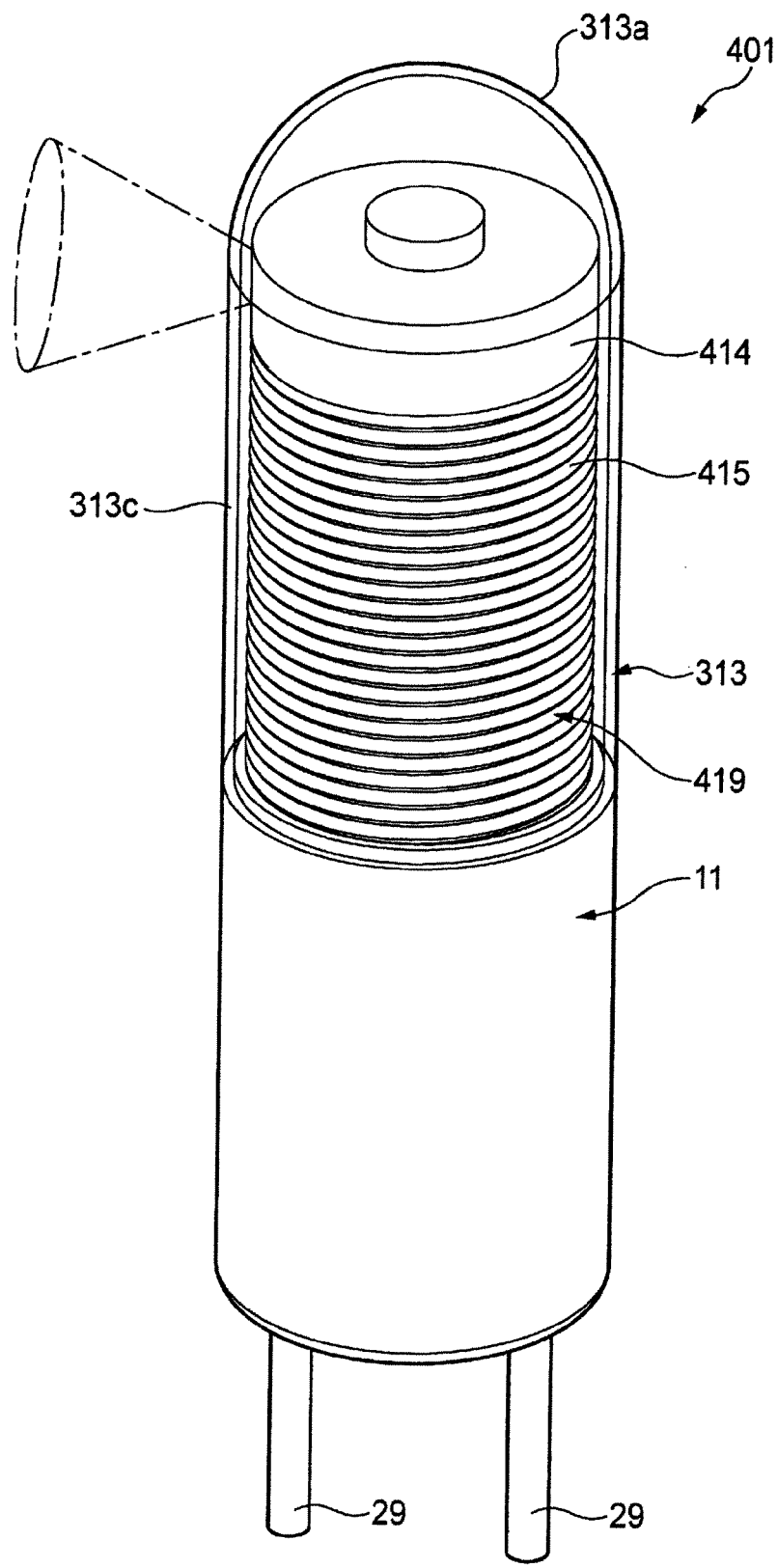
FIG. 29 is an external appearance perspective view of another example of an electronic endoscope used for describing an embodiment of the present invention.
Figure 30:
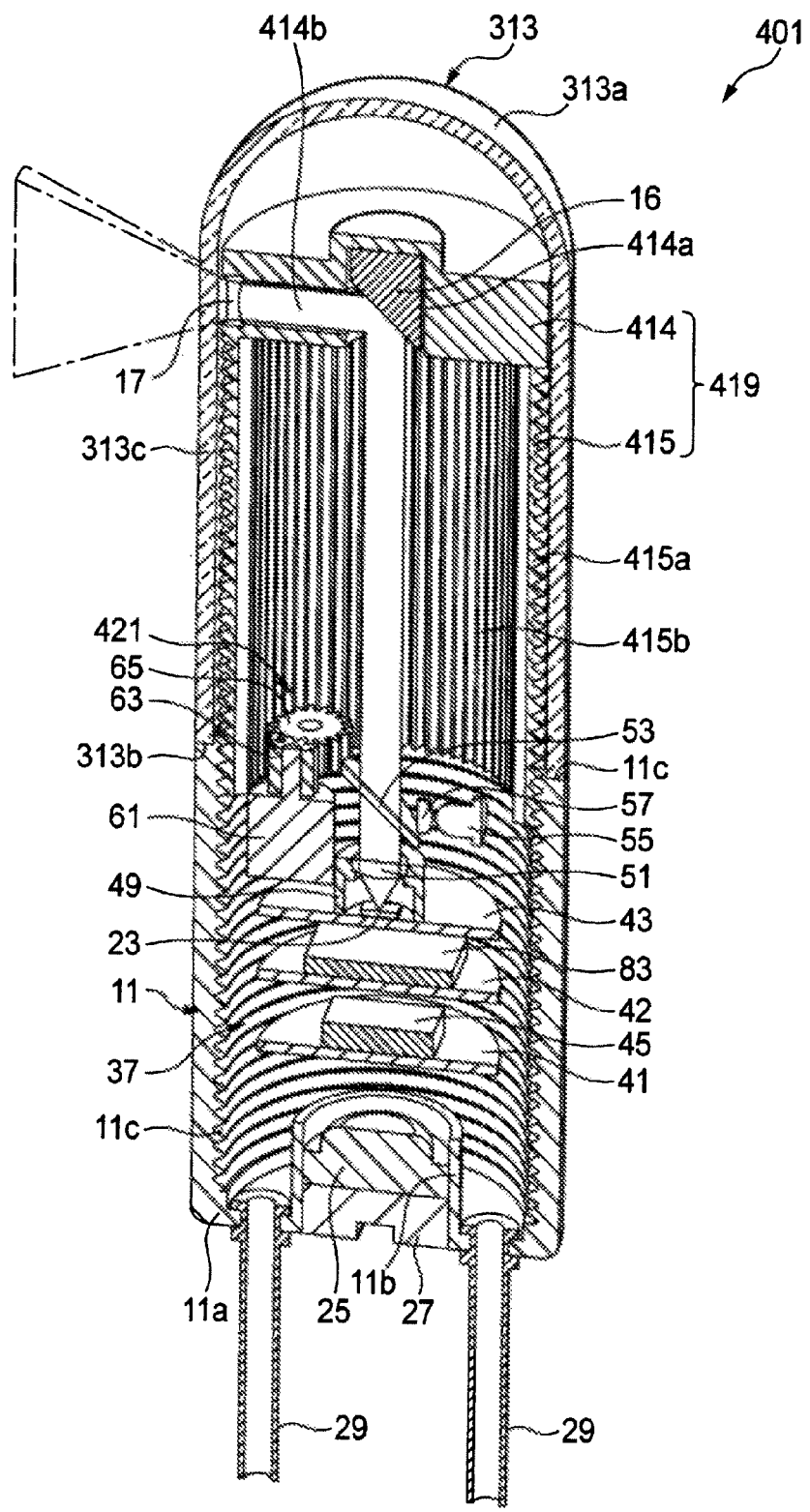
FIG. 30 is a longitudinal sectional view of an endoscope shown in FIG. 29.
Figure 31:
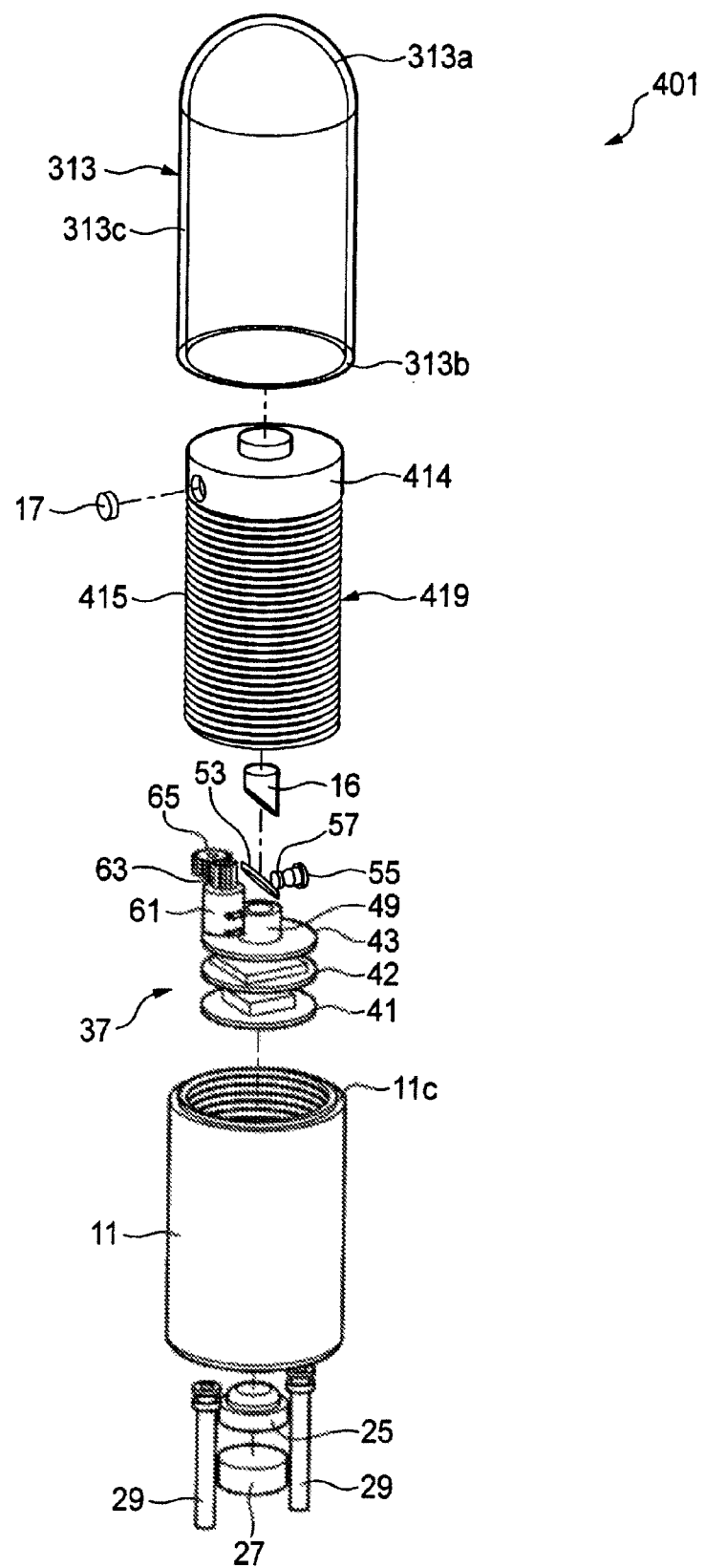
FIG. 31 is an exploded perspective view of an endoscope shown in FIG. 29.

An electronic endoscope 401 shown in FIGS. 29 to 31 has an outer shell constructed from a body part 11 and a transparent cover 313. Then, its inside is provided with: a lens holder 419 that holds an objective lens 17 for focusing object light through the transparent cover 313; a driving section 421 for moving the lens holder 419 inside the outer shell; and a solid-state imaging device 23 that receives the object light acquired through the objective lens 17 and then converts the light into an electric signal. Here, like members to those of the electronic endoscope 1 or 301 described above are designated by like numerals, and functionally common members are designated by appropriately corresponding numerals. Then, their description is omitted or simplified.

The lens holder 419 is formed from resin material or the like and has: an objective lens mount part 414 formed in an approximately disk shape; and a tube-shaped part 415 formed in a cylindrical shape having the same diameter as the objective lens 414. The tube-shaped part 415 is arranged such that its center axis agrees with the center axis of the transparent cover 313, that is, the center axis of the outer shell. The objective lens mount part 414 is provided at the tip of the tube-shaped part 415 coaxially to the tube-shaped part 415.

In the objective lens mount part 414 and the tube-shaped part 415, their outer diameter is formed somewhat smaller than the inner diameter of the cylindrical part 313c of the transparent cover 313. Thus, the objective lens mount part 414 is allowed to move in the inside of the transparent cover 313 smoothly without chattering along the center axis of the transparent cover 313, that is, the enter axis of the outer shell.

In the inner peripheral surface of the tube-shaped part 415, an internal-tooth gear 415a is formed. The gear teeth of the internal-tooth gear 415a extend in parallel to the center axis of the tube-shaped part 415, and are formed at equal intervals in the circumferential direction. Further, in the outer peripheral surface of the tube-shaped part 415, a male screw 415b is formed that is screwed into the thread groove formed in the inner peripheral surface of the body part 11.

In the objective lens mount part 414, a cylindrical hole 414a is formed that is continuous to the tip opening of the tube-shaped part 415 and extends in the axial direction of the tube-shaped part 415. Then, an objective mirror 16 is accommodated in the cylindrical hole 414a. Further, in the objective lens mount part 414, an image pick-up hole 414b is formed that extends in a radial direction and whose one end opens in the outer peripheral surface and whose the other end faces the reflecting surface of the objective mirror 16 in a radial direction and communicates with the cylindrical hole 414a. Then, an objective lens 17 is mounted in the opening part on the outer periphery side of the image pick-up hole 414b.

Object light is focused along the cylindrical part 313c of the transparent cover 313 by the objective lens 17 so as to travel to the objective mirror 16 in the form of a parallel light beam. Then, the object light is reflected by the reflecting surface of the objective mirror 16, and then travels along the center axis of the tube-shaped part 415 in parallel to the center axis of the outer shell, with maintaining the form of a parallel light beam.

In the inside of the body part 11, an image pick-up drive unit part 37 is arranged at a position located on an extended line of the center axis of the tube-shaped part 415 of the lens holder 419. The image pick-up drive unit part 37 is the satyr as that of the electronic endoscope 1 described above. Thus, description is omitted.

Here, in the lens holder 419 whose tube-shaped part 415 is screwed into the thread groove formed in the inner peripheral surface of the body part 11, movement is guided along the center axis of the body part 11, that is, along the center axis of the outer shell. The driving section 421 for moving the lens holder 419 along the center axis of the outer shell is described below in detail with reference to FIG. 30.

A stepping motor 61 is fixed inside the body part 11. Further, an idle gear wheel 65 is provided that is located between and engaging with both of the motor gear wheel 63 of the stepping motor 61 and the internal-tooth gear 415a formed in the tube-shaped part 415 of the lens holder 419. The revolution of the stepping motor 61 is transmitted through the motor gear wheel 63 and the idle gear wheel 65 to the lens holder 419.

In the lens holder 419, the tube-shaped part 415 is fit into the body part 11. Thus, when revolution of the stepping motor 61 is transmitted, the lens holder 419 revolves about the center axis of the body part 11. At the same time, the tube-shaped part 415 is screwed into the thread groove formed in the inner peripheral surface of the body part 11 by means of the male screw 415b formed in the outer peripheral surface. Thus, in association with revolution about the center axis of the body part 11, the lens holder 419 moves along the center axis of the body part 11.

Figure 32:
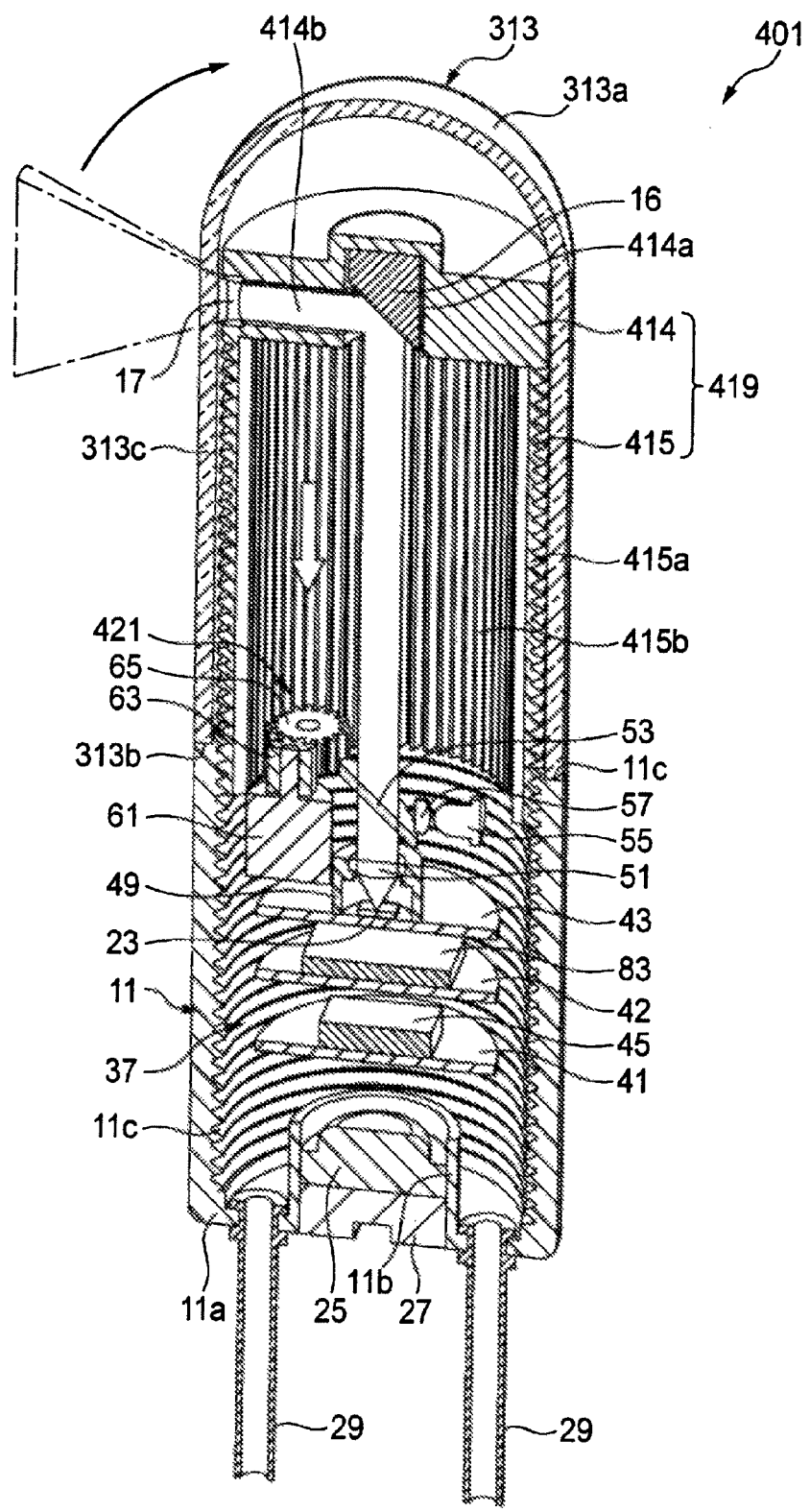
FIG. 32 is a longitudinal sectional view used for describing operation of a lens holder for holding an objective lens in an endoscope shown in FIG. 29.
Figure 33:
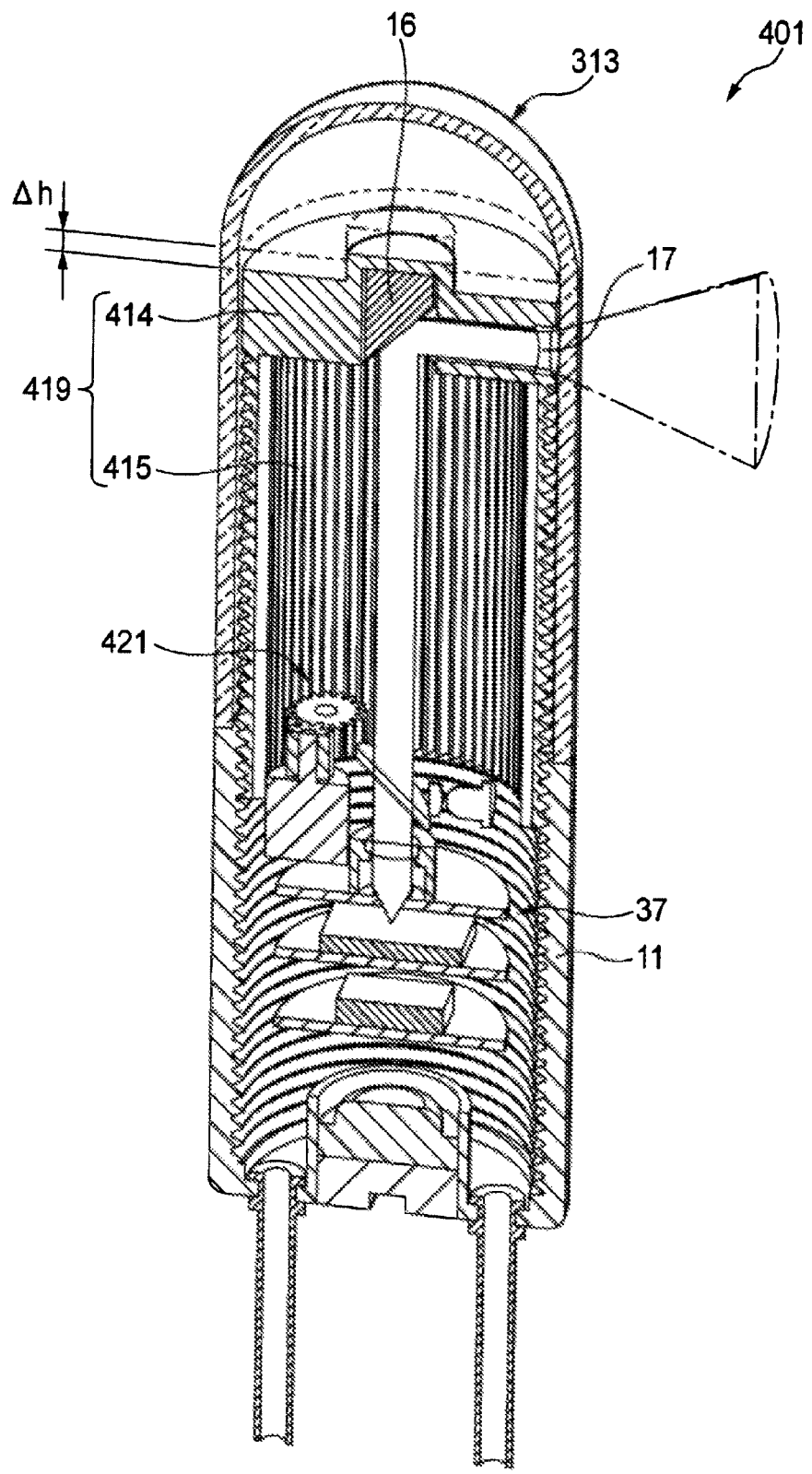
FIG. 33 is a longitudinal sectional view used for describing operation of a lens holder for holding an objective lens in an endoscope shown in FIG. 29.

For example, in a situation that the lens holder 419 is located at a raised position shown in FIG. 32, the stepping motor 61 is revolved in a predetermined direction so that the lens holder 419 is revolved via the motor gear wheel 63 and the idle gear wheel 65. As a result, as shown in FIG. 33, the lens holder 419 revolves about the center axis of the body part 11 so as to go lower by Δh along the center axis of the body part 11. In accordance with the revolution of the lens holder 419, the objective lens 17 is also revolved so that the field of view of image pick-up moves in the circumferential direction.

The operation of the electronic endoscope 401 is similar to that of the electronic endoscope 301 described above. That is, the driving section 421 causes the lens holder 419 that holds the objective lens 17 to move in the axial and the circumferential directions sequentially. Then, in the course of this motion, image pick-up is performed in the entire directions.

According to the electronic endoscope 401, in the guiding of the movement of the lens holder 419, the inner peripheral surface of the body part 11 is used in place of the feed screw 367 of the electronic endoscope 301 described above. This reduces the number of components and, at the same time, permits such a configuration that the image pick-up drive unit part 37 and the like are accommodated inside the tube-shaped part 415 guided by the inner peripheral surface of the body part 11. Accordingly, efficient space utilization is achieved and size reduction of the electronic endoscope is realized.

As described above with reference to the electronic endoscopes 1, 101, 201, 301, and 401 serving as examples, the present specification has disclosed an electronic endoscope characterized in that: an outer shell that is formed in a tube shape and whose peripheral wall is provided with a transparent window part extending in an axial direction; a solid-state imaging device that is provided inside the outer shell; an objective optical system that includes an objective lens for focusing object light through the window part and that forms an image onto the solid-state imaging device; and a drive mechanism that causes at least the objective lens in the objective optical system to move along an axis of the outer shell.

Further, the present specification has disclosed an electronic endoscope characterized in that the drive mechanism includes a lens holder for supporting the objective lens, a feed screw extending along the axis of the outer shell, and a motor for driving and revolving the feed screw, and wherein the lens holder engages with a thread groove of the feed screw and revolution about the feed screw as an axis of revolution is restricted.

Further, the present specification has disclosed an electronic endoscope characterized in that the drive mechanism includes a lens holder for supporting the objective lens, a feed screw extending along the axis of the outer shell, and a motor for driving and revolving the lens holder about the feed screw as an axis of revolution, and wherein the lens holder engages with a thread groove of the feed screw.

Further, the present specification has disclosed an electronic endoscope characterized in that the outer shell is formed in a cylindrical shape and a thread groove is formed in its inner peripheral surface, wherein the driving section includes a lens holder for supporting the objective lens and a motor for driving and revolving the lens holder about the axis of the outer shell as an axis of revolution, and wherein the lens holder engages with the thread groove of the outer shell.

Further, the present specification has disclosed an electronic endoscope characterized by comprising a control section that reads an image pick-up signal from the solid-state imaging device and that generates image data, and a memory that stores the image data are further included in the outer shell.

Figure 34:
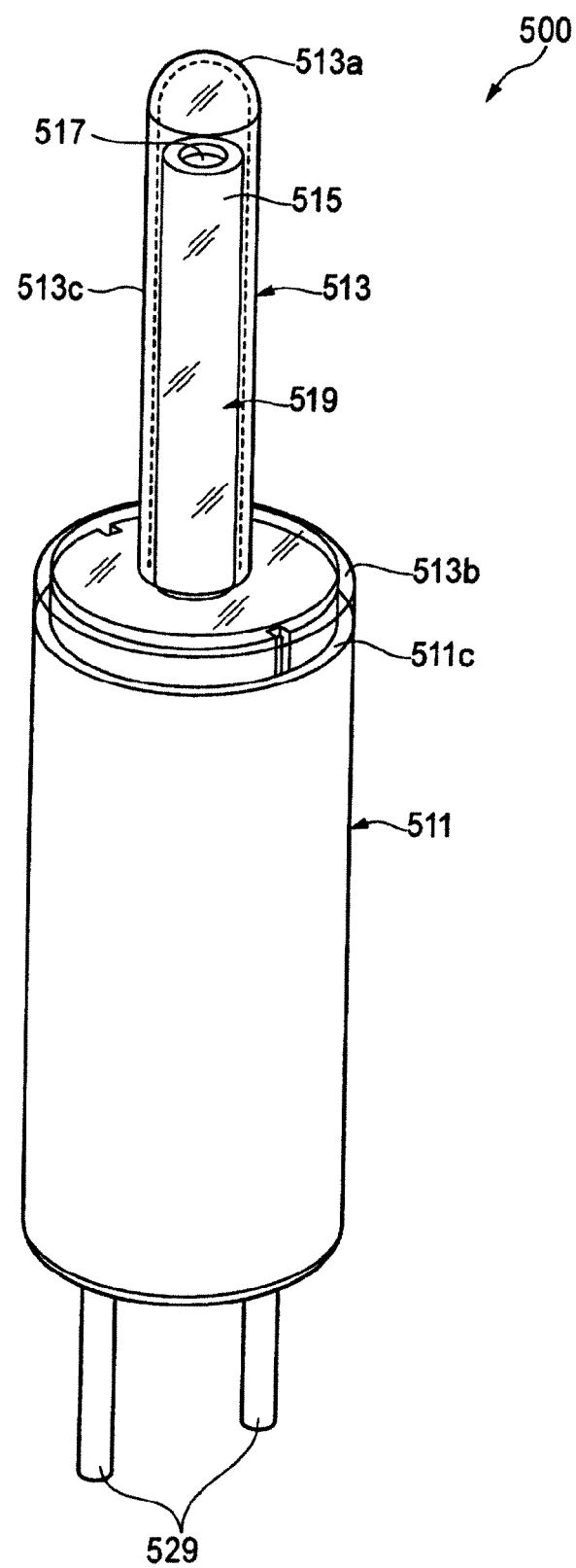
FIG. 34 is an external appearance perspective view of another example of an electronic endoscope used for describing an embodiment of the present invention.
Figure 35:
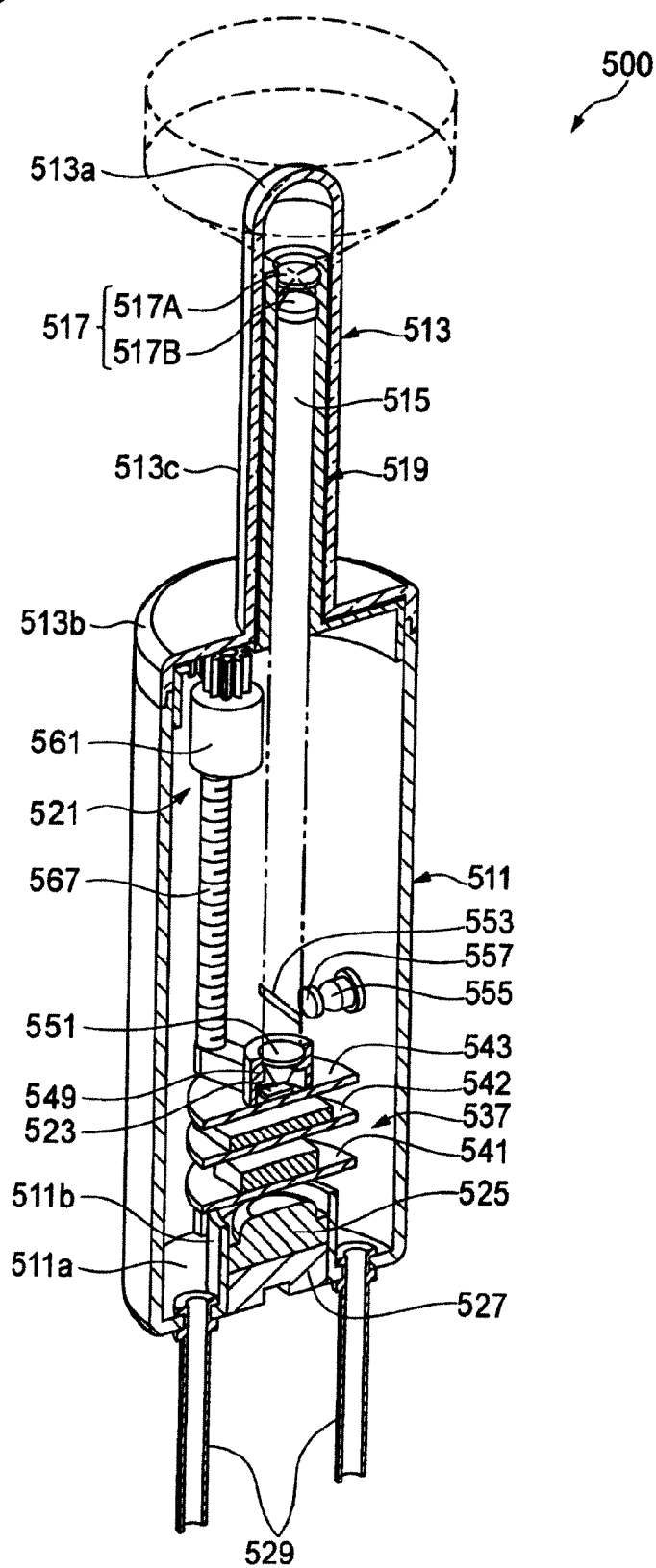
FIG. 35 is a longitudinal sectional view of an endoscope shown in FIG. 34.
Figure 36:
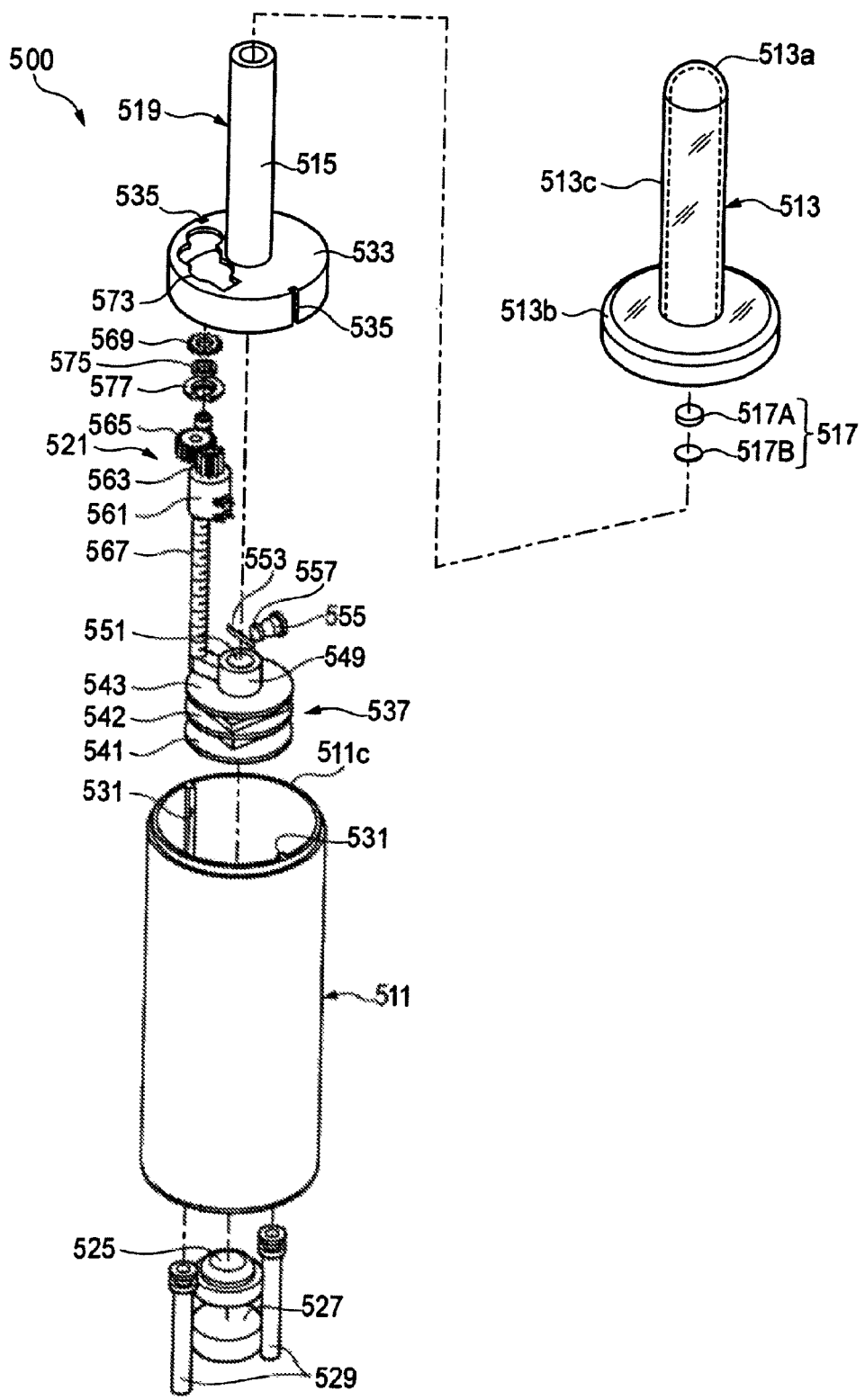
FIG. 36 is an exploded perspective view of an endoscope shown in FIG. 34.

The electronic endoscope 500 shown in FIGS. 34 to 36 comprises: a body part 511 and a transparent cover 513 serving as an outer shell; a lens holder 519 that is accommodated inside the body part 511 and that is provided with an objective lens group 517 serving as a wide-angle lens arranged on one-end side of the tube-shaped part 515; a raising and lowering driving section 521 for moving the lens holder 519 in the inside of the transparent cover 513 and the body part 511 in the optical axis direction of the objective lens group 517; and a solid-stare imaging device 523 that receives the object light acquired through the objective lens group 517 and then converts the light into an electric signal.

The body part 511 is formed in a closed-bottom cylindrical shape fabricated from resin material or the like having light shielding property. Its bottom part (lower side in FIG. 35) 511*a* is provided with a tube-shaped battery accommodating part 511*b*. After a power battery 525 is mounted, the battery accommodating part 511*b* is airtightly closed by a battery lid 527. That is, the power battery 525 is built in the body part 511 so that the necessity of power supply from the outside is avoided. This avoids the necessity of connection of a power supply cable to the body part, and hence enhances the easy handling of the electronic endoscope 500 itself. Here, the shape of the body part 511 is not limited to a cylinder, and may be a tube of another kind, a hollow shape, or the like.

Further, in the bottom part 511*a*, in the example shown in the figure, two hard wiring protection tribes 529 fabricated from resin are fixed in a protruding manner toward the outside. Then, wiring for outputting an image signal or the like is allowed to be inserted through the wiring protection tubes 529. Here, at the time of use of the electronic endoscope 500, the wiring protection tubes 529 serve also as grip pipes used for inserting or extracting the entirety of the electronic endoscope 500 into or from a hole or an abdominal cavity serving as a subject.

In the inner peripheral surface of the body part 511, ribs 531 extending in the longitudinal direction of the body part 511 are formed and engage with engagement groove 535 formed in the flange 533 of the lens holder 519, so that revolution of the lens holder 519 is stopped.

The transparent cover 513 is formed from hard transparent resin. The apex part on the tip side is formed in a smooth hemispherical shape that permits easy insertion into the inside of a subject. An open end part 513*b* that is located on the side opposite to the hemispherical part 513*a* and has an expanded diameter and an open end part 511*c* of the body part 511 are aligned to each other and fixed by bonding. The transparent cover 513 may be fabricated by integral molding, or alternatively by joining the hemispherical part 513*a* and the open end part 511*c* by bonding. Further, light shielding property may be imparted to the hemispherical part 513*a* so that it may be prevented that external light is introduced directly into the objective lens group 517. Here, it is sufficient that the transparent resin is transparent to light at a particular wavelength. That is, the material need not be transparent to visible light.

The hemispherical part 513*a* of the transparent cover 513 and the cylindrical part 513*c* extending from the hemispherical part 513*a* to the open end part 513*b* have a smaller diameter than the open end part 513*b* that has almost the same diameter as the external shape of the body part 511. As such, since the hemispherical part 513*a* and the cylindrical part 513*c* are formed in a smaller diameter, they are easily inserted into a narrow inside of a subject. This expands the range of application of the electronic endoscope 500. Here, the cylindrical part 513*c* of the transparent cover 513 may be in the form of a frontward-tapered shape. In this case, the tip of the transparent cover 513 is easily inserted into a small hole or a small abdominal cavity. Further, the hemispherical part 513*a* and the cylindrical part 513*c* may be formed in a diameter that is equal to the external shape of the body part 511 and that is the same as the open end part 513*b*. In this case, no tapered tip is formed. Thus, the strength of the electronic endoscope 500 is improved and its robustness is improved.

The lens holder 519 is fabricated from resin material or the like and formed in an outer surface shape that follows the inner surface of the transparent cover 513. The objective lens group (a wide-angle lens 517A and a lens 51713) is fixed to one-end side of the tube-shaped part 515 so as to close the opening of the one-end side apex part. Preferably, the wide-angle lens 517A is composed of a fish-eye lens. In this case, a circular fish-eye lens is suitable for observation in the entire circumferential directions where the inclination angle (angle relative to the lens optical axis) is large. That is, the wide-angle lens is a wide-angle lens having an observational field of view that permits observation in dr entire side circumferential directions around the optical axis (the center axis of the tube-shaped part 515) of the objective lens group 517. Here, in addition to this configuration, the wide-angle lens 517A may be composed of a diagonal fish-eye lens, a common wide-angle lens, or the like. The optical axis of the objective lens group 517 fixed to the lens holder 519 agrees with the center axis direction of the tube-shaped part 515 of the lens holder 519. Then, in the tube-shaped part 515 of the lens holder 519, its outer diameter is formed somewhat smaller than the inner diameter of the cylindrical part 513c of the transparent cover 513. Thus, the tube-shaped part 515 is allowed to move inside the transparent cover 513 smoothly without chattering.

At a position on an extended line of the center axis of the cylindrical part 513c extended toward the bottom part 511a of the body part 511, an image pick-up drive unit part 537 is arranged. The image pick-up drive unit part 537 is mounted and fixed in the inside of the body part 511 by using a stay member (not shown) in a state that the peripheral wall of the battery accommodating part 511b provided in the bottom part 511a of the body part 511 serves as a supporting column. In the example shown in the figure, the image pick-up drive unit part 537 has three base plates 541, 542 and 543.

Figure 37:
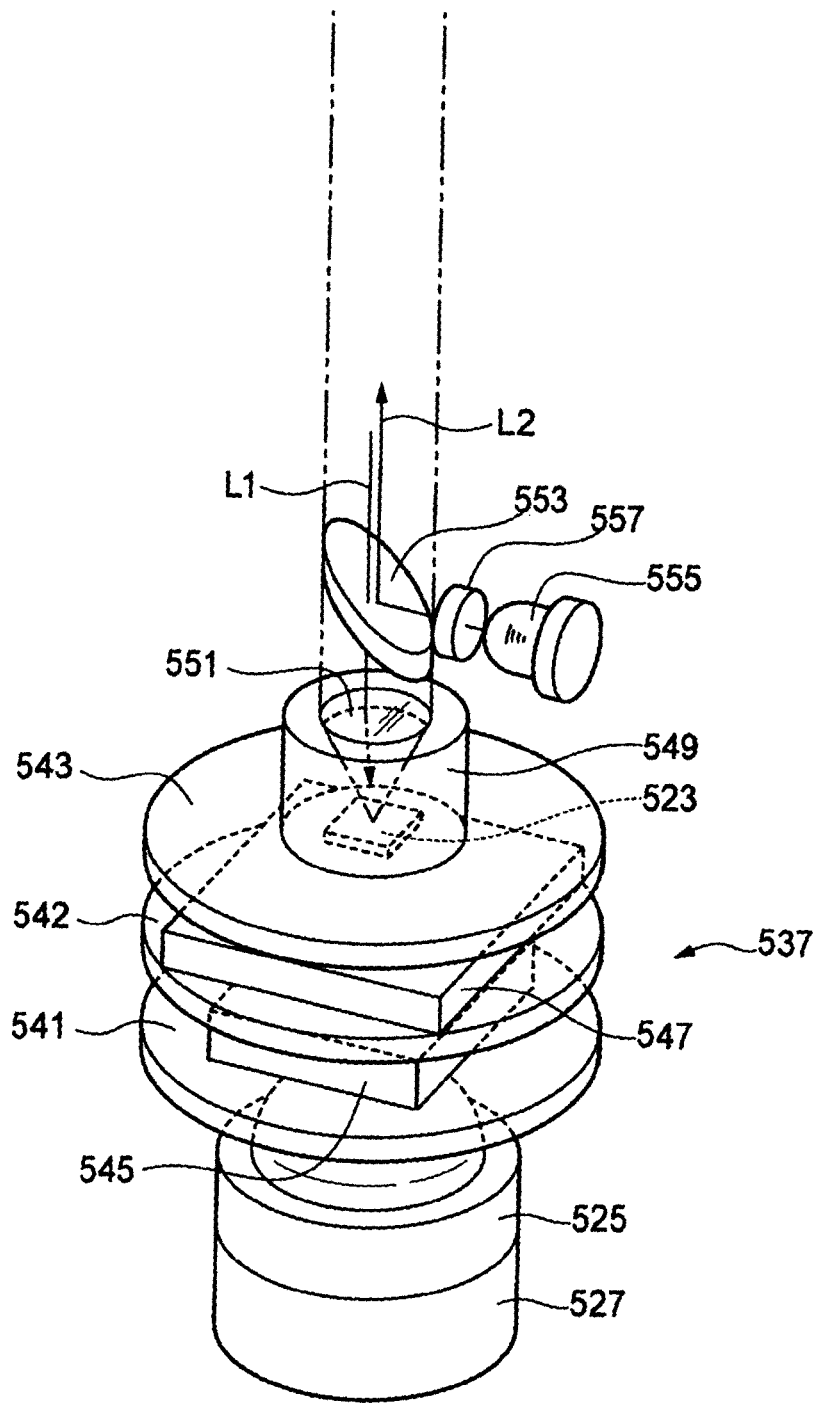
FIG. 37 is an enlarged perspective view of a part containing an image pick-up drive unit part of an endoscope.

FIG. 37 shows an enlarged perspective view of a part containing the image pick-up drive unit part 537. The base plate 541 in the lowermost layer (on the bottom part 511a side) is provided with a control unit 545 containing a driver circuit for the stepping motor and other circuits. The middle layer the base plate 542 is provided with an image memory 547 for storing pick-up image data. The upper layer base plate 543 is provided with an imaging device 523 composed of a solid-state imaging device such as a CCD type imaging device and a CMOS type imaging device.

In the center part of the base plate 543 containing the center axis of the cylindrical part 513c, a focusing lens holder 549 formed in a cylindrical shape is arranged. Then, the focusing lens holder 549 accommodates the imaging device 523 in the inside. Then, a focusing lens 551 is arranged in the upper-end opening part of the focusing lens holder 549. Thus, the parallel light beam (object light) L1 guided along the center axis is focused onto the light acceptance surface of the imaging device 523 by the focusing lens 551 so that an image is formed.

Further, a half mirror 553 is arranged in the middle of the optical path between the objective lens group 517 and the imaging device 523. Then, emitted light from a light emitting diode (LED) 555 serving as a light emitting body is directed to the objective lens group 517 by reflection in the half minim 553, and then projected as light for illumination L2. That is, the half 553 is arranged at a position in the immediate upstream of the focusing lens 551 within the parallel light beam entering the focusing lens 551 in a state that the half mirror 553 is inclined by 45 degrees relative to the optical axis of the parallel light beam (the center axis of the cylindrical part 513c). Then, an illumination lens 557 for deflecting the light for illumination into the form of a parallel light beam toward the half mirror 553 is provided between the LED 555 and the half mirror 553. The half mirror 553, the illumination lens 557, and the LED 555 are fixed inside the body part 511 individually by appropriate support members.

Figure 38A:
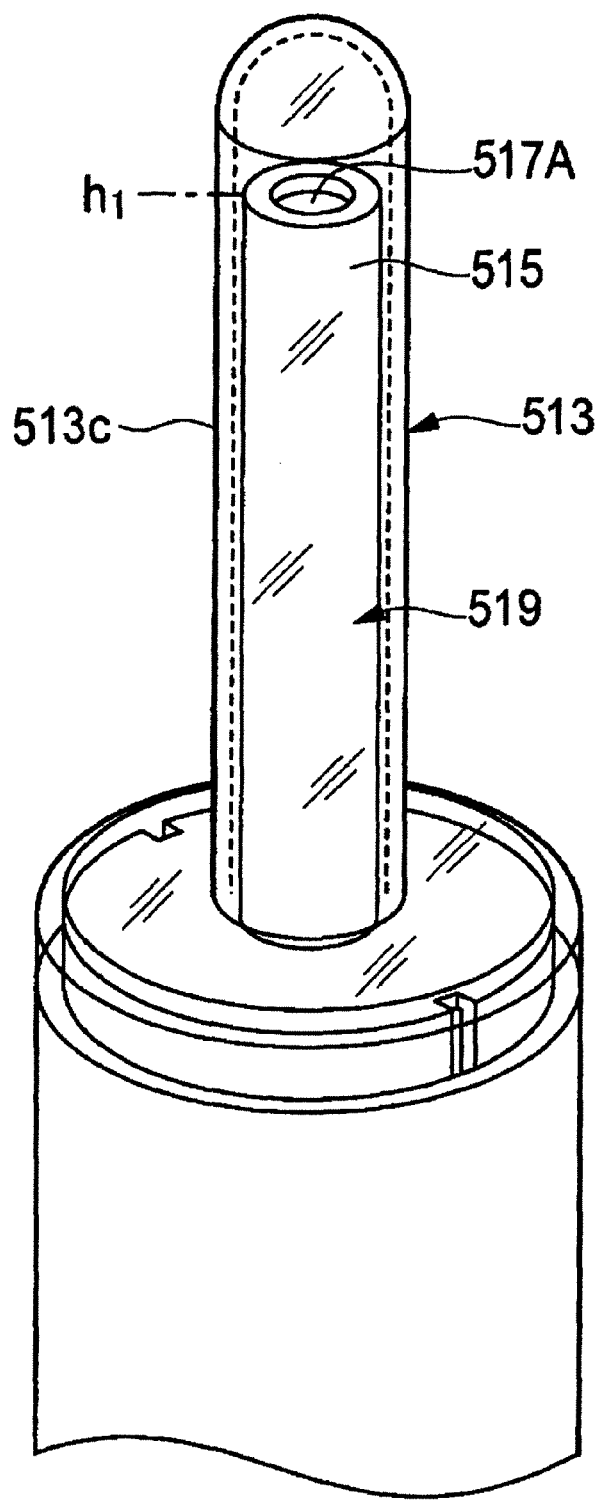
FIG. 38A is an enlarged perspective view showing a situation of movement of a lens holder inside a transparent cover in a state that the lens holder is located at an upper end position.
Figure 38B:
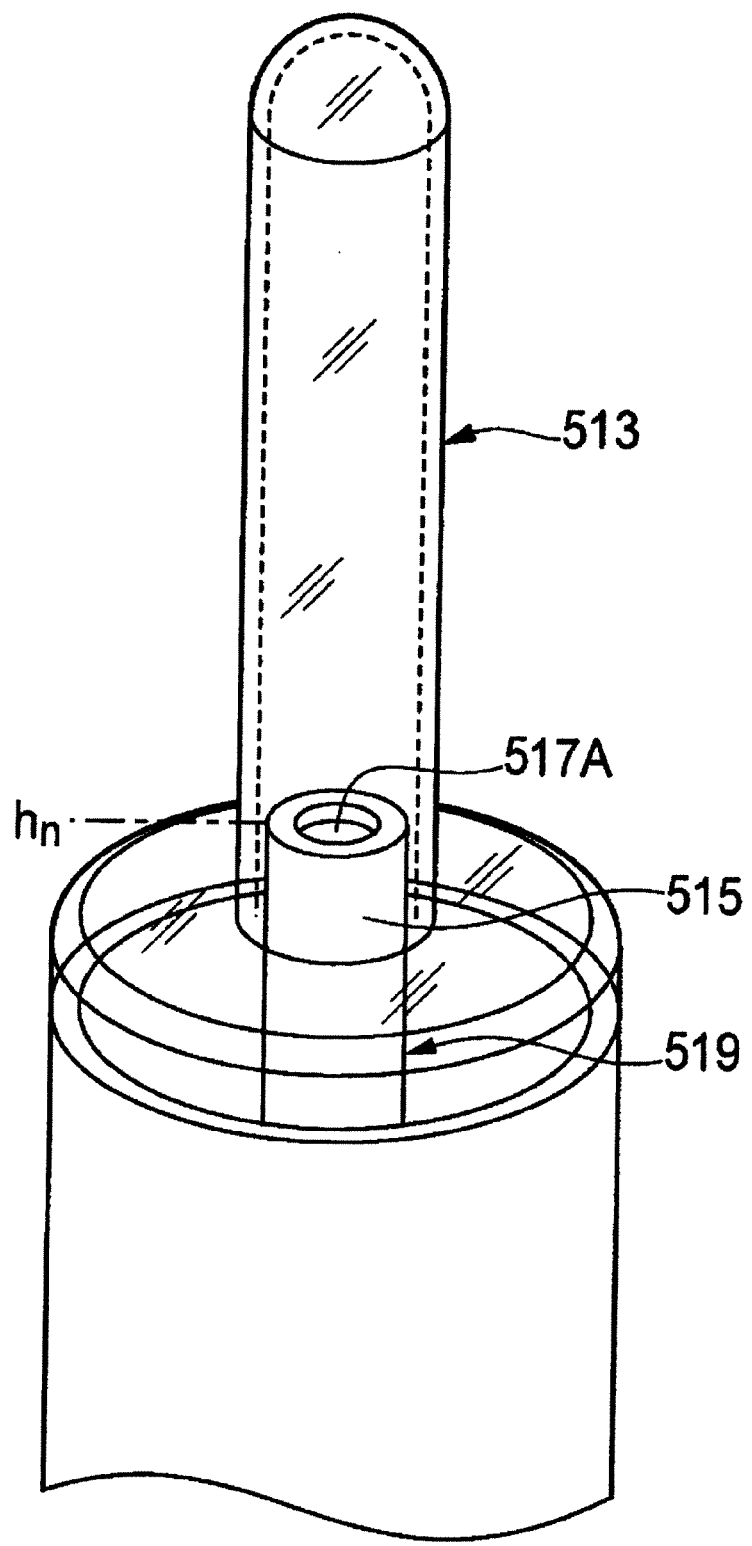
FIG. 38B is an enlarged perspective view showing a situation of movement of a lens holder inside a transparent cover in a state that the lens holder is located at a lower end position.

Here, as shown in FIGS. 38A and 38B, the tube-shaped part 515 of the lens holder 519 provided with the objective lens group 517 is allowed to move in the inside of the transparent cover 513 and the body part 511 in the optical axis direction of the objective lens group 517 (the center axis direction of the tube-shaped part 515). That is, the position of the wide-angle lens 517A can be set up arbitrarily between height h1 shown in FIG. 38A and height hn shown in FIG. 38B.

Means for moving the lens holder 519 is described below in detail with reference to FIGS. 35, 39A, and 39B. A motor holding member (not shown) is provided in the inside of the body part 511. Then, the stepping motor 561 is attached to this motor holding member. The shaft of the stepping motor 561 is in parallel to the center axis of the tube-shaped part 515 (the optical axis of the parallel light beam). A motor gear wheel (spur wheel) 563 is attached to the shaft of the stepping motor 561. Then, the motor gear wheel 563 engages with an idle gear wheel 565 composed of a spur wheel. Then, the idle gear wheel 565 engages with a gear wheel 569 fixed to one-end side of the feed screw 567 by press fit or bonding. Thus, the revolving force of the stepping motor 561 is transmitted through the motor gear wheel 563, the idle gear wheel 565, and the gear wheel 569 to the feed screw 567. Here, the idle gear wheel 565 has a larger number of gear teeth than the motor gear wheel 563. Thus, the revolution speed of the stepping motor 561 is reduced and then transmitted to the idle gear wheel 565. Here, the stepping motor 561 for driving the feed screw 567 is not limited to a motor operated by pulse drive, and may be a motor of a diverse kind such as a servo motor provided with an encoder, or alternatively may be a power source of another type.

Figure 40:
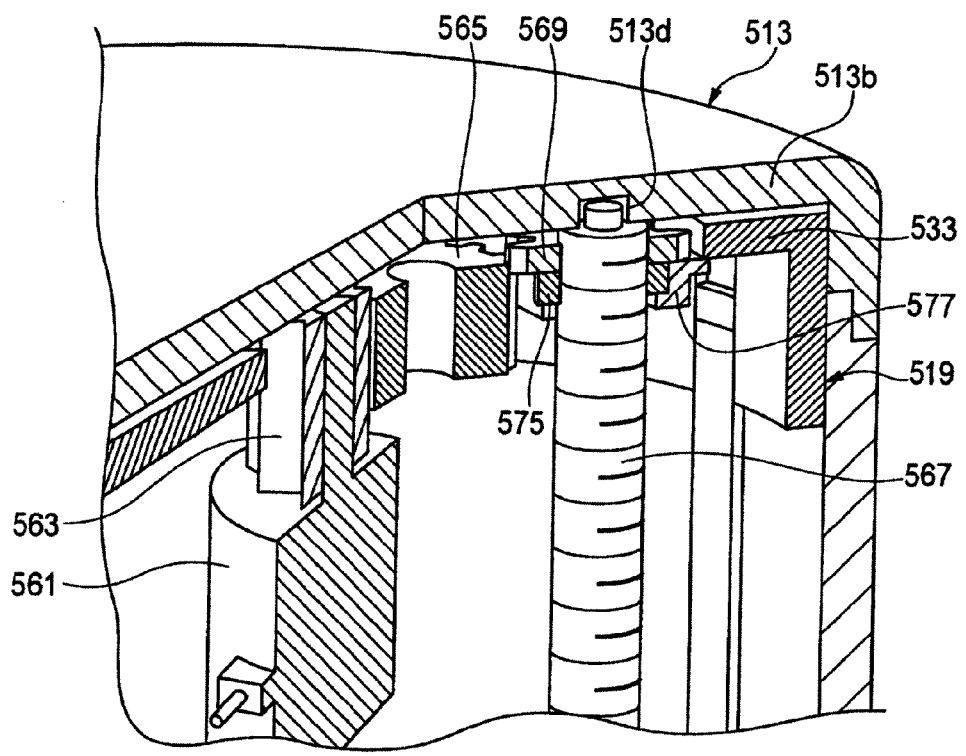
FIG. 40 is a sectional perspective view of a part showing a mode of supporting an upper end of a feed screw shown in FIG. 39A.

As shown in the sectional part view of FIG. 40, in the feed screw 567, the tip on one-end side is inserted into the shaft hole 513d formed in the flange face of the open end part 513b of the transparent cover 513. Further, the-other-end side of the feed screw 567 is supported in a revolvable manner by the support arm 571 provided in the side face of the focusing lens holder 549 of the image pick-up drive unit part 537. Thus, the feed screw 567 driven and revolved by the revolution of the stepping motor 561. Here, the stepping motor 561, the motor gear wheel 563, the idle gear wheel 565, and the gear wheel 569 stay at the same height position inside the body part 511 regardless of the movement of the lens holder 519.

Figure 39A:
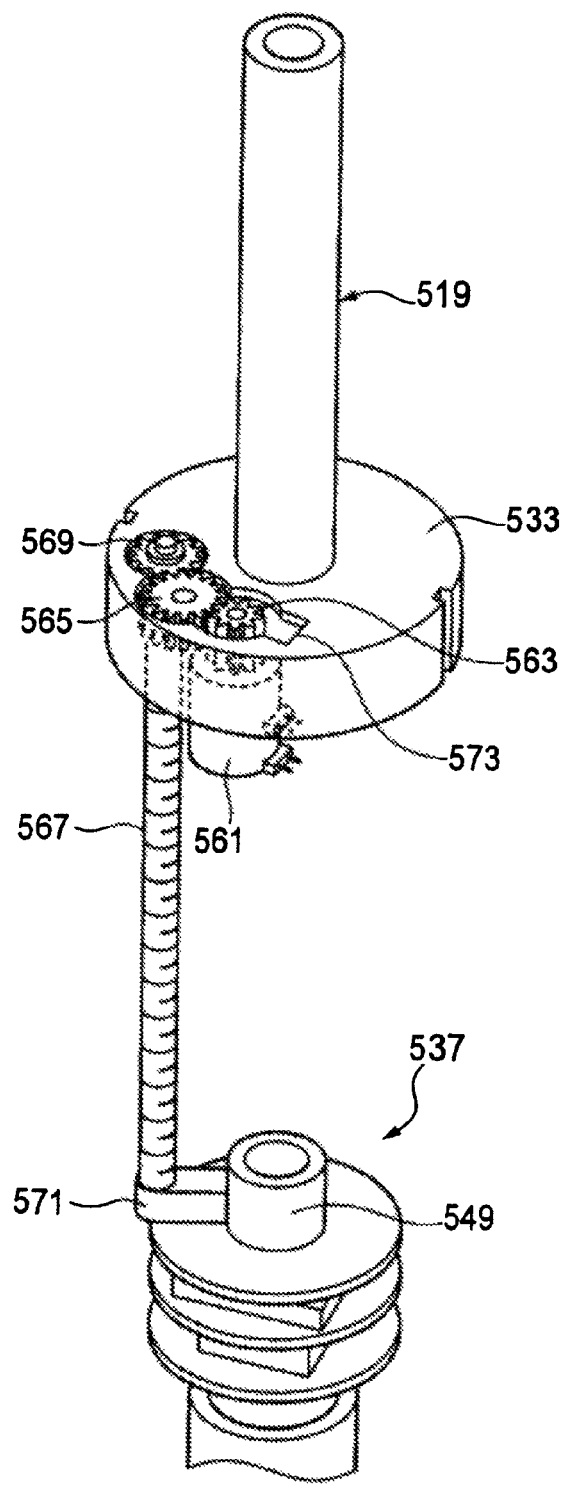
FIG. 39A is an enlarged perspective view showing a main part of a moving mechanism for a lens holder in a state that the lens holder is located at an upper end position.
Figure 39B:
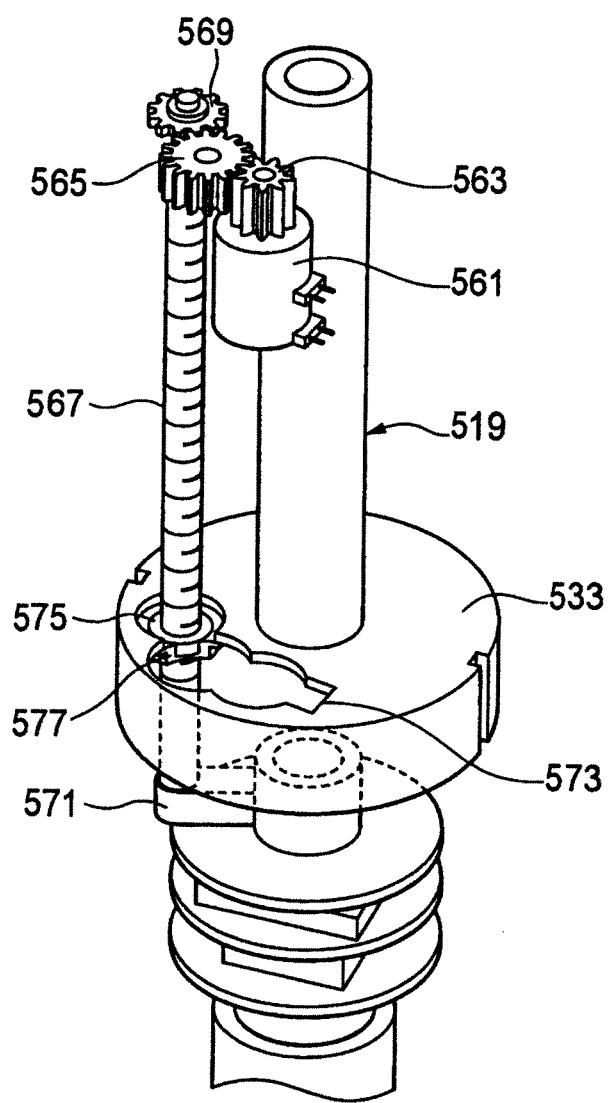
FIG. 39B is an enlarged perspective view showing a main part of a moving mechanism for a lens holder in a state that the lens holder is located at a lower end position.

On the other hand, the flange 533 of the lens holder 519 is provided with an opening 573 for avoiding interference with the motor gear wheel 563, the idle gear wheel 565, the gear wheel 569, and the like at a raised position of the lens holder 519 shown in FIG. 39A. Then, a feed nut 575 screwed onto the feed screw 567 is fixed to the flange 533 by a nut holding piece 577.

According to the above-mentioned configuration, the feed screw 567 and the lens holder 519 provided with the feed nit 575 serve as a linear movement mechanism for moving the lens holder 519 in the axial direction of the feed screw 567 in association with the revolution operation of the feed screw 567.

For example, when the stepping motor 561 is driven starting from the raised position of the lens holder 519 shown in FIG. 39A, the feed screw 567 is driven and revolved via the motor gear wheel 563, the idle gear wheel 565, and the gear wheel 569. When the feed screw 567 is driven and revolved, the feed nut 575 screwed onto this is moved relative to the feed screw 567. As a result, as shown in FIG. 39B, the lens holder 519 is lowered down from the raised position.

Figure 41:
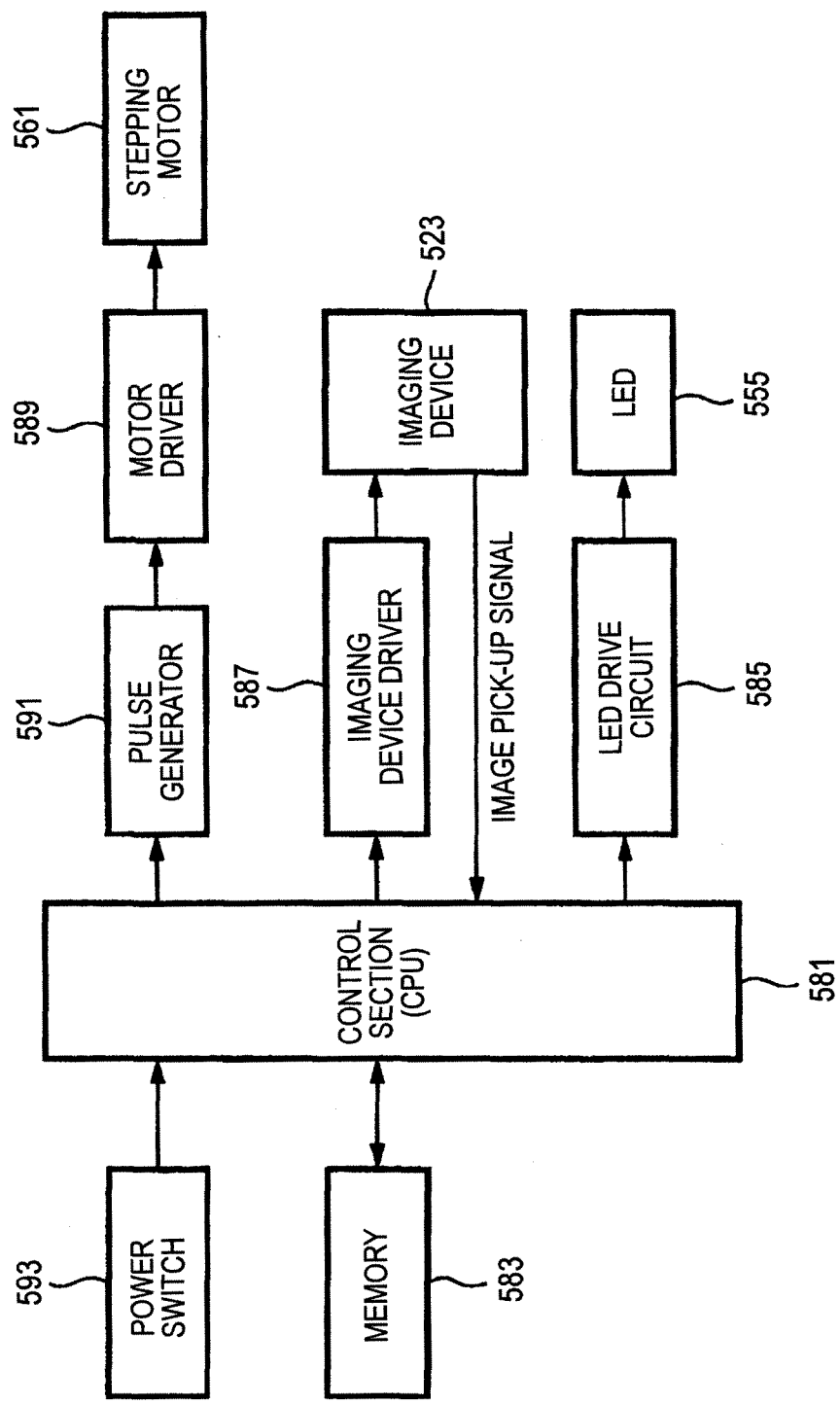
FIG. 41 is a functional block diagram showing an image pick-up drive unit part.

FIG. 41 is a functional block diagram showing the image pick-up drive unit part 537. The control section (CPU) 581 for collectively controlling the entire system is connected to: a memory 583 that stores a control program and serves also as a work memory and that contains the image memory 547 provided on the base plate 542 described in FIG. 37; an LED drive circuit 585 for driving the LED 555; an imaging device driver 587 for driving the imaging device 523; and a pulse generator 591 for providing driving pulses to the motor driver 589 for driving the stepping motor 561. Image data obtained by image processing in the control section 581 is stored into the image memory 547 built in the body part 511. This permits acquisition of an image by the electronic endoscope 500 in a stand alone mode. Thus, easy handling is enhanced.

Further, the electronic endoscope 500 has a power switch 593. When the power switch 593 is turned ON, electric power from the power battery 525 is supplied through wiring (not shown) to the individual parts of the image pick-up drive unit part 537, so that image pick-up operation and drive operation are performed as described later.

For example, the power switch 593 may be provided in the bottom part 511a of the body part 511, and may be turned ON or OFF by manual operation. Alternatively, a switch terminal that follows magnetism may be built in the body part 511. Then, from the outside of the electronic endoscope 500, a magnet may be brought close or apart so that the switch terminal may be turned ON or OFF.

Next, the operation of the electronic endoscope 500 is described below. As shown in FIGS. 35 and 41, when the power switch 593 is turned ON, electric power is supplied from the power battery 525 to the individual parts so that their operation is started and hence the stepping motor 561 is driven and revolved. Thus, the lens holder 519 moves in the inside of the electronic endoscope 511) in the center axis direction of the tube-shaped part 515, and then stops at a home position (for example, a raised-end position of the lens holder 519). Further, emitted light from the LED 555 is brought into the form of a parallel light beam by the illumination lens 557. Then, the parallel light beam is reflected to the direction of the objective lens group 517 by the half mirror 553, and then projected through the objective lens group 517 over the entire circumference of the directions (the side face directions relative to the direction of insertion into the subject) that are approximately perpendicular to the center axis of the tube-shaped part 515. As such, the light serves as light for illumination.

Figure 42:
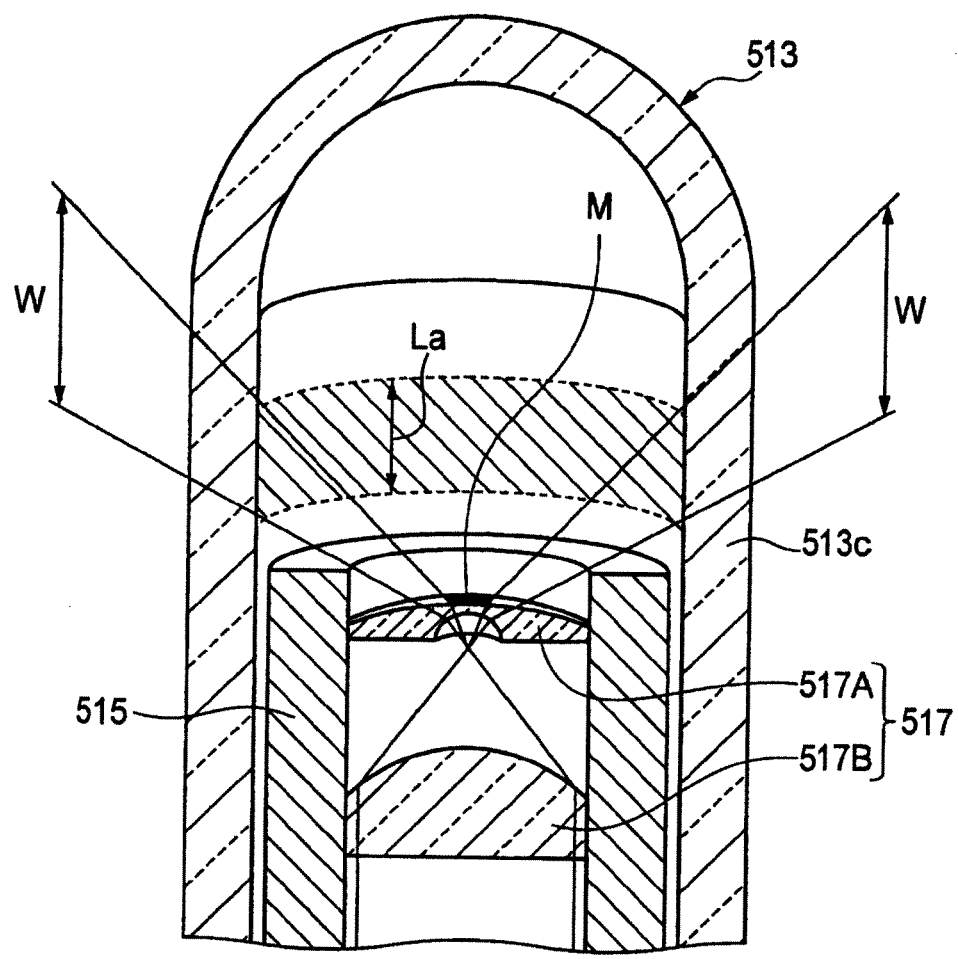
FIG. 42 is an explanation diagram showing a situation of a view field region of an objective lens group.

The reflected light from the image-taking object is acquired through the objective lens group 517 into the electronic endoscope 500. Then, the optical image of the image-taking object travels to the focusing lens 551 in the form of a parallel light beam. And then, an image is formed onto the light acceptance surface of the imaging device 523 by the focusing lens 551. FIG. 42 shows the situation of the view field region W formed by the objective lens group 517. The light for illumination emitted from the wide-angle lens 517A is projected onto the region indicated as the view field region W. Among the reflected light from the image-taking object illuminated by the light for illumination, the part of light belonging to the view field region W is used in image formation and then acquired by the imaging device 523. Here, in the center part of the optical axis of the wide-angle lens 517A, a light shielding mask M for defining the upper end of the view field region W is provided. In this example, a light shielding mask M having a circular shape whose radius is set up in correspondence to the view field region W is provided in the outer surface (the surface on the light exit side) of the wide-angle lens 517A.

The image pick-up signal of the image-taking object acquired by the imaging device 523 is inputted to the control section (CPU) 581 and then undergoes image processing. Then, the obtained data, for example, in the form of JPEG image data is stored into the memory 583 (the image memory 547).

Figure 43:
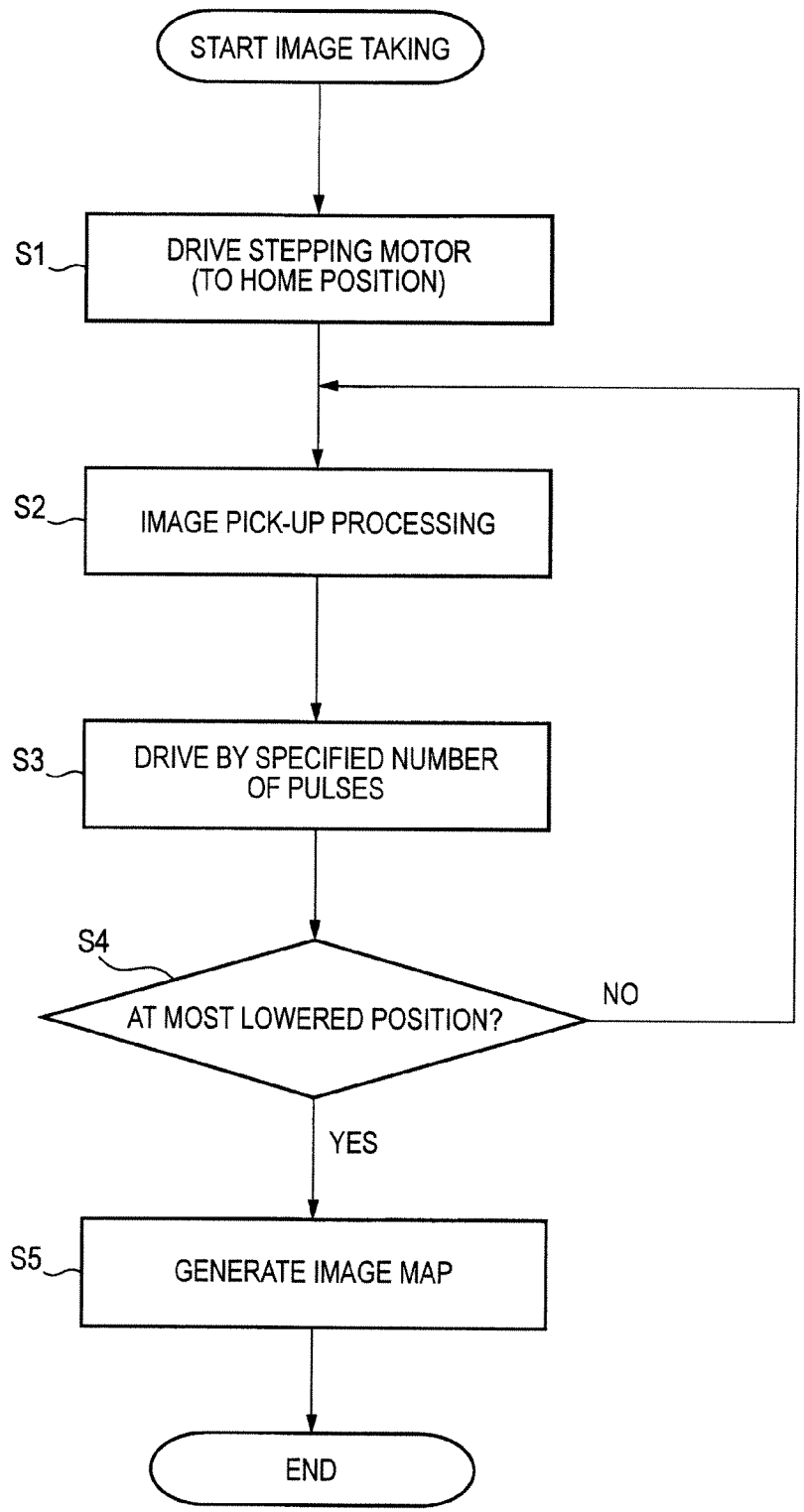
FIG. 43 is a flow chart showing a processing procedure of a control program.

FIG. 43 is a flow chart showing the processing procedure of a control program stored in the memory 583. When the power switch 593 is turned ON, this control program is invoked. Then, first, the stepping motor 561 is driven so that the lens holder 519 is moved toward the home position (the raised end position) (S1). The home position is defined, for example, as a position where the objective lens group 517 is located on the tip side of the electronic endoscope 500 as shown in FIGS. 34 and 38A. However, the definition is not limited to this, and may be the position on the pedestal side opposite to the tip side (the position of the lens holder shown in FIG. 38B).

After the lens holder 519 reaches the home position, image pick-up processing is performed (S2). The image pick-up processing inch ides: processing that the LED 555 is turned ON so that light for illumination is projected through the objective lens group 517, and then light reflected from the image-taking object is acquired through the objective lens group 517 into the electronic endoscope 500 so that an image is formed onto the light acceptance surface of the imaging device 523; and processing that the imaging device 523 generates an image pick-up signal, then the image pick-up signal of the image-taking object undergoes image processing, and then the obtained data is stored into the memory 583 (the image memory 547).

Then the stepping motor 561 is driven by a specified number of pulses (S3), so that the lens holder 519 is lowered by a predetermined distance. The predetermined distance indicates a step distance by which the lens holder 519 is to be moved stepwise in order that the view field region W shown in FIG. 42 should cover stepwise the movable region of the lens holder 519. For example, the predetermined distance may be the height La of a part contained in the view field region W in the cylindrical part 513c of the transparent cover 513.

Figure 44:
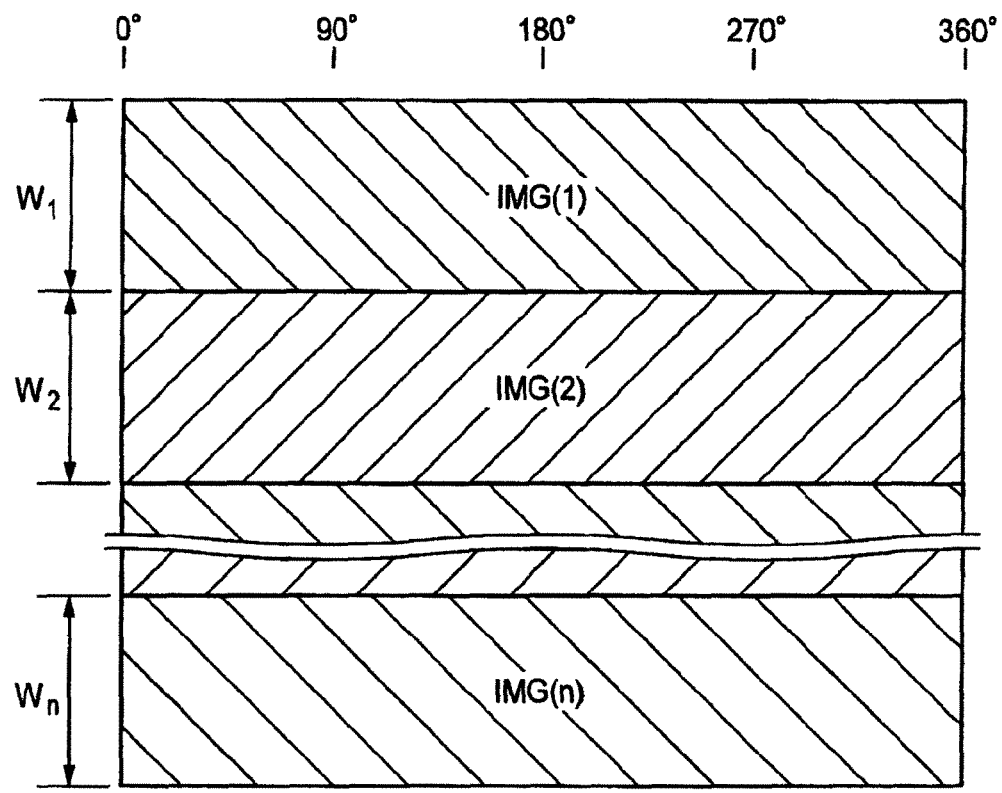
FIG. 44 is an explanation diagram showing a situation that an image map is generated from a plurality of pick-up images.

Until the destination reaches the most lowered position of the lens holder 519 (S4), image pick-up processing is performed at each destination of the movement (S2). Then, S2 and S3 are repeated so that an image map as shown in FIG. 44 is generated by combining the pick-up images obtained by individual occasions of image pick-up (S5). That is, the pick-up image data IMG(1) of the first occasion is image data of the view field region W1 over the entire circumferential directions (circumferential angle from 0 degree to 360 degrees) in a situation that the wide-angle lens 517A of the objective lens group 517 is located at height h1 shown in FIG. 38A. The pick-up image data IMG(2) of the second occasion is image data of the view field region W2 over the entire circumferential directions in a situation that the wide-angle lens 517A has been lowered down together with the lens holder 519 from the position of height h1 by a predetermined distance and hence is located at height h2. As such, plural sheets of image data IMG(1) to IMG(n) each obtained at each position of the movement of the lens holder 519 are combined into a substantially single sheet of image data (image map) by linking the data pieces with each other in the height direction. Here, in a configuration that a part of the view field region of an image taking occasion overlaps with the view field region of the next image taking occasion, even junction regions of the images are acquired without a missing part. This provides image data without a gap.

After the image map is generated from the above-mentioned pick-up image data IMG(1) to IMG(n), the accumulated data is read to the outside from the memory 583 (see FIG. 41) storing the image map. This read operation may be performed by wireless, or alternatively by using a wiring inserted through the wiring protection tubes 529 shown in FIG. 34. Alternatively, the memory 583 may be provided in a removable manner from the electronic endoscope 500. Then, the removed memory 583 may be read by a personal computer provided separately.

Further, the electronic endoscope 500 may transmit the pick-up image data to an external monitor, so that the pick-up image may be observed on line through the external monitor. In addition, operation instructions may be inputted from the outside. In this case, without performing image processing, the control section 581 transmits the image pick-up signal acquired from the imaging device 523, to an external video processor in an intact manner. Then, an object image obtained by image processing by the video processor is displayed on the external monitor. The communication between the external video processor, the external monitor, and the control section 581 may be of cable or wireless. In a case that the communication is of cable, an external power source becomes employable when a power source line is included in the wiring.

Further, as another example of the control program, a control program may be employed that, in addition to the control procedure shown in the flow chart of FIG. 43, allows the view field region of the objective lens group 517 to be moved to an arbitrary position in accordance with an operation instruction from the outside. In this case, selective image pick-up of a desired site is achieved in accordance with the purpose of image pick-up, and hence more detailed observation of the site is allowed.

As described above with reference to the electronic endoscope 500 serving as an example, the present specification has disclosed an electronic endoscope that is inserted into a subject and then acquires an image inside the subject, characterized in that a lens holder that has a tube-shaped part; a wide-angle lens that is mounted on the lens holder and that is arranged on one-end side of the tube-shaped part in a state that an optical axis is aligned to a center axis of the tube-shaped part so that an observational field of view extends to a sideward region of the tube-shaped part; an imaging device that receives light acquired through the wide-angle lens and that converts the light into an electric signal; a transparent cover that covers one-end side of the tube-shaped part and at least whose part facing the observational field of view of the wide-angle lens has transparency; a tube-shaped body part that is connected to the transparent cover on the-other-end side of the tube-shaped part; and a driving section that is arranged inside the body part and that causes the lens holder to advance or retreat in the center axis direction.

According to this electronic endoscope, the lens holder inside the transparent cover advances or retreats by virtue of the driving section. This permits image pick-up at different positions along the center axis of the tube-shaped part of the lens holder, and hence image information to be acquired through the wide-angle lens is allowed to be acquired accurately within the moving range of the lens holder. Thus, without the necessity of moving the electronic endoscope within the subject, a continuous image of a large region is acquired easily.

Further, the present specification has disclosed an electronic endoscope characterized in that the imaging device receives light from an entire sideward circumference of a direction of insertion into the subject.

According to this electronic endoscope, image information for the entire sideward circumference of the direction of insertion into the subject is acquired, and then the image information is combined to each other so that a single sheet of entire sideward circumferential image is generated easily.

Further, the present specification has disclosed an electronic endoscope characterized in that the wide-angle lens is composed of a circular fish-eye lens.

According to this electronic endoscope, since the circular fish-eye lens is employed, an image of the entire sideward circumference of the optical axis of the wide-angle lens is obtained efficiently. Further, this permits image pick-up from a direction almost perpendicular to the observation surface of the subject.

Further, the present specification has disclosed an electronic endoscope characterized by comprising: a half mirror that is arranged in the course of the optical path between the wide-angle lens and the imaging device; and a light emitting body that emits light for illumination to be projected through the wide-angle lens after reflection by the half mirror and thereby illuminates the subject.

According to this electronic endoscope, the emitted light from the light emitting body is reflected toward the subject by the half mirror. Then, this reflected light serves as light for illumination that illuminates the entire sideward circumference of the subject.

Further, the present specification has disclosed an electronic endoscope characterized in that the tube-shaped part of the lens holder and a tip part of the transparent cover that covers the tube-shaped part are formed in a smaller diameter than the body part.

According to this electronic endoscope, image information is acquired by the tip part having a smaller diameter than the body part. This permits easy insertion even into a narrow region of the subject and hence easy observation of the inside of the subject. This expands the range of application of the electronic endoscope.

Further, the present specification has disclosed an electronic endoscope characterized in that the driving section includes: a feed screw which is supported inside the body part in a revolvable manner in parallel to the optical axis direction of the wide-angle lens, a feed nut which is fixed to the lens holder in a screwed manner onto the feed screw, and a motor which drives and revolves the feed screw.

According to this electronic endoscope, the feed screw is revolved by the motor so that the feed nut screwed onto the feed screw is moved in the axial direction of the feed screw. By virtue of this, the lens holder is advanced or retreated in parallel to the optical axis direction of the wide-angle lens.

Further, the present specification has disclosed an electronic endoscope characterized in that a control section that performs image processing on an image signal obtained by image pick-up performed by the imaging device and an image memory that stores image data obtained by image processing performed by the control section are included in the inside of the body part.

According to this electronic endoscope, image data obtained by image processing in the control section is stored into the image memory built in the body part. This permits acquisition of an image by the electronic endoscope in a stand alone mode. Thus, easy handling is enhanced.

Further, the present specification has disclosed an electronic endoscope characterized in that a power battery for supplying electric power to the imaging device and the driving section is built inside the body part.

According to this electronic endoscope, the power battery is built in the body part. This avoids the necessity of power supply from the outside, and hence avoids the necessity of a power supply cable connected from the outside of the body part. Thus, easy handling is enhanced.

Figure 45:
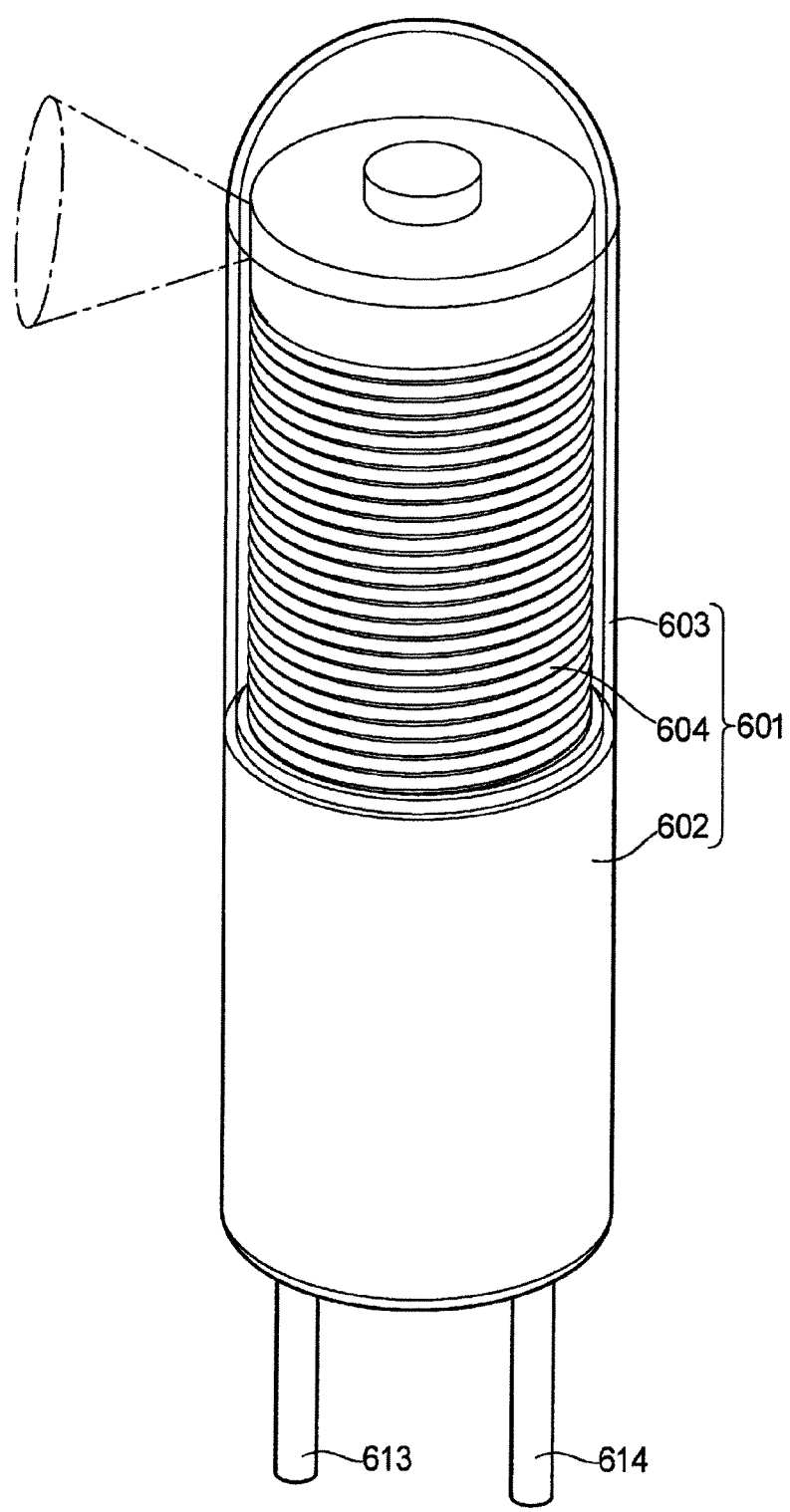
FIG. 45 is an external appearance perspective view of another example of an electronic endoscope used for describing an embodiment of the present invention.

The electronic endoscope 601 shown in FIG. 45 is of side-viewing type and, at the same time, of hard type. The electronic endoscope 601 is constructed from: a body part 602 and a transparent capsule (transparent cover) 603 serving as an outer shell; and a moving lens frame section (lens holder) 604 accommodated inside and an image pick-up drive unit part 605 described later.

Figure 46:
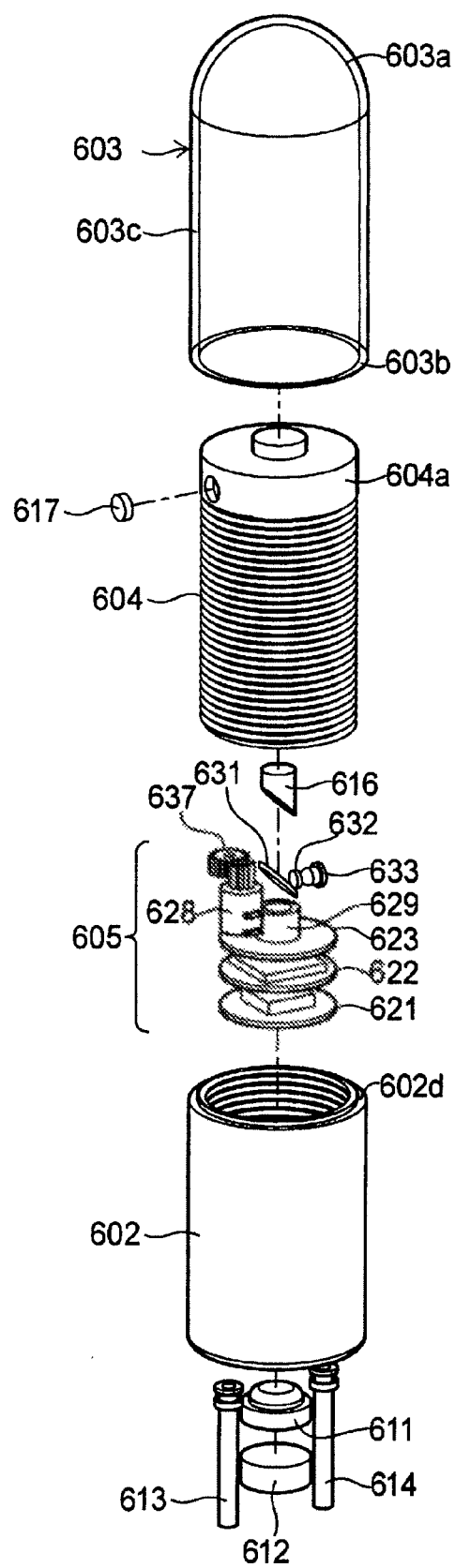
FIG. 46 is an exploded perspective view of an electronic endoscope shown in FIG. 45.
Figure 47:
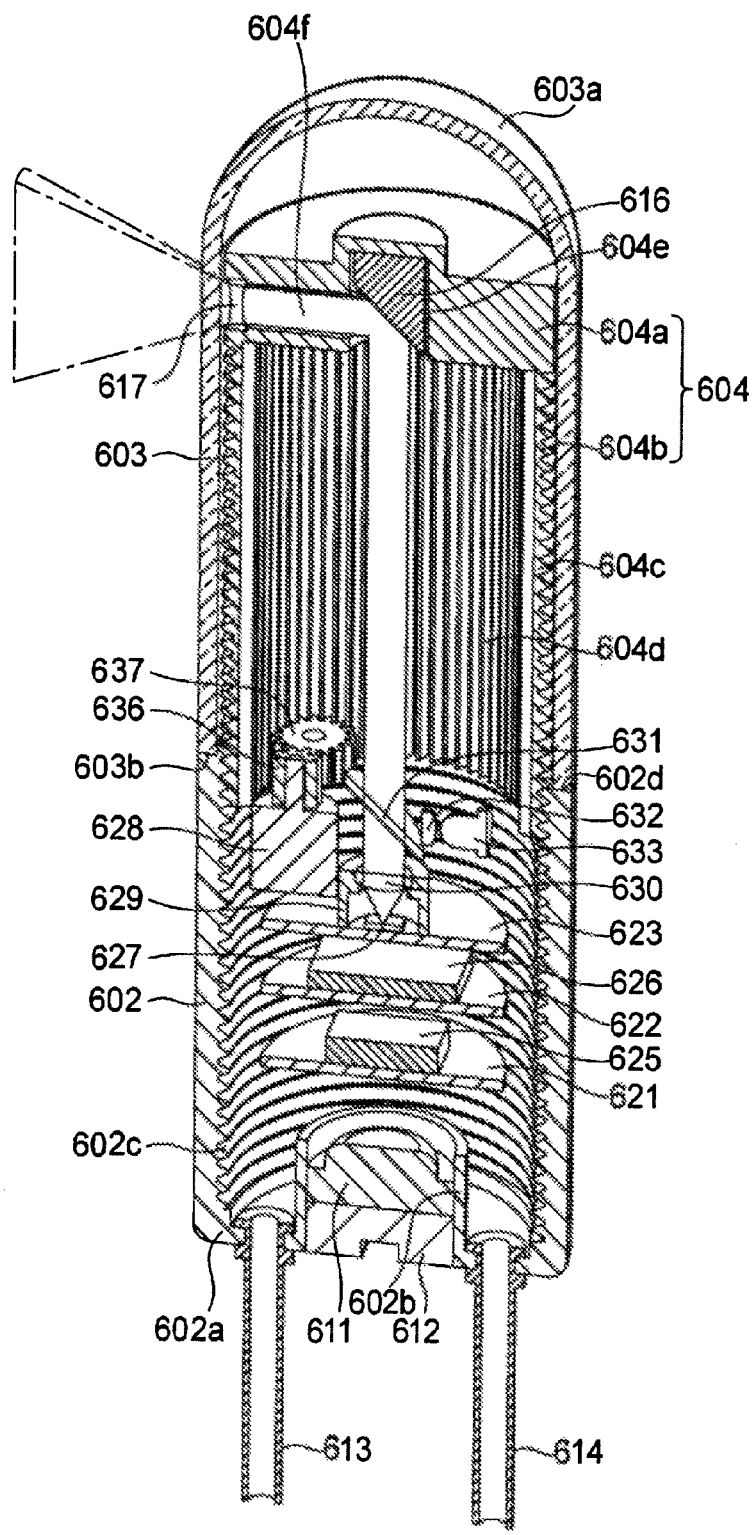
FIG. 47 is a longitudinal sectional view of an electronic endoscope shown in FIG. 45.

FIG. 46 is an exploded perspective view of the electronic endoscope 601. FIG. 47 is a longitudinal sectional view of the electronic endoscope 601.

The body part 602 is formed in a closed-bottom cylindrical shape by using resin material or the like. Then, a tube-shaped battery accommodating part 602b is provided in its bottom part (lower side in FIG. 46) 602a. Then, after a power battery 611 is mounted, the battery accommodating part 602b is closed airtightly by a battery lid 612. That is, the electronic endoscope 601 is provided with the power battery 611 in the inside, and hence does not require other power supply from the outside. Thus, the electronic endoscope 601 need not be connected to a power supply cable, and hence permits easy handling.

Further, in the bottom part 602a, in the example shown in the figure, two hard grip pipes 613 and 614 fabricated from resin are fixed in a protruding manner toward the outside. Then, when the grip pipes 613 and 614 are manipulated by hand, the entirety of the electronic endoscope 601 is inserted into or extracted from a hole or an abdominal cavity serving as a subject. The electronic endoscope 601 may be used in a configuration that wiring is inserted through the grip pipes 613 and 614.

In the inner peripheral surface of the body part 602, a precision female screw 602c is engraved about the axis of the body part 602. Then, the moving lens frame section 604 provided with a male screw is screwed in and revolved so that the member 604 advances or retreats in the axial direction.

The transparent capsule 603 is formed in the form of a tube body fabricated from hard transparent resin. Its one-end side (tip side) is formed hemispherical. Then, the open end part 603b on the side opposite to the hemispherical part 603a is bonded and fixed to the open end part 602d of the body part 602 in an aligned orientation. In the example shown in the figure, the entirety of the capsule section 603 is formed from transparent resin. However, it is sufficient that at least the part of the cylindrical part 603c serving as an observation window is transparent. The hemispherical part 603a may be opaque. The observation window indicates the part faced by a later-described objective lens 617 in association with revolution of the moving lens frame section. Further, in place of a configuration that the hemispherical part 603a and the cylindrical part 603c are formed integrally from the sane material, they may be formed as separate members and then joined and integrated. Here, it is sufficient that the transparent resin is transparent to light at particular wavelengths such as infrared light. That is, the material need not be transparent to visible light.

Such a configuration may be employed that the hemispherical part 603a is formed in a yet smaller diameter than that shown in the figure and that the tip part of the cylindrical part 603c of the transparent capsule 603 is reduced into a tapered shape and then connected continuously and smoothly to the hemispherical part 603a. According to this configuration, the tip part of the transparent capsule 603 is easily inserted even into a smaller hole or a smaller abdominal cavity. Here, the outer diameter of the cylindrical part 603c of the transparent capsule 603 and the outer diameter of the body part 602 are completely identical. Thus, no level difference occurs between these.

The moving lens frame section 604 includes: an objective lens mount part 604a formed in a disk shape by using resin material; and a cylindrical member 604b having almost the same diameter as the objective lens mount part 604a. Then, the objective lens mount part 604a is bonded and fixed integrally at the upper open end part (in the direction to the tip of the electronic endoscope 601) of the cylindrical member 604b, so that the open end part is closed. The outer diameter of the objective lens mount part 604a is formed somewhat smaller than the inner diameter of the transparent capsule 603. This allows the objective lens mount part 604a to move inside the transparent capsule 603 smoothly without chattering.

In the outer peripheral surface of the cylindrical member 604b, a precision male screw 604c screwed into the female screw 602c engraved in the inner peripheral surface of the body part 602 is engraved over the entire length in the axial direction of the cylindrical member 604b. Further, an internal-tooth gear 604d is formed in the inner peripheral surface of the cylindrical member 604b. The internal-tooth gear 604d is formed such that gear teeth parallel to the axis and extending over the entire length in the axial direction of the cylindrical member 604b are arranged at equal intervals in the circumferential direction.

In the center axis part of the objective lens mount part 604a, a cylindrical hole 604e is formed that has a bottom part in the upper end direction (the direction of the tip of the electronic endoscope 601). Then, an objective mirror 616 is accommodated in the cylindrical hole 604e. The objective mirror 616 has a shape obtained by cutting a cylindrical glass material obliquely at 45 degrees. Then, a reflection film is formed on the obliquely cut surface at 45 degrees.

In the objective lens mount part 604a, an image pick-up hole 604f for image pick-up is formed that extends straight in a radial direction of the disk-shaped member. Then, one-end of the image pick-up hole 604f is open in the peripheral side face of the objective lens mount part 604a, and then an objective lens 617 composed of a concave lens is provided in this opening part. The other end of the image pick-up hole 604f is open toward the cylindrical hole 604e. Thus, the object light having entered the image pick-up hole 604f through the objective lens 617 travels in the form of a parallel light beam, then is reflected by the above-mentioned 45-degree-oblique reflecting surface of the objective mirror 616, and then travels along the center axis of the cylindrical member foal) in the form of a parallel light beam.

Here, in FIG. 47, in order that the inside of the image pick-up hole 604f and the above-mentioned parallel light be should be seen clearly, illustration is omitted for the gear teeth of the internal-tooth gear 604d which are to be seen on the far side of the parallel light beam. Then, the parallel light beam is shown as a white part.

The image pick-up drive unit part 605 is mounted and fixed in the inside of the body part 602 by using a stay member (not shown) in a state that the peripheral wall of the battery accommodating part 602b provided in the bottom part 602a of the body part 602 serves as a supporting column. In the example shown in the figure, the image pick-up drive unit part 605 has three base plates 621, 622, and 623.

The base plate 621 in the lowermost layer (on the bottom part 602a side) is provided with a control unit 625 containing a driver circuit for the stepping motor and other circuits. The middle layer the base plate 622 is provided with an image memory 626 for storing pick-up image data. The upper layer base plate 623 is provided with a solid-state imaging device 627 such as a CCD type imaging device and a CMOS type imaging device and a stepping motor 628.

In the center part of the base plate 623, a lens holder 629 formed in a cylindrical shape is provided. Then, the solid-state imaging device 627 is accommodated in the inside. Then, a focusing lens 630 is mounted in the upper-end opening part of the lens holder 629. Then, the above-mentioned parallel light beam (object light) entering along the center axis is focused onto the light acceptance surface of the solid-state imaging device 627 by the focusing lens 630 so that an image is formed.

Figure 48:
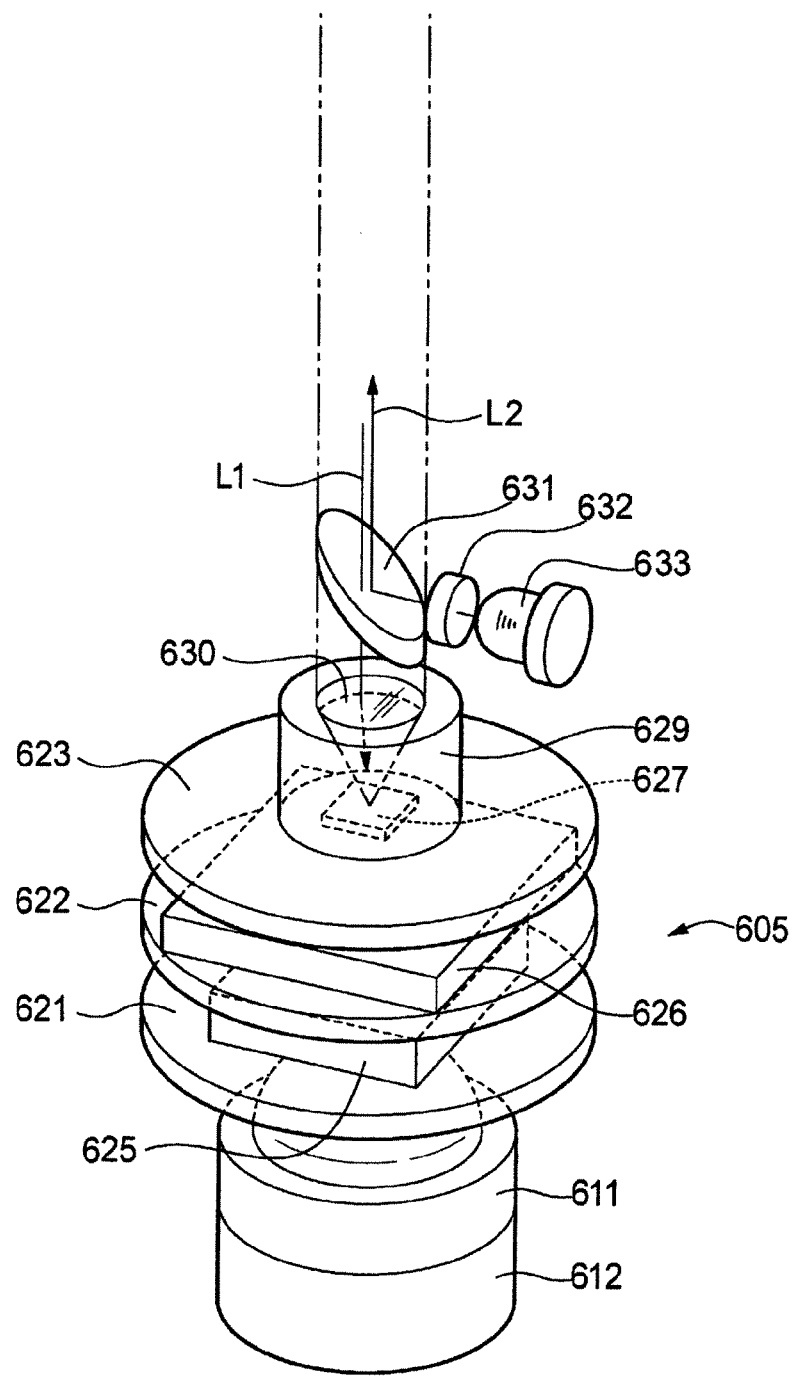
FIG. 48 is an enlarged perspective view of a part containing an image pick-up drive unit part of an electronic endoscope shown in FIG. 45.

Further, with reference to FIG. 48, in a part in the immediate upstream of the focusing lens 630 within the parallel light beam entering the focusing lens 630, a half mirror 631 is provided that is arranged oblique to the optical axis of the parallel light beam (the center axis of the cylindrical member 604b). In the example shown in the figure, the reflecting surface of the half mirror 631 is inclined at 45 degrees relative to the optical axis of the parallel light beam. However, the inclination angle may be arbitrary as long as the reflecting surface does not intersect the optical axis at right angles. The half mirror 631 is an optical member that allows a part of the incident light to transmit through and that reflects the remaining part of the incident light. The ratio of transmission and reflection may be set up appropriately. Further provided are: an LED 633 for emitting light for illumination toward the half mirror 631; and an illumination lens 632 that intervenes between the half mirror 631 and the LED 633 and that projects the light for illumination from the LED 633, toward the half mirror 631 in the form of a parallel light beam. The half mirror 631, the illumination lens 632, and the LED 633 are fixed to the base plate 623.

The stepping motor 628 is fixed in the periphery part of the base plate 623. Then, a motor gear wheel (spur wheel) 636 is attached to the shaft of the stepping motor 628. The shaft of the stepping motor 628 is oriented in parallel to the center axis of the cylindrical member 604b (the optical axis of the parallel light beam). Urn, the motor gear wheel 636 engages with an idle gear wheel 637 composed of a spur wheel.

The shaft of the idle gear wheel 637 is pivotally supported in a revolvable manner in a direction perpendicular to the base plate 623. The idle gear wheel 637 has a larger number of gear teeth than the motor gear wheel 636. Thus, the revolution of the stepping motor 628 is slowed down and then transmitted to the idle gear wheel 637. The idle gear wheel 637 engages with the internal-tooth gear 604d provided in the inner peripheral surface of the cylindrical member 604b.

When the stepping motor 628 revolves, the idle gear wheel 637 revolves. Then, in association with this, the cylindrical member 6046 revolves. When the cylindrical member 6046 revolves, the cylindrical member 604b of the moving lens frame section 604 is screwed into or out from the body part 602 depending on the direction of revolution. That is, the moving lens frame section 604 advances or retreats in the axial direction.

Further, the electronic endoscope 601 has a power switch (not shown). When the power switch is turned ON, electric power from the power battery 611 is supplied through wiring (not shown) to the individual parts of the image pick-up drive unit part 605, so that image pick-up operation and drive operation are performed as described later.

For example, the power switch may be provided in the bottom part 602a of the body part 602, and may be turned ON or OFF by manual operation. Alternatively, a switch terminal that follows magnetism may be built in the body part 602. Then, from the outside of the electronic endoscope 601, a magnet may be brought close or apart so that the switch terminal may be turned ON or OFF.

Figure 49:
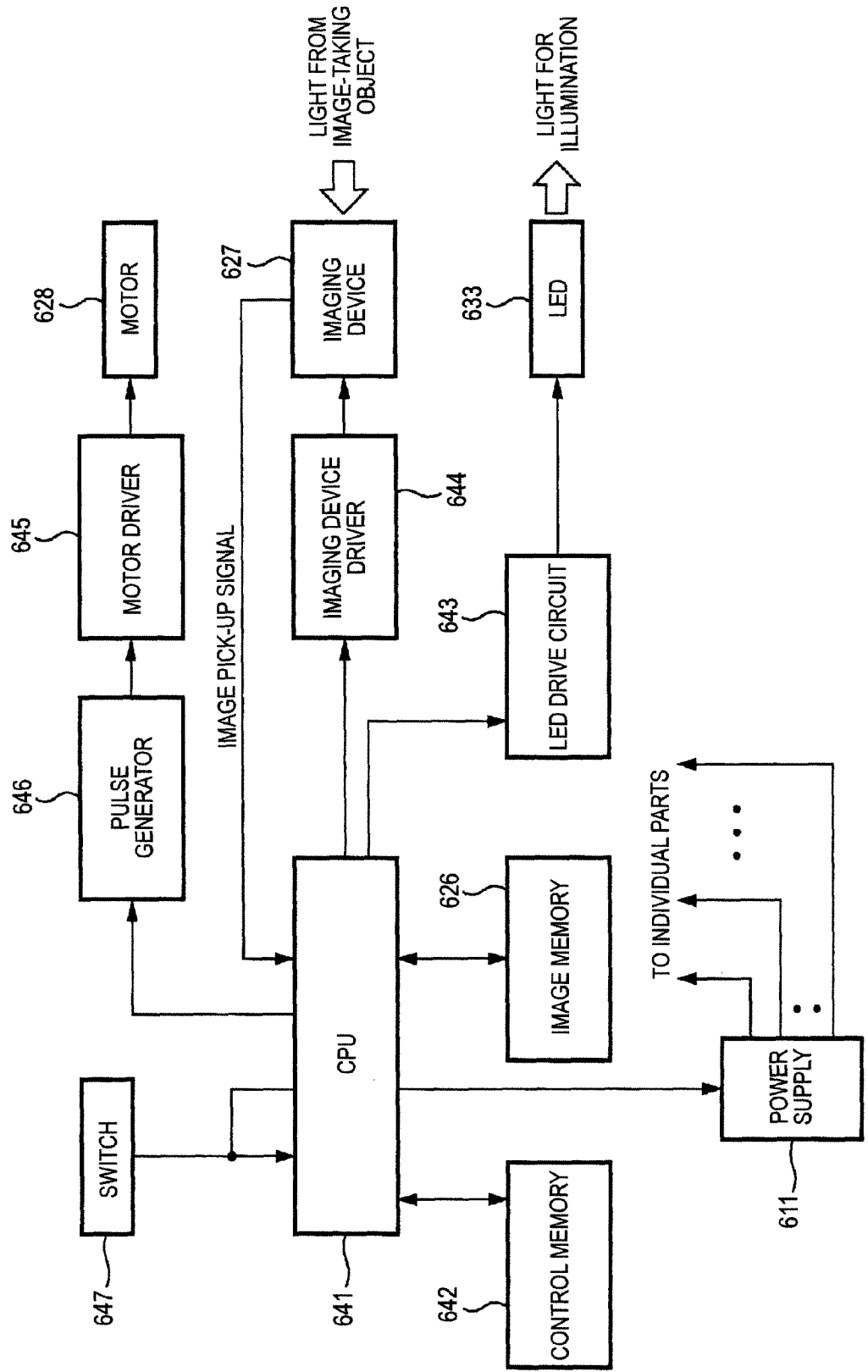
FIG. 49 is a functional block diagram showing a control unit mounted on an electronic endoscope shown in FIG. 45.

FIG. 49 is a functional block diagram showing the image pick-up drive unit part 605. The CPU 641 for collectively controlling the entire system is connected to: a control memory 642 that stores a control program and serves also as a work memory; an image memory 626 provided on the base plate 622 described in FIG. 47; an LED drive circuit 643 for driving the LED 633; an imaging device driver 644 for driving the imaging device 627; and a pulse generator 646 for providing driving pulses to the motor driver 645 for driving the stepping motor 628.

When the power switch 647 is turned ON, electric power is supplied from the power battery 611 to the individual parts so that operation is started. Thus, the stepping motor 628 is driven and revolved. Accordingly, the moving lens frame section 604 is revolved in the inside of the electronic endoscope 601 so as to advance or retreat in the axial direction.

With reference to FIGS. 47 and 48, the light for illumination from the LED 633 is brought into the form of a parallel light beam by the illumination lens 632, then enters the half mirror 631, and then is reflected toward the objective mirror 616. The light for illumination having entered the objective mirror 616 is reflected toward the objective lens 617 with maintaining the form of a parallel light beam. Then, the light for illumination having entered the objective lens 617 is projected through the objective lens 617 toward the image-taking object, so as to serve as light for illumination that illuminates the image-taking object contained in the view field region of the objective lens 617. That is, the illumination lens 632, the half mirror 631, the objective mirror 616, and the objective lens 617 constitute an illumination optical system.

The light for illumination is reflected by the image-taking object. Then, a part of the reflected light serving as object light enters the objective lens 617. The object light having entered the objective lens 617 is brought into the form of a parallel light beam, then travels to the objective mirror 616, then is reflected by the objective mirror 616, then transmitting through the half mirror 631 with maintaining the form of a parallel light beam, and then travels to the focusing lens 630. Then, the object light is focused onto the light acceptance surface of the solid-state imaging device 627 by the focusing lens 630 so that an image is formed. That is, the objective lens 617, the objective mirror 616, the half mirror 631, and the focusing lens 630 constitute an objective optical system.

As such, the objective optical system and the illumination optical system share the optical path of the interval between the half mirror 631 and the objective lens 617. Thus, the light for illumination emitted from the LED 633 travels, in the reverse direction, the optical path of the object light in the objective optical system, then enters the objective lens 617, and then projected toward the image-taking object. Thus, the image-taking object contained in the view field region of the objective lens 617 is illuminated reliably.

Here, in the electronic endoscope 601, the LED 633 is arranged on the reflected light path of the object light reflected from the half mirror 631, and the solid-state imaging device 627 is arranged on the transmitted light path of the object tight transmitted through the half mirror 631. However, the employed configuration is not limited to this. That is, the LED 633 may be arranged on the transmitted light path, and the solid-state imaging device 627 may be arranged on the reflected light path.

The image pick-up signal of the image-taking object acquired by the imaging device 627 is acquired into the CPU 641 so as to undergo image processing, and then stored into the image memory 626, for example, in the form of JPEG image data.

Figure 50:
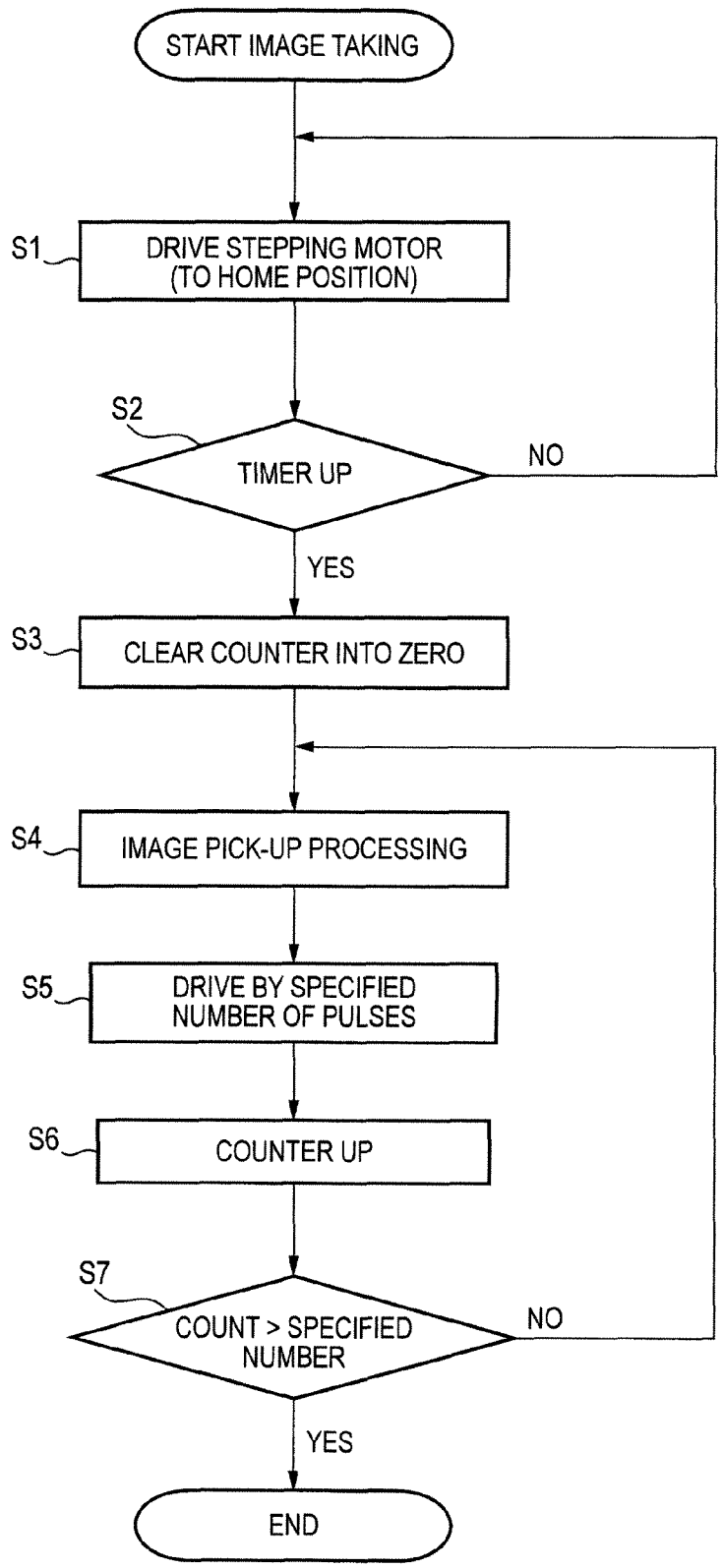
FIG. 50 is a flow chart showing a processing procedure of a control program executed by a CPU shown in FIG. 49.

FIG. 50 is a flow chart showing the processing procedure of a control program stored in the control memory 642. When the power switch 647 is turned ON, this control program is started. Then, first, the stepping motor 628 is driven to the home position side (step S1). Here, the home position side indicates, for example, the state shown in FIG. 47 where the objective lens 617 is located on the tip side of the electronic endoscope 601.

In the electronic endoscope 601, for the purpose of cost reduction, a sensor is not provided that detects whether the stepping motor 628 has reached the home position. Thus, at the next step S2, it is judged whether a timer for counting a predetermined time has counted up. Then, when the predetermined time has not yet elapsed, step S1 is executed repeatedly. In a configuration that a sensor for detecting reaching to the home position is provided, step S1 is merely executed repeatedly until reaching to the home position is detected by the sensor.

Figure 52:
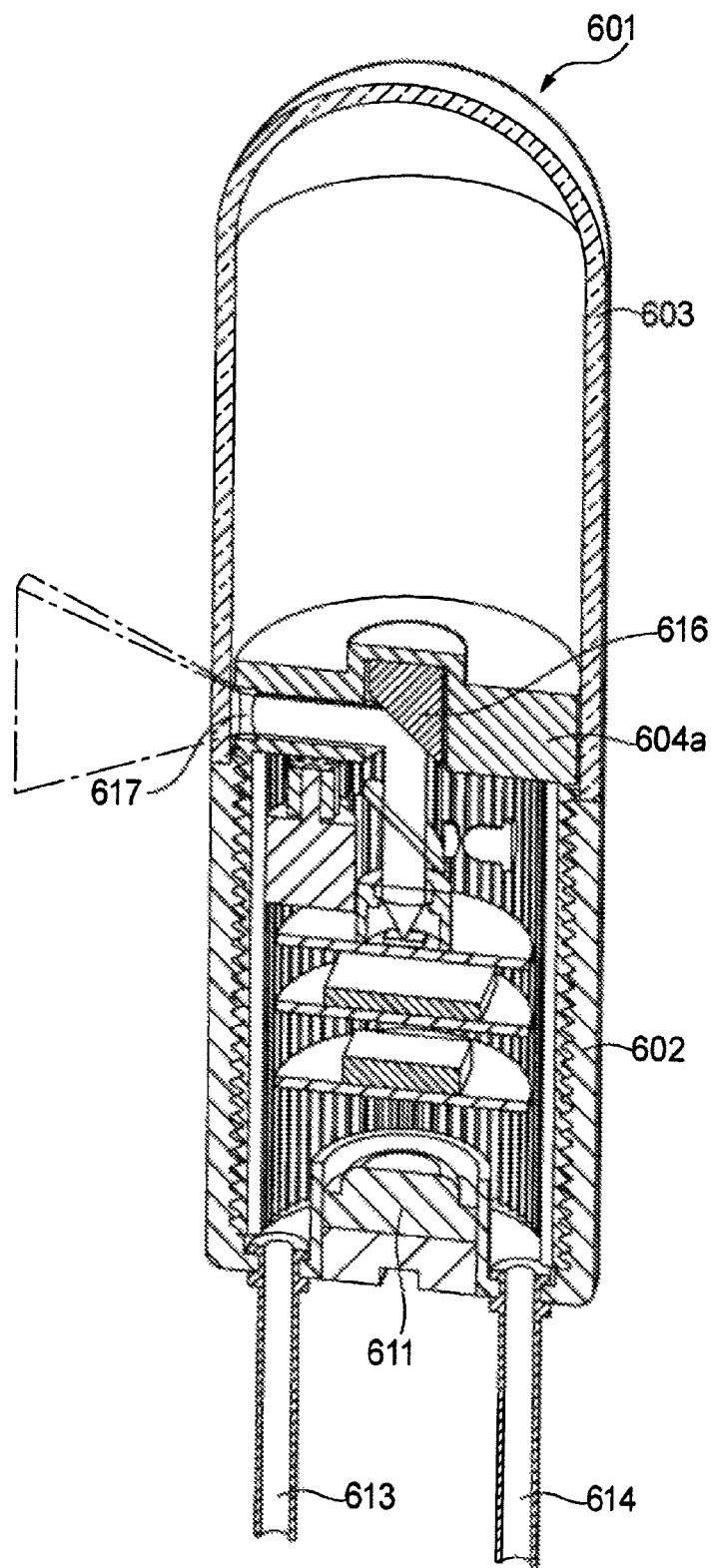
FIG. 52 is a longitudinal sectional view showing a state that a lens holder shown in FIG. 51 has been lowered to an image pick-up completion position.

It is sufficient that the predetermined time is defined as the longest time necessary for the stepping motor 628 to reach the home position. For example, the state shown in FIG. 52 is a state that the moving lens frame section 604 has revolved and moved to the lowermost position. Thus, the predetermined time may be defined as the time necessary from this state to a state that the moving lens frame section 604 has revolved in association with the revolution of the stepping motor 628 so as to have reached the home position (a position where the moving lens frame section 604 abuts against the inner peripheral surface of the hemispherical part 603a and hence cannot move further in this direction) shown in FIG. 47.

By virtue of this, even in a case that the moving lens frame section 604 is located wherever in the middle between the state shown in FIG. 47 and the state shown in FIG. 52 (a state that the lower end of the cylindrical member 604b abuts against the bottom part 602a of the body part 602), the objective lens 617 necessarily reaches the home position when the stepping motor 628 is driven in the home position direction by the predetermined time.

When the timer has counted the predetermined time, the procedure goes from step S2 to step S3 where the contents of a counter described later is cleared into zero. Then, the procedure goes to step S4 where image pick-up processing is performed. In the image pick-up processing: the LED 633 is turned ON so that light for illumination is projected through the objective lens 617; tight reflected from the image-taking object is acquired through the objective lens 617 into the electronic endoscope 601; and then the incident light from the image-taking object is focused onto the light acceptance surface of the imaging device 627 so that an image is formed.

Then, the CPU 641 drives the imaging device 627 via the imaging device driver 644 so as to acquire from the imaging device 627 the image pick-up signal of the image-taking object obtained by the imaging device 627, then performs image processing on the signal, and then stores the data into the image memory 626.

At the next step S5, the stepping motor 628 is driven by a specified number of pulses. At the next step S6, this specified number of pulses is added to the count value in the counter. At the next step S7, the total count value in the counter is compared with a specified number.

Then, when the total count value in the counter does not reach the specified number, the procedure returns from step S7 to step S4 so that image pick-up processing is performed. After that, the processing loop of steps S4 to S7 is executed repeatedly. When the total count value in the counter has reached the specified number, the processing shown in FIG. 50 is terminated.

FIG. 53 is a diagram illustrating the movement of the field of view of image pick-up of the objective lens 617 in a case that step S4 in FIG. 50 is executed repeatedly. In the first occasion of image pick-up processing performed at the home position, an object image in the field of view indicated by "No. 001" in FIG. 53 is acquired from the imaging device 627.

After the image pick-up for the object image of the field of view "No. 001", the stepping motor 628 is driven at step S5 by a specified number of pulses. Thus, the cylindrical member 604b revolves by the specified number of pulses. As a result, the cylindrical member 604b is screwed and withdrawn into the body part 602. Thus, the next field of view is located at "No. 002" in FIG. 53. Then, an object image in this field of view is taken, and then the obtained image data is accumulated in the image memory 626.

Figure 51:
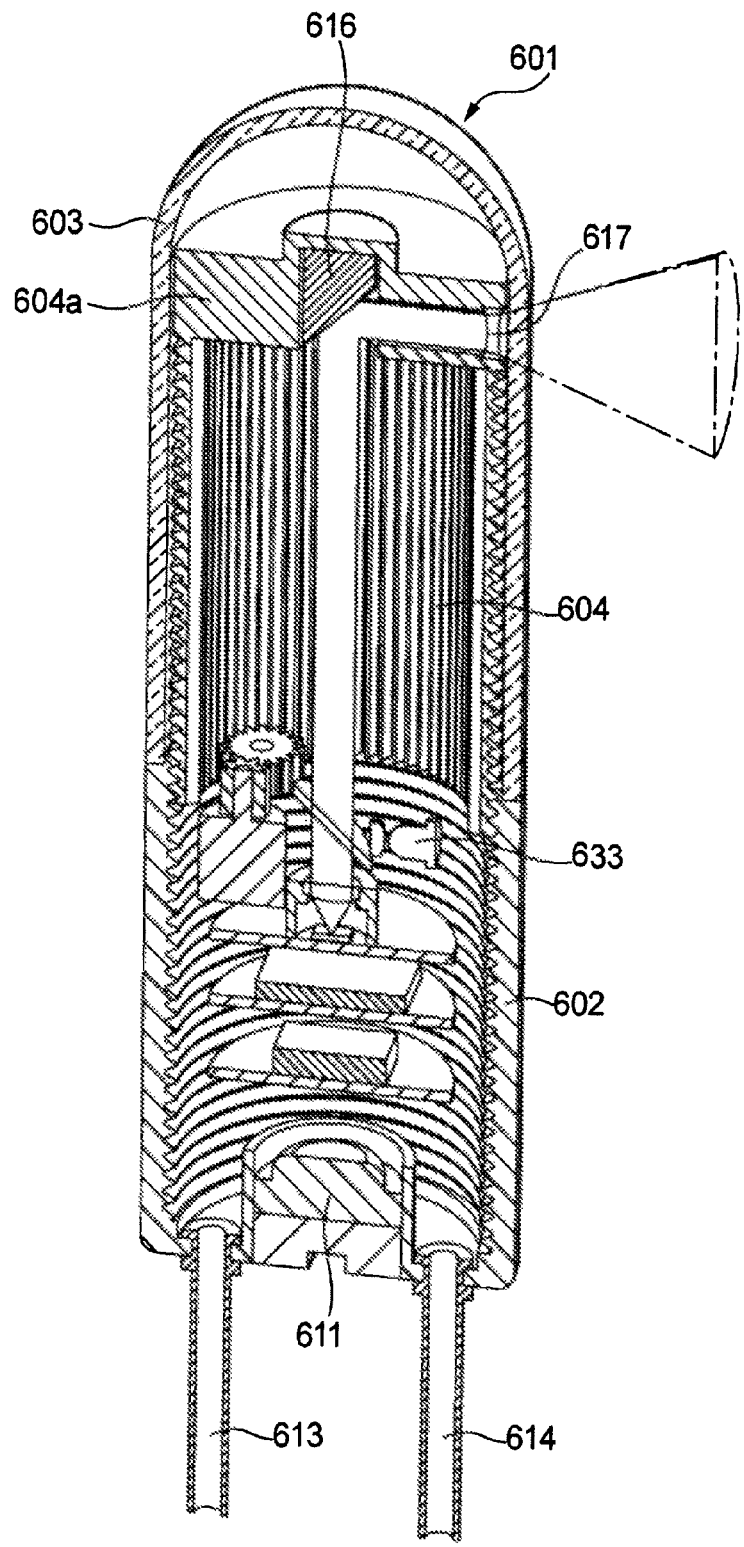
FIG. 51 is a longitudinal sectional view showing a state that a lens holder has gone half around from a state shown in FIG. 47.

After that, during the operation of moving the field of view like No. 003→No. 004→No. 005 . . . , image pick-up processing and image data accumulation into the memory 626 are repeated. FIG. 51 shows a state that the moving lens frame section 604 has gone half around inside the transparent capsule 603 starting from the state shown in FIG. 47. When the moving lens frame section 604 has gone one around from the home position inside the transparent capsule 603, the field of view of image pick-up is located at No. 011 in FIG. 53. In case of having gone around twice, the field of view of image pick-up is located at No. 021 in FIG. 53.

Further, FIG. 52 shows a state that the lower end of the cylindrical member 604b abuts against the bottom part 602a of the body part 602 and hence cannot move further in this direction. When the state shown in FIG. 52 is reached, the processing loop of repeating the image pick-up processing (step S4) is terminated. Accordingly, the "specified number" used at step S7 in FIG. 50 is equal to the total number of pulses necessary for reaching from the home position to the state shown in FIG. 52.

In the example of movement of the field of view of image pick-up illustrated in FIG. 53, the specified number of pulses at step S5 in FIG. 50 is set up such that in the direction of revolution of the moving lens frame section 604 serving as a lens holder, adjacent fields of view of image pick-up are positioned such that their left and right edge parts should be in contact with each other or overlapping somewhat with each other. Further, the pitch of the screw threads provided in the inner peripheral surface of the body part 602 and the outer peripheral surface of the cylindrical member 604b is designed such that axially adjacent fields of view of image pick-ups are positioned such that their upper and lower edge parts should be in contact with each other or overlapping somewhat with each other.

By virtue of this, without a missing part over the entirety of the cylindrical field of view region of the inner peripheral surface of the image-taking object serving as an observation object, image pick-up is achieved so that image data is acquired. Obviously, the number of pulses for the stepping motor may be set up, or alternatively the pitch of the screws 602c and 604c may be designed such that larger overlapping parts should be generated in the fields of view of image pick-up.

Once image pick-up by the electronic endoscope 601 is completed, the data accumulated in the image memory 626 shown in FIG. 49 is to be read to the outside. This read operation may be performed by wireless, or alternatively by using a wiring inserted through the grip pipes 613 and 614 shown in FIG. 45. Alternatively, the image memory 626 may be provided in a removable manner from the electronic endoscope 601. Then, the removed image memory 626 may be read by a personal computer provided separately.

Figure 54:
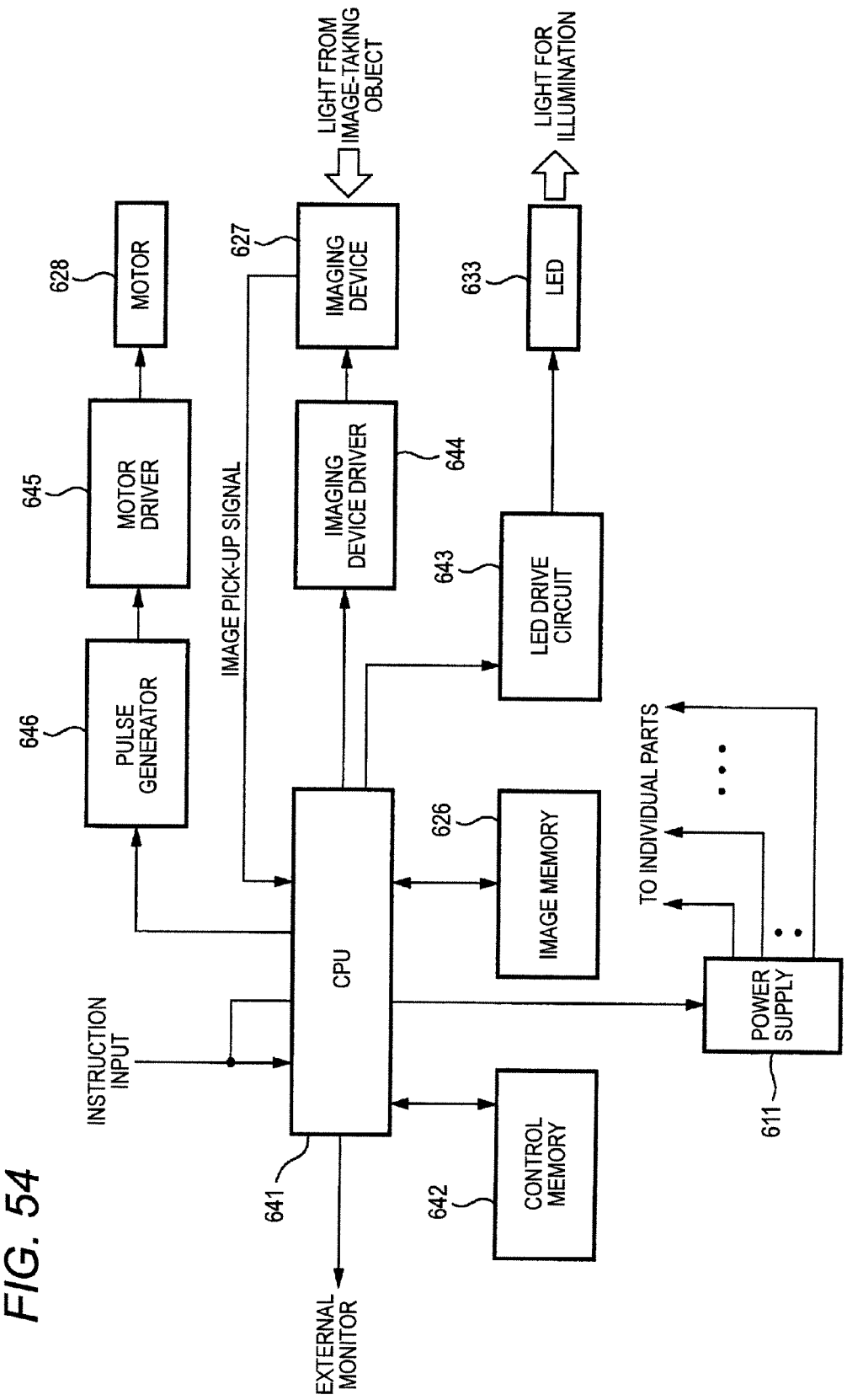
FIG. 54 is a functional block diagram showing a control unit serving as an alternative of that shown in FIG. 49.

FIG. 54 is a functional block diagram showing a modification of the image pick-up drive unit part 605. The only difference from the image pick-up drive unit part 605 shown in FIG. 49 is that pick-up image data is transmitted to an external monitor so that the pick-up image is observed on the external monitor on line and that an operation instruction is allowed to be inputted from the outside.

In this case, without performing image processing, the CPU 641 transmits the image pick-up signal acquired from the imaging device 627, to an external video processor in an intact manner. Then, the object image obtained by image processing in the video processor may be displayed on an external monitor. The communication between the external video processor, the external monitor, and the CPU 641 may be of cable or wireless. In a case that the communication is of cable, an external power source becomes employable when a power source line is included in the wiring.

Further, as a control program additional to the control program shown in FIG. 50, a control program is preferably installed that in accordance with an operation instruction from the outside, for example, the view field position of the objective lens 617 it moved to an arbitrary image pick-up view field position shown in FIG. 53.

Here, in the electronic endoscope 601 described above, the moving lens frame section 604 is driven and revolved by the stepping motor 628. However, obviously, in place of such a stepping motor, a motor of any type may be employed as long as the revolution angle and the revolution length are controlled accurately.

As described above with reference to the electronic endoscope 601 serving as an example, the present specification has disclosed an electronic endoscope characterized in that a cylindrical transparent cover at least whose observation window in a cylindrical pan is transparent; a body part that has a cylindrical part provided continuously to the cylindrical part of the transparent cover; a lens holder that revolves about the center axis of the transparent cover in the inside of the transparent cover and the body part and that moves in the direction of the center axis; an objective mirror that is provided in the lens holder and that reflects, toward the body part, light entering through an objective lens provided at a position facing the cylindrical part of the transparent cover; an imaging device that receives light reflected from the objective mirror and that converts the light into an electric signal; and a driving section that is provided inside the body part and that drives and revolves the lens holder so as to drive the lens holder in the center axis direction.

Further, the present specification has disclosed an electronic endoscope characterized in that the lens holder includes: a disk-shaped member on which the objective lens is mounted and the objective mirror is mounted; and a cylindrical member which is provided integrally and continuously to the body part side of the disk-shaped member.

Further, the present specification has disclosed an electronic endoscope characterized by comprising: a female screw which is formed spirally in the inner peripheral surface of the body part; and a male screw that is engraved spirally in the outer peripheral surface of the cylindrical member and engaging with the female screw and that, when the cylindrical member is driven and revolved by the driving section, moves the cylindrical member in the center axis direction.

Further, the present specification has disclosed an electronic endoscope characterized in that an optical axis of the objective lens is provided in a direction perpendicular to an axis of revolution of the lens holder.

Further, the present specification has disclosed an electronic endoscope characterized in that the objective mirror reflects light entering through the objective lens, toward the body part along an optical path going along the center axis.

Further, the present specification has disclosed an electronic endoscope characterized by comprising a half mirror that is provided in a course of an optical path of light reflected from the objective mirror, and a light emitting body for emitting light for illumination, which is to be reflected by the half mirror and then reflected by the objective mirror, so as to illuminate a image-taking object through the objective lens.

Further, the present specification has disclosed an electronic endoscope characterized in that a control section which performs image processing on an image signal obtained by image pick-up performed by the imaging device and an image memory which stores pick-up image data obtained by image processing performed by the control section are built in.

Further, the present specification has disclosed an electronic endoscope characterized in that a battery accommodating part which accommodates a power battery for supplying electric power to the imaging device and the driving section is built in the body part.

Figure 55:
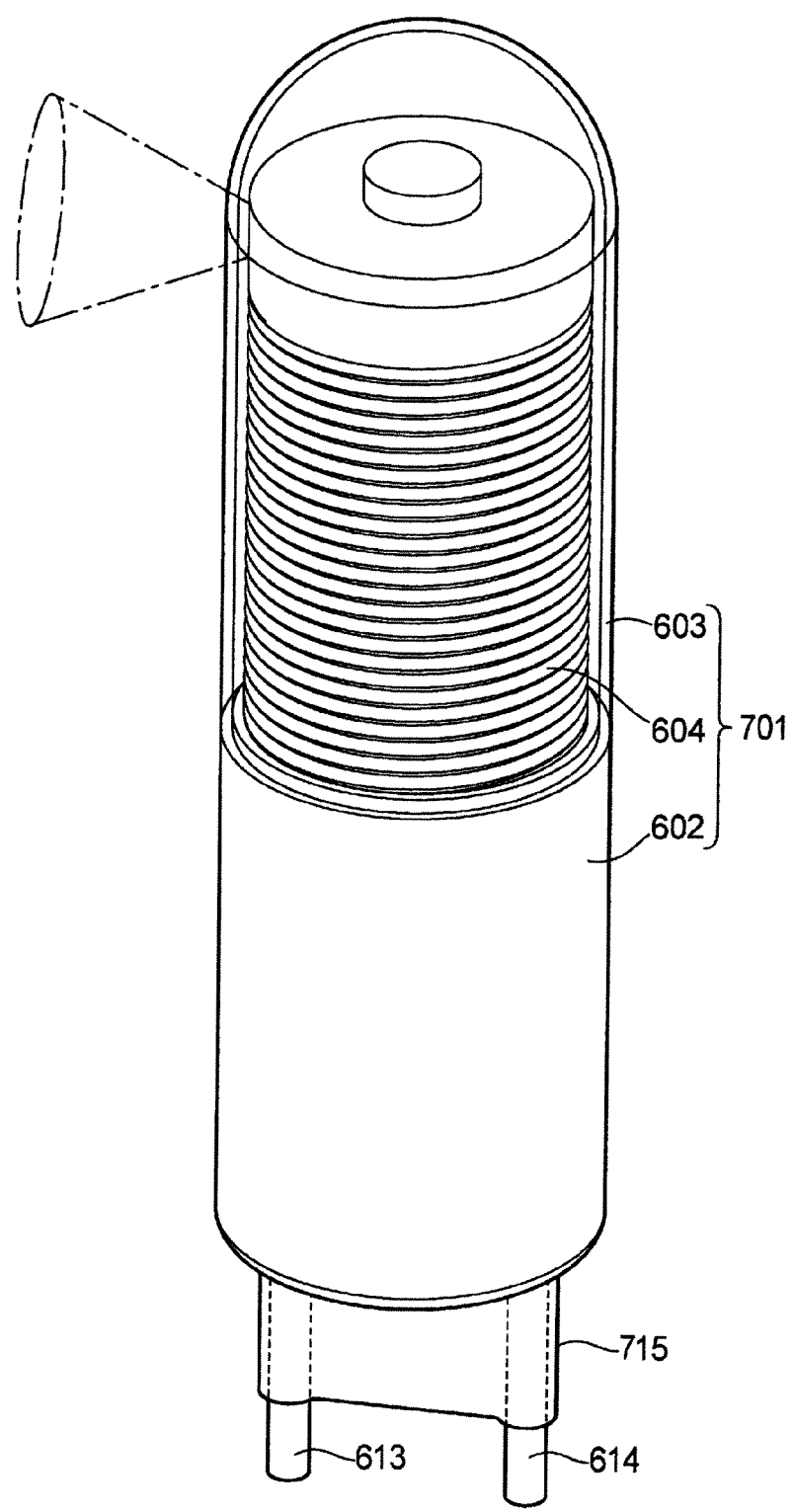
FIG. 55 is an external appearance perspective view of another example of an electronic endoscope used for describing an embodiment of the present invention.
Figure 56:
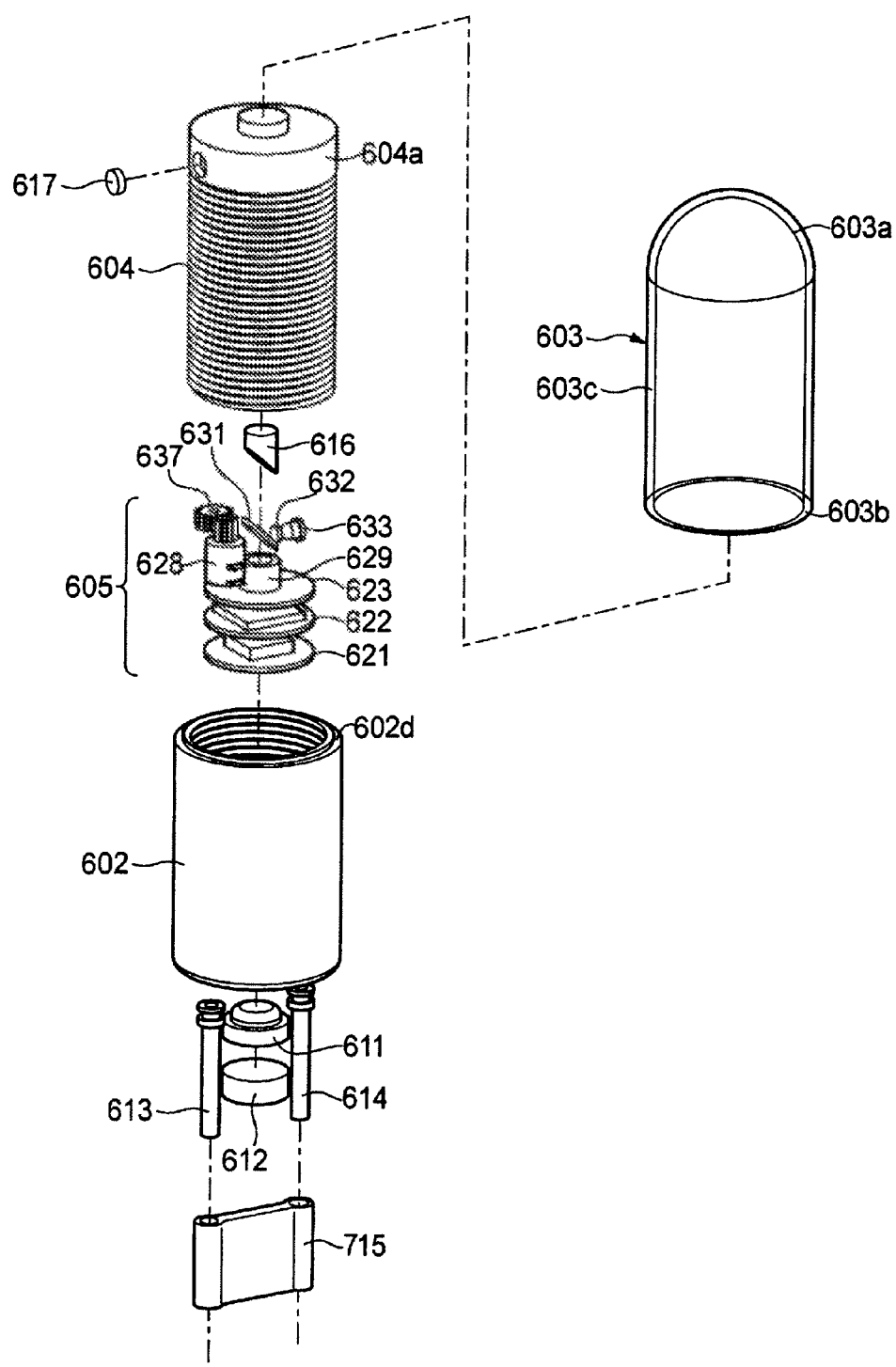
FIG. 56 is an exploded perspective view of an electronic endoscope shown in FIG. 55.
Figure 57:
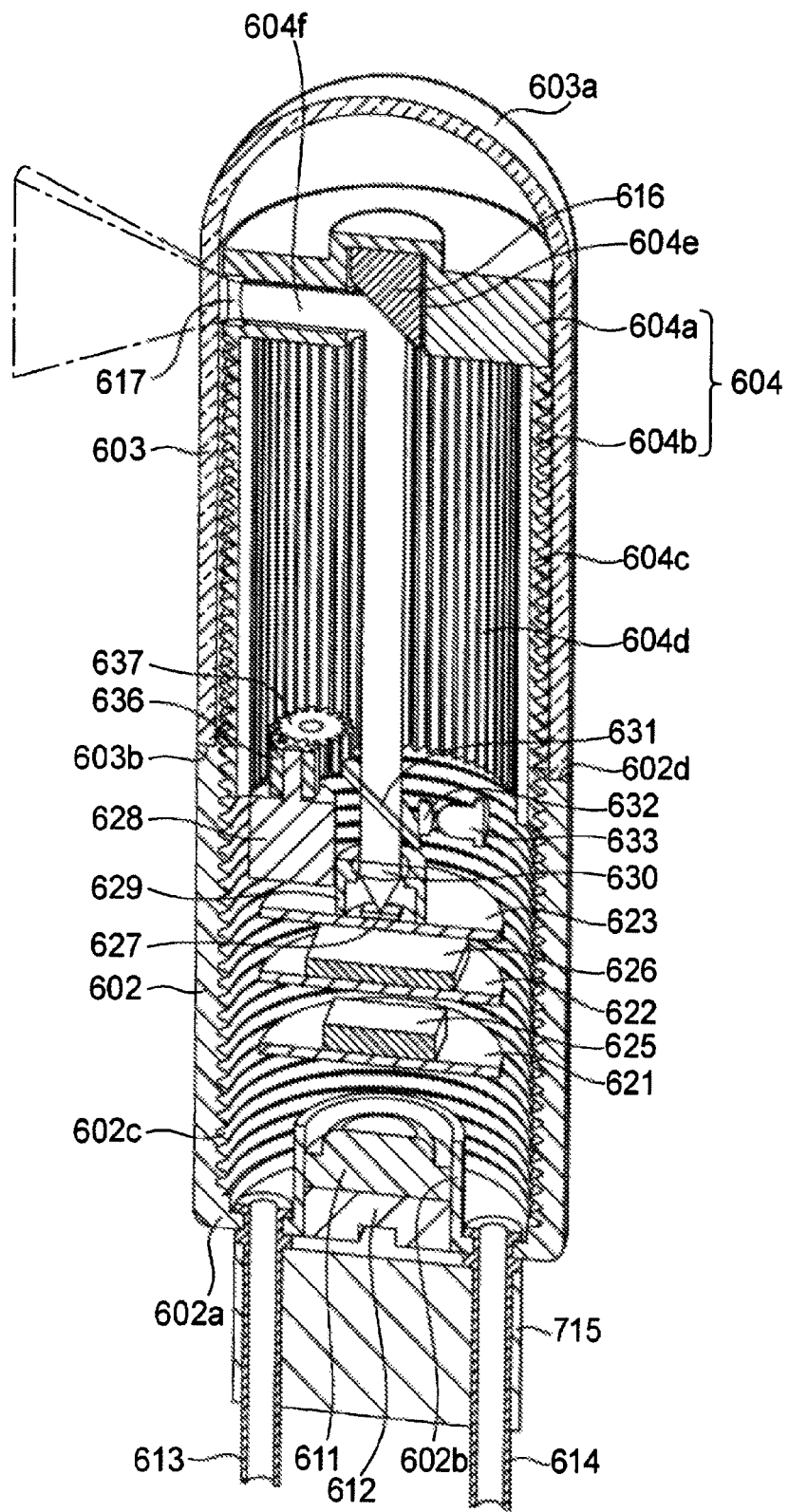
FIG. 57 is a longitudinal sectional view of an electronic endoscope shown in FIG. 55.

An electronic endoscope 701 shown in FIGS. 55 to 57 includes: a body part 602 and a transparent capsule 603 serving as an outer shell; and a moving lens frame section 604 and an image pick-up drive unit part 605 accommodated in the inside. Here, like members to those of the electronic endoscope 601 described above are designated by like numerals, and functionally common members are designated by appropriately corresponding numerals. Then, their description is omitted or simplified.

In the electronic endoscope 701, a hard grip plate 715 fabricated from resin is bridged between the two grip pipes 613 and 614 fixed in and protruding from the bottom part 602a of the body part 602. The two grip pipes 613 and 614 and the grip plate 715 constitute a manipulation part used for revolving the outer shell about the axis of the outer shell. The two grip pipes 613 and 614 are provided approximately symmetric with respect to the axis of the outer shell. When the grip plate 715 is twisted such that the grip pipes 613 and 614 are twisted to each other, a torque about the axis of the outer shell is applied on the outer shell via the grip pipes 613 and 614. Here, the configuration of the manipulation part may be arbitrary as long as a torque about the axis of the outer shell is allowed to be applied on the outer shell.

Similarly to the case of the electronic endoscope 601 described above, in the electronic endoscope 701, the stepping motor 628 is driven by a specified number of pulses so that the moving lens frame section 604 is revolved inside the electronic endoscope 701 so as to advance or retreat in the axial direction. In association with this, the field of view is moved like No. 001→No. 002→No. 003 . . . as shown in FIG. 53. In this manner, image pick-up processing and image data accumulation into the memory 626 are repeated so that image pick-up is achieved.

Once image pick-up by the electronic endoscope 701 is completed, the data accumulated in the image memory 626 is read to the outside. Then, when an abnormality such as disease and a wound is recognized in the image generated from the read-out data, the image pick-up site where the image data was acquired need be identified. Thus, in the beginning of image pick-up, the attitude angle of the outer shell about the axis of the outer shell of the electronic endoscope 701 is set up at a predetermined angle relative to the hole serving as a subject by manipulating the manipulation part composed of the grip pipes 613 and 614 and the grip plate 715.

Figure 58:
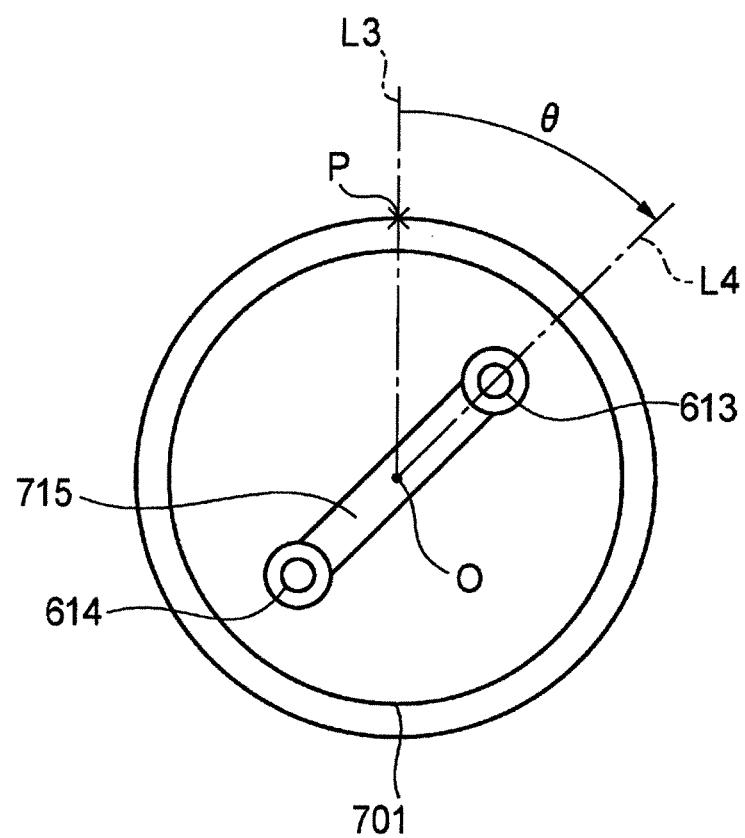
FIG. 58 is a plan view for describing a method of image pick-up performed using an electronic endoscope shown in FIG. 55.

For example, in the state that the moving lens frame section 604 is located at the home position shown in FIG. 57, the field of view of the electronic endoscope 701 is directed to the one grip pipe 613 side in the direction of arrangement of the two grip pipes 613 and 614. Here, as shown in FIG. 58, a segment L3 is defined as the segment obtained by joining a reference point P set up arbitrarily at a position on the open end part of the hole serving as a subject to the axis O of the housing of the electronic endoscope 701. Further, a segment L4 is defined as the segment obtained by joining the grip pipe 613 to the axis O. Then, the angle (attitude angle) θ formed by the segment L3 and the segment LA is set up at a predetermined angle. By virtue of this, the image pick-up site where the image data was acquired is identified on the basis of the attitude angle θ, the order of image pick-up of the image data, and the amounts of displacement of the field of view in the axial direction and the circumferential direction at predetermined image pick-up intervals.

As described above with reference to the electronic endoscope 701 serving as an example, the present specification has disclosed an electronic endoscope that is inserted into a hole and then acquires an image of the inner peripheral surface of the hole, characterized by comprising: an outer shell that is formed in a cylindrical shape and whose peripheral wall is provided with a transparent window part extending in an axial direction; a solid-state imaging device that is provided inside the outer shell; an objective optical system that includes an objective lens for focusing object light through the window part and that forms an image onto the solid-state imaging device; and a drive mechanism that causes at least the objective lens in the objective optical system to move along an axis of the outer shell, wherein a manipulation part used for revolving the outer shell about the axis of the outer shell is provided in the bottom part of the outer shell which faces the opening of the hole.

Further, the present specification has disclosed an electronic endoscope characterized in that the window part is provided over the entire circumference of the outer shell, and that the drive mechanism causes at least the objective lens in the objective optical system to revolve about the axis of the outer shell and thereby moves along the axis of the outer shell.

Further, the present specification has disclosed an electronic endoscope characterized in that the manipulation part includes a plate member which is provided such as to protrude from the bottom part of the outer shell, and wherein the plate member is arranged on the axial of the outer shell.

Further, the present specification has disclosed a method of image pick-up characterized by comprising the steps of: inserting an electronic endoscope into a hole; manipulating a manipulation part provided in the bottom part of the outer shell that faces the opening of the hole so as to set up the attitude angle of the outer shell about the axis of the outer shell relative to the hole to a predetermined angle; and acquiring an image of the inner peripheral surface of the hole in the course that the drive mechanism moves the objective lens along the axis of the outer shell.

Further, the present specification has disclosed a method of image pick-up characterized in that the window part is provided over the entire circumference of the outer shell, and wherein the drive mechanism causes at least the objective lens in the objective optical system to revolve about the axis of the outer shell and thereby moves along the axis of the outer shell.

Figure 59:
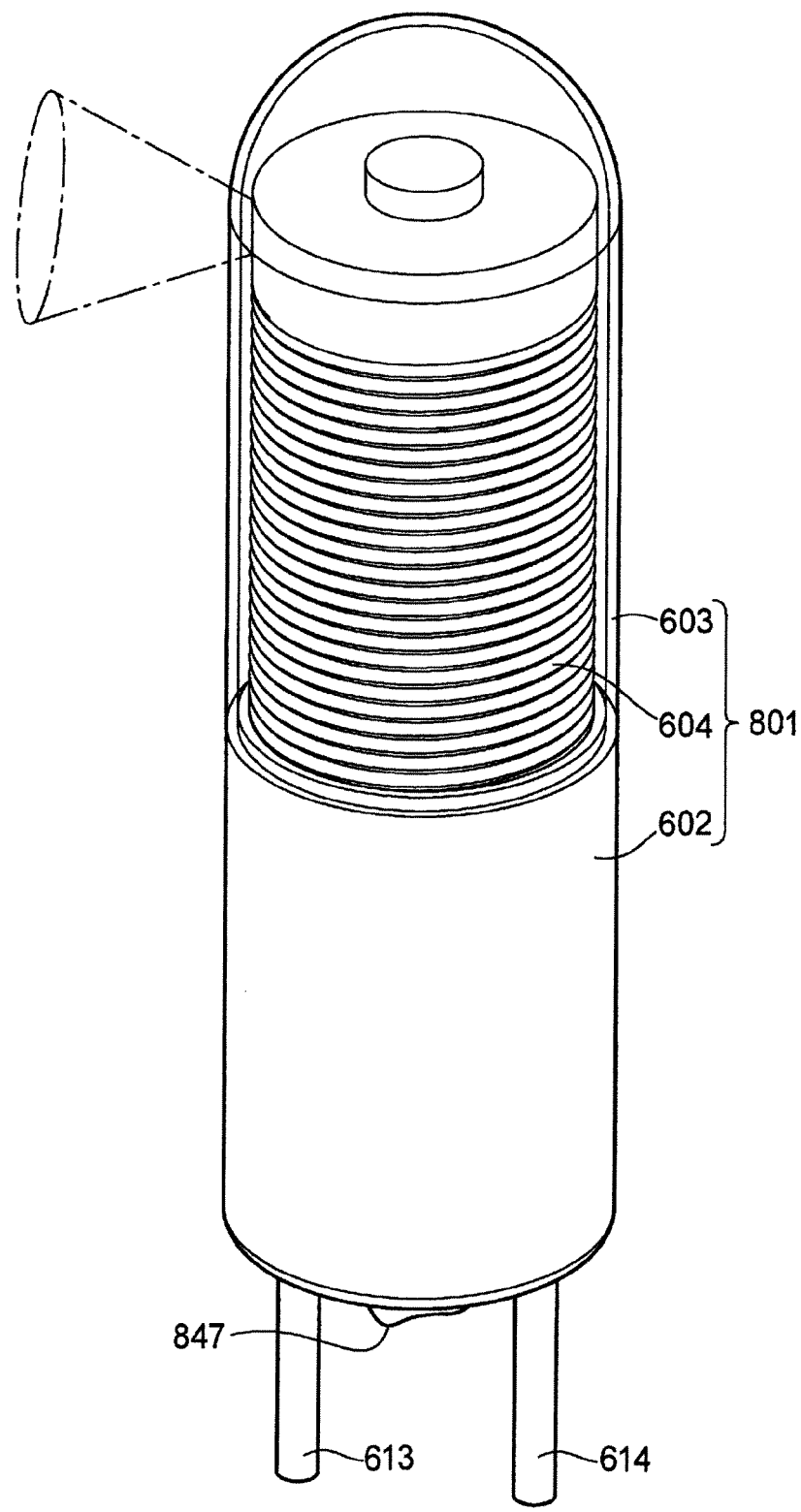
FIG. 59 is an external appearance perspective view of another example of an electronic endoscope used for describing an embodiment of the present invention.
Figure 60:
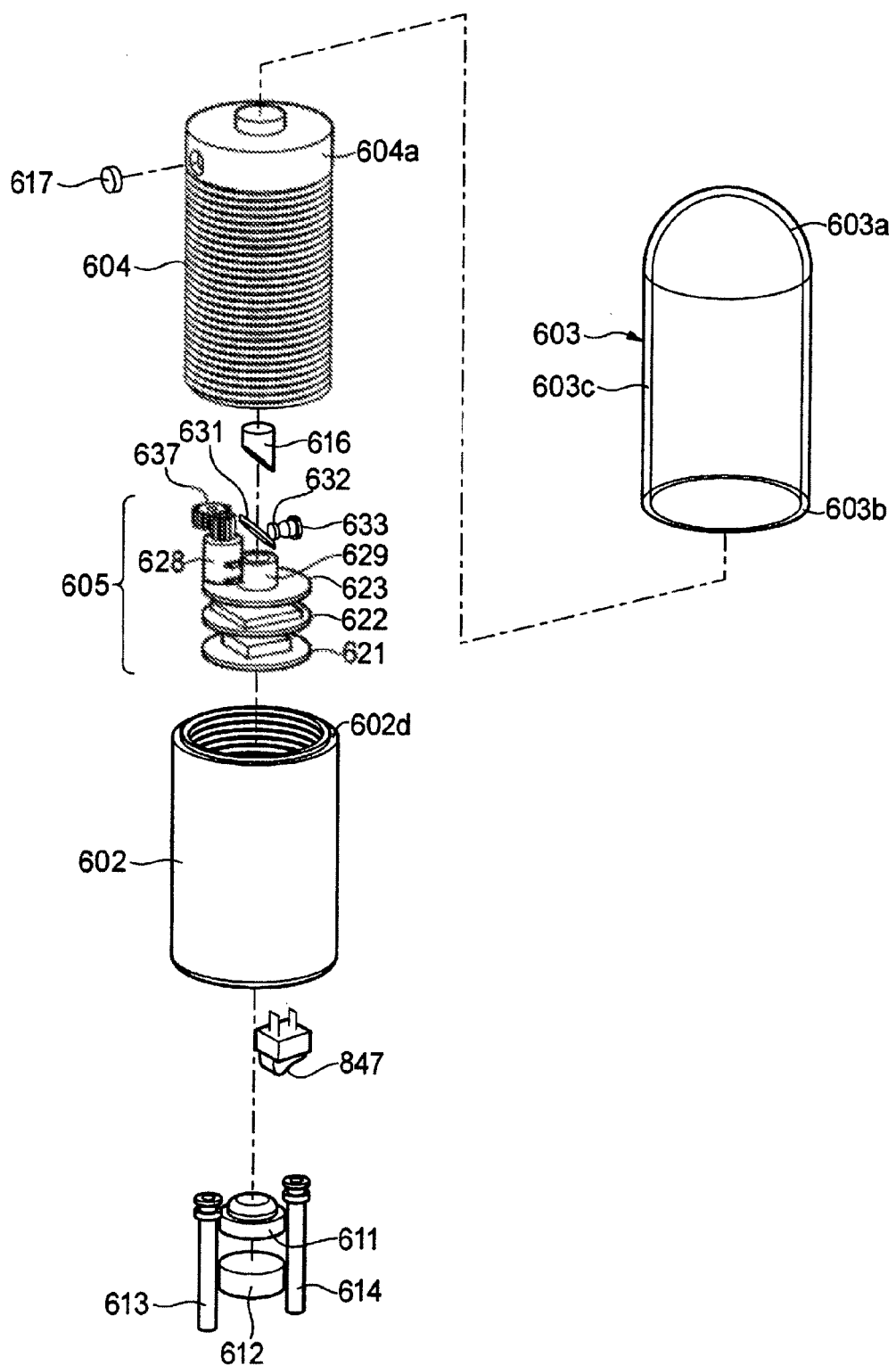
FIG. 60 is an exploded perspective view of an electronic endoscope shown in FIG. 59.

An electronic endoscope 801 shown in FIGS. 59 and 60 includes: an outer shell having a body part 602 and a transparent capsule 603; and a moving lens franc section 604 and an image pick-up drive unit part 605 accommodated in the inside of the outer shell. Here, like members to those of the electronic endoscope 601 described above are designated by like numerals, and functionally common members are designated by appropriately corresponding numerals. Then, their description is omitted or simplified.

Figure 61:
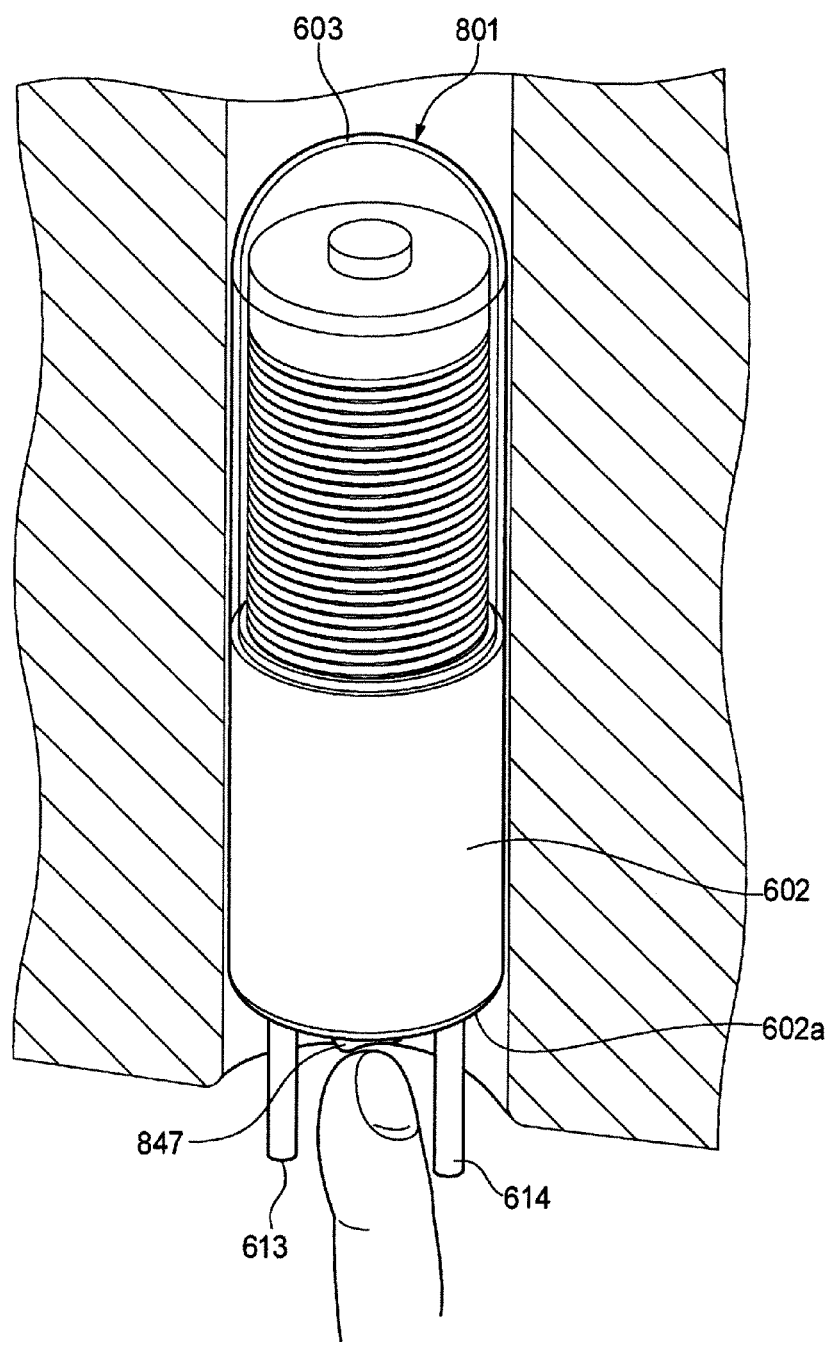
FIG. 61 is a schematic diagram showing a state that an electronic endoscope shown in FIG. 59 is inserted into a hole serving as a subject.

In the electronic endoscope 801, a power switch 847 is provided. As shown in FIG. 61, in the state that the electronic endoscope 801 is inserted into a hole serving as a subject, the power switch 847 can be operated from the outside of the hole. In the example shown in the figure, the power switch 847 is turned ON or OFF by manual operation, and is provided in the bottom part 602a of the body part 602 that faces the opening of the hole. Here, the power switch 847 may be provided in the battery lid 612 that is fitted in the opening pan of the battery accommodating part 602b formed in the bottom part 602a and that constitutes a part of the bottom part 602a.

In another exemplary configuration for the power switch, a remote code may be extracted from the body part 602 to the outside of the hole and then a manipulation part used for performing ON-OFF operation may be provided in the end part. In yet another exemplary configuration for the power switch, a switch terminal that follows magnetism may be built in the body part 602. Then, from the outside of the hole, a magnet is brought close to or apart from the body part 602 so that the switch terminal may be turned ON or OFF.

Figure 62:
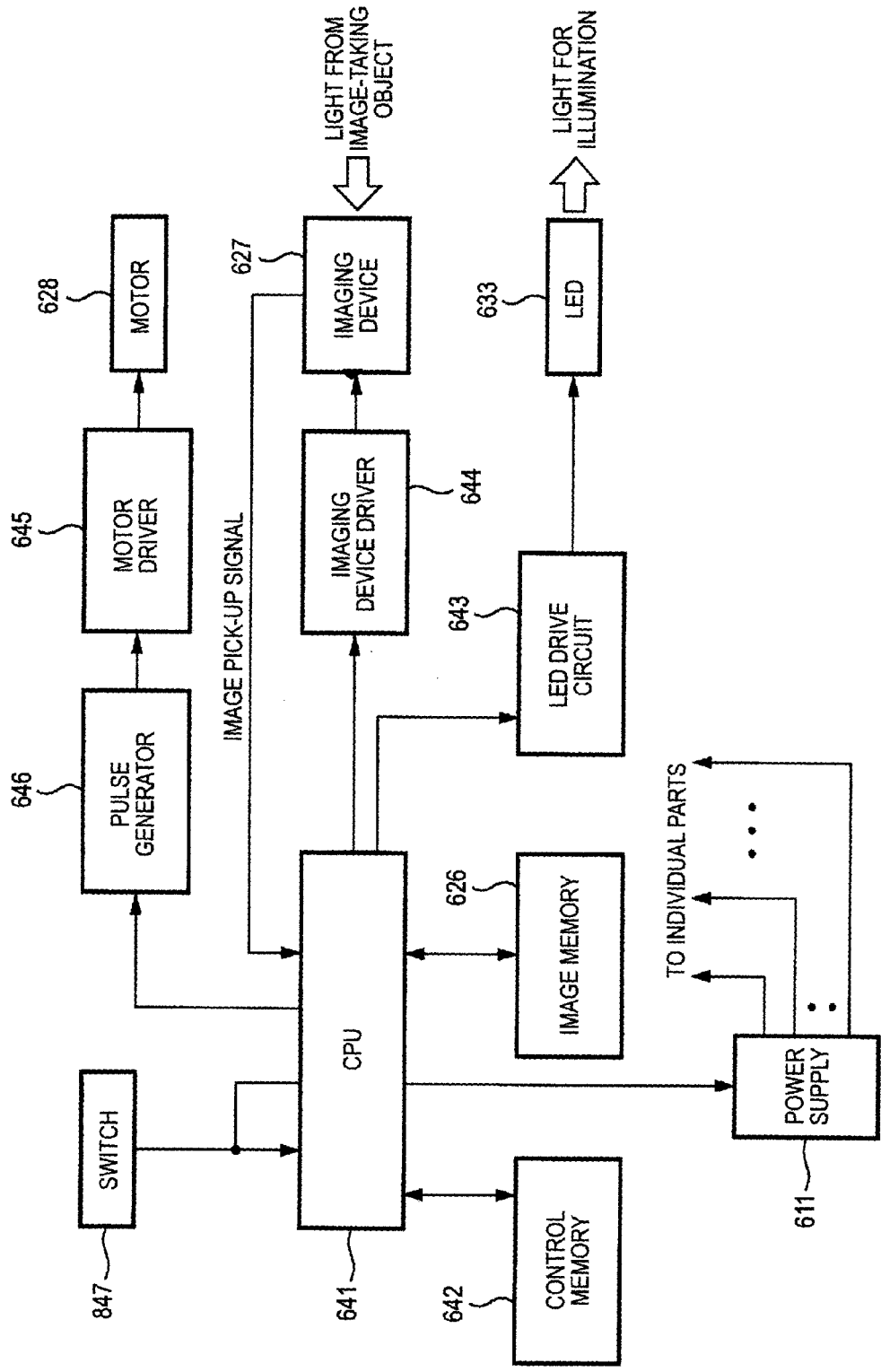
FIG. 62 is a functional block diagram showing a control unit mounted on an electronic endoscope shown in FIG. 59.

When the power switch 847 is turned ON, as shown in FIG. 62, electric power from the power battery 611 is supplied through wiring (not shown) to the individual parts of the image pick-up drive unit part 605, so that image pick-up operation and drive operation are performed similarly to the case of the electronic endoscope 601 described above.

As described above with reference to the electronic endoscope 801 serving as an example, the present specification has disclosed an electronic endoscope that is inserted into a hole and then acquires an image of the inner peripheral surface of the hole, characterized by comprising: an outer shell that is formed in a cylindrical shape and whose peripheral wall is provided with a transparent window part extending in an axial direction; a solid-state imaging device that is provided inside the outer shell; an objective optical system that includes an objective lens for focusing object light through the window part and that forms an image onto the solid-state imaging device; a drive mechanism that causes at least the objective lens in the objective optical system to move along an axis of the outer shell; a control section that controls the solid-state imaging device and the drive mechanism and an operation switch that operates the control section, wherein in a state that the electronic endoscope is inserted into the hole, the operation switch is allowed to be operated from the outside of the hole.

Further, the present specification has disclosed an electronic endoscope characterized in that the operation switch is provided in the bottom part of the outer shell that faces the insertion opening of the hole.

Further, the present specification has disclosed an electronic endoscope characterized in that the window part is provided over the entirety of the circumferential wall of the outer shell, and wherein the drive mechanism causes at least the objective lens in the objective optical system to revolve about the axis of the outer shell and thereby moves along the axis of the outer shell.

Further, the present specification has disclosed an electronic endoscope characterized in that the outer shell is formed in a cylindrical shape and a thread groove is formed in the inner peripheral surface of the circumferential wall, wherein the drive mechanism inch vies a lens holder which supports the objective lens and a motor which drives and revolves the lens holder about the axis of the outer shell, and wherein the lens holder engages with the thread groove of the outer shell.

Further, the present specification has disclosed an electronic endoscope characterized in that the control section reads an image pick-up signal from the solid-state imaging device and generates image data, and wherein a memory which stores the image data is further included in the inside of the outer shell.

Further, the present specification has disclosed an electronic endoscope characterized in that the drive mechanism is driven by electric power, and wherein a power battery which supplies electric power to the solid-state imaging device, the drive mechanism, and the control section is further provided inside the outer shell.

Figure 63:
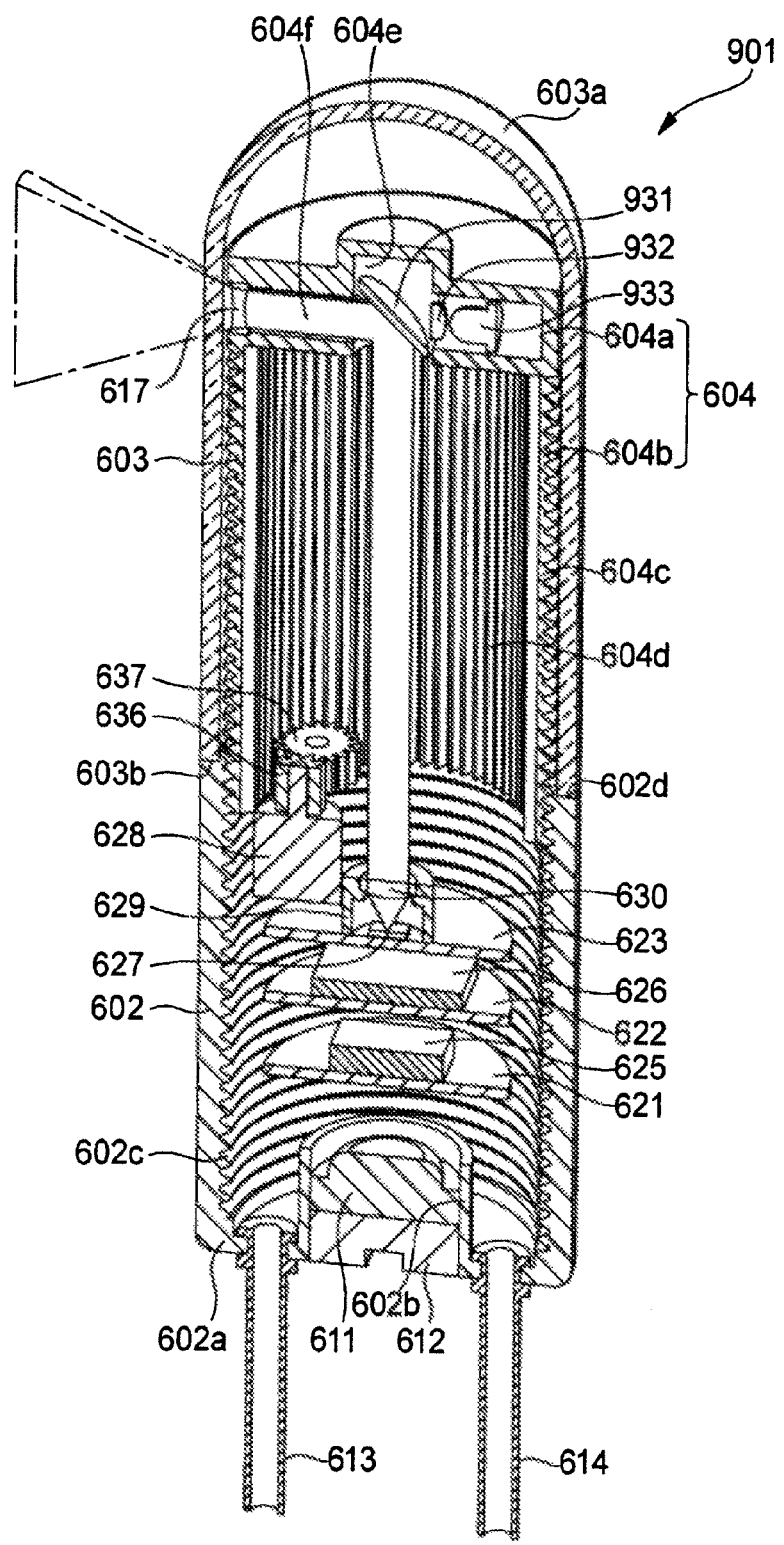
FIG. 63 is an external appearance perspective view of another example of an electronic endoscope used for describing an embodiment of the present invention.

In the electronic endoscope 901 shown in FIG. 63, in place of the objective mirror 616 in the electronic endoscope 601 described above, a half mirror 931 is arranged in the cylindrical hole 604e of the objective lens mount part 604a. Then, an illumination lens 932 and an LED 933 is provided behind the half mirror 931. Here, like members to those of the electronic endoscope 601 described above are designated by like numerals, and functionally common members are designated by appropriately corresponding numerals. Then, their description is omitted or simplified.

In the electronic endoscope 601 described above, the LED 633 is arranged on the reflected light path of the object light reflected from the half mirror 631, and the solid-state imaging device 627 is arranged on the transmitted light path of the object light transmitted through the half mirror 631. In contrast, in the electronic endoscope 901, the LED 933 is arranged on the transmitted light path of the object light transmitted through the half mirror 931, and the solid-state imaging device 627 is arranged on the reflected light path of the object light reflected through the half mirror 931. Even in this configuration, light for illumination is projected through the objective lens 617 onto the image-taking object.

As described above with reference to the electronic endoscopes 601 and 901 serving as examples, the present specification has disclosed an electronic endoscope characterized by comprising: an outer shell that is formed in a tube shape and whose peripheral wall is provided with a transparent window part extending in an axial direction; a light source and a solid-state imaging device that are provided inside the outer shell; an illumination optical system that projects light for illumination from the light source through the window part onto an image-taking object an objective optical system that includes an objective lens which focuses object light through the window part and that forms an image onto the solid-state imaging device; and a drive mechanism that causes at least the objective lens in the objective optical system to move along an axis of the outer shell, wherein the illumination optical system projects the tight for illumination onto the image-taking object through the objective lens.

Further, the present specification has disclosed an electronic endoscope characterized in that the illumination optical system includes a half mirror, the half mirror is arranged on the optical path of the object light in an inclined manner relative to the optical axis of the object light in the objective optical system; the light source is arranged on any one of the transmitted light path of the object light transmitted through the half mirror and the reflected tight path of the object light reflected from the half mirror; and the solid-stare imaging device is arranged on the other one of the transmitted light path and the reflected light path.

Further, the present specification has disclosed an electronic endoscope characterized in that the window part is provided over the entirety of the circumferential wall of the outer shell, and wherein the drive mechanism causes at least the objective lens in the objective optical system to revolve about the axis of the outer shell and thereby moves along the axis of the outer shell.

Further, the present specification has disclosed an electronic endoscope characterized in that the outer shell is formed in a cylindrical shape and a thread groove is formed in the inner peripheral surface of the circumferential wall, wherein the drive mechanism includes a lens holder which supports the objective lens and a motor which drives and revolves the lens holder about the axis of the outer shell, and wherein the lens holder engages with the thread groove of the outer shell.

Further, the present specification has disclosed an electronic endoscope characterized in that a control section which reads an image pick-up signal from the solid-stare imaging device and which generates image data and a memory which stores the image data are further included in the inside of the outer shell.

Further, the present specification has disclosed an electronic endoscope characterized in that the drive mechanism is driven by electric power, and wherein a power battery which supplies electric power to the solid-state imaging device and the drive mechanism is further provided inside the outer shell.

Figure 64:
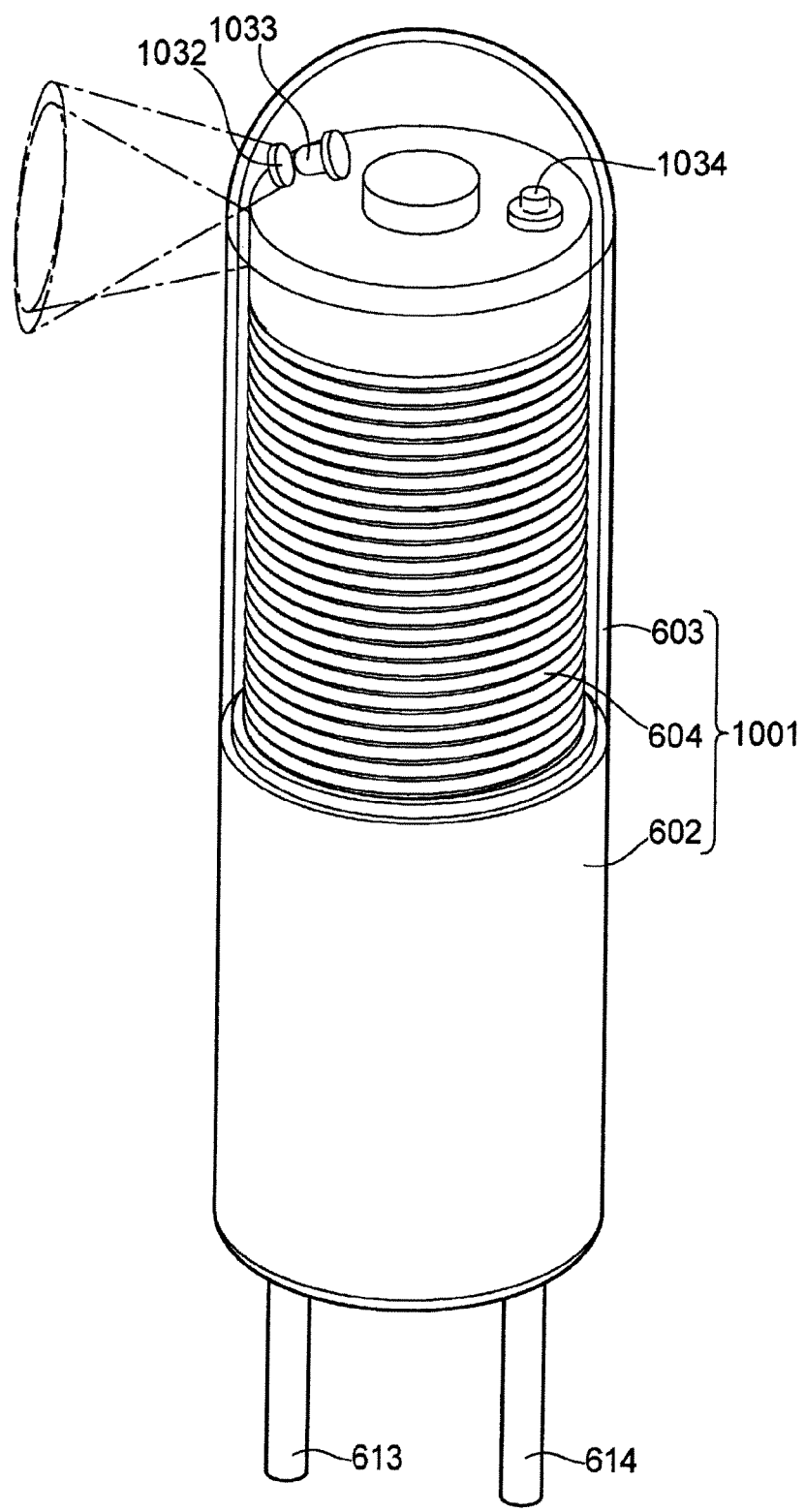
FIG. 64 is an external appearance perspective view of another example of an electronic endoscope used for describing an embodiment of the present invention.
Figure 65:
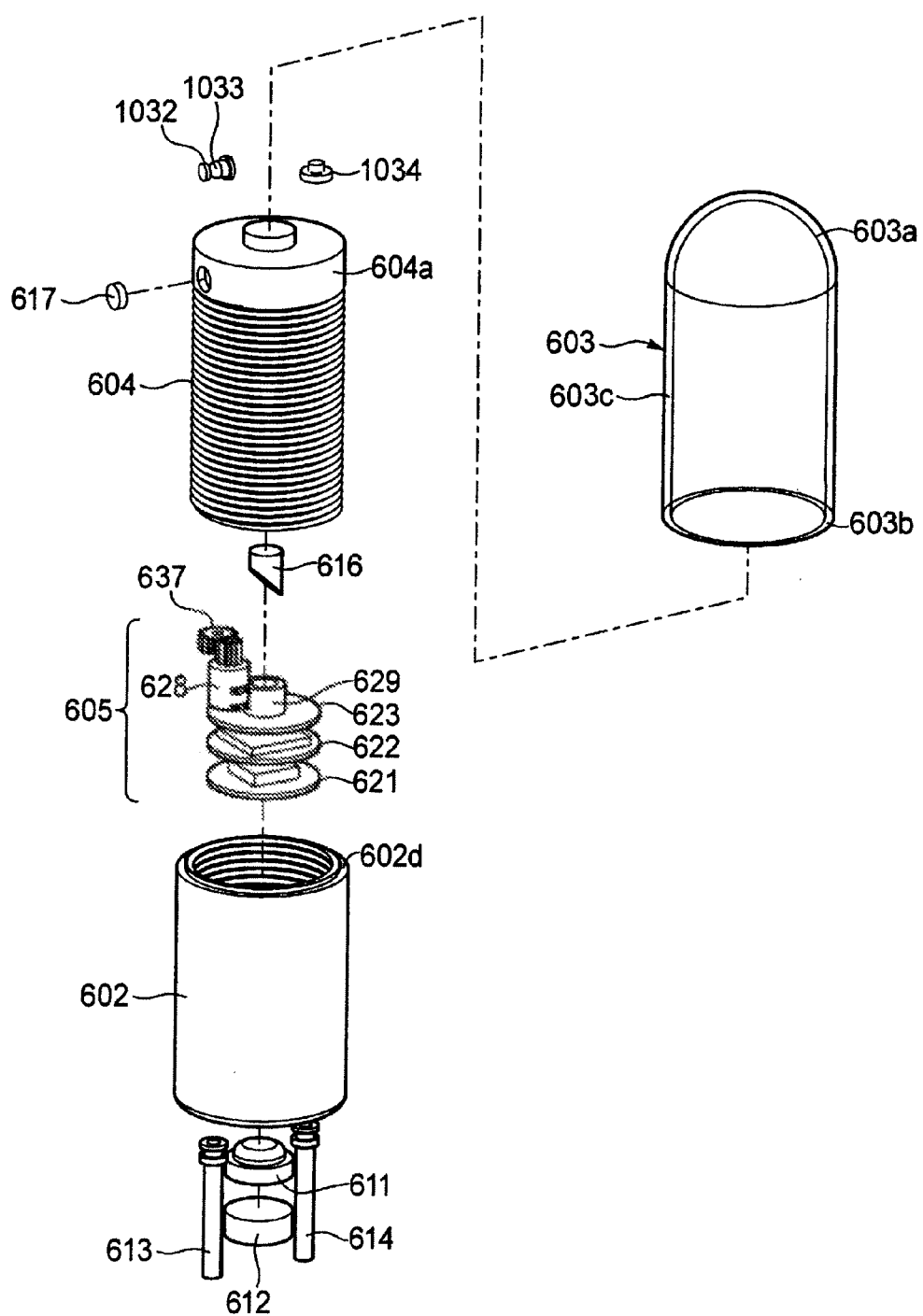
FIG. 65 is an exploded perspective view of an electronic endoscope shown in FIG. 64.
Figure 66:
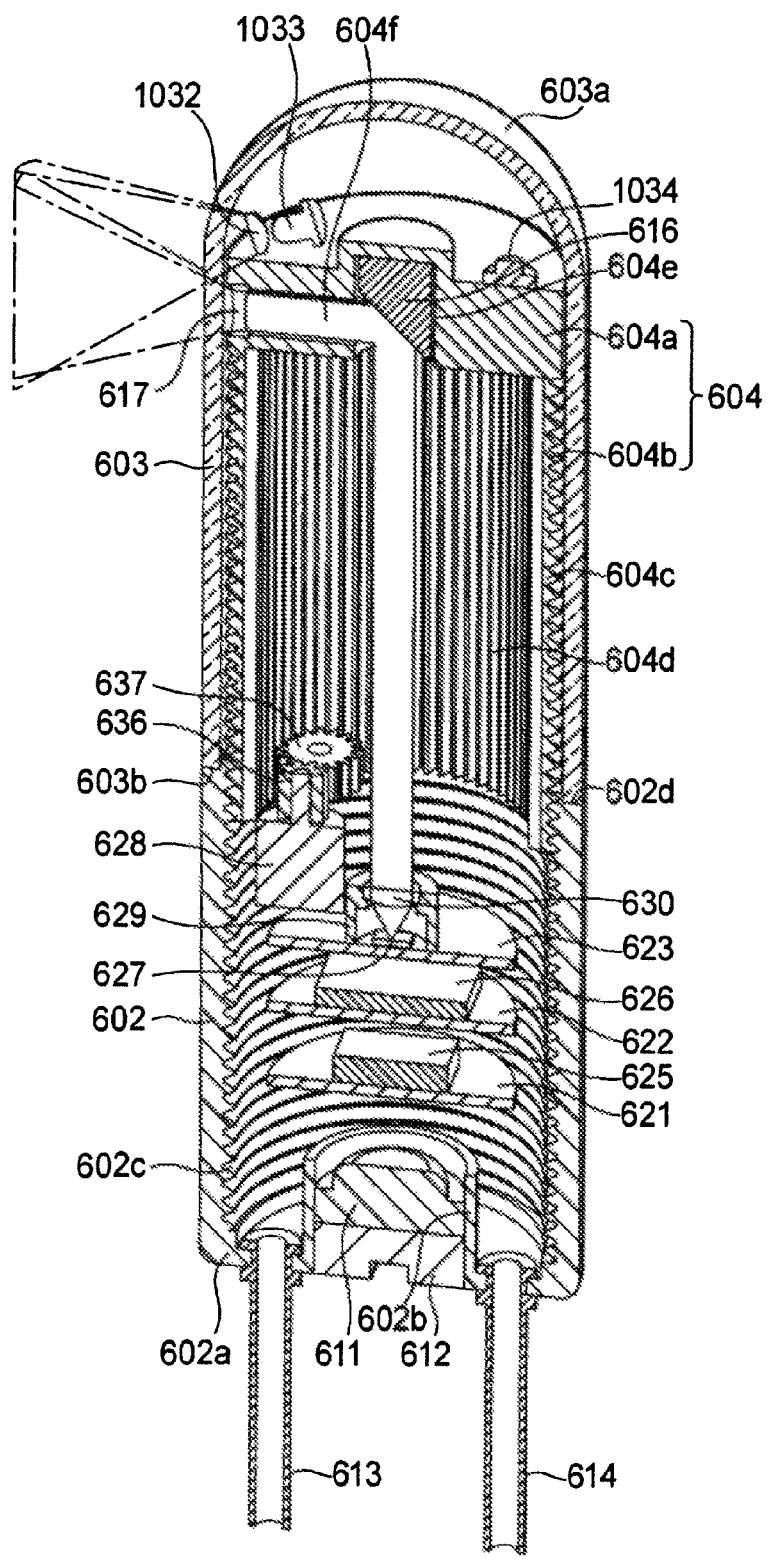
FIG. 66 is a longitudinal sectional view of an electronic endoscope shown in FIG. 64.

An electronic endoscope 1001 shown in FIGS. 64 to 66 includes: an outer shell having a body part 602 and a transparent capsule 603; and a moving lens franc section 604 and an image pick-up drive unit part 605 accommodated in the inside of the outer shell. Here, like members to those of the electronic endoscope 601 described above are designated by like numerals, and functionally common members are designated by appropriately corresponding numerals. Then, their description is omitted or simplified.

Then, in place of the illumination optical system of the above-mentioned electronic endoscope 601 which is constructed from the LED 633, the illumination lens 632, the half mirror 631, the objective mirror 616, and the objective lens 617, in the electronic endoscope 1001, the upper part of the objective lens mount part 604a of the moving lens frame section 604 is provided with: a light emitting diode (LED) 1033 for emitting light for illumination; an illumination lens 1032 for facing the light for illumination from the LED 1033 and then projects the light onto the image-taking object; and a battery 1034 for supplying electric power to the LED 1033.

The illumination lens 1032 serving as a projection exit of the light for illumination is arranged above the objective lens 617 such that the lens optical axis of the illumination lens 1032 is in parallel to the lens optical axis of the objective lens 617 or alternatively such that the lens optical axis of the illumination lens 1032 approaches the lens optical axis of the objective lens 617 when going outward from the outer shell. The light for illumination projected from the illumination 1032 onto the image-taking object illuminates the region containing the view field region of the objective lens 617. The LED 1033, the illumination lens 1032, and the battery 1034 are fixed to the objective lens mount part 601e by fixing members (not shown).

Here, the illumination lens 1032 serving as a projection exit of the light for illumination is preferably arranged at a position adjacent to the objective lens 617 in the axial direction of the outer shell. By virtue of this, for example, in a case that an image-taking object located extremely close is to be taken, illumination of the region containing the view field region of the objective lens 617 becomes easy.

In the above-mentioned configuration that the LED 1033 and the illumination lens 1032 are exposed to the outside of the objective lens mount part 604a, its ON-OFF stare is easily checked through the transparent capsule 603 and hence a possible trouble is recognized easily. Further, electric power to the LED 1033 is supplied from the battery 1034 separate from the power battery 611. Thus, even in a case that the LED 1033 is of high luminance, its relatively high power consumption among those of LEDs is satisfactorily covered by the battery 1034. Thus, this configuration realizes a clear image.

In the electronic endoscope 1001, a power switch (not shown) is provided. When the power switch is turned ON, electric power from the power battery 611 is supplied through wiring (not shown) to the individual parts of the image pick-up drive unit part 605. Further, electric power from the battery 1034 is supplied through wiring (not shown) to the LED 1033. By virtue of this, image pick-up operation and drive operation are performed.

Figure 67:
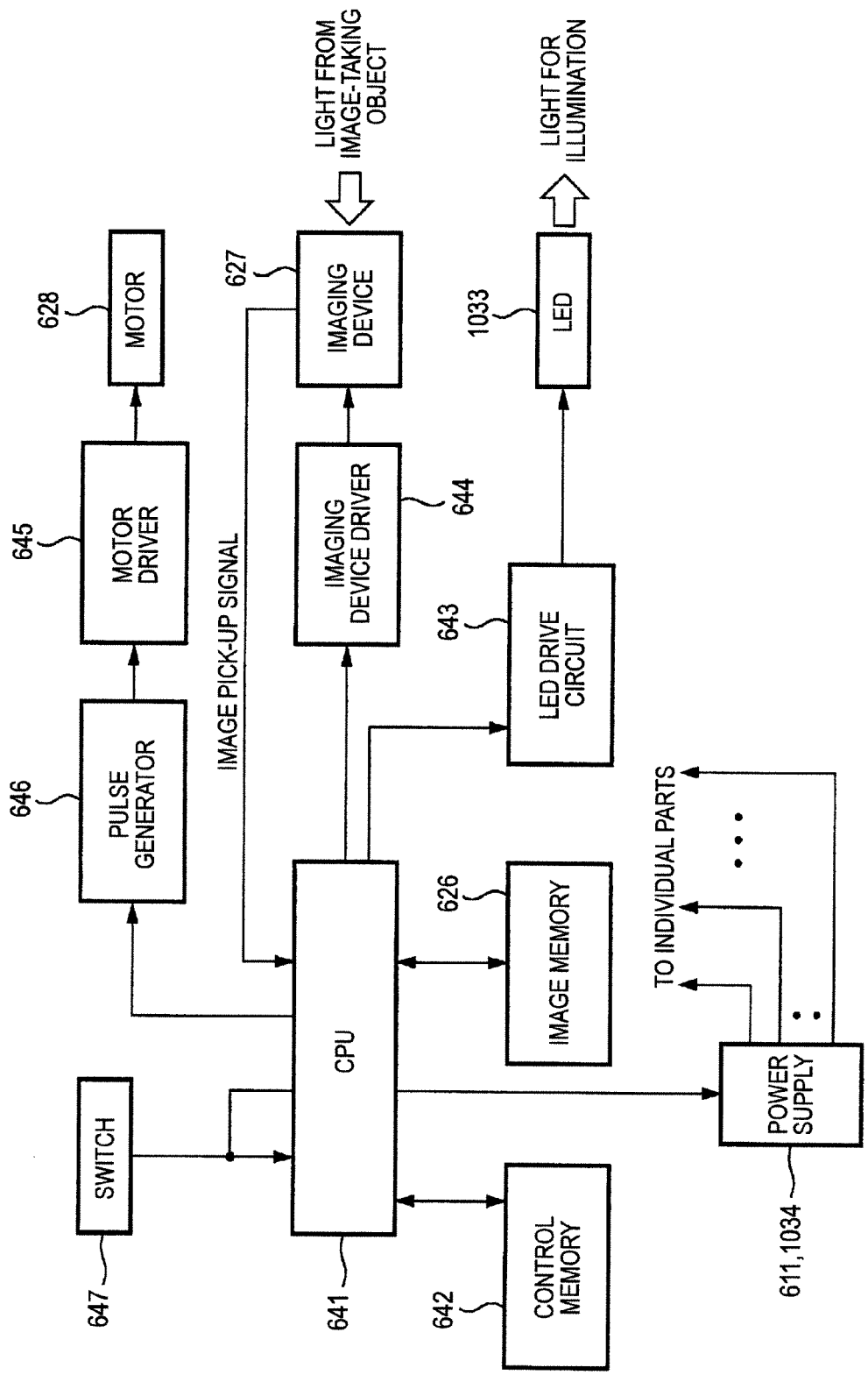
FIG. 67 is a functional block diagram showing a control unit mounted on an electronic endoscope shown in FIG. 64.

FIG. 67 is a functional block diagram showing the image pick-up drive unit put 605. The CPU 641 for collectively controlling the entire system is connected to: a control memory 642 that stores a control program and serves also as a work memory, an image memory 626 provided on the base plate 622; an LED drive circuit 643 for driving the LED 1033; an imaging device driver 644 for driving the imaging device 627; and a pulse generator 646 for providing driving pulses to the motor driver 645 for driving the stepping motor 628.

When the power switch 647 is tuned ON, electric power is supplied from the power batteries 611 and 1034 to the individual parts so that operation is started. Thus, the stepping motor 628 is driven and revolved. Accordingly, the moving lens frame section 604 is revolved in the inside of the electronic endoscope 1001 so as to advance or retreat in the axial direction.

With reference to FIG. 66, the light for illumination from the LED 1033 enters the illumination lens 1032. Then, the light for illumination having entered the illumination lens 1032 is transmitted through the transparent capsule 603 and then projected toward the image-taking object so as to serve as light for illumination that illuminates the image-taking object contained in the view field region of the objective lens 617. That is, the illumination lens 1032 constitutes an illumination optical system.

The light for illumination is reflected by the image-taking object. Then, a part of the reflected light serving as object light enters the objective lens 617.

The object light having entered the objective lens 617 is brought into the form of a parallel light beam, then travels to the objective mirror 616, and then is reflected by the objective mirror 616 so as to travel to the focusing lens 630 with maintaining the form of a parallel light beam. Then, the object light is focused onto the light acceptance surface of the solid-state imaging device 627 by the focusing lens 630 so that an image is formed.

The image pick-up signal of the image-taking object acquired by the imaging device 627 is acquired into the CPU 641 so as to undergo image processing, and then stored into the image memory 626, for example, in the form of JPEG image data.

Similarly to the case of the electronic endoscope 601 described above, in the electronic endoscope 1001, the stepping motor 628 is driven by a specified number of pulses so that the moving lens frame section 604 is revolved inside the electronic endoscope 1001 so as to advance or retreat in the axial direction. In association with this, the field of view is moved like No. 001→No. 002→No. 003 ... as shown in FIG. 53. In this manner, image pick-up processing and image data accumulation into the memory 626 are repeated so that image pick-up is achieved.

After the image pick-up of an object image of the field of view "No. 001" shown in FIG. 53, the stepping motor 628 is driven by a specified number of pulses. Thus, the moving lens frame section 604 is revolved by the specified number of pulses. As a result, the moving lens frame section 604 is screwed and retreats into the body part 602. In association with this, the objective lens 617 held by the moving lens frame section 604 is moved so that the field of view moves to "No. 002" shown in FIG. 53. At that time, the LED 1033 and the illumination lens 1032 mounted on the moving lens frame section 604 are also moved similarly to the objective lens 617, and thereby follows the moving field of view so as to illuminate the field of view "No. 002". Then, an object image in this field of view is taken, and then the obtained image data is accumulated in the image memory 626.

Figure 68:
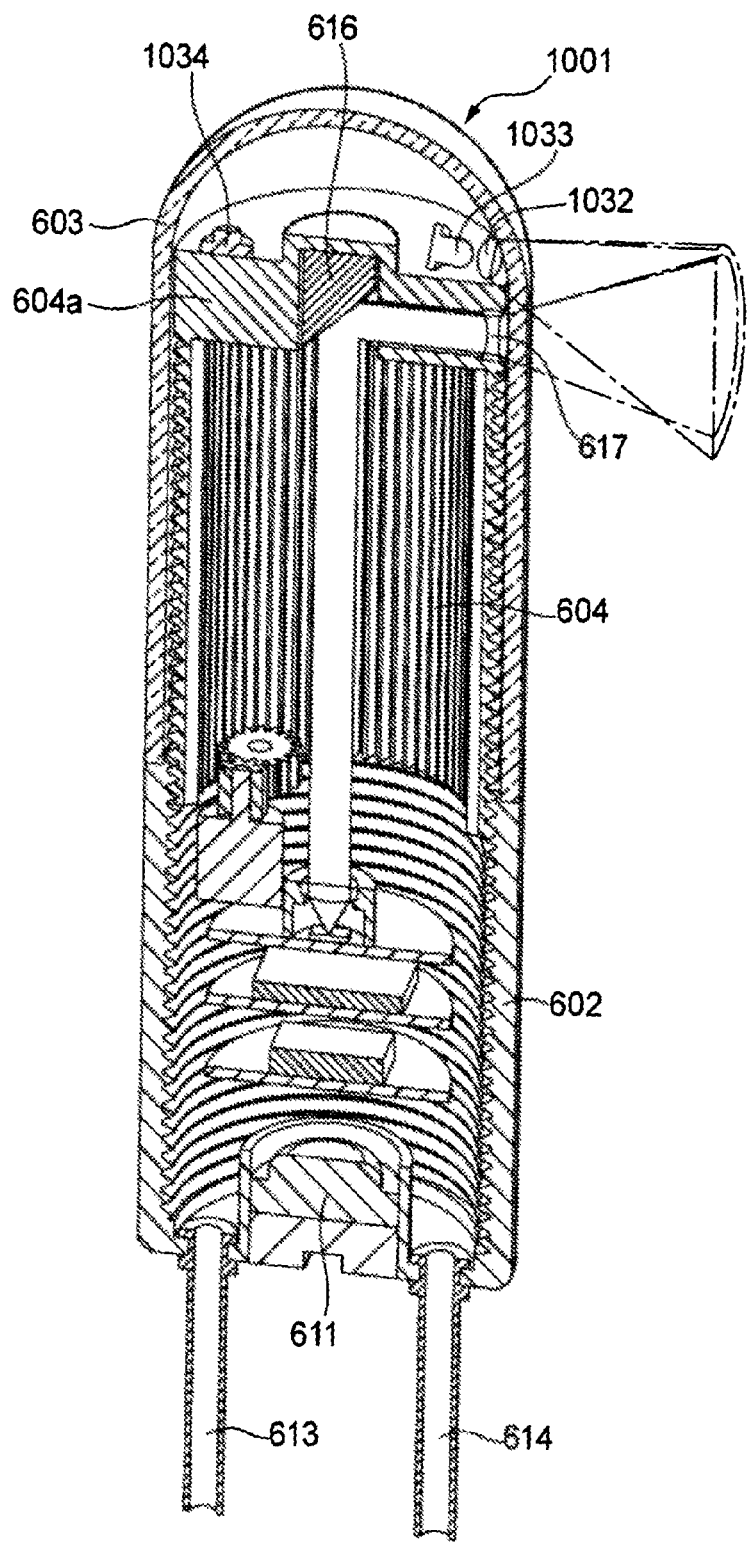
FIG. 68 is a longitudinal sectional view showing a state that a lens holder has gone half around from a state shown in FIG. 66.

FIG. 68 shows a state that the moving lens frame section 604 has gone half around inside the transparent capsule 603 starting from the state shown in FIG. 66. When the moving lens frame section 604 has gone one around from the home position inside the transparent capsule 603, the field of view of image pick-up is located at No. 011 in FIG. 53. In case of having gone around twice, the field of view of image pick-up is located at No. 021 in FIG. 53.

Figure 69:
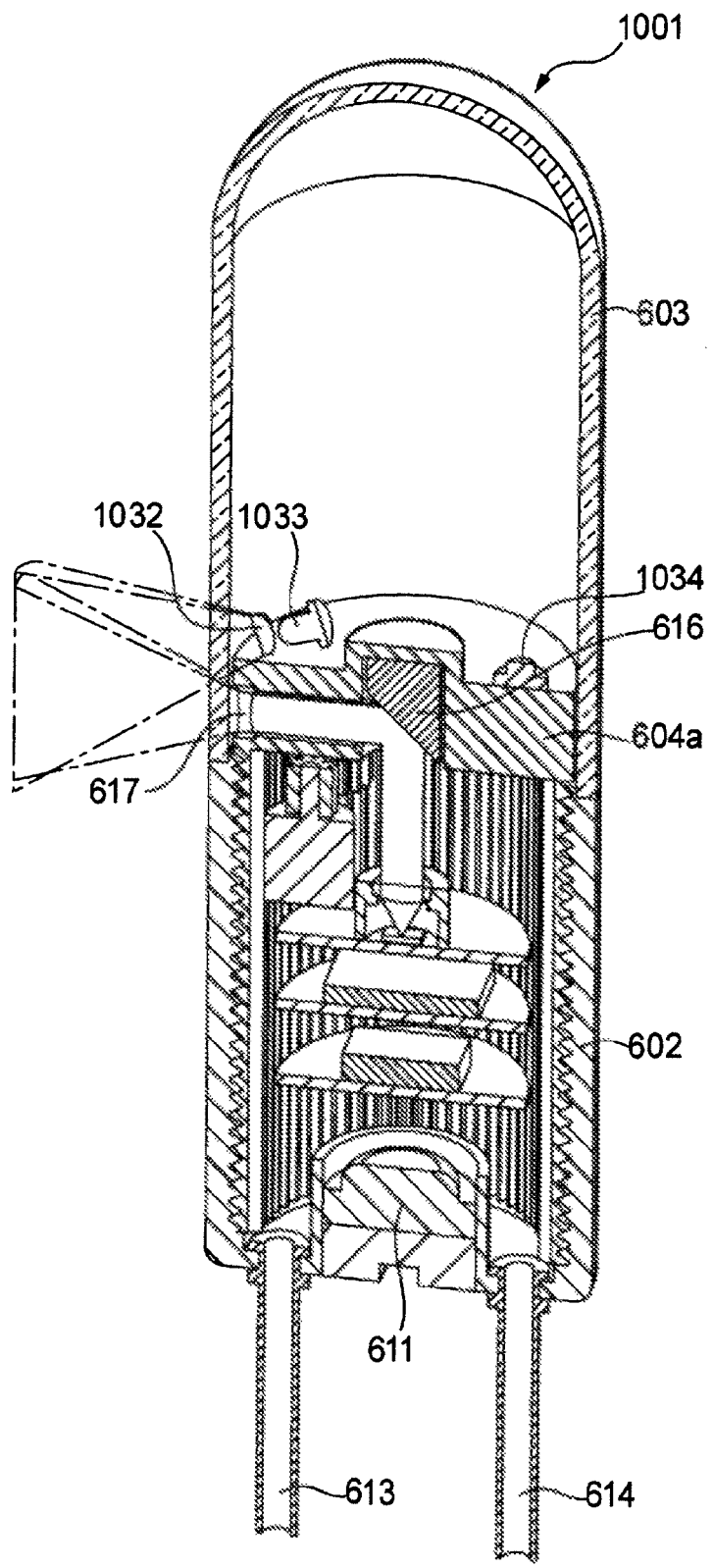
FIG. 69 is a longitudinal sectional view showing a state that a lens holder shown in FIG. 66 has been lowered to an image pick-up completion position.

Further, FIG. 69 shows a state that the lower end of the cylindrical member 604b abuts against the bottom part 602a of the body pan 602 and hence cannot move further in this direction. When the state shown in FIG. 69 is reached, the processing loop of repeating the image pick-up processing is terminated.

Once image pick-up by the electronic endoscope 1001 is completed, the data accumulated in the image memory 626 is to be read to the outside.

As described above with reference to the electronic endoscope 1001 serving as an example, the present specification has disclosed an electronic endoscope characterized by comprising: an outer shell that is formed in a tube shape and whose peripheral wall is provided with a transparent window part extending in an axial direction; a light source and a solid-state imaging device that are provided inside the outer shell; an illumination optical system that projects light for illumination from the light source through the window part onto an image-taking object, an objective optical system that includes an objective lens which focuses object light through the window part and that forms an image onto the solid-state imaging device; a lens holder that holds at least the objective lens in the objective optical system; and a driving section that moves the lens holder along the axis of the outer shell, wherein the light source and the illumination optical system are integrally fixed and supported by the lens holder.

Further, the present specification has disclosed an electronic endoscope characterized in that the projection exit of the illumination optical system is arranged at a position adjacent to the objective lens in the axial direction of the outer shell.

Further, the present specification has disclosed an electronic endoscope characterized in that the window part is provided over the entire circumference of the peripheral wall of the outer shell, and wherein the driving section causes the lens holder to revolve about the axis of the outer shell and thereby moves along the axis of the outer shell.

Further, the present specification has disclosed an electronic endoscope characterized in that the outer shell is formed in a cylindrical shape and its inner peripheral surface is provided with a thread groove, wherein the driving section includes a motor which drives and revolves the lens holder about the axis of the outer shell, and wherein the lens holder engages with the thread groove of the outer shell.

Further, the present specification has disclosed an electronic endoscope characterized in that a control section which reads an image pick-up signal from the solid-state imaging device and then generates image data and a memory which stores the image data are further included in the inside of the outer shell.

Further, the present specification has disclosed an electronic endoscope characterized in that the driving section is driven by electric power, and wherein a power battery which supplies electric power to the light source, the solid-state imaging device, and the driving section are further provided inside the outer shell.

Figure 70:
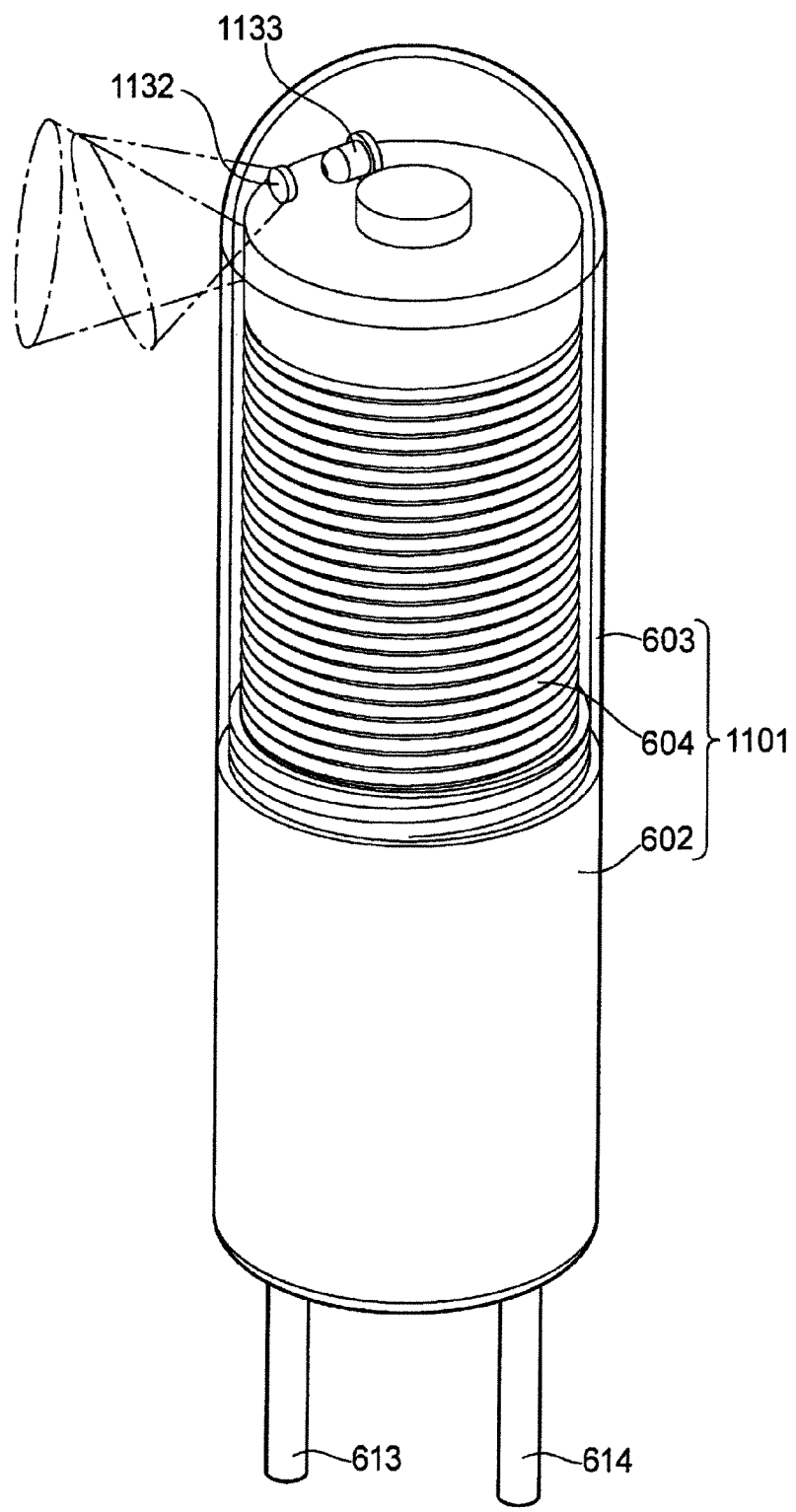
FIG. 70 is an external appearance perspective view of another example of an electronic endoscope used for describing an embodiment of the present invention.
Figure 71:
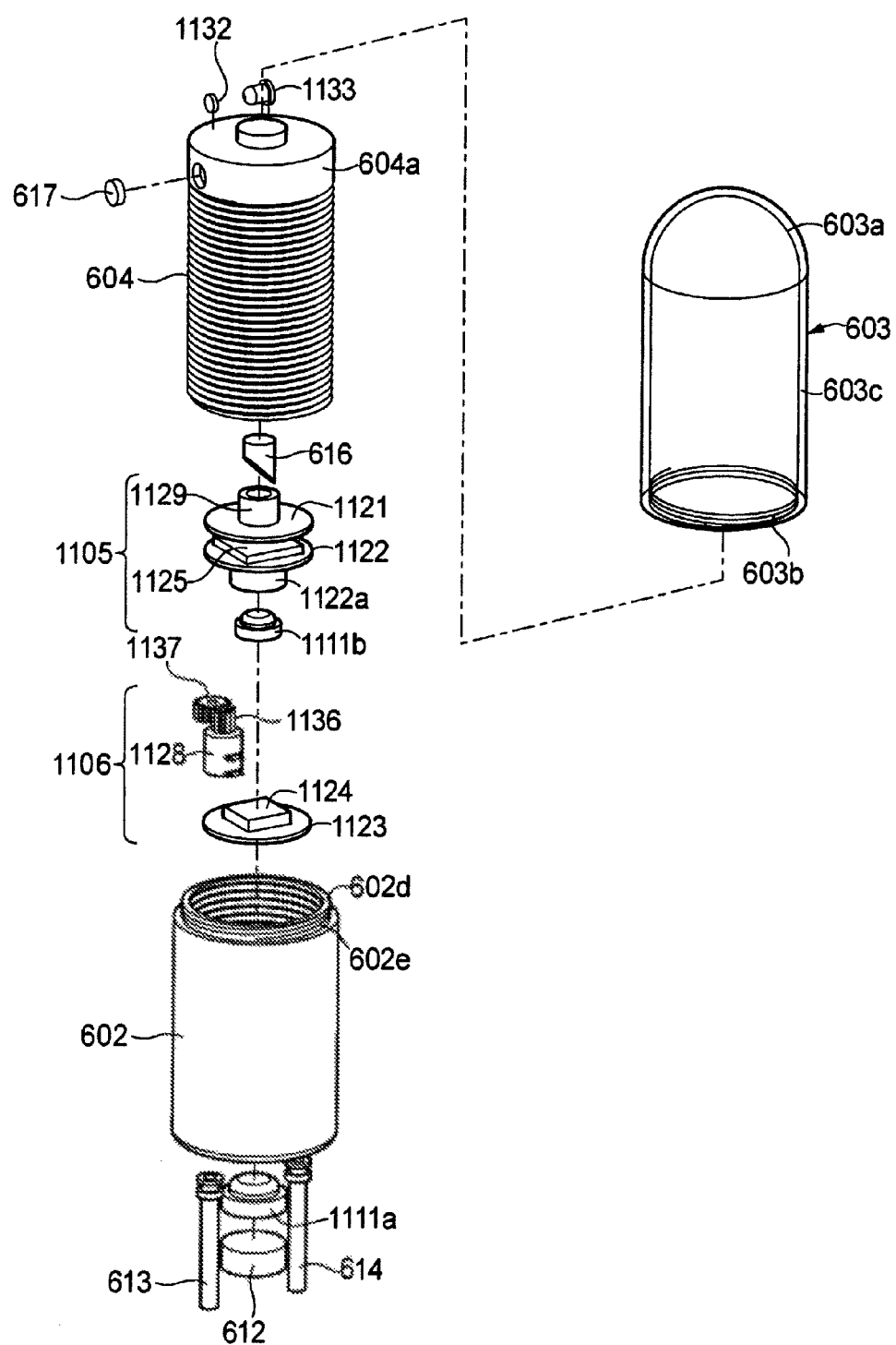
FIG. 71 is an exploded perspective view of an electronic endoscope shown in FIG. 70.

An electronic endoscope 1101 shown in FIGS. 70 to 72 includes: a body part 602 and a transparent capsule 603 that constitute an outer shell; a moving lens frame section 604 accommodated in the inside; and an imaging unit part 1105 and a storage and driving section 1106 described later. Here, like members to those of the electronic endoscope 601 described above are designated by like numerals, and functionally common members are designated by appropriately corresponding numerals. Then, their description is omitted or simplified.

In the electronic endoscope 601 described above, the body part 602 and the transparent capsule 603 were fixed to each other by bonding. In contrast, in the electronic endoscope 1101, the body part 602 and the transparent capsule 603 are fixed to each other by screwing. That is, a screwing protrusion part 602e having a somewhat smaller diameter than the body part 602 protrudes from the open end part 602d of the body part 602. Then, a male screw is engraved spirally in the outer peripheral surface of the screwing protrusion part 602e. Further, in the inner peripheral surface of the open end part 603b on the side opposite to the hemispherical part 603a of the transparent capsule 603, a female screw is engraved spirally that screws into the male screw in the screwing protrusion part 602e on the body part 602 side.

The imaging unit 1105 individual colors base plates 1121 and 1122. The base plates 1121 and 1122 are mounted on and fixed to the objective lens mount part 604a inside the cylindrical member 604b at a position departing from the cylindrical member 604b. In the base plate 1121 arranged on the upper side (the objective lens mount part 604a side), a cylindrical lens holder 1129 is arranged in the center part. Then, a solid-state imaging device 1127 is mounted on the base plate 1121 in the inside.

A focusing lens 1130 is mounted in the upper opening of the lens holder 1129. Then, the parallel light beam reflected by the objective mirror 616 is focused by the focusing lens 1130 so that an image is formed onto the light acceptance surface of the solid-state imaging device 1127.

The moving lens frame section 604 includes: an LED 1133 installed on the upper part of the objective lens mount part 604a; and an illumination lens 1132 arranged in front of the LED 1133. The LED 1133 emits light for illumination. Then, the light for illumination focused by the illumination lens 1132 illuminates an image-taking object located in front of the objective lens 617.

A first control unit 1125 described later is mounted on the base plate 1122 arranged on the lower side. A battery accommodating part 1122a is provided in the lower surface of the base plate 1122. Then, a second power battery 1111b is accommodated here. The second power battery 1111b is mounted in the battery accommodating part 1122a in a situation that the screwing between the female screw 603b of the transparent capsule 603 and the male screw 602e of the body part 602 is released so that the electronic endoscope 1101 is disassembled.

The first control unit 1125 receives driving power from the second power battery 1111b. Further, the LED 1133 receives driving power from the second power battery 1111b through wiring (not shown).

The storage and driving section 1106 is mounted and fixed in the inside of the body part 602 by using a stay member (not shown) in a state that the peripheral wall of the battery accommodating part 602b provided in the bottom part 602a of the body part 602 serves as a supporting column. The storage and driving section 1106 has a base plate 1123.

On the base plate 1123, a second control unit 1124 is fixed and mounted, and a stepping motor 1128 is also fixed and mounted. Then, a motor gear wheel (spur wheel) 1136 is attached to the shaft of the stepping motor 1128. The shaft of the stepping motor 1128 is oriented in parallel to the center axis of the cylindrical member 604b (the optical axis of the parallel light beam). Then, the motor gear wheel 1136 engages with an idle gear wheel 1137 composed of a spur wheel.

The shaft of the idle gear wheel 1137 is pivotally supported in a revolvable manner in a direction perpendicular to the base plate 1123. The idle gear wheel 1137 has a larger number of gear teeth than the motor gear wheel 1136. Thus, the revolution of the stepping motor 1128 is slowed down and then transmitted to the idle gear wheel 1137. The idle gear wheel 1137 engages with the internal-tooth gear 604d provided in the inner peripheral surface of the cylindrical member 604b.

When the stepping motor 1128 revolves, the idle gear wheel 1137 revolves. Then, in association with this, the cylindrical member 604b revolves. When the cylindrical member 604b revolves, the cylindrical member 604b of the moving lens frame section 604 is screwed into or out from the body part 602 depending on the direction of revolution. That is, the moving lens frame section 604 advances or retreats in the axial direction.

In the electronic endoscope 1101, a power switch (not shown) is provided. When the power switch is turned ON, electric power from the first power battery 1111a is supplied to the individual parts of the storage and driving section 1106 through wiring (not shown) so that drive operation is performed.

Further, in the imaging unit 1105, a switch terminal that follows magnetism is built in. When a magnet is brought close or apart in the outside of the electronic endoscope 1101, the switch terminal is turned ON or OFF so that power supply from the second power battery 1111b to the imaging unit 1105 is turned ON or OFF.

Figure 73:
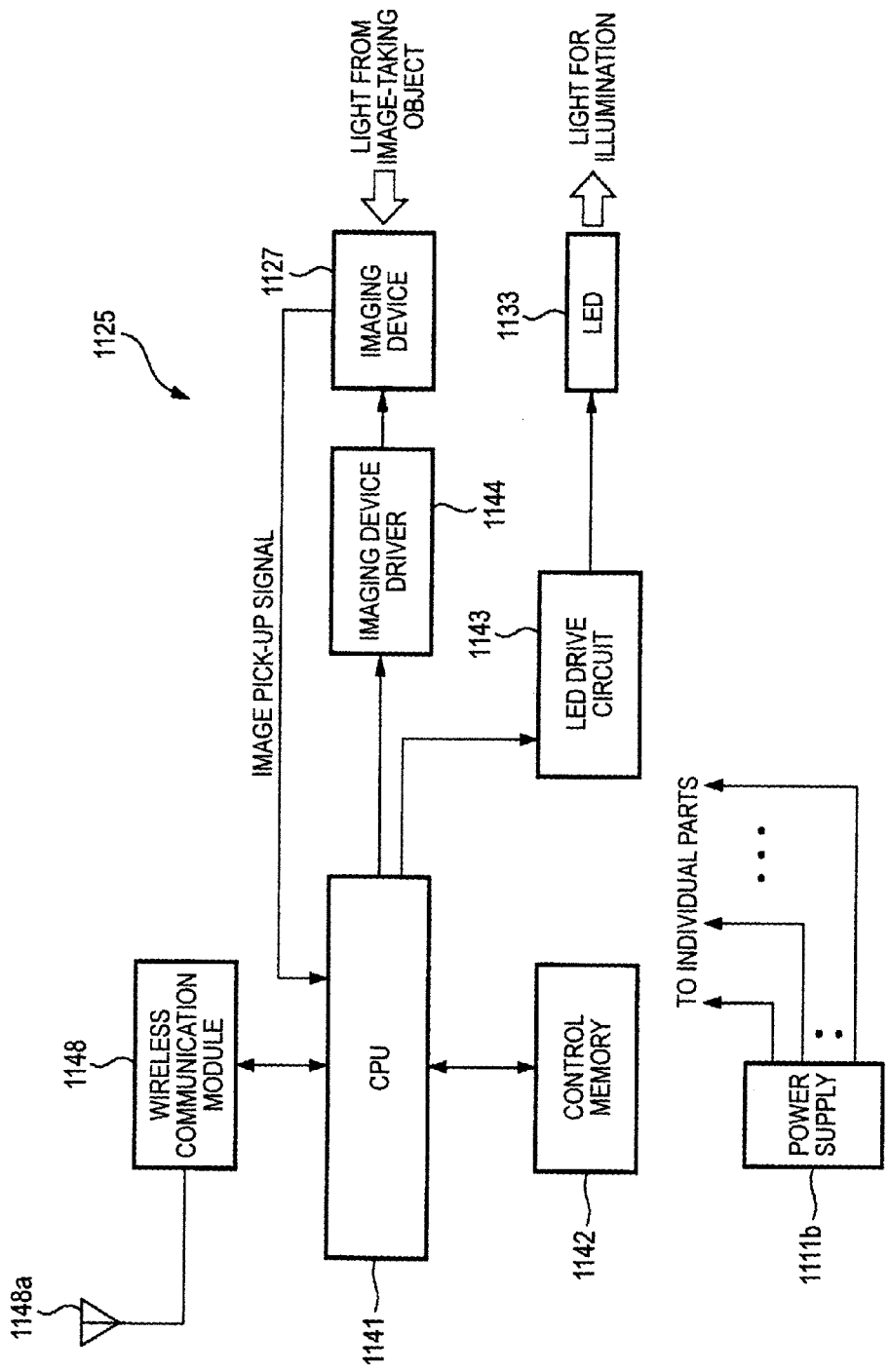
FIG. 73 is a functional block diagram showing a first control unit mounted on an electronic endoscope shown in FIG. 70.

FIG. 73 is a functional block diagram showing the first control unit 1125 The CPU 1141 for collectively controlling the imaging unit 1105 is connected to: a control memory 1142 for storing a control program and serving also as a work memory; an LED drive circuit 1143 for driving the LED 1133; an imaging device driver 1144 for driving the imaging device 1127; and a wireless communication module 1148 for performing wireless communication with the second control unit 1124. An antenna 1148a is provided in the wireless communication module 1148.

Figure 74:
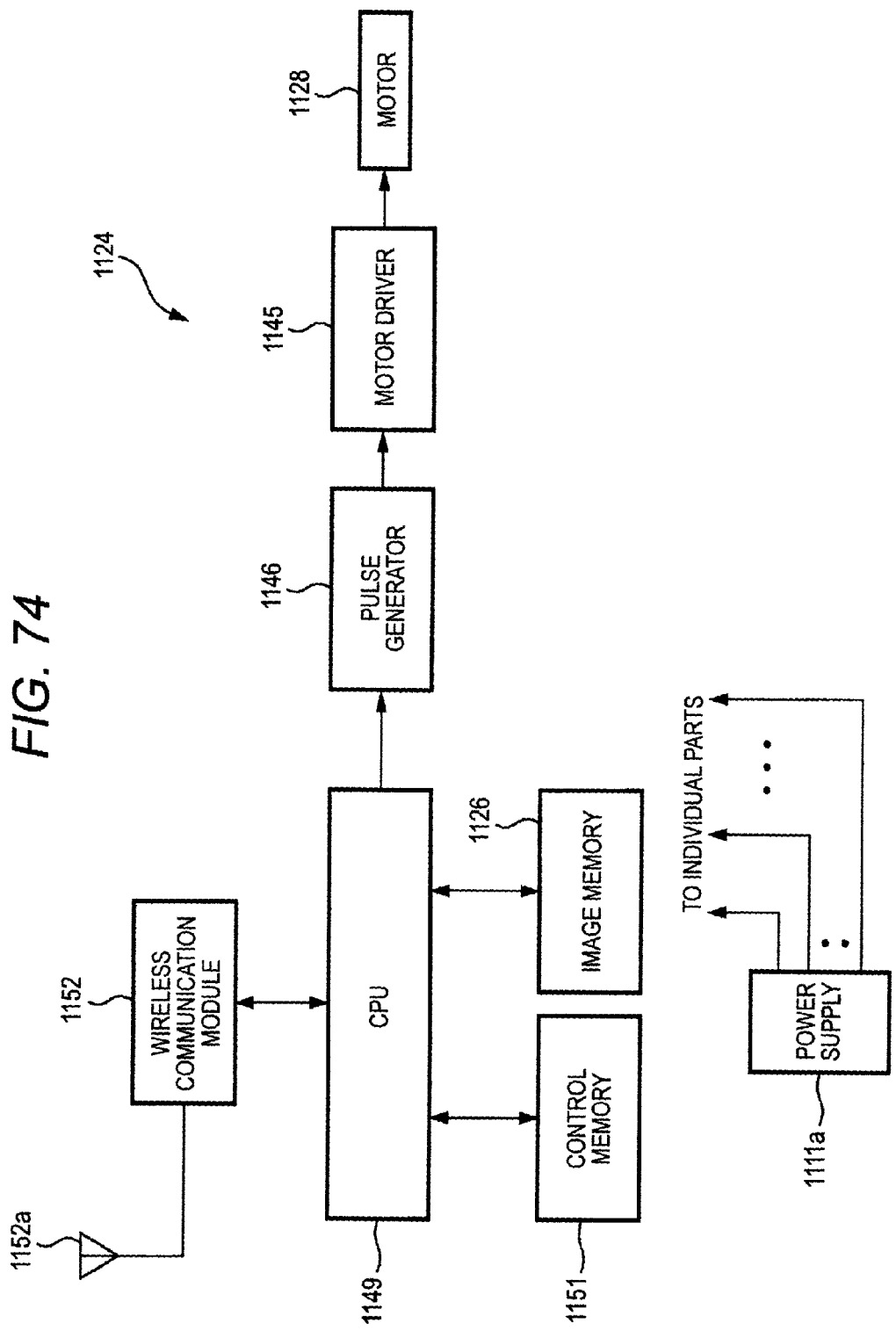
FIG. 74 is a functional block diagram showing a second control unit mounted on an electronic endoscope shown in FIG. 70.

FIG. 74 is a functional block diagram showing the second control unit 1124. The CPU 1149 for collectively controlling the entire system is connected to: a control memory 1151 for storing a control program and serving also as a work memory; an image memory 1126 for storing image data received from the imaging unit 1105 by wireless; a pulse generator 1146 for providing driving pulses to a motor driver 1145 for driving the stepping motor 1128; and a wireless communication module 1152 for performing wireless communication with the first control unit 1125. An antenna 1152a is provided in the wireless communication module 1152.

The CPU 1149 of the second control unit 1124 cooperates with the CPU 1141 of the first control unit 1125 via wireless communication.

When the power switch described above is turned ON, electric power is supplied from the first power battery 1111a and the second power battery 1111b to the individual parts so that operation is started. Then, the motor 1128 is driven and revolved. Accordingly, the moving lens frame section 604 is revolved in the inside of the electronic endoscope 1101 so as to advance or retreat in the axial direction. Further, the emitted light from the LED 1133 is focused by the illumination lens 1132, and then projected toward the image-taking object so as to serve as light for illumination.

The reflected light from the image-taking object is acquired through the objective lens 617 into the electronic endoscope 1101. Then, the optical image of the image-taking object reflected by the objective mirror 616 travels to the focusing lens 1130 in the form of a parallel light beam, and then is focused onto the light acceptance surface of the solid-state imaging device 1127 by the focusing lens 1130 so that an image is formed.

The image pick-up signal of the image-taking object acquired by the imaging device 1127 is acquired into the CPU 1141 and then undergoes image processing so as to be converted, for example, into JPEG image data. The obtained data is acquired into the CPU 1149 via wireless communication modules 1148 and 1152, and then stored into the image memory 1126.

Figure 75:
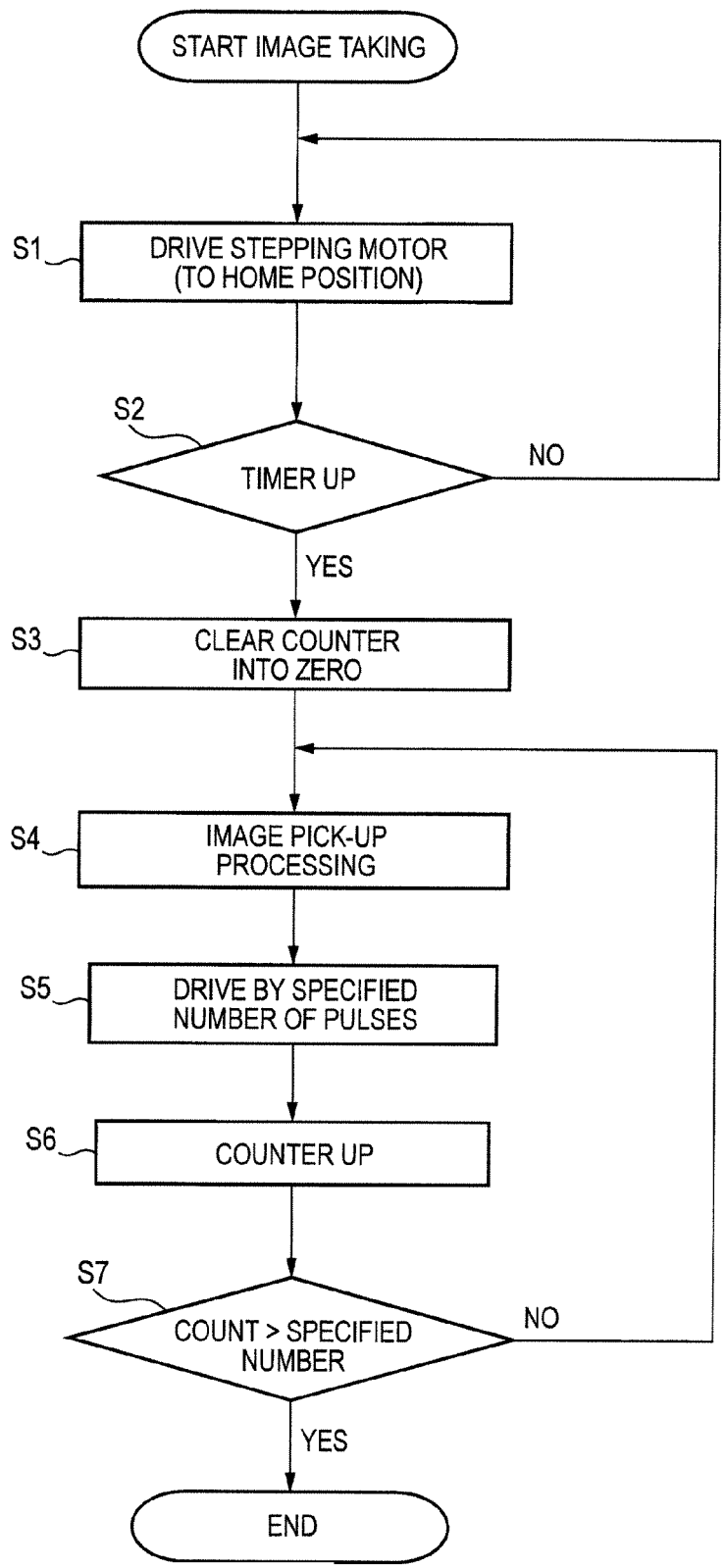
FIG. 75 is a flow chart showing a processing procedure of a control program executed by a CPU shown in FIG. 74.

FIG. 75 is a flow chart showing the processing procedure of a control program stored in the control memory 1151. When the power switch is turned ON, this control program is started. Then, first, the stepping motor 1128 is driven to the home position side (step S1). Here, the home position side indicates, for example, the state shown in FIG. 72 where the objective lens 617 is located on the tip side of the electronic endoscope 1101.

In this embodiment, for the purpose of cost reduction, a sensor is not provided that detects whether the stepping motor 1128 has reached the home position. Thus, at the next step S2, it is judged whether a timer for counting a predetermined time has counted up. Then, when the predetermined time has not yet elapsed, step S1 is executed repeatedly. In a configuration that a sensor for detecting reaching to the home position is provided, step S1 is merely executed repeatedly until reaching to the hone position is detected by the sensor.

Figure 76:
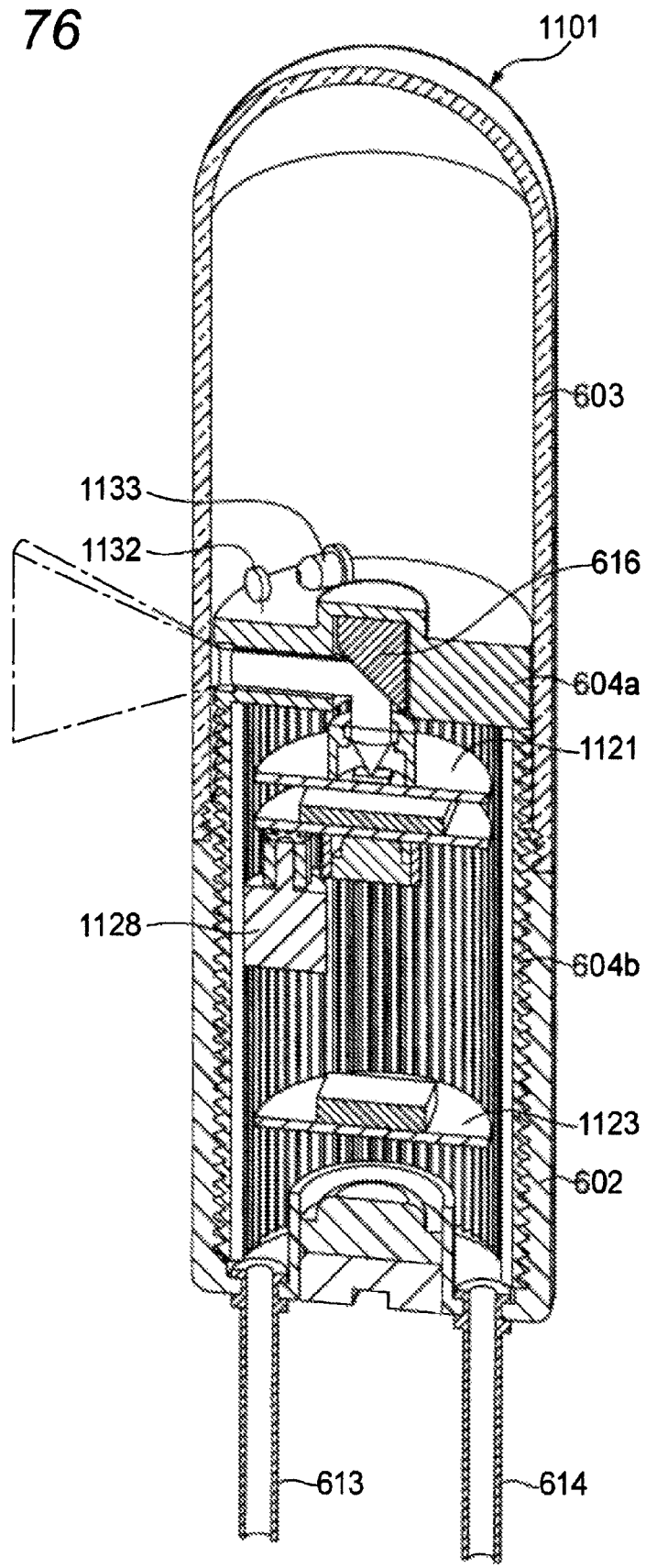
FIG. 76 is a longitudinal sectional view showing a state that a lens holder has been lowered to an image pick-up completion position.

It is sufficient that the predetermined time is defined as the longest time necessary for the stepping motor 1128 to reach the home position. For example, the state shown in FIG. 76 is a stare that the moving lens frame section 604 has revolved and moved to the lowermost position. Thus, the predetermined time may be defined as the time necessary from this state to a state that the moving lens frame section 604 has revolved in association with the revolution of the stepping motor 1128 so as to have reacted the home position (a position where the moving lens frame section 604 abuts against the inner peripheral surface of the hemispherical part 603a and hence cannot move further in this direction) shown in FIG. 72.

Figure 72:
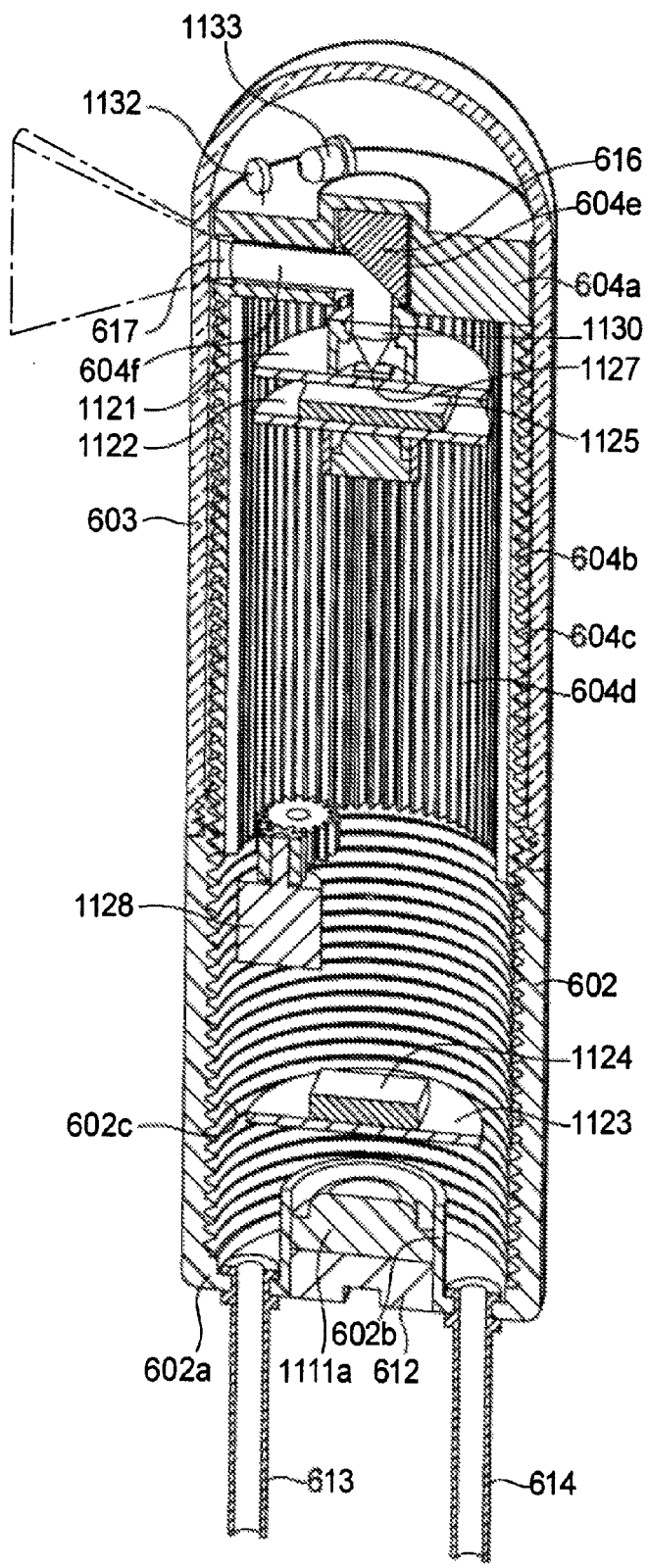
FIG. 72 is a longitudinal sectional view of an electronic endoscope shown in FIG. 70.

By virtue of this, even in a case that the moving lens frame section W4 is located wherever in the middle between the state shown in FIG. 72 and the state shown in FIG. 76 (a state that the lower end of the cylindrical member 604b abuts against the bottom part 602a of the body part 602), the objective lens 617 necessarily reaches the home position when the stepping motor 1128 is driven in the home position direction by the predetermined time.

When the timer has counted the predetermined time, the procedure goes from step S2 to step S3 where the contents of a counter described later is cleared into zero. Then, the procedure goes to step S4 where image pick-up processing is performed. In the image pick-up processing: the LED 1133 is turned ON so that light for illumination is projected through the objective lens 617; light reflected from the image-taking object is acquired through the objective lens 617 into the electronic endoscope 1101; and then the incident light from the image-taking object is focused onto the light acceptance surface of the imaging device 1127 so that an image is formed.

Then, the CPU 1141 drives the imaging device 1127 via the imaging device driver 1144 so as to acquire from the imaging device 1127 the image pick-up signal of the image-taking object obtained by the imaging device 1127, then performs image processing, and then transmits the obtained data to the second control unit 1124. Then, the CPU 1149 of the second control unit 1124 stores the data into the image memory 1126.

At the next step S5, the stepping motor 1128 is driven by a specified number of pulses. At the next step S6, this specified number of pulses is added to the count value in the counter. At the next step S7, the total count value in the counter is compared with a specified number.

Then, when the total count value in the counter does not reach the specified number, the procedure returns from step S7 to step S4 so that image pick-up processing is performed. After that, the processing loop of steps S4 to S7 is executed repeatedly. When the total count value in the counter has reached the specified number, the processing shown in FIG. 75 is terminated.

FIG. 77 is a diagram illustrating the movement of the field of view of image pick-up of the objective lens 617 in a case that step S4 in FIG. 75 is executed repeatedly. In the first occasion of image pick-up processing performed at the home position, an object image in the field of view indicated by "No. 001" in FIG. 77 is acquired from the imaging device 1127.

After the image pick-up for the object image of the field of view "No. 001", the stepping motor 1128 is driven at step S5 by a specified number of pulses. Thus, the cylindrical member 604b revolves by the specified number of pulses. As a result, the cylindrical member 604b is screwed and withdrawn into the body part 602. Thus, the next field of view is located at "No. 002" in FIG. 77. Then, an object image in this field of view is taken, and then the obtained image data is accumulated in the image memory 1126.

Figure 78:
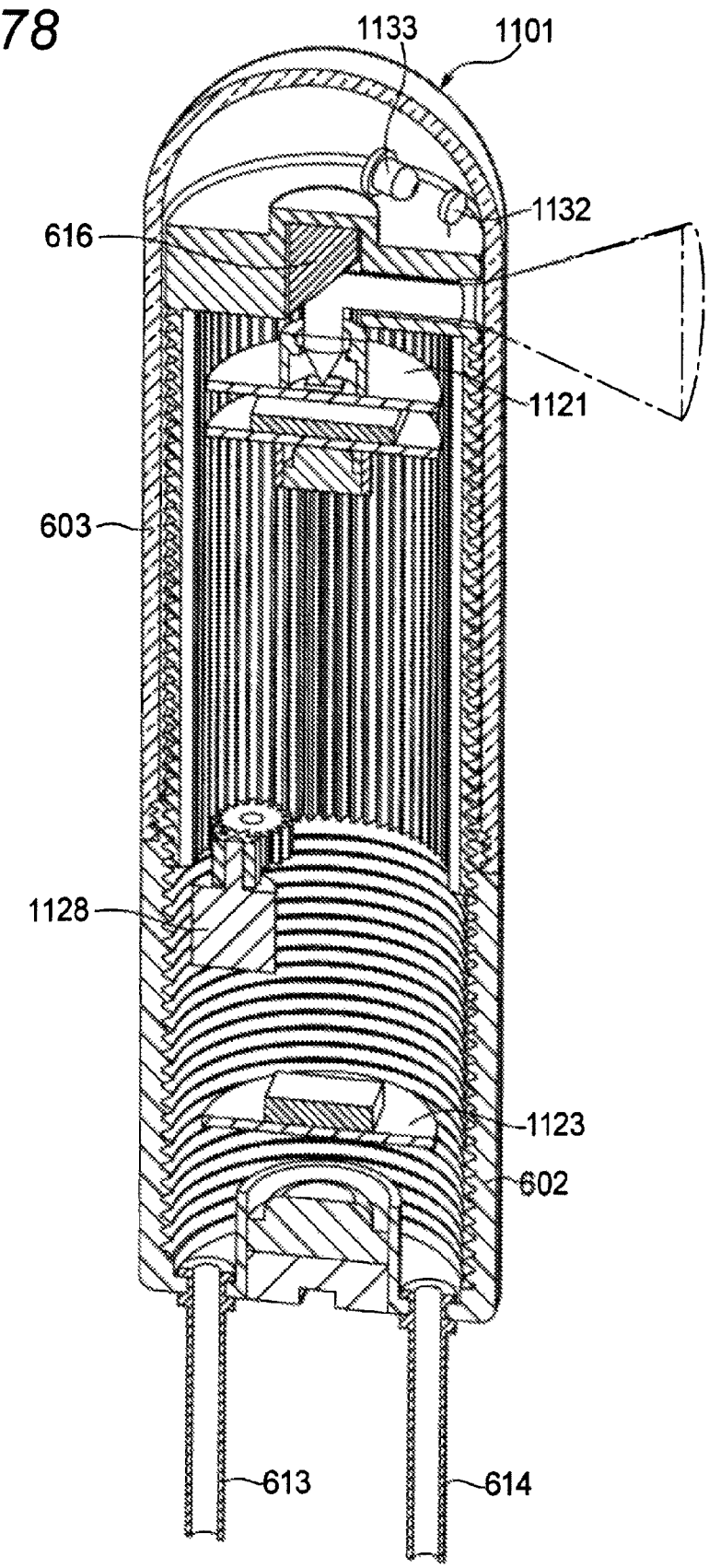
FIG. 78 is a longitudinal sectional view showing a state that a lens holder has gone half around from a state shown in FIG. 72.
Figure 79:
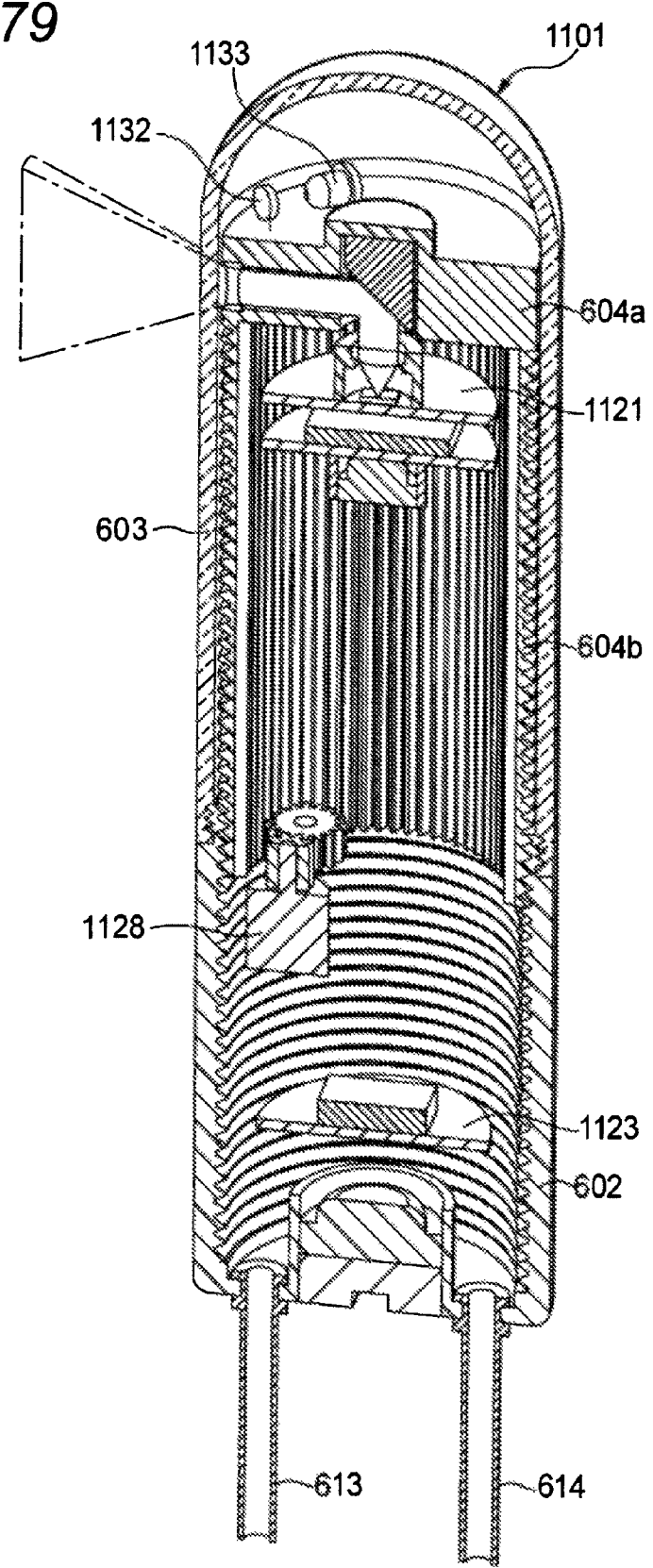
FIG. 79 is a longitudinal sectional view showing a state that a lens holder has gone one around from a state shown in FIG. 72.

After that during the operation of moving the field of view like No. 003→No. 004→No. 005 . . . , image pick-up processing and image data accumulation into the memory 1126 are repeated. FIG. 78 shows a state that the moving lens frame section 604 has gone half around inside the transparent capsule 603 starting from the state shown in FIG. 72. FIG. 79 shows a state of one around starting from the state shown in FIG. 72.

When the moving lens frame section 604 has gone one around from the home position within the transparent capsule 603, the field of view of image pick-up is located at No. 011 in FIG. 77. In case of having gone around twice, the field of view of image pick-up is located at No. 021 in FIG. 77.

Further, FIG. 76 shows a state that the lower end of the cylindrical member 604b abuts against the bottom part 602a of the body part 602 and hence cannot move further in this direction. When the state shown in FIG. 76 is reached, the processing loop of repeating the image pick-up processing (step S4) is terminated. Accordingly, the "specified number" used at step S7 in FIG. 75 is equal to the total number of pulses necessary for reaching from the home position to the state shown in FIG. 76.

Once image pick-up by the electronic endoscope 1101 is completed, the data accumulated in the image memory 1126 is to be read to the outside.

In the electronic endoscope 1101 described above, the objective mirror 616 is provided on the center axis. Then, the light acceptance surface of the imaging device 1127 is provided on this center axis, and the image pick-up hole 604f is provided straight in a radial direction. By virtue of this, the objective mirror 616 bends the optical path by 90 degrees so that the light beam enters the imaging device 1127 on the center axis. In contrast, in the present example, the mutual positional relation between the objective lens 617, the objective mirror 616, and the imaging device 1127 is fixed regardless of the revolution of the moving lens frame section 604. Thus, the position of the imaging device 1127, the position of the objective mirror 616, its reflection angle, and the direction of the image pick-up hole 604f may be set up arbitrarily as long as they do not interfere with the revolution motion of the moving lens frame section 604.

Further, the above-mentioned description has been given for a case that the incident light is brought into the form of a parallel light beam by the objective lens 617 and then is reflected by the objective mirror 616 with maintaining the form of a parallel light beam. However, since the mutual position relation between the objective lens 617, the objective mirror 616, and the imaging device 1127 is fixed, the form of the light beam is not limited to a parallel beam. Thus, a zoom lens may be inserted in the middle of the optical path so that an enlarged image corresponding to the original image may be acquired.

As described above with reference to the electronic endoscope 1101 serving as an example, the present specification has disclosed an electronic endoscope characterized by comprising: a transparent cover at least whose observation window in a cylindrical part is transparent; a body part that has a cylindrical part provided continuously to the cylindrical part of the transparent cover; a lens holder that revolves about the center axis of the transparent cover in the inside of the transparent cover and the body part so as to move in the direction of the center axis; an objective mirror that is provided in the lens holder and that reflects, toward the body part, light entering through an objective lens provided at a position facing the cylindrical part of the transparent cover; an imaging device that is fixed and mounted in the lens holder and that receives the light reflected from the objective mirror so as to convert the light into an electric signal; and a driving section that is provided inside the body part and that drives and revolves the lens holder so as to drive the lens holder in the center axis direction.

Further, the present specification has disclosed an electronic endoscope characterized in that the lens holder includes: a disk-shaped member on which the objective lens is mounted and the objective mirror is mounted; and a cylindrical member provided integrally and continuously to the body part side of the disk-shaped member.

Further, the present specification has disclosed an electronic endoscope characterized by comprising: a female screw that is engraved spirally in the inner peripheral surface of the body part; and a male screw that is engraved spirally in the outer peripheral surface of the cylindrical member, that engages with the female screw and that, when the cylindrical member is driven and revolved by the driving section, moves the cylindrical member in the center axis direction.

Further, the present specification has disclosed an electronic endoscope characterized in that a control section that performs image processing onto the image signal acquired by image pick-up performed by the imaging device and that transmits by wireless the image data having undergone the image processing is fixed and mounted in the lens holder.

Further, the present specification has disclosed an electronic endoscope characterized in that an image memory which receives and stores the image data transmitted by wireless as described above is provided in the body part.

Further, the present specification has disclosed an electronic endoscope characterized in that the transparent cover and the body part are provided continuously to each other by screwing in a manner permitting disassembly.

Further, the present specification has disclosed an electronic endoscope characterized in that the drive power supply for the imaging device and the drive power supply for the driving section are provided as separate members.

Figure 80:
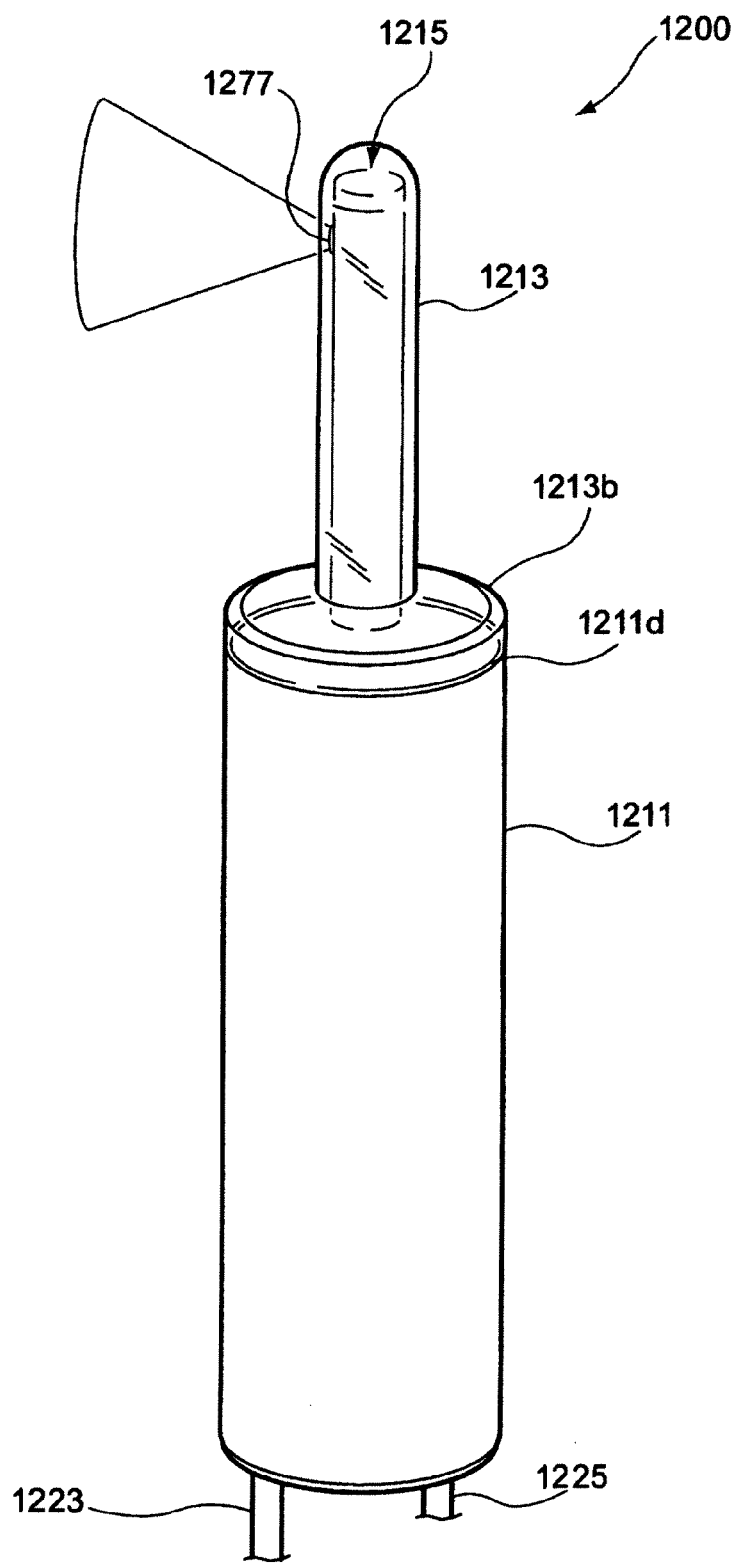
FIG. 80 is an external appearance perspective view of another example of an electronic endoscope used for describing an embodiment of the present invention.

The electronic endoscope 1200 shown in FIG. 80 includes: a body part 1211 serving as an outer shell; a transparent cover 1213 having a tube body at least whose side surface has transparency; an introductory optical part 1215 accommodated inside the outer shell; and an image pick-up drive unit part 1217 (see FIG. 81) serving as an image pick-up section described later.

Figure 81:
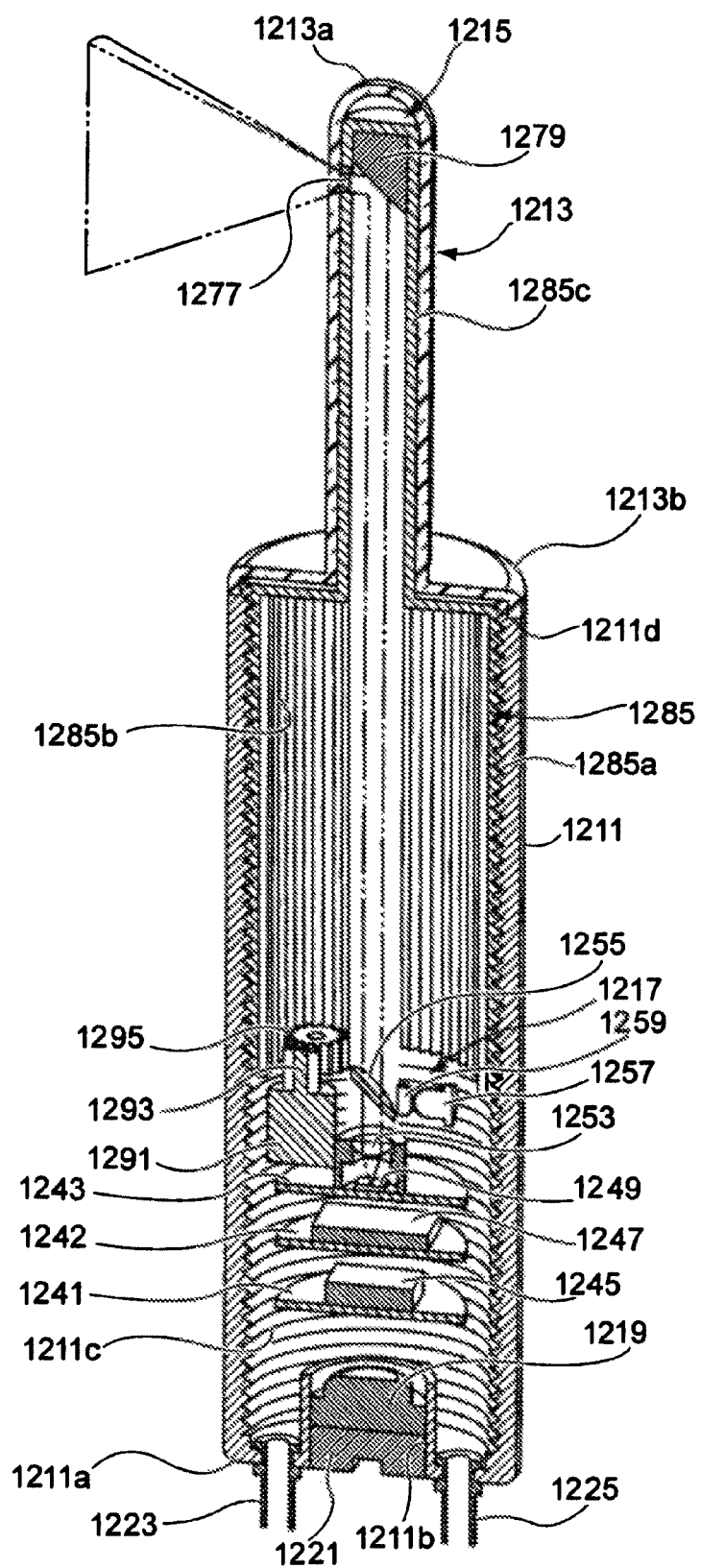
FIG. 81 is a longitudinal sectional view of an electronic endoscope shown in FIG. 80.
Figure 82:
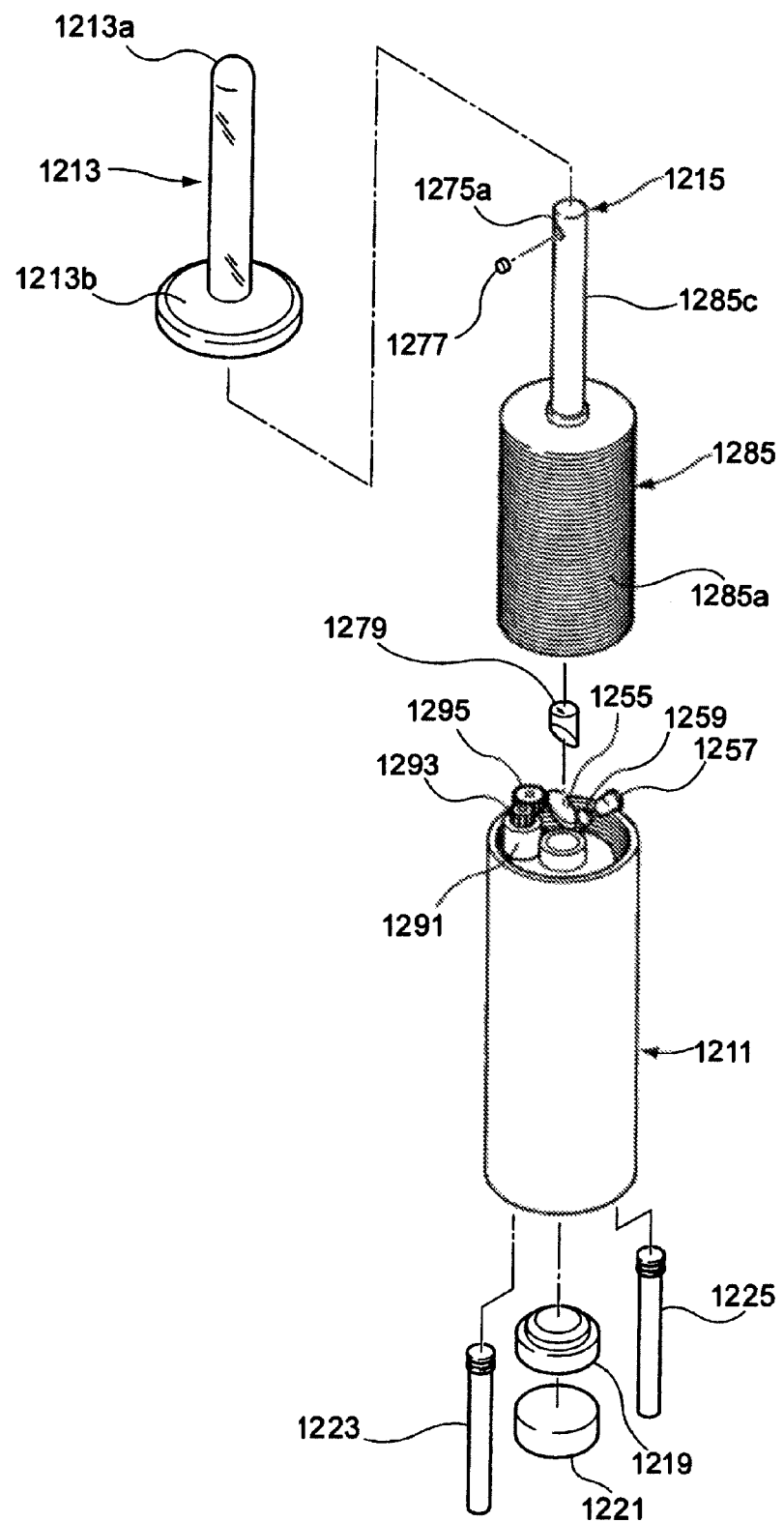
FIG. 82 is an exploded perspective view of an electronic endoscope shown in FIG. 80.

FIG. 81 is a longitudinal sectional view of the electronic endoscope 1200. FIG. 82 is an exploded perspective view of the electronic endoscope 1200. The body part 1211 is formed in a closed-bottom cylindrical shape fabricated from resin material or the like. Its bottom part (lower side in FIG. 81) 1211a is provided with a tube-shaped battery accommodating part 1211b. After a power battery 1219 is mounted, the battery accommodating part 1211b is airtightly closed by a battery lid 1221.

Further, in the bottom part 1211a, in the example shown in the figure, two hard grip pipes 1223 and 1225 fabricated from resin are fixed in a protruding manner toward the outside. Then, when the grip pipes 1223 and 1225 are manipulated by hand, the entirety of the electronic endoscope 1200 is inserted into or extracted from a hole or an abdominal cavity serving as a subject. The electronic endoscope 1200 may be used in a configuration that wiring is inserted through the grip pipes 1223 and 1225.

The transparent cover 1213 is formed from hard transparent resin. Its one-end part (tip part) is closed and formed in a smooth hemispherical shape that permits easy insertion into the inside of a subject. An open end part 1213b that is located on the side opposite to the hemispherical part 1213a and has an expanded diameter and an open end part 1211d of the body part 1211 are aligned to each other and fixed by bonding. The transparent cover 1213 may be fabricated by integral molding. Alternatively, the hemispherical part 1213a, the open end part 1213b, and the lace may be fixed to the transparent cylinder body by bonding in a multi-piece configuration. Further, light shielding property may be imparted to the hemispherical part 1213a so that it may be prevented that external light is introduced directly into the objective lens 1277. Here, it is sufficient that the transparent resin is transparent to light at a particular wavelength. That is, the material need not be transparent to visible light.

The transparent cover 1213 having the above-mentioned configuration so as to cover the introductory optical part 1215 is formed in a smaller diameter than the body part 1211. Further, one-end side of the transparent cover 1213 in the form of a tube body has a smaller diameter than the body part 1211. Thus, a stepped part (open end part 1213b) whose diameter expands in the radial direction of the transparent cover 1213 is formed in a part of the outer shell. That is, the stepped part is formed by the diameter difference between the transparent cover 1213 and the body part 1211. When the diameter is reduced in the tip of the electronic endoscope 1200 as described here, observation of the inside of the subject becomes easy. This extends the range of application of the electronic endoscope, like observation of a site having an extremely small diameter in the subject. Here, the transparent cover 1213 may be in the form of a frontward-tapered shape having a stepped part. This configuration permits much easier insertion of the tip insert part of the body part 1211 into a small hole or a small abdominal cavity.

In the inside of the body part 1211, a lens drive ring 1285 serving as a cylindrical revolving body is arranged. On the transparent cover 1213 side (upper side in the figure) of the lens drive ring 1285, a moving lens frame 1285*c* connected to the introductory optical part 1215 is provided continuously. On the tip side of the moving lens frame 1285*c*, objective lens holding hole 1275*a* serving as an image pick-up hole is formed. Then, an objective lens 1277 is fixed to the objective lens holding hole 1275*a* and then acquire light (object light) from the transparent cover 1213 side. The light acquired from the sideward region through the objective lens 1277 is brought into the form of a parallel light beam, then projected onto the objective mirror 1279 fixed to the inner surface of the moving lens frame 7285*c*, then reflected by the 45-degree-oblique reflecting surface of the objective mirror 1279, and then travels toward the imaging device 1249 along the center axis of the transparent cover 1213 with maintaining the form of a parallel light beam.

Figure 83:
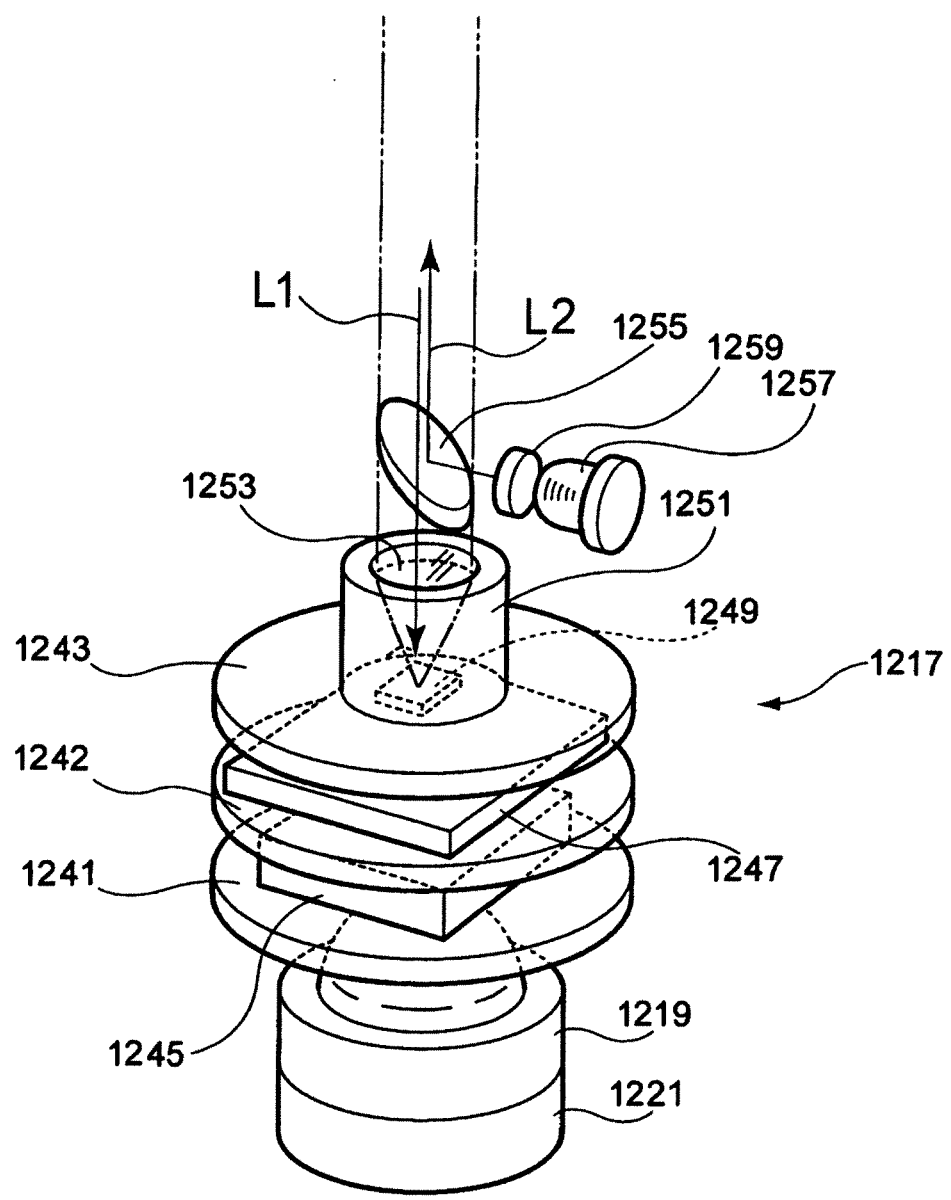
FIG. 83 is an enlarged perspective view showing a main part of an electronic endoscope shown in FIG. 80.

FIG. 83 shows an enlarged perspective view of a part containing the image pick-up drive unit part 1217. On the base plate 1241 in the lowermost layer (on the bottom part 1211*a* side), a control unit 1245 is arranged that includes a driver circuit for the stepping motor serving as a driving source of the raising and lowering driving section. On the base plate 1242 in the middle layer, an image memory 1247 for storing pick-up image data is arranged. On the base plate 1243 in the upper layer, an imaging device 1249 is arranged that is composed of a solid-state imaging device such as a CCD type imaging device and a CMOS type imaging device.

On the base plate 1243, a focusing lens holder 1251 formed in a cylindrical shape is arranged. Then, the imaging device 1249 is accommodated inside the focusing lens holder 1251. Then, a focusing lens 1253 is arranged in the upper-end opening part of the focusing lens holder 1251. Thus, the guided parallel light beam (object light) L1 is focused onto the light acceptance surface of the imaging device 1249 by the focusing lens 1253 so that an image is formed.

Further, a half mirror 1255 is arranged in the middle of the optical path between the introductory optical part 1215 and the imaging device 1249 so that an illumination optical system is added. In the illumination optical system, the emitted light from the light emitting diode (LED) 1257 serving as a light emitting body is projected as light for illumination L2 toward the introductory optical part 1215 after the reflection by the half mirror 1255. That is, the half mirror 1255 is arranged at a position in the immediate upstream of the focusing lens 1253 within the parallel light beam entering the focusing lens 1253 in a state that the half mirror 1255 is inclined by 45 degrees relative to the optical axis of the parallel light beam (the center axis of the body part 1211). Then, an illumination lens 1259 for bringing the light for illumination the form of a parallel light beam is arranged between the LED 1257 and the half mirror 1255. The half mirror 1255, the illumination lens 1259, and the LED 1257 are fixed inside the body part 1211 individually by appropriate support members (not shown).

Figure 84A:
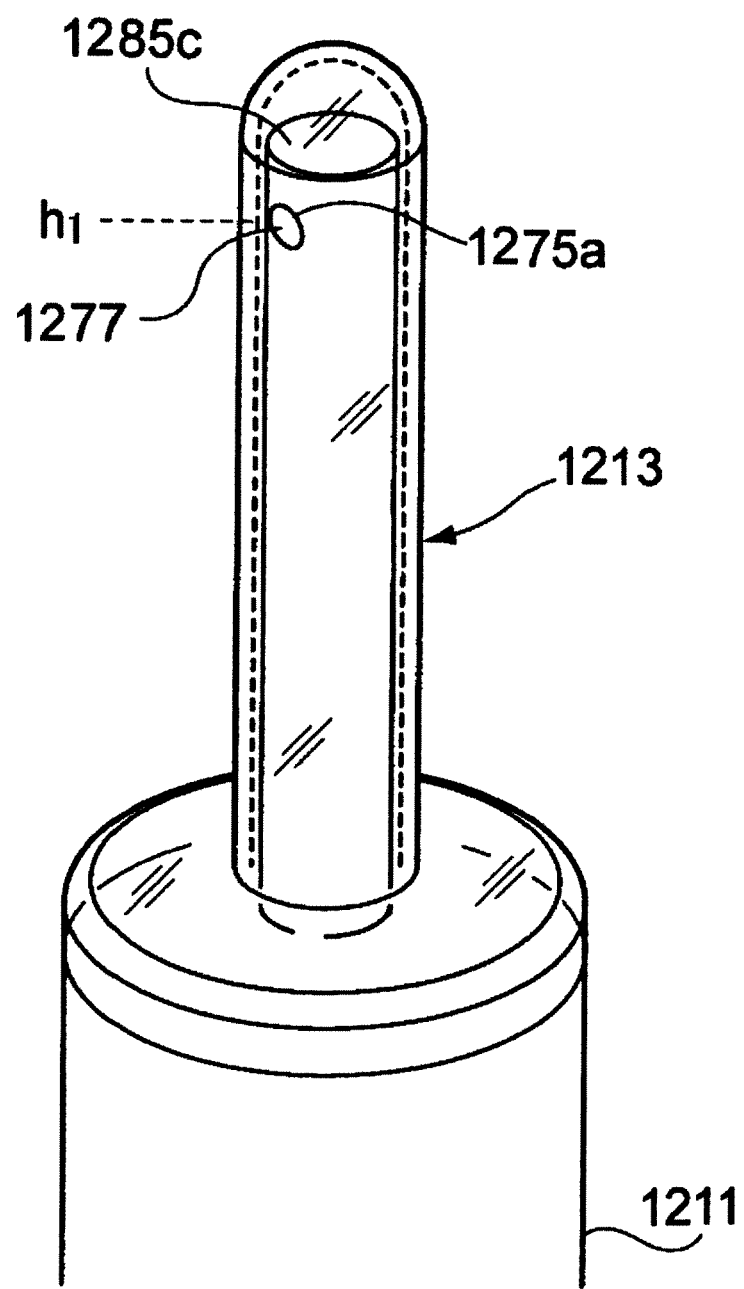
FIG. 84A is an enlarged perspective part view showing operation of a moving lens frame provided with an objective lens in a state that the moving lens frame is located at a raised position.
Figure 84B:
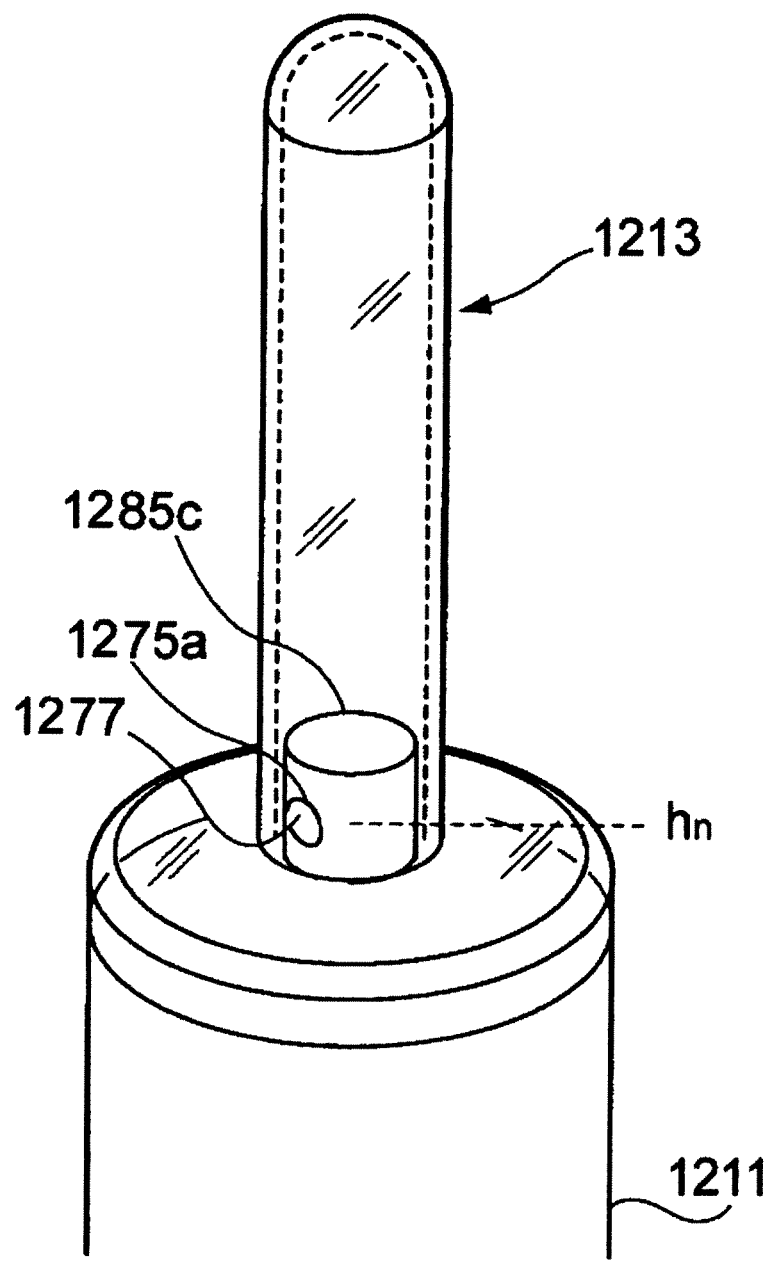
FIG. 84B is an enlarged perspective part view showing operation of a moving lens frame provided with an objective lens in a state that the moving lens frame is located at a lowered position.

FIGS. 84A and 84B are diagrams showing operation of the moving lens frame provided with the objective lens. FIG. 84A is an enlarged perspective view of a pan showing a raised position. FIG. 84B is an enlarged perspective view of a part showing a lowered position. The introductory optical part 1215 revolves about the center axis of the transparent cover 1213 and, in accordance with this rises or goes lower in the axis direction in the inside of the transparent cover 1213. The introductory optical part 1215 is provided at the tip of the tube-shaped moving lens frame 1285*c*, and projects light for illumination toward the side along a spiral trajectory formed in association with the motion that the objective lens 1277 arranged on the side part of the moving lens frame 1285*c* revolves and moves in the axis direction. At the same time, the introductory optical part 1215 acquires reflected light from the sideward region so as to transfer the object light to the imaging device 1249. As shown in FIGS. 81 and 82, the introductory optical part 1215 is integrated with the lens drive ring 1285 via the cylindrical moving lens frame 1285*c*, and hence moves in linkage with the revolution motion and the raising and lowering motion of the lens drive ring 1285.

Next, a movement mechanism for the lens drive ring 1285 having the introductory optical part 1215 is described below. As shown in FIGS. 81 and 82, in the inner peripheral surface of the body part 1211, a precision female screw 1211*c* is engraved about the axis of the body part 1211. Then, the lens drive ring 1285 provided with a male screw 1285*a* is screwed into the female screw 1211*c*. Then, in association with its revolution, the lens drive ring 1285 advances or retreats in the axial direction. Further, an annular gear 1285*b* is formed in the inner peripheral surface of the lens drive ring 1285. In the annular gear 1285*b*, gear teeth that are in parallel to the axis and that extend over the entire length in the axial direction of the lens drive ring 1285 are formed in the circumferential direction at equal intervals.

A stepping motor 1291 is mounted on the base plate 1243 in the uppermost layer (on the side opposite to the bottom part 1211*a* side). Then, a motor gear wheel (spur wheel) 1293 is attached to the shaft of the stepping motor 1291. The axis of revolution of the stepping motor 1291 is oriented in parallel to the center axis of the lens drive ring 1285 (the optical axis of the parallel light beam). The motor gear wheel 1293 engages with an idle gear wheel 1295 composed of a spur wheel.

The shaft of the idle gear wheel 1295 is pivotally supported in a revolvable manner in a direction perpendicular to the base plate 1243. The idle gear wheel 1295 has a larger number of gear teeth than the motor gear wheel 1293. Thus, the revolution of the stepping motor 1291 is slowed down and then transmitted to the idle gear wheel 1295. The idle gear wheel 1295 engages with the annular gear 1285*b* provided in the inner peripheral surface of the lens drive ring 1285.

Figure 85A:
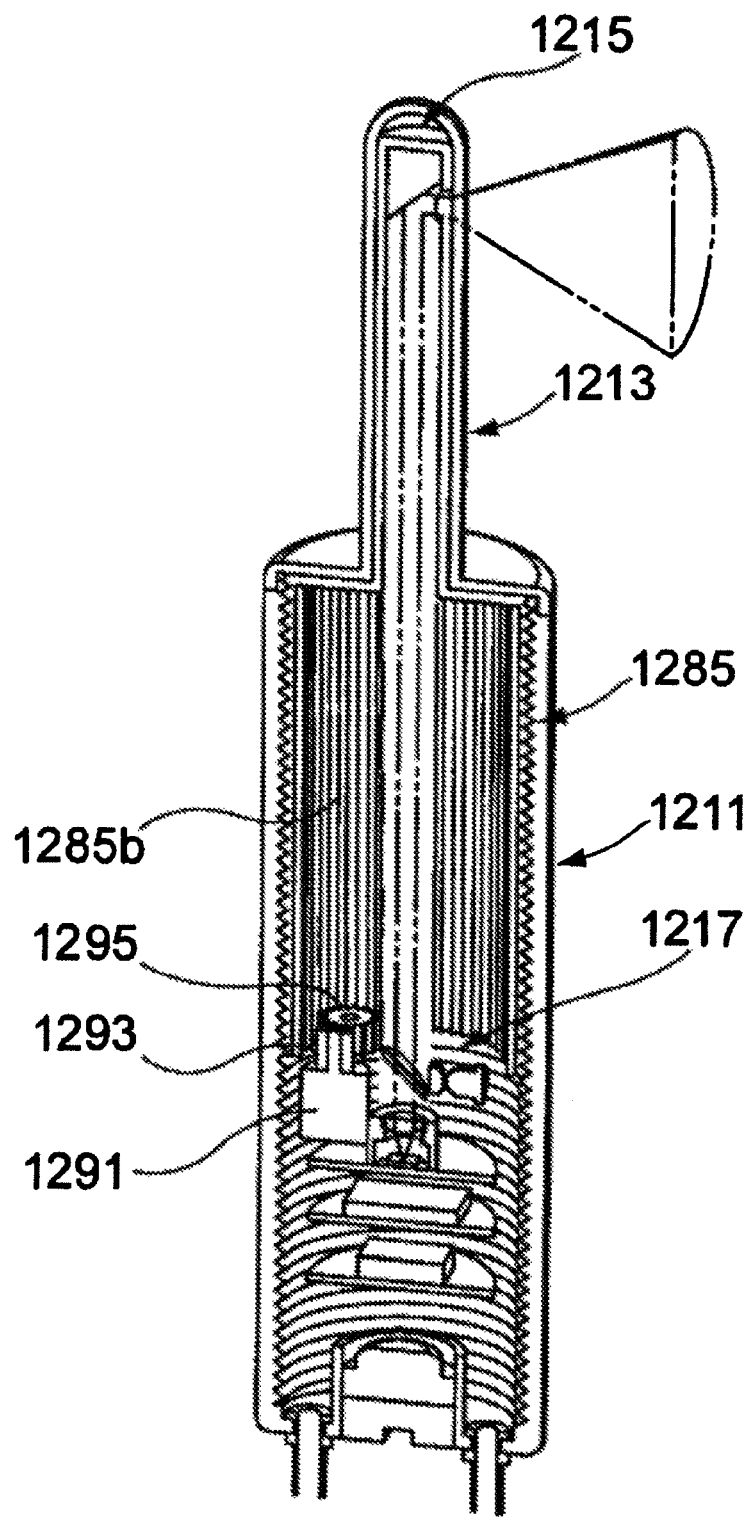
FIG. 85A is a sectional view showing operation of a moving lens frame provided with an objective lens in a state of having gone half around from a revolution start position.
Figure 85B:
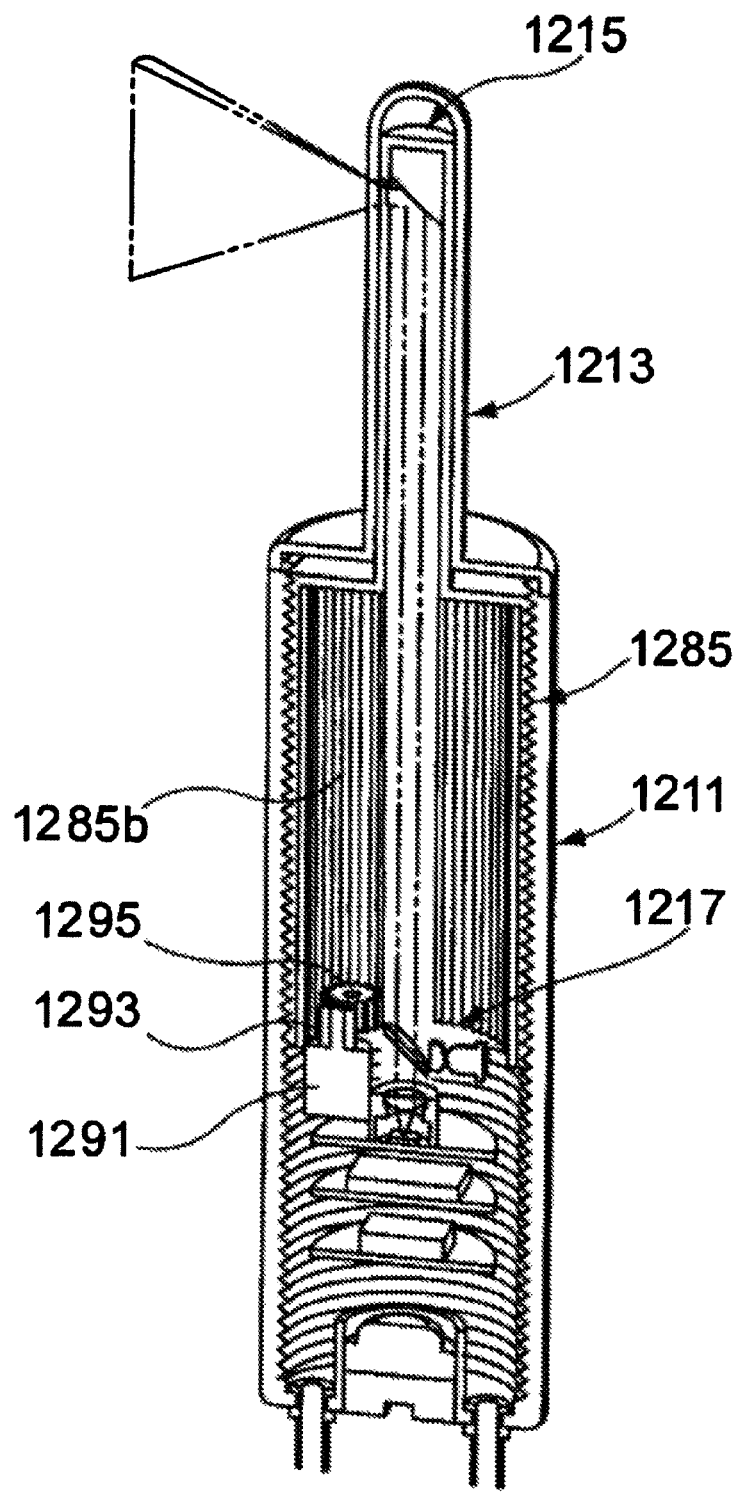
FIG. 85B is a sectional view showing operation of a moving lens frame provided with an objective lens in a state of having gone one around from a revolution start position.
Figure 85C:
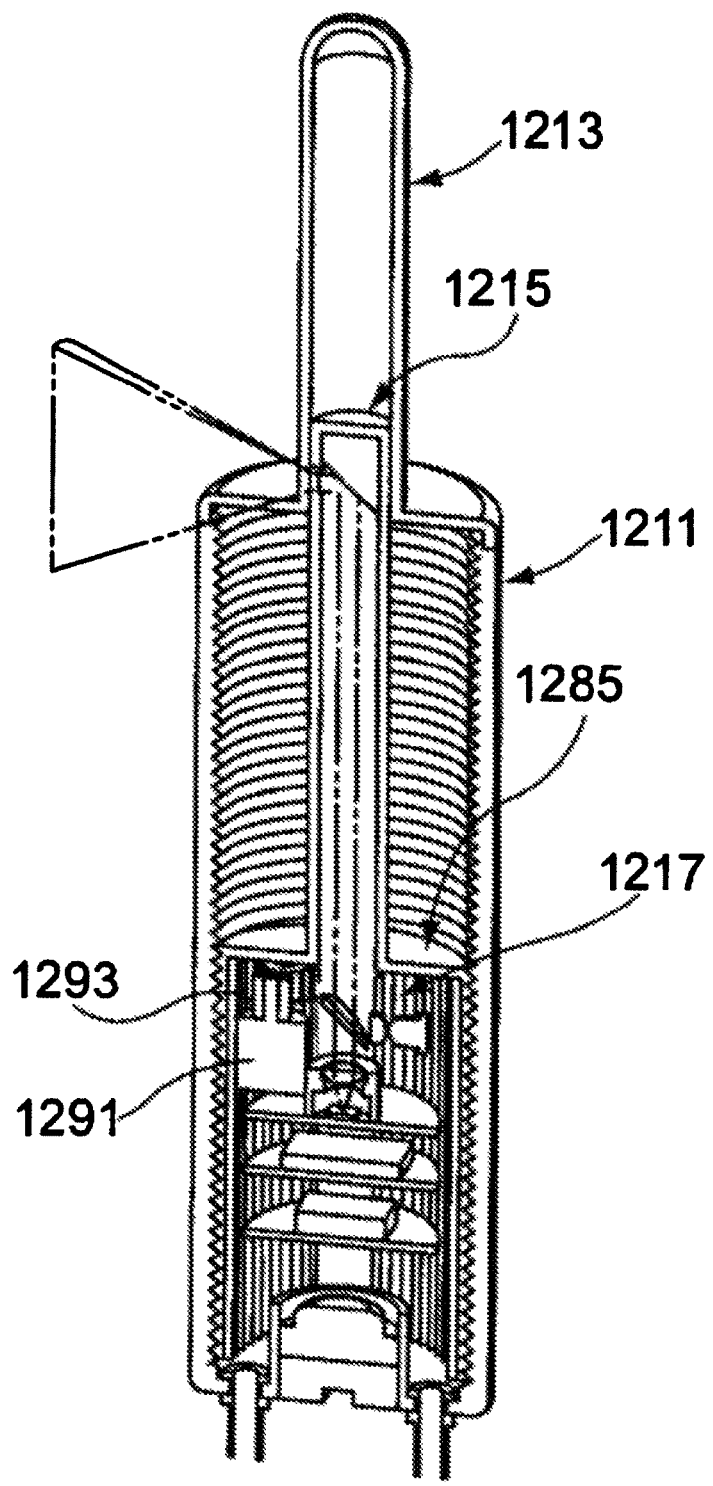
FIG. 85C is a sectional view showing operation of a moving lens frame provided with an objective lens in a state of being located at a retarded position where revolution has been completed.

FIGS. 85A to 85C are explanation diagrams for the operation of the electronic endoscope 1200. FIG. 85A shows a state that the lens drive ring 1285 has gone half around from the revolution start position. FIG. 85B shows a state that the lens drive ring 1285 has gone one around from the revolution start position. FIG. 85C shows a retreated position where the lens drive ring 1285 has terminated the revolution. When the stepping motor 1291 is driven so that the motor gear wheel 1293 is revolved, the idle gear wheel 1295 revolves so that the lens drive ring 1285 revolves. When the lens drive ring 1285 revolves, depending on the direction of the revolution, the lens drive ring 1285 is raised or lowered in the axial direction in the inside of the body part 1211. As such, the moving lens frame 1285*c* revolves, and moves in the axial direction in the inside of the transparent cover 1213. Thus, the moving lens frame 1285*c* revolves, and goes straight gradually. By virtue of this, information on the entire field is reflected by the objective mirror 1279, and then acquired through the focusing lens 1253 into the imaging device 1249. The information on the imaging device 1249 is transmitted to the image memory 1247 in appropriate timing, so that information on the entire field is obtained.

As described above, the annular gear 1285*b*, the motor gear wheel 1293, the idle gear wheel 1295, and the stepping motor 1291 constitute a raising and lowering driving section serving as a revolution driving section. Further, the female screw 1211*c*, the lens drive ring 1285, the male screw 1285*a*, and the raising and lowering driving section constitute a driving section.

The electronic endoscope 1200 has a power switch (not shown). When the power switch is turned ON, electric power from the power battery 1219 is supplied through wiring (not shown) to the individual parts of the image pick-up drive unit part 1217, so that image pick-up operation and drive operation are performed as described later.

For example, the power switch may be provided in the bottom part 1211a of the body part 1211, and may be turned ON or OFF by manual operation. Alternatively, a switch terminal that follows magnetism may be built in the body part 1211. Then, from the outside of the electronic endoscope 1200, a magnet may be brought close or apart so that the switch terminal may be turned ON or OFF.

Figure 86:
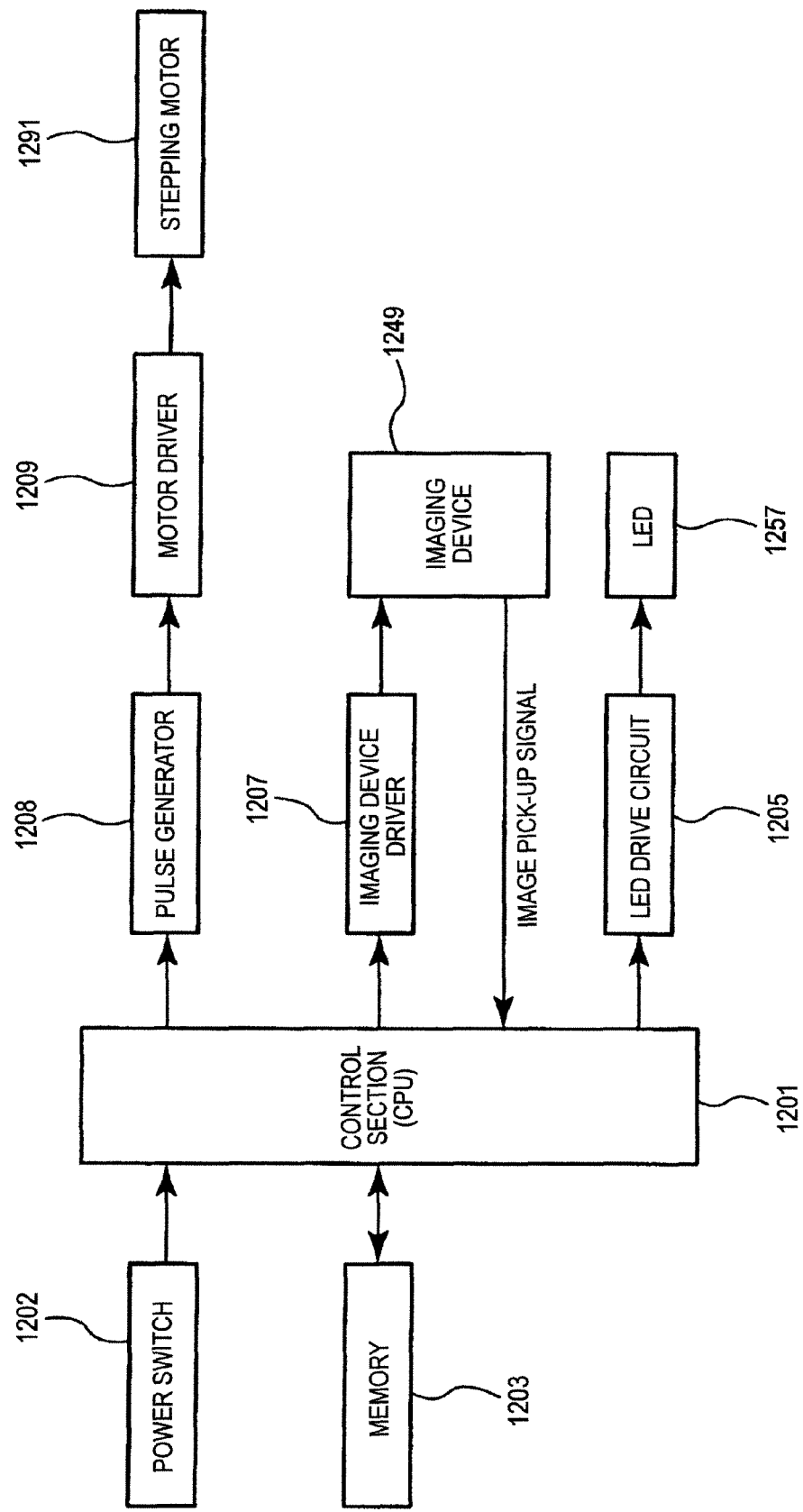
FIG. 86 is a functional block diagram showing an image pick-up drive unit part.

FIG. 86 is a functional block diagram showing the image pick-up drive unit part 1217. The control section (CPU) 1201 for collectively controlling the entire system is connected to a memory 1203 that stores a control program and serves also as a work memory and that contains the image memory 1247 provided on the base plate 1242 described in FIG. 83; an LED drive circuit 1205 for driving the LED 1257; an imaging device driver 1207 for driving the imaging device 1249; and a pulse generator 1208 for providing driving pulses to the motor driver 1209 for driving the stepping motor 1291. Image data obtained by image processing in the control section 1201 is stored into the image memory 1247 built in the body part 1211. This permits acquisition of an image by the electronic endoscope 1200 in a stand alone mode. Thus, operability is improved in comparison with a system where the image data is sequentially transmitted to the outside.

When the power switch 1202 is turned ON, electric power is supplied from the power battery 1219 to the individual parts so that operation is started. Thus, the stepping motor 1291 is driven and revolved. Accordingly, the moving lens frame 1285c is revolved in the inside of the electronic endoscope 1200 so as to advance or retreat in the axial direction. Further, emitted light from the LED 1257 is focused into the form of a parallel light beam by the illumination lens 1259. Then, the parallel light beam is reflected toward the objective mirror 1279 by the half mirror 1255, and then the parallel light beam reflected by the objective mirror 1279 is projected toward the image-taking object through the objective lens 1277 so as to serve as light for illumination.

The reflected light from the image-taking object is acquired through the objective lens 1277 into the electronic endoscope 1200. Then, the optical image of the image-taking object reflected by the objective mirror 1279 travels to the focusing lens 1253 in the form of a parallel light beam, and then is focused onto the light acceptance surface of the solid-state imaging device 1249 by the focusing lens 1253 so that an image is formed.

The image pick-up signal of the image-taking object acquired by the imaging device 1249 is acquired into the CPU 1201 so as to undergo image processing, and then stored into the image memory 1247, for example, in the form of JPEG image data.

Figure 87:
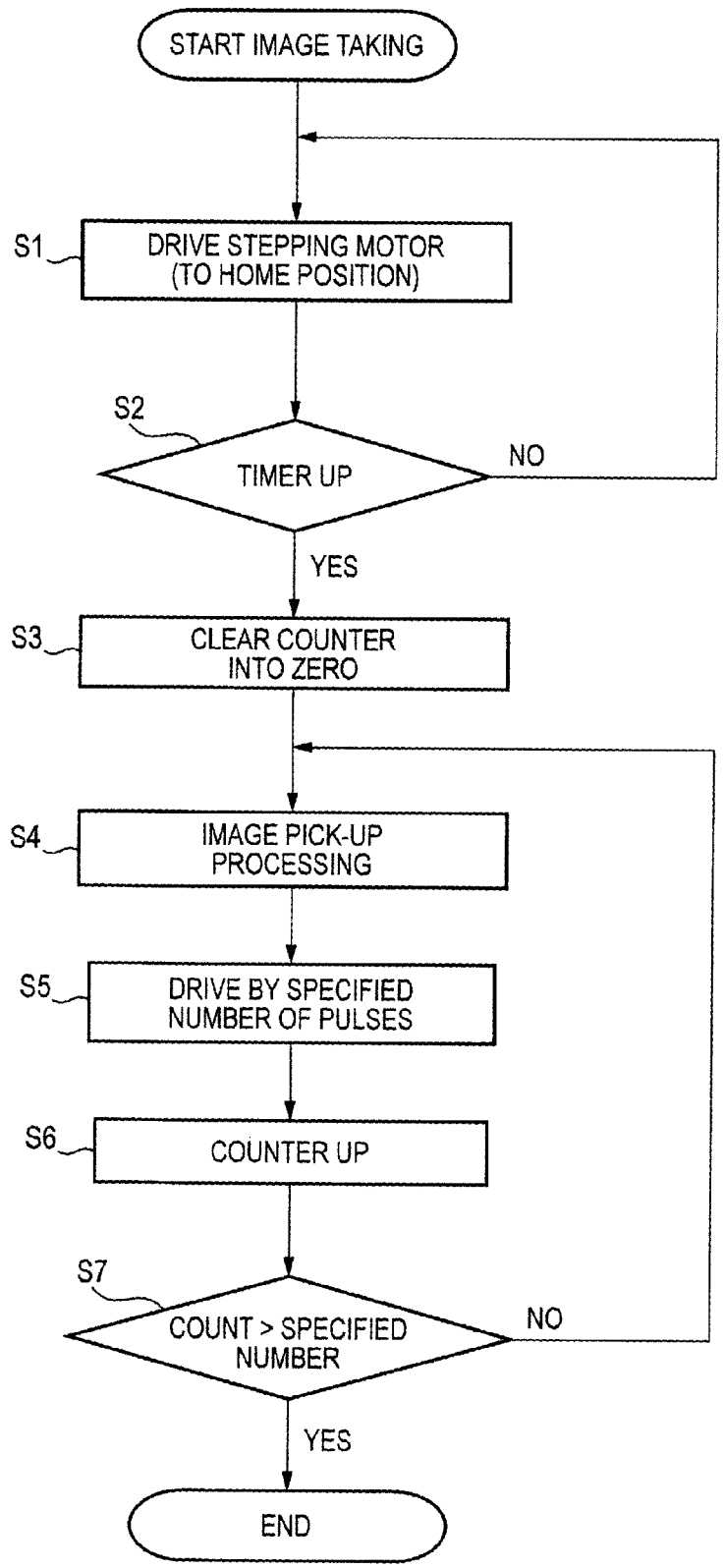
FIG. 87 is a flow chart showing a processing procedure of a control program stored in a memory.

FIG. 87 is a flow chart showing the processing procedure of a control program stored in the memory 1203. When the power switch 1202 is turned ON, this control program is started. Then, first, the stepping motor 1291 is driven to the home position side (step S1). Here, the home position side indicates, for example, the state shown in FIG. 84A where the objective lens 1277 is located on the tip side of the electronic endoscope 1200.

In the electronic endoscope 1200, a sensor is not provided that detects whether the stepping motor 1291 has reached the home position. Thus, at the next step S2, it is judged whether a timer for counting a predetermined time has counted up.

Then, when the predetermined time has not yet elapsed, step S1 is executed repeatedly. In a configuration that a sensor for detecting reaching to the home position is provided, step S1 is merely executed repeatedly until reaching to the home position is detected by the sensor.

It is sufficient that the predetermined time is defined as the longest time necessary for the stepping motor 1291 to reach the home position. For example, the state shown in FIG. 84B is that the moving lens frame 1285c has revolved and thereby reached the lowermost position hn. Then, the predetermined time may be defined as the time necessary for a process that, starting from the lowermost position, the moving lens frame 1285c revolves in association with the revolution of the stepping motor 1291 so as to reach the home position (a position where the moving lens frame 1285c is not allowed to travel further in that direction, for example, because of abutting against the tip of the transparent cover 1213) h1 shown in FIG. 84A.

By virtue of this, even in a case that the moving lens frame 1285c is located wherever in the middle between the state shown in FIG. 84A and the state shown in FIG. 84B (a state that the lower end of the lens drive ring 1285 abuts against the bottom part 1211a of the body part 1211), the objective lens 1277 necessarily reaches the home position when the stepping motor 1291 is driven in the home position direction by the predetermined time.

When the timer has counted the predetermined titre, the procedure goes from step S2 to step S3 where the contents of a counter described later is cleared into zero. Then, the procedure goes to step S4 where image pick-up processing is performed. In the image pick-up processing: the LED 1257 is turned ON so that light for illumination is projected through the objective lens 1277; light reflected from the image-taking object is acquired through the objective lens 1277 into the electronic endoscope 1200; and then the incident light from the image-taking object is focused onto the light acceptance surface of the imaging device 1249 so that an image is formed.

Then, the CPU 1201 drives the imaging device 1249 via the imaging device driver 1207 so as to acquire from the imaging device 1249 the image pick-up signal of the image-taking object obtained by the imaging device 1249, then performs image processing on the signal, and then stores the data into the image memory 1247.

At the next step S5, the stepping motor 1291 is driven by a specified number of pulses. At the next step S6, this specified number of pulses is added to the count value in the counter. At the next step S7, the total count value in the counter is compared with a specified number.

Then, when the total count value in the counter does not reach the specified number, the procedure returns from step S7 to step S4 so that image pick-up processing is performed. After that, the processing loop of steps S4 to S7 is executed repeatedly. When the total count value in the counter has reached the specified number, the processing shown in FIG. 87 is terminated.

FIG. 88 is a diagram illustrating the movement of the field of view of image pick-up of the objective lens 1277 in a case that step S4 in FIG. 87 is executed repeatedly. In the first occasion of image pick-up processing performed at the home position, an object image in the field of view indicated by "No. 001" in FIG. 88 is acquired from the imaging device 1249.

After the image pick-up for the object image of the field of view "No. 001", the stepping motor 1291 is driven at step S5 by a specified number of pulses. Thus, the lens drive ring 1285 revolves by the specified number of pulses. As a result, the lens drive ring 1285 is screwed and withdrawn into the body part 1211. Thus, the next field of view is located at "No. 002" in FIG. 88. Then, an object image in this field of view is taken, and then the obtained image data is accumulated in the image memory 1247.

After that, during the operation of moving the field of view like No. 003→No. 004→No. 005 . . . , image pick-up processing and image data accumulation into the memory 1203 are repeated. FIG. 85A shows a state that the moving lens frame 1285c has gone half around inside the transparent cover 1213 starting from the state shown in FIG. 85B. When the moving lens frame 1285c has gone one around from the home position inside the transparent cover 1213, the field of view of image pick-up is located at No. 011 in FIG. 88. In case of having gone around twice, the field of view of image pick-up is located at No. 021 in FIG. 88.

Further, FIG. 85C shows a state that the lower end of the lens drive ring 1285 abuts against the bottom part 1211a of the body part 1211 and hence cannot move further in this direction. When the state shown in FIG. 85C is reached, the processing loop of repeating the image pick-up processing (step S4) is terminated. Accordingly, the "specified number" used at step S7 in FIG. 87 is equal to the total number of pulses necessary for reaching from the home position to the state shown in FIG. 85C.

In the example of movement of the field of view of image pick-up illustrated in FIG. 88, the specified number of pulses at step S5 in FIG. 87 is set up such that in the direction of revolution of the moving lens frame 1285c serving as a revolving body, adjacent fields of view of image pick-up are positioned such that their left and right edge pans should be in contact with each other or overlapping somewhat with each other. Further, the pitch of the screw threads provided in the inner peripheral surface of the body part 1211 and the outer peripheral surface of the lens drive ring 1285 is designed such that axially adjacent fields of view of image pick-ups are positioned such that their upper and lower edge parts should be in contact with each other or overlapping somewhat with each other.

By virtue of this, without a missing part over the entirety of the cylindrical field of view region of the inner peripheral surface of the image-taking object serving as an observation object, image pick-up is achieved so that image data is acquired. The number of pulses for the stepping motor 1291 may be set up, or alternatively the pitch of the female screw 1211c and the male screw 1285a may be designed such that larger overlapping parts should be generated in the fields of view of image pick-up.

Once image pick-up by the electronic endoscope 1200 is completed, the data accumulated in the image memory 1247 shown in FIG. 83 is to be read to the outside. This read operation may be performed by wireless, or alternatively by using a wiring inserted through the grip pipes 1223 and 1225 shown in FIG. 80. Alternatively, the image memory 1247 may be provided in a removable manner from the electronic endoscope 1200. Then, the removed image memory 1247 may be read by a personal computer provided separately.

In the electronic endoscope 1200, pick-up image data may be transmitted to an external monitor so that the pick-up image may be observed on line through the external monitor. In addition, operation instructions may be inputted from the outside. In this case, without performing image processing, the CPU 1201 transmits the image pick-up signal acquired from the imaging device 1249, to an external video processor in an intact manner. Then, the object image obtained by image processing in the video processor may be displayed on an external monitor. The communication between the external video processor, the external monitor, and the CPU 1201 may be of cable or wireless. In a case that the communication is of cable, an external power source becomes employable when a power source line is included in the wiring.

According to the electronic endoscope 1200 of the present embodiment described above, a stepped part (the open end part 1213b of the transparent cover 1213) is formed in a part of the outer shell of the electronic endoscope 1200. Then, for example, when insertion is performed until the stepped part is pressed against the wall surface of the subject, the tube body is simply and reliably allowed to reach a narrow and small site located at the observation position. This permits easy insertion of the electronic endoscope tip into a narrow and small site, and still permits easy and accurate acquisition of detailed entire circumferential image information over a large region. In place of the configuration that the stepped part is provided in the transparent cover 1213, the transparent cover 1213 may be formed in a straight shape and the stepped part may be provided in the body part 1211. As such, the stepped part may be provided at an arbitrary position in the shaped outer shell. However, the position of the stepped part is preferably set up with taking into consideration the insertion length into the destination of insertion.

Further, in a case that the stepped part is formed in an annular shape whose diameter is expanded isotropically relative to the electronic endoscope 1200, the electronic endoscope is constructed compact in comparison with a decentered configuration. Further, in the case of an annular stepped part, even when the electronic endoscope 1200 is inserted into the subject in an arbitrary orientation, any circumferential position of the stepped part is reliably pressed against the wall surface of the subject. Thus, the tube body of the tip of the electronic endoscope is allowed to reliably reach a desired observation position.

Figure 89A:
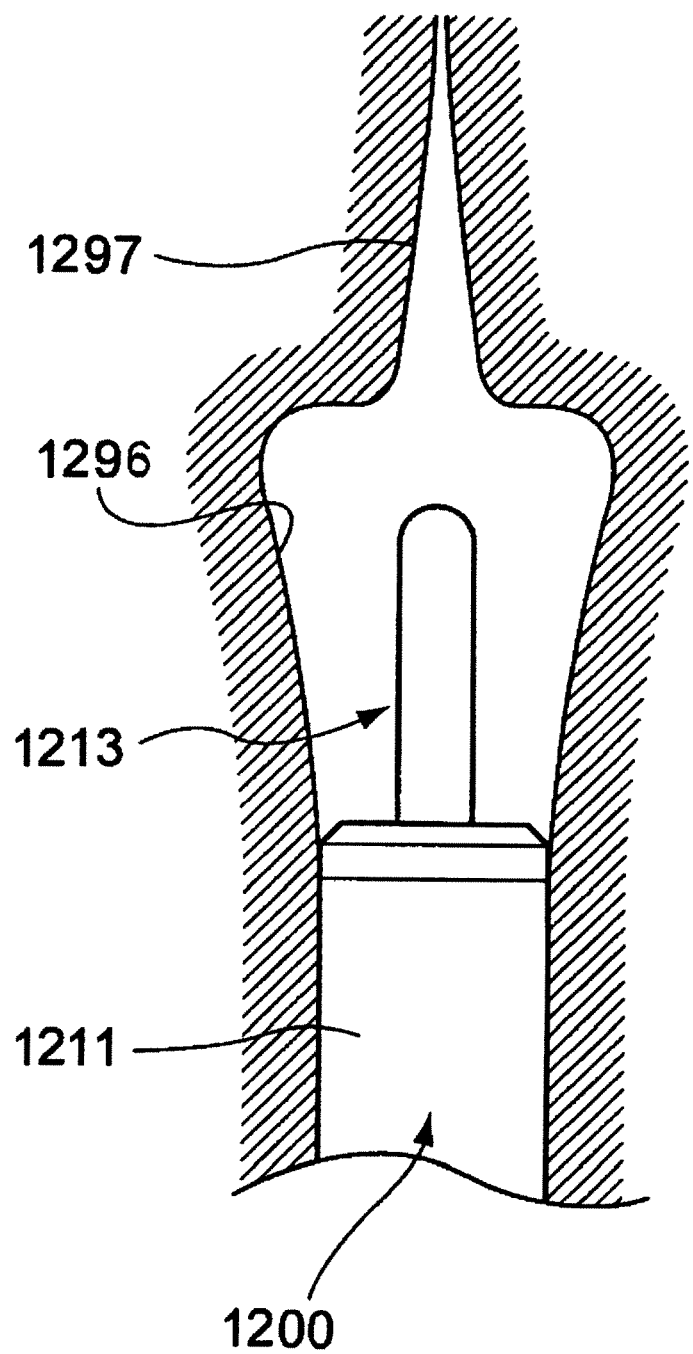
FIG. 89A is a schematic diagram showing a situation that the inside of a subject is observed.
Figure 89B:
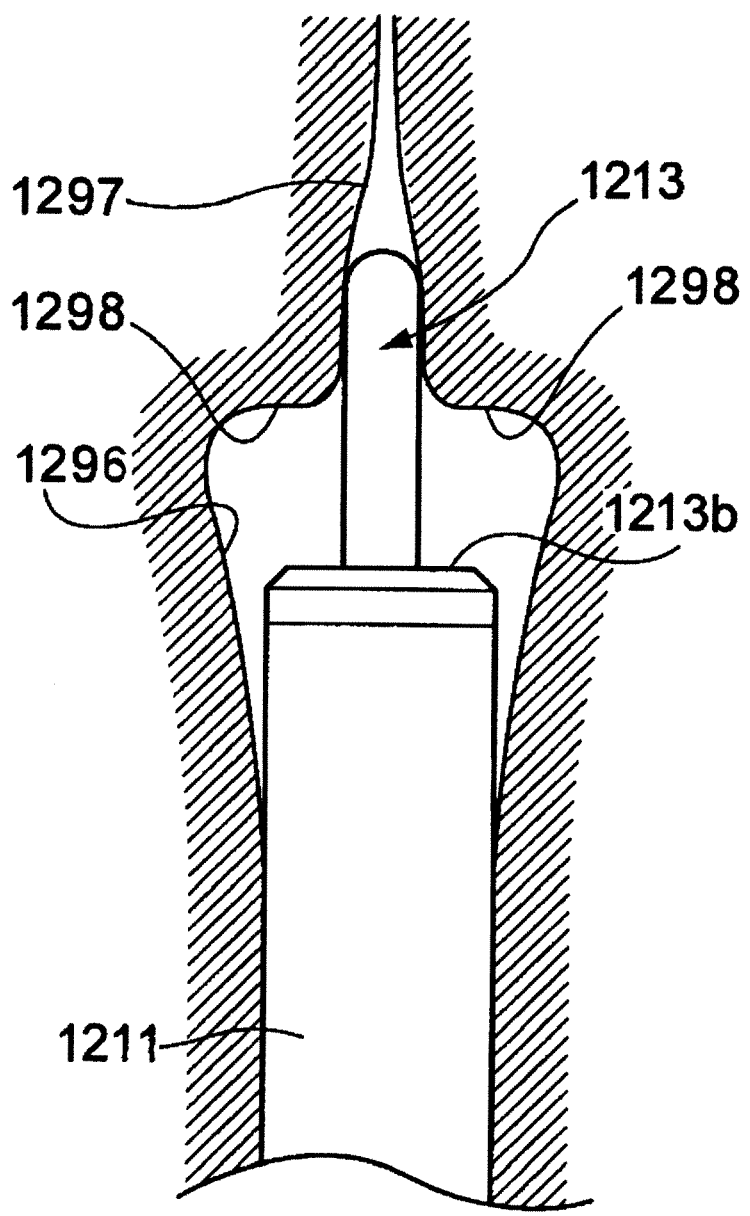
FIG. 89B is a schematic diagram showing a situation that the inside of a subject is observed.
Figure 89C:
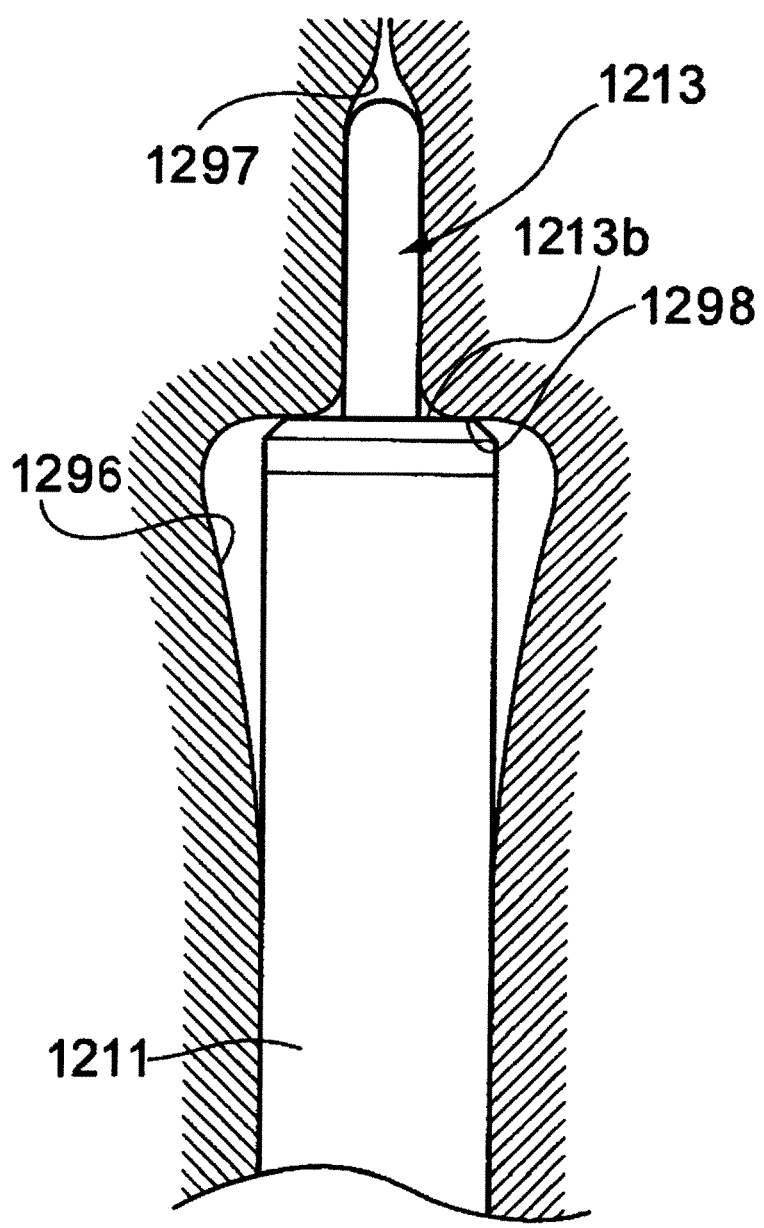
FIG. 89C is a schematic diagram showing a situation that the inside of a subject is observed.

That is, as shown in FIG. 89, when the inside of a small-diameter hole 1297 located on the deep side of a hole 1296 serving as a subject is to be observed, in a straight-pipe shaped electronic endoscope, it is difficult for the tip part to reach the small-diameter hole 1297. However, in the electronic endoscope 1200, since the transparent cover serving as an observation window having a smaller diameter is provided at the tip, insertion into the small-diameter hole 1297 is guided so that the insertion operation becomes easy. Further, starting the insertion from the state shown in FIGS. 89A and 89B, when the inner wall surface 1298 of the entrance of the small-diameter hole 1297 abuts against the open end part 1213b of the transparent cover 1213 serving as a stepped part as shown in FIG. 89C, deeper insertion is prevented. As such, the insertion length is restricted by the stepped part. Thus, the electronic endoscope 1200 is reliably located at the target observation position by easy operation in comparison with a case that insertion operation is performed with paying attention to the detailed insertion amount. By virtue of this, at the target observation position, detailed entire circumferential image information is acquired simply and accurately.

Here, in place of the form of a flat surface extending in a direction perpendicular to the direction of insertion of the electronic endoscope 1200, the stepped part may be formed in an appropriately arbitrary shape, like a tapered surface whose diameter is reduced toward the insertion tip side. For example, in place of construction from a single flat surface, the stepped part may be constructed from a plurality of surfaces.

As described above with reference to the electronic endoscope 1200 serving as an example, the present specification has disclosed an electronic endoscope for acquiring an image of the inside of a subject the electronic endoscope characterized by comprising: a tube body whose one-end part is closed and whose at least side surface has transparency; a body part that is provided continuously to the-other-end side of the tube body so as to form an outer shell; an introductory optical part that guides external light acquired through the side of the tube body within the tube body, toward the axis direction of the tube body; an image pick-up section that receives the external light introduced from the introductory optical part so as to convert the light into an electric signal; and a driving section that causes the introductory optical part to advance or retreat in the axis direction of the tube body, wherein the one-end side of the tube body is formed in a smaller diameter than the body part so that a stepped part which is constructed from the diameter difference between the tube body and the body part is formed.

According to this electronic endoscope, since the stepped part is formed in a part of the outer shell, for example, when insertion is performed until the stepped part is pressed against the wall surface of the subject, the tube body is simply and reliably allowed to reach a narrow and small site located at the observation position. This permits easy positioning of the electronic endoscope tip to a desired position of a narrow and small site, and still permits easy and accurate acquisition of detailed entire circumferential image information over a large region.

Further, the present specification has disclosed an electronic endoscope characterized in that the stepped part is composed of an annular stepped part whose diameter is expanded isotropic relative to the center axis of the tube body.

According to this electronic endoscope, since the annular stepped part whose diameter is expanded isotropic, even when the electronic endoscope is inserted into a subject in an arbitrary orientation, any circumferential position of the stepped part is reliably pressed against the wall surface of the subject. Thus, the tube body of the tip of the electronic endoscope is allowed to reliably reach a desired observation position. Further, the isotropic diameter expansion realizes a compact shape of the electronic endoscope.

Further, the present specification has disclosed an electronic endoscope characterized in that the driving section includes: a female screw which is formed in the inner peripheral surface of the cylindrical part of the body part; a revolving body whose one-end part is connected to the introductory optical part and whose pedestal part is arranged in the cylindrical part, wherein a male screw to be screwed into the female screw is formed in the outer peripheral surface of the pedestal part; and a revolution driving section which drives and revolves the revolving body about the center axis of the cylindrical part so as to move the revolving body in the center axis direction.

According to this electronic endoscope, light of the sideward region relative to the direction of insertion into the subject is acquired continuously in the circumferential direction by a simple configuration composed of screwing between the male screw and the female screw.

Further, the present specification has disclosed an electronic endoscope characterized in that the revolution driving section includes: an annular gear whose face width direction is in parallel to the center axis of the cylindrical part and which is formed in the inner peripheral surface of the revolving body; a gear wheel which is arranged inside the revolving body and which engages with the annular gear; and a motor which drives and revolves the gear wheel.

According to this electronic endoscope, when the motor revolves, the gear wheel revolves. Then, in accordance with this, the revolving body revolves so as to move in the axial direction in the inside of the body part. In association with this motion, the introductory optical part linked to the revolving body revolves and moves in the axial direction in the inside of the tube body.

Further, the present specification has disclosed an electronic endoscope characterized in that, in the introductory optical part, an image pick-up hole is formed in the peripheral surface, an objective lens is mounted in the open end part of the image pick-up hole, and a mirror is mounted that deflects the optical path to the optical axis of the objective lens.

According to this electronic endoscope, external light acquired from the sideward region of the tube body via the objective lens is deflected to the tube body axial direction by the mirror in the vicinity of the objective lens. Thus, the optical path is constructed compact, and hence diameter reduction of the tube body is allowed.

Further, the present specification has disclosed an electronic endoscope characterized by comprising, a half mirror that is arranged in the middle of the optical path between the introductory optical part and the imaging device; and a light emitting body that emits light to be projected through the introductory optical part after reflection by the half mirror and thereby illuminates the subject.

According to this electronic endoscope, the emitted light from the light emitting body is reflected toward the subject by the half mirror. Then, this reflected light serves as light for illumination that illuminates the entire sideward circumference of the subject.

Further, the present specification has disclosed an electronic endoscope characterized in that a control section which performs image processing on an image signal obtained by image pick-up performed by the image pick-up section and an image memory which stores image data obtained by image processing performed by the control section are included in the inside of the body part.

According to this electronic endoscope, image data obtained by image processing in the control section is stored into the image memory built in the body part. This permits acquisition of an image by the electronic endoscope in a stand alone mode. Thus, easy handling is enhanced.

Further, the present specification has disclosed an electronic endoscope characterized in that a power battery which supplies electric power to the image pick-up section and the driving section is built inside the body part.

According to this electronic endoscope, the power battery is built in the body part. This avoids the necessity of power supply from the outside, and hence avoids the necessity of a power supply cable connected from the outside of the body part. Thus, easy handling is enhanced.

Figure 90:
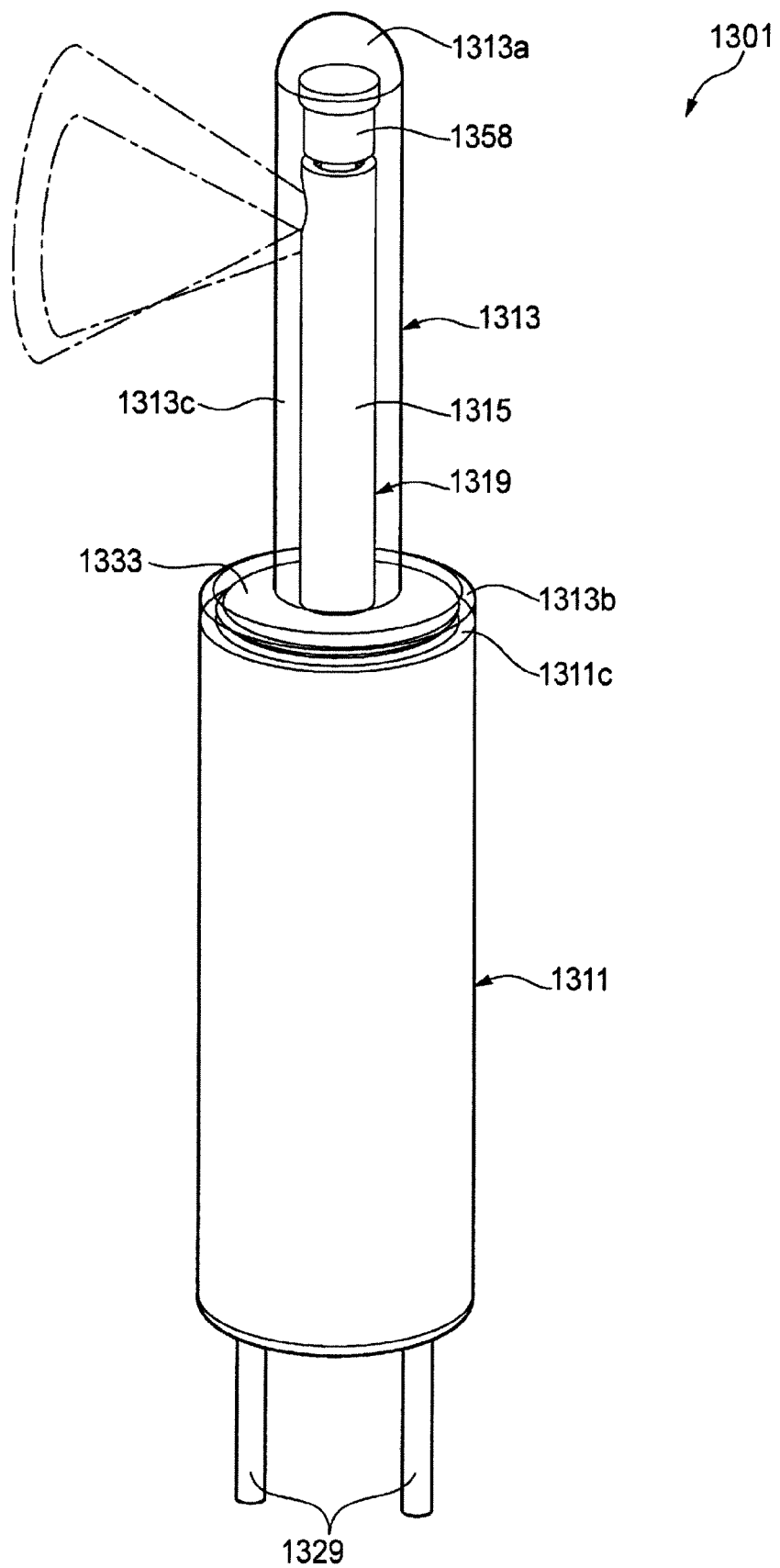
FIG. 90 is an external appearance perspective view of another example of an electronic endoscope used for describing an embodiment of the present invention.
Figure 91:
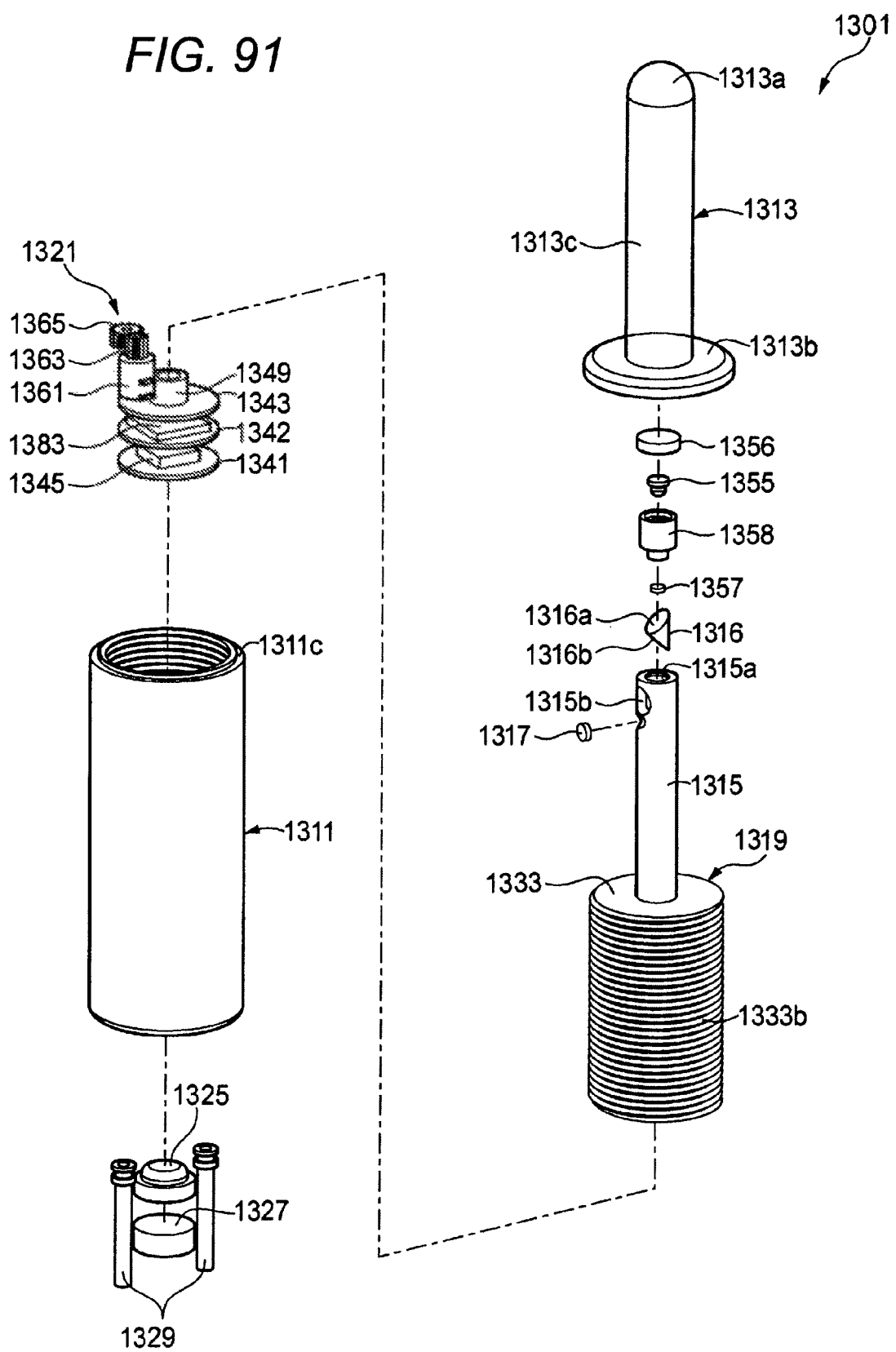
FIG. 91 is an exploded perspective view of an electronic endoscope shown in FIG. 90.
Figure 92:
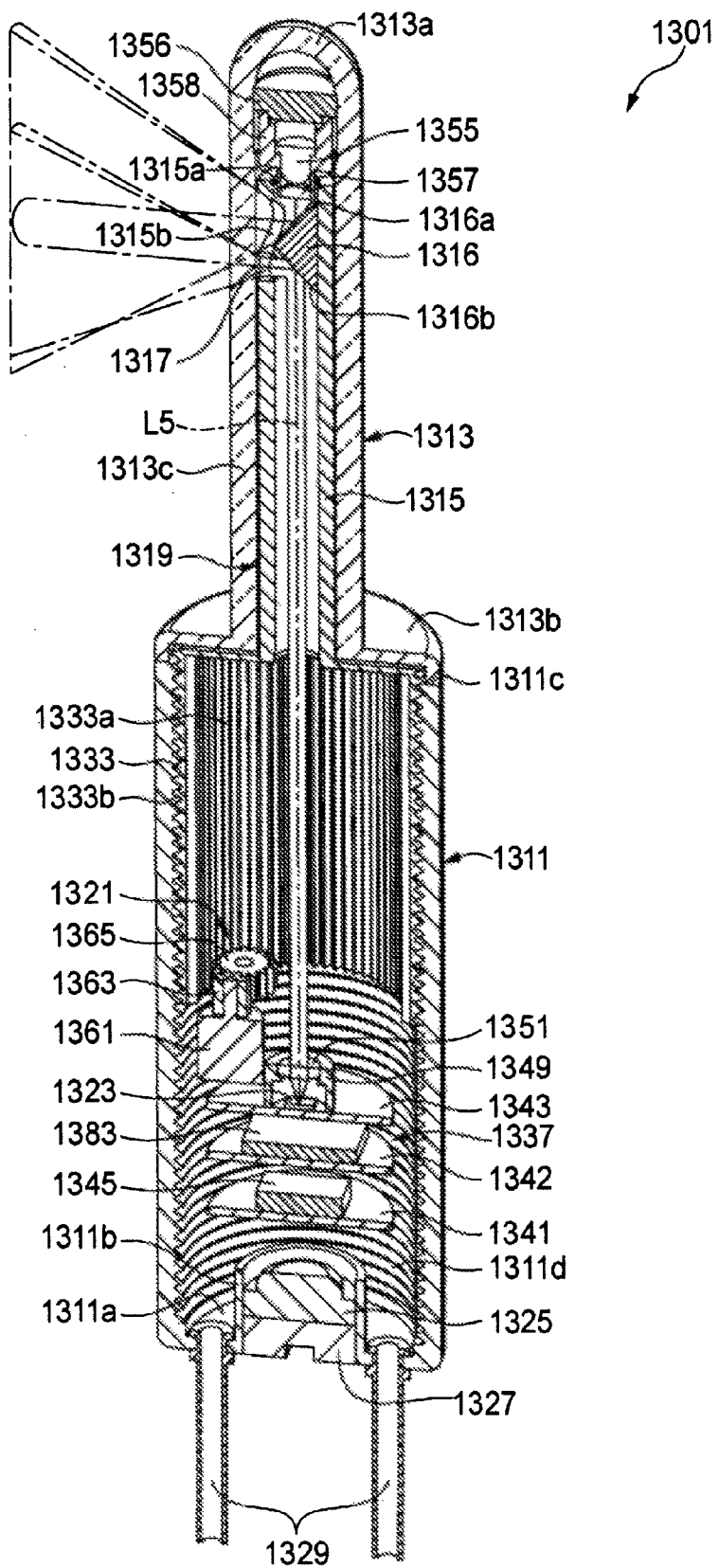
FIG. 92 is a longitudinal sectional view of an electronic endoscope shown in FIG. 90.

The electronic endoscope 1301 shown in FIGS. 90 to 92 includes an outer shell composed of the body part 1311 and the transparent cover 1313. Then, its inside is provided with: a lens holder 1319 that holds an objective lens 1317 for focusing object light through the transparent cover 1313; a driving section 1321 for moving the lens holder 1319 in the inside of the outer shell; and a solid-state imaging device 1323 that receives the object light acquired through the objective lens 1317 and then converts the light into an electric signal.

The body part 1311 constituting a part of the outer shell is fabricated from resin material or the like having light shielding property and formed into a cylindrical shape whose one-end part 1311a is closed and whose the other end pan 1311c is open. The closed end part (bottom part) 1311a is provided with a tube-shaped battery accommodating part 1311b. The battery accommodating part 1311b is closed by a battery lid 1327 after a power battery 1325 is mounted.

In the example shown in the figure, in the bottom part 1311a, two pipes 1329 protrude outward from the outer shell. For example, in a case that image data and an image map stored in a memory 1383 described later are to be transferred to an external device, data transfer cables are inserted through and protected by the pipes 1329. The pipes 1329 may be fabricated from soft material, or alternatively may be fabricated from hard material so as to serve as a grip used for inserting or extracting the electronic endoscope 1301 into or from a hole serving as a subject during the use of the electronic endoscope 1301.

The transparent cover 1313 formed in a cylindrical shape whose one-end part 1313b is open. In the transparent cover 1313, the open end part 1313b is aligned with the open end part 1311c of the body part 1311, and then fixed to the body part 1311 by appropriate means such as bonding.

The other end part (tip part) 1313a of the transparent cover 1313 is formed in a smooth hemispherical shape permitting easy insertion into a hole serving as a subject. Then, the tip part 1313a and the open end part 1313b are connected by a cylindrical part 1313c having the same diameter as the tip part 1313a. In the electronic endoscope 1301, the tip part 1313a and the cylindrical pan 1313c are formed in a smaller diameter than the open end part 1313b. As such, since the hemispherically formed tip part 1313a and the cylindrical part 1313c are formed in a small diameter, easy insertion into a narrow hole is achieved so that the range of application of the electronic endoscope 1301 is expanded.

The transparent cover 1313 having the above-mentioned configuration is fabricated from transparent resin material or the like by integral molding or the like. Alternatively, the hemispherically formed tip part 1313a, the open end part 1313b, and the cylindrical pan 1313c may be fabricated as separate members, and then may be joined to each other by appropriate means as such bonding. In this case, at least the cylindrical part 1313c serving as a window part facing the inner peripheral surface of a hole serving as a subject is formed transparent. Here, in the present invention, the term "transparent" indicates that the material is transparent to light at a particular wavelength sensitive to the imaging device 1323. That is, the material need not be transparent to visible light.

The lens holder 1319 is formed from resin material or the like and has: a cylindrical to-be-driven section 1333 fit into the body part 1311; and a cylindrical support part 1315 that is formed in a smaller diameter than the to-be-driven section 1333 and that can enter the cylindrical part 1313c of the transparent cover 1313.

In the outer peripheral surface of the to-be-driven section 1333 of the lens holder 1319, a male screw 1333b is formed that is screwed into the thread groove 1311d formed in the inner peripheral surface of the body part 1311. Further, in the inner peripheral surface of the to-be-driven section 1333, an internal-tooth gear 1333a is formed. The gear teeth of the internal-tooth gear 1333a extend in parallel to the center axis of the to-be-driven section 1333, and are formed at equal intervals in the circumferential direction.

Further, in the support part 1315 of the lens holder 1319, its outer diameter is formed somewhat smaller than the inner diameter of the cylindrical part 1313c of the transparent cover 1313 so that the support part 1315 moves in the inside of the cylindrical part 1313c along the center axis of the outer shell smoothly without chattering.

In the tip part of the support pan 1315, a 1316 is accommodated. The mirror 1316 is formed in an approximately cylindrical shape. Its lower end has a shape having been cut by a plane intersecting the center axis at 45 degrees. This inclined cut plane is formed into an objective reflecting surface 1316b by formation of a reflection film or the like.

Then, an image pick-up hole is formed at a site in the support part 1315 facing in a radial direction the objective reflecting surface 1316b of the mirror 1316. Then, the objective lens 1317 is attached in this image pick-up hole. Then, object light is focused along the cylindrical part 1313c of the transparent cover 1313 by the objective lens 1317 so as to travel to the 1316 in the form of a parallel light beam. Then, the object light is reflected by the objective reflecting surface 1316b of the mirror 1316, travels along the center axis of the support part 1315 that agrees with the center axis of the outer shell with maintaining the form of a parallel light beam.

In the inside of the body part 1311, an image pick-up drive unit part 1337 is arranged at a position located on an extended line of the center axis of the support part 1315 of the lens holder 1319. The image pick-up drive unit part 1337 is fixed inside the body part 1311 by a fixing member (not shown). In the example shown in the figure, the image pick-up drive unit pan 1337 has three base plates 1341, 1342, and 1343.

The solid-state imaging device 1323 is provided on a base plate 1343 arranged most adjacent to the lens holder 1319. The imaging device 1323 may be a CCD type imaging device, a CMOS type imaging device, or the like. A memory 1383 is mounted on a base plate 1342 arranged under the base plate 1343 (on the bottom part 1311a side of the body part 1311). The memory 1383 stores image data and the like generated from image pick-up signals read out from the imaging device 1323. Further, a control unit 1345 is mounted on a base plate 1341 arranged under the base plate 1342. The control unit 1345 performs, for example, read of image pick-up signals from the imaging device 1323 and generation of image data on the basis of the read-out image pick-up signals.

The imaging device 1323 is arranged on the base plate 1343 at a position located on an extended line of the center axis of the support part 1315 of the lens holder 1319. Then, a focusing lens 1351 is arranged at a position located above the imaging device 1323 and located on an extended line of the center axis of the support part 1315. The focusing lens 1351 is held by a focusing lens holder 1349 provided on the base plate 1343 in a manner of surrounding the imaging device 1323. The focusing lens 1351 causes the object light traveling in the form of a parallel light beam along the center axis of the support part 1315 to be focused on the light acceptance surface of the imaging device 1323 so that image formation is achieved. As such, the objective lens 1317, the objective reflecting surface 1316b of the mirror 1316, and the focusing lens 1351 constitute an objective optical system.

The electronic endoscope 1301 includes a light emitting diode (LED) 1355 serving as a light source for emitting light for illuminating the image-taking object. The LED 1355 is accommodated in the tip part 1313a of the transparent cover 1313 in such a manner that the LED 1355 is departing from the solid-state imaging device 1323 in the axial direction of the outer shell and that the lens holder 1319 intervenes between the LED 1355 and the imaging device 1323. Further, in the inside of the tip part 1313a, accommodated are: a battery 1356 for supplying electric power to the LED 1355; and an illumination lens 1357 for focusing the light for illumination from the LED 1355. The LED 1355, the battery 1356, and the illumination lens 1357 are fixed to the tip part 1313a of the transparent cover 1313 by a holding member 1358.

At the tip of the support part 1315 of the lens holder 1319, a through-hole 1315a is formed that exposes the upper end part of the mirror 1316 accommodated in the tip part. The upper end part of the mirror 1316 has a shape having been cut by a plane intersecting the center axis. The inclined cut plane is formed into an illumination reflecting surface 1316*a* by formation of a reflection film or the like. The light for illumination from the LED 1355 transmits through the illumination lens 1357, then travels along the extended line of the center axis of the support part 1315, and then enters the illumination reflecting surface 1316*a* of the mirror 1316 exposed through the through-hole 1315*a*.

The illumination reflecting surface 1316*a* of the mirror 1316 is inclined approximately symmetrically to the objective reflecting surface 1316*b* with respect to a virtual surface that is located in between relative to the objective reflecting surface 1316*b* and that is perpendicular to the center axis. Then, in the support part 1315 of the lens holder 1319, a projection exit 1315*b* is formed at a site that is located above the objective lens 1317 and that faces the illumination reflecting surface 1316*a* of the mirror 1316 in a radial direction. The light for illumination having entered the illumination reflecting surface 1316*a* is reflected by the illumination reflecting surface 1316*a* toward the projection exit 1315*b*, and then projected from the projection exit 1315*b* through the cylindrical part 1313*c* of the transparent cover 1313 onto the image-taking object.

The inclination angle of the illumination reflecting surface 1316*a* is set up appropriately such that the optical axis of the light for illumination projected from the projection exit 1315*b* is in parallel to the lens optical axis of the objective lens 1317 or alternatively approaches the lens optical axis of the objective lens 1317 when going outward from the outer shell. The aperture diameter of the projection exit 1315*b* is also set up appropriately. Thus, the light for illumination projected from the projection exit 1315*b* onto the image-taking object illuminates the region containing the view field region of the objective lens 1317. Here, the projection exit 1315*b* is preferably arranged at a position adjacent to the objective lens 1317 in the axial direction of the outer shell. By virtue of this, for example, in a case that an image-taking object located extremely close is to be taken, illumination of the region containing the view field region of the objective lens 1317 becomes easy.

As such, the illumination lens 1357, the illumination reflecting surface 1316*a* of the mirror 1316, and the projection exit 1315*b* constitute an illumination optical system. Here, the objective reflecting surface 1316*b* of the objective optical system and the illumination reflecting surface 1316*a* of the illumination optical system are formed in the mirror 1316. Thus, the optical member is shared by the objective optical system and the illumination optical system. This reduces the number of components and hence realizes size reduction.

In the lens holder 1319 in which the male screw 1333*b* formed in the outer peripheral surface of the to-be-driven section 1333 is screwed into the thread groove 1311*d* formed in the inner peripheral surface of the body part 1311, its movement is guided along the center axis of the body part 1311, that is, along the center axis of the outer shell. The driving section 1321 for moving the lens holder 1319 along the center axis of the outer shell is described below in detail.

A stepping motor 1361 is fixed inside the body part 1311. Further, an idle gear wheel 1365 is provided that is located between and engaging with both of the motor gear wheel 1363 of the stepping motor 1361 and the internal-tooth gear 1333*a* formed in the to-be-driven section 1333 of the lens holder 1319. The revolution of the stepping motor 1361 is transmitted through the motor gear wheel 1363 and the idle gear wheel 1365 to the lens holder 1319. Here, as the source of power for driving and revolving the lens holder 1319 is not limited to a stepping motor operated by pulse drive, and may be a motor of a diverse kind such as a servo motor provided with an encoder, or alternatively may be a power source of another type.

In the lens holder 1319, the to-be-driven section 1333 is fit into the body part 1311. Thus, when revolution of the stepping motor 1361 is transmitted, the lens holder 1319 revolves about the center axis of the body part 1311. At the same time, by using the male screw 1333*b* formed in the outer surface, the to-be-driven section 1333 is screwed into the thread groove 1311*d* formed in the inner peripheral surface of the body part 1311 Thus, in association with revolution about the center axis of the body part 1311, the lens holder 1319 moves (is raised or lowered) along the center axis of the body part 1311.

Figure 93:
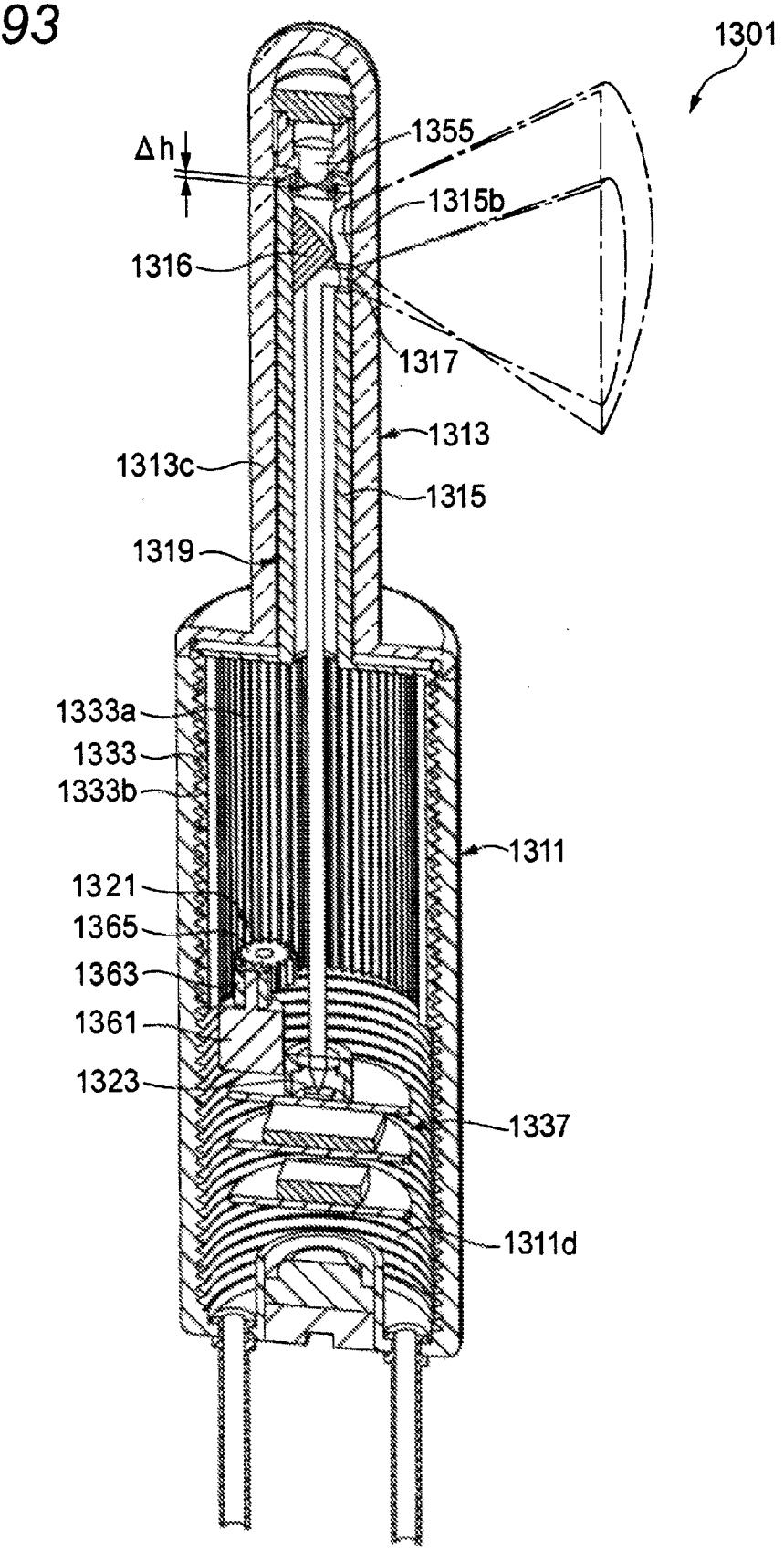
FIG. 93 is a longitudinal sectional view showing a state that a lens holder of an electronic endoscope shown in FIG. 90 has gone half around from a state shown in FIG. 92.
Figure 94:
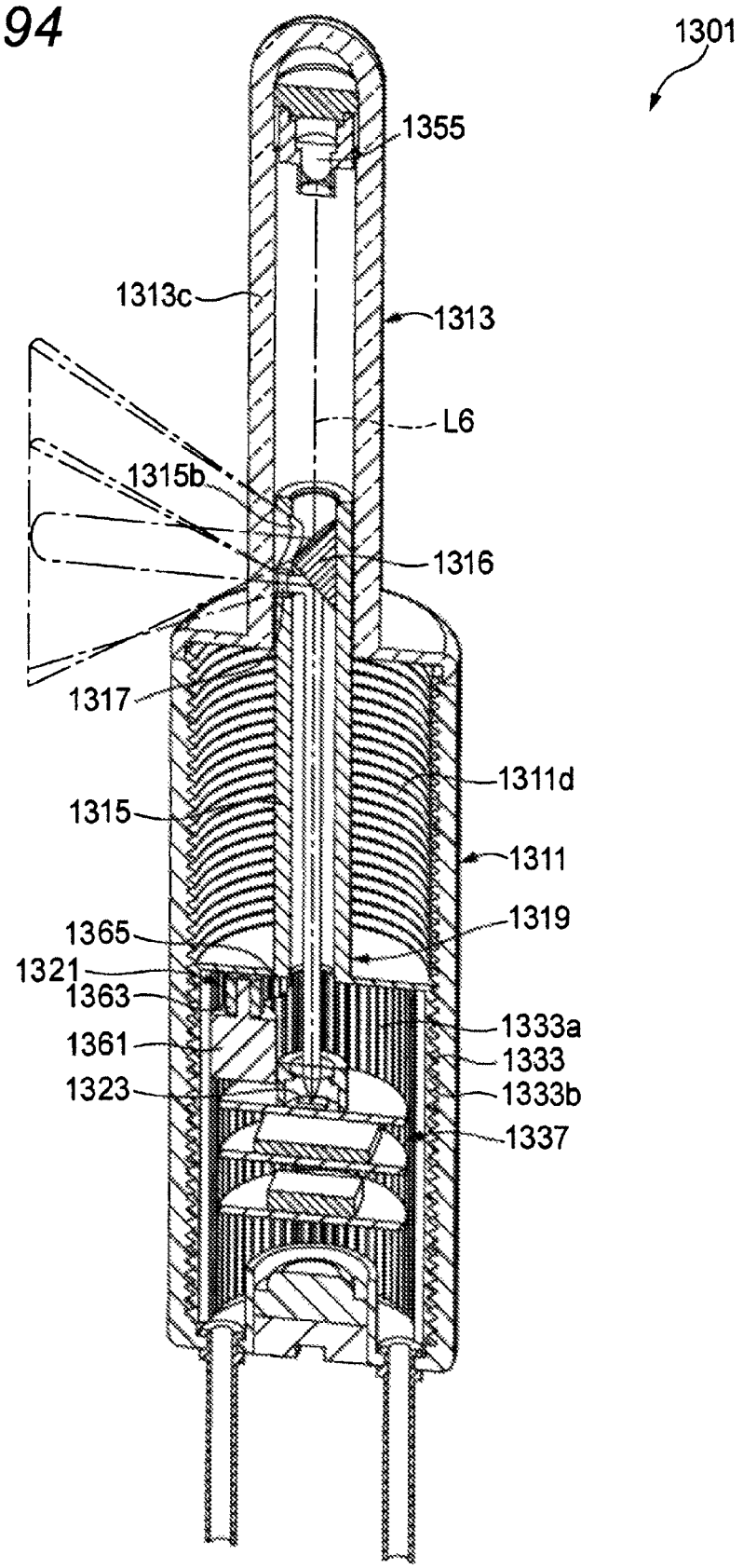
FIG. 94 is a longitudinal sectional view showing a state that a lens holder of an electronic endoscope shown in FIG. 90 has gone to a most lowered position.

For example, in a situation that the lens holder 1319 is located at a raised position shown in FIG. 92, the stepping motor 1361 is revolved in a predetermined direction so that the lens holder 1319 is revolved via the motor gear wheel 1363 and the idle gear wheel 1365. FIG. 93 shows a state that the lens holder 1319 has gone half around. As shown in FIG. 93, the lens holder 1319 revolves about the center axis of the body part 1311 so as to be lowered by Δh along the center axis of the body part 1311. Then, in accordance with the revolution of the lens holder 1319, the objective lens 1317 is also revolved so that the field of view of image pick-up moves in the circumferential direction. The lens holder 1319 is allowed, in association with the revolution, to be lowered along the center axis of the body part 1311 up to the lowermost position shown in FIG. 94, that is, a position where the lower end of the male screw 1333*b* of the to-be-driven section 1333 reaches the lower end of the thread groove 1311*d* of the body part 1311.

Figure 95:
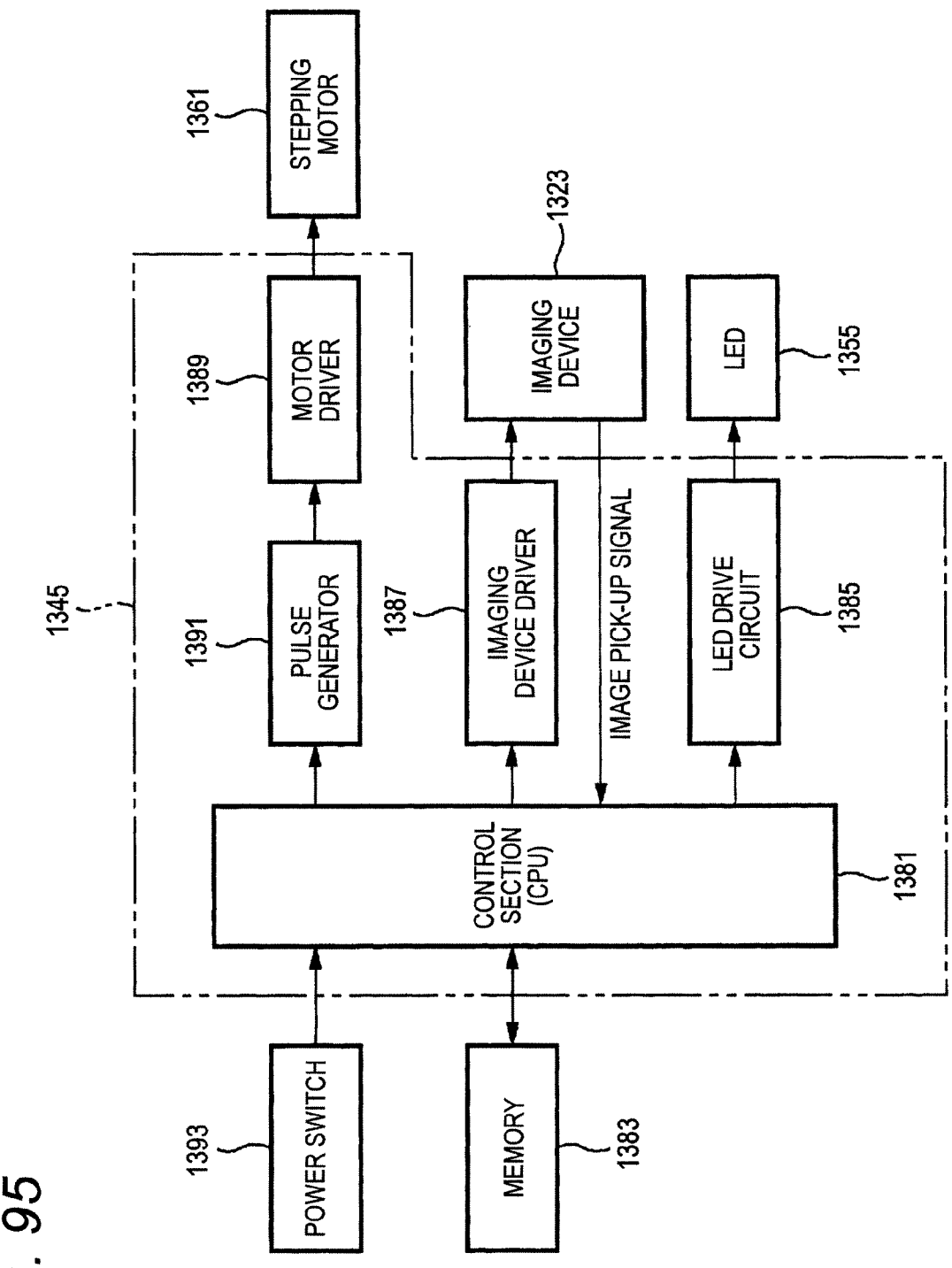
FIG. 95 is a functional block diagram showing an electronic endoscope shown in FIG. 90.

FIG. 95 is a functional block diagram showing the image pick-up drive unit part 1337. In the image pick-up drive unit part 1337, the control unit 1345 includes: an LED drive circuit 1385 for driving the LED 1355; an imaging device driver 1387 for driving the imaging device 1323; a motor driver 1389 for driving the stepping motor 1361; a pulse generator 1391 for providing driving pulses to the motor driver 1389; and a control section (CPU) 1381 for controlling the operation of the LED drive circuit 1385, the imaging device driver 1387, and the pulse generator 1391. Further, the memory 1383 stores a control program for the control unit 1345. Here, the memory 1383 stores a control program, stores image data, and serves also as a work memory. The control section 1381 performs appropriate image processing onto image pick-up signals read from the imaging device 1323, so as to generate image data, and then stores the generated image data into the memory 1383. This configuration allows the electronic endoscope 1301 in a stand alone mode to acquire and save images of image-taking objects. This provides excellence in easy handling.

When the power switch 1393 of the electronic endoscope 301 is closed, electric power from the power battery 1325 and the battery 1356 is supplied to the individual parts of the electronic endoscope 1301 through wiring (not shown) so that image pick-up is performed. For example, the power switch 1393 may be provided in the bottom part 1311*a* of the body part 1311, and may be opened or closed by manual operation. Alternatively, a switch terminal that follows magnetism may be built in the body part 1311. Then, from the outside of the electronic endoscope 1301, a magnet may be brought close or apart so that the switch terminal may be opened or closed.

Next, the operation of the electronic endoscope 1301 is described below. When the power switch 1393 is turned ON, electric power is supplied from the power battery 1325 and the battery 1356 to the individual parts of the electronic endoscope 1301. Then, the light for illumination from the LED 1355 is projected from the projection exit 1315b through the cylindrical part 1313c of the transparent cover 1313 toward the sideward region so that the image-taking object is illuminated. Reflected light from the image-taking object is acquired into the electronic endoscope 1301 through the cylindrical part 1313c and the objective lens 1317 of the transparent cover 1313, so that an image is formed onto the light acceptance surface of the imaging device 1323 by the focusing lens 1351. Then, charge accumulated in the imaging device 1323 as a result of photoelectric conversion is read as an image pick-up signal by the control section 1381 of the control unit 1345. The control section 1381 performs appropriate image processing onto the read-out image pick-up signal so as to generate image data, and then stores the generated image data into the memory 1383.

Figure 96:
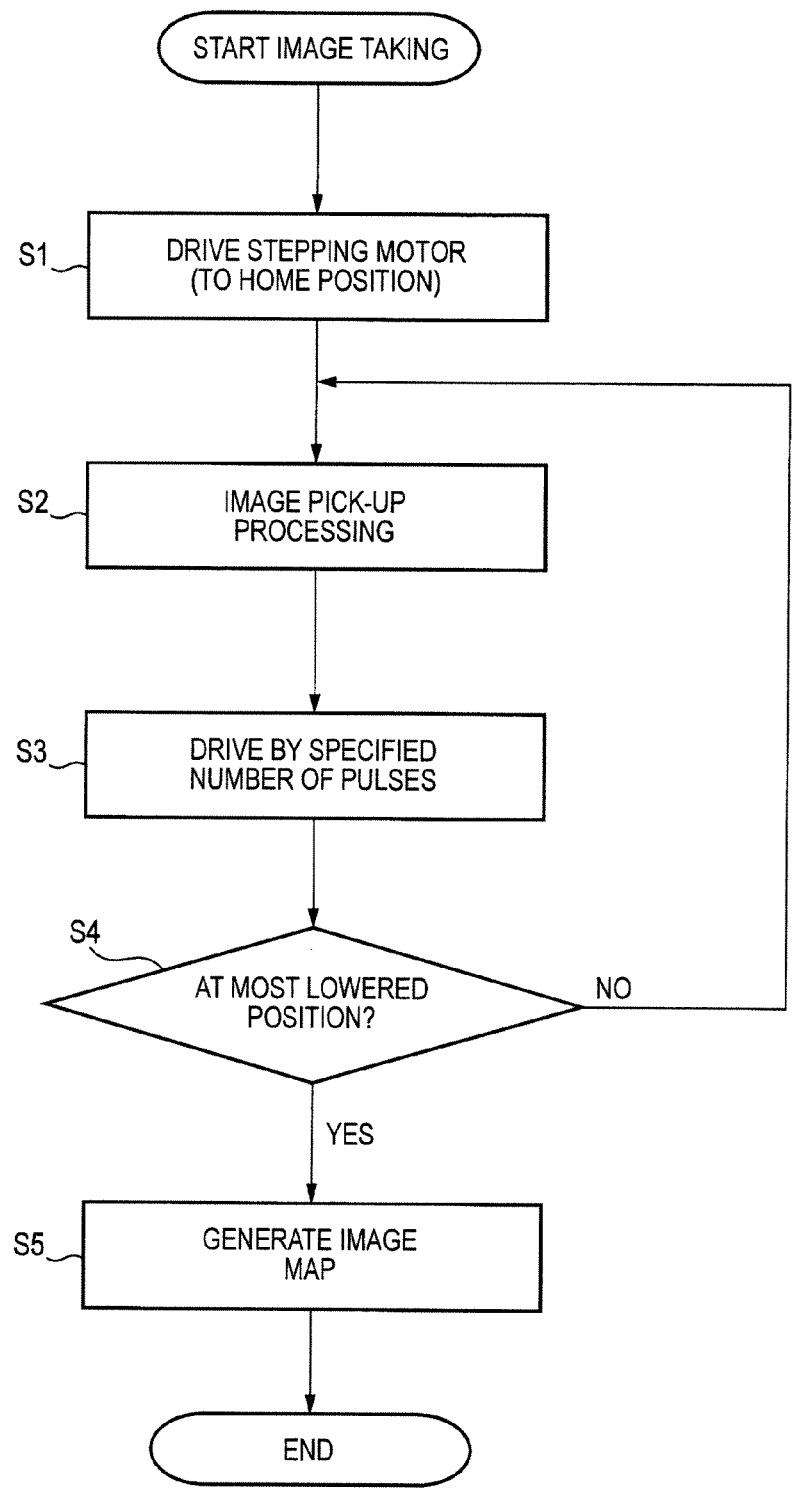
FIG. 96 is a flow chart showing a processing procedure of a control program executed by a control section of an electronic endoscope shown in FIG. 90.

FIG. 96 is a flow chart showing the processing procedure of a control program of the control unit 1345. When the power switch 1393 is turned ON, first, the stepping motor 1361 is driven and revolved, so that the lens holder 1319 goes along the center axis of the outer shell of the electronic endoscope 1301 to a home position (step S1). Here, in the following description, the home position is defined as a position where, for example, as shown in FIG. 92, the objective lens 1317 is located on the tip side of the electronic endoscope 1301. However, the definition is not limited to this, and may be the opposite position where the objective lens 1317 is located on the pedestal side (the position shown in FIG. 94).

After the lens holder 1319 is set at the home position, image pick-up processing is performed (step S2). The image pick-up processing includes such processes that the LED 1355 is driven so as to emit light for illumination; object light is acquired through the objective lens 1317 into the electronic endoscope 1301 so that an image is formed onto the light acceptance surface of the imaging device 1323; and on the basis of the image pick-up signal read from the imaging device 1323, image data is generated and then stored into the memory 1383.

Then, the stepping motor 1361 is driven by a specified number of pulses (step S3), so that the lens holder 1319 is lowered by a predetermined distance. Until the lens holder 1319 reaches the most lowered position (step S4), image pick-up processing is performed at each destination of the movement (step S2). When the lens holder 1319 reaches the most lowered position, the lowering operation of the lens holder 1319 and the image pick-up processing are terminated (step S4).

FIG. 97 is a diagram illustrating the movement of the field of view of image pick-up achieved when the above-mentioned steps S2 to S4 are executed repeatedly. In the first occasion of image pick-up processing performed at the home position, image pick-up is performed in the field of view "No. 001", and hence image data of the field of view "No. 001" is generated from the image pick-up signal read from the imaging device 1323.

Once the image pick-up processing in the field of view "No. 001" is completed, the stepping motor 1361 is driven at step S3 by a specified number of pulses so that the lens holder 1319 is lowered and revolved. In association with this, the objective lens 1317 held by the lens holder 1319 is moved so that the field of view moves to "No. 002" in FIG. 97. At that time, the projection exit 1315b provided in the lens holder 1319 is moved similarly to the objective lens 1317 and thereby follows the moving field of view so as to illuminate the field of view "No. 002". Then, image pick-up is performed in this field of view, and hence image data of the field of view "No. 002" is generated from the image pick-up signal read from the imaging device 1323.

Here, the lens holder 1319 is located in between the LED 1355 and the solid-state imaging device 1323 separated in the axial direction of the outer shell, and is moved along the axis of the outer shell. Thus, the optical path length from the LED 1355 to the solid-state imaging device 1323 is approximately fixed regardless of the movement of the lens holder 1319. For example, when the lens holder 1319 is located at the home position shown in FIG. 92, the objective optical system (the objective lens 1317 the objective reflecting surface 1316b of the mirror 1316 the focusing lens 1351 the solid-state imaging device 1323) has a longer optical path length than the illumination optical system (the illumination reflecting surface 1316a the projection exit 1315b of the LED 1355→the illumination lens 1357→the mirror 1316). In contrast, when the lens holder 1319 is located at the lowermost position shown in FIG. 94, the optical path length of the illumination optical system is extended, and the optical path length of the objective optical system is reduced by the same amount. Thus, the optical path length L5 from the LED 1355 to the solid-state imaging device 1323 in a situation that the lens holder 1319 is located at the home position is almost equal to the optical path length L6 from the LED 1355 to the solid-state imaging device 1323 in a situation of the lowermost position. As a result, the intensity of light attenuation by scattering and the like occurring in the course from the LED 1355 to the solid-state imaging device 1323 becomes almost the same for these two optical paths. Thus, the intensity of light entering the solid-state imaging device 1323 is fixed approximately.

After that, image pick-up processing is repeated with moving the field of view like "No. 003"→"No. 004"→"No. 005" . . . . When the lens holder 1319 has gone one around from the home position, the field of view of image pick-up is located at "No. 011" in FIG. 97. In case of having gone around twice, the field of view of image pick-up is located at "No. 021" in FIG. 97. In the present embodiment, plural pieces of image data stored in the memory 1383 are arranged similarly to the exemplary movement of the field of view shown in FIG. 97 so that an image map is generated (step S5).

Here, for example, the number of pulses provided to the stepping motor 1361 at step S3 may be adjusted appropriately, or alternatively the screw pitch of the thread groove 1311d of the body part 1311 and the male screw 1333b of the to-be-driven section 1333 may be adjusted appropriately, so that circumferentially adjacent fields of view of image pick-up may be positioned such that their left and right edge parts should be in contact with each other or overlapping somewhat with each other, and so that axially adjacent fields of view of image pick-up may be positioned such that their upper and lower edge pans should be in contact with each other or overlapping somewhat with each other. According to this configuration, image taking of an object is achieved without a missing pan in the axial and the circumferential directions. Thus, an image map without a gap is obtained.

When the above-mentioned image map has been generated, the image map is to be read from the memory 1383 to the outside. This read may be performed by wireless, or alternatively through a cable in a configuration that a data transfer cable is inserted through the pipe 1329 shown in FIG. 90 and connected to the image pick-up drive unit part 1337. Alternatively, the memory 1383 may be provided in a removable manner from the electronic endoscope 1301. Then, the removed memory 1383 may be read by a personal computer provided separately.

As described above with reference to the electronic endoscope 1301 serving as an example, the present specification has disclosed an electronic endoscope characterized by comprising: an outer shell that is formed in a tube shape and whose peripheral wall is provided with a transparent window part extending in an axial direction; a light source and a solid-state imaging device that are provided inside the outer shell; an illumination optical system that projects light for illumination from the light source through the window pan onto an image-taking object; an objective optical system that includes an objective lens which focuses object light through the window part and that forms an image onto the solid-state imaging device; a lens holder that holds at least the objective lens in the objective optical system; and a driving section that moves the lens holder along the axis of the outer shell, wherein the light source is arranged departing from the solid-state imaging device in the axial direction of the outer shell, wherein the lens holder is moved between the light source and the solid-state imaging device along the axis of the outer shell, and wherein the projection exit of the illumination optical system is provided in the lens holder.

Further, the present specification has disclosed an electronic endoscope characterized in that the projection exit of the illumination optical system is arranged at a position adjacent to the objective lens in the axial direction of the outer shell.

Further, the present specification has disclosed an electronic endoscope characterized in that: the illumination optical system includes a first reflecting surface which reflects the light for illumination toward the projection exit; the objective optical system includes a second reflecting surface which reflects the object light toward the solid-state imaging device; the light source and the solid-state imaging device are arranged on the same axis; and the first reflecting surface and the second reflecting surface are formed in a single optical member arranged on the axis.

Further, the present specification has disclosed an electronic endoscope characterized in that the window part is provided over the entire circumference of the peripheral wall of the outer shell, and wherein the driving section causes the lens holder to revolve about the axis of the outer shell and thereby move along the axis of the outer shell.

Further, the present specification has disclosed an electronic endoscope characterized in that the outer shell is formed in a cylindrical shape and the inner peripheral surface of its inner wall is provided with a thread groove, wherein the driving section includes a motor which drives and revolves the lens holder about the axis of the outer shell, and wherein the lens holder engages with the thread groove of the outer shell.

Further, the present specification has disclosed an electronic endoscope characterized in that a control section which reads an image pick-up signal from the solid-state imaging device and then generates image data and a memory which stores the image data are further included in the inside of the outer shell.

Further, the present specification has disclosed an electronic endoscope characterized in that the driving section is driven by electric power and wherein a power battery which supplies electric power to the light source, the solid-state imaging device, and the driving section is further provided inside the outer shell.

Next, preferred examples of use of the electronic endoscopes described above are given below.

(i) Example of Use as Hysteroscope

In recent years, the lowering trend in the age of women suffering from cervical cancer is growing. In case that cervical cancer is found at early stages, serious results are avoided by partial extirpation. Thus, early detection is important. Nevertheless, women hesitate to expose their own bodies, and hence the population who receive medical checkup is not growing.

Each electronic endoscope described above is effective in medical checkup for cervical cancer, when the dimensions and the shape are designed appropriately. When the electronic endoscope is inserted into the vaginal cavity of a woman and then the electronic endoscope is inserted from the apex part into the uterine cervix such that a series of the field of view of image pick-up positions should reach the uterine cervix, image pick-up is achieved for the situation of the inner peripheral surface of the uterine cervix without a missing part.

As a mode of use, for example, the electronic endoscope may be inserted into the uterine cervix by the patient herself in the consultation room. Further, the doctor staying in another room may instruct the insertion position and check the pick-up image through a monitor on line. This eases the patient's mental burden, and hence contributes to an increase in the population who receive medical checkup.

In particular, at the time when the electronic endoscope 1200 described above is inserted from the inside of the vaginal cavity further into the canal of the cervix, the inner wall of the vaginal portion of the cervix at the entrance of the canal of the cervix abuts against the stepped part of the electronic endoscope 1200 so that the amount of insertion of the electronic endoscope 1200 is restricted. Thus, the tip of the electronic endoscope 1200 is reliably positioned at the inner wall surface of the canal of the cervix. Further, also from the perspective of the insertion length, the insertion is stopped at an appropriate position.

Further, in each electronic endoscope described above, when the power switch is turned ON, the objective lens returns to the home position automatically and then image pick-up processing is performed automatically. Thus, the electronic endoscope may be lent to the patient, and then the patient herself may acquire an image of her own uterine cervix in her home. Then, the doctor receives the electronic endoscope and then checks the pick-up image data in the memory so that diagnosis is performed.

(ii) Example of Use as Electronic Endoscope for Large Intestine and Rectum

When medical checkup is performed for the large intestine or the rectum, in the prior art, observation has been performed by using an electronic endoscope in which an imaging device is mounted on the tip part. Thus, the diseased part has been observed obliquely from the above. In contrast, when any one of the electronic endoscopes described above is inserted to the diseased part position and then observation is performed, the diseased part is observed perpendicularly from the above. This permits more detailed observation and accurate diagnosis.

(iii) Example of Use as Industrial Endoscope

Each electronic endoscope described above may be used as an industrial endoscope, for example, used for observing a fine crack in a thin piping. At the time, an electronic endoscope is prepared that has dimensions and a shape in accordance with the size of the opening of a hole or a gap serving as an observation object as well as with the insertion depth. As described above, observation of the crack or the like is performed from the above perpendicularly to the inner peripheral surface of the hole, and hence more detailed observation is achieved. Further, once the electronic endoscope is inserted, observation is allowed for a large region. This reduces the rate of overlooking small cracks.

INDUSTRIAL APPLICABILITY

According to the present invention, detailed image information over a large region is acquired easily and accurately.

The present invention has been described above in detail with reference to particular embodiments. However, it is clear for the person skilled in the art that various modifications and variations can be made without departing from the spirit and the scope of the present invention. The present application is based on Japanese Laid-Open Patent Application Nos. 2008-157991, 2008-157992, 2008-157993, 2008-157999, 2008-158000, 2008-158002, 2008-158004, 2008-158005, 2008-158006, and 2008-158013 filed on Jun. 17, 2008. Their contents are incorporated herein by reference.

REFERENCE SIGNS LIST 1 endoscope
11 body part (outer shell)
13 transparent cover (outer shell)
13c cylindrical part (window pan)
16 objective mirror (objective optical system)
17 objective lens (objective optical system)
19 lens holder
21 driving section
23 solid-state imaging device
25 power battery
51 focusing lens (objective optical system)
61 stepping motor
67 feed screw
81 control section
83 memory
500 electronic endoscope
511 body part
511a bottom part
511b battery accommodating part
511c open end part
513 transparent cover section
513a hemispherical part
513b open end part
513c cylindrical part
513d shaft hole
515 tube-shaped part
517 objective lens group
517A wide-angle lens
517B lens
519 lens holder
521 raising and lowering driving section
523 imaging device
525 power battery
527 battery lid
529 wiring protection tube
531 rib
533 flange
535 engagement groove
537 image pick-up drive unit part
541, 542, 543 base plate
545 control unit
547 image memory
549 focusing lens holder
551 focusing lens
553 half mirror or
555 light emitting diode
557 illumination lens
561 stepping motor
563 motor gear wheel
565 idle gear wheel
567 feed screw
569 gear wheel
571 support arm
573 opening
575 feed nut
577 nut holding piece
581 control section
583 memory
585 LED drive circuit
587 imaging device driver
591 pulse generator
593 power switch
W view field region
601 electronic endoscope
602 body part
602a bottom part
602b battery accommodating part
602c female screw provided in the inner peripheral surface
603 transparent capsule (transparent cover)
603a hemispherical part at tip
603c cylindrical part
604 moving lens frame section (lens holder)
604a disk-shaped objective lens mount pan
604b cylindrical member
604c male screw provided in outer peripheral surface
604d internal-tooth gear
604f image pick-up hole
605 image pick-up drive unit part
611 power battery
612 battery lid
613, 614 grip pipe
616 objective mirror
617 objective lens
621, 622, 623 base plate
626 image memory
627 solid-state imaging device
628 stepping motor
629 lens holder
630 focusing lens
631 half mirror
632 illumination lens
633 LED (light emitting body)
636 motor gear wheel
637 idle gear wheel
641 control device (CPU)
647 power switch

The invention claimed is:

1. An electronic endoscope comprising:
a cylindrical transparent cover at least whose observation window in a cylindrical part is transparent;
a body part that has a cylindrical part provided continuously to the cylindrical part of the transparent cover;
a lens holder that revolves about a center axis of the transparent cover in an inside of the transparent cover and the body part and that moves in a direction of the center axis;
an objective mirror that is provided in the lens holder and that reflects, toward the body part, light entering through an objective lens provided at a position facing the cylindrical part of the transparent cover;
an imaging device that receives light reflected from the objective mirror and that converts the light into an electric signal; and a driving section that is provided inside the body part and that drives and revolves the lens holder so as to drive the lens holder in the center axis direction.

2. The electronic endoscope according to claim 1, wherein the lens holder includes:

a disk-shaped member on which the objective lens is mounted and the objective mirror is mounted; and a cylindrical member which is provided integrally and continuously to the body part side of the disk-shaped member.

3. The electronic endoscope according to claim 2, comprising:

a female screw that is formed spirally in an inner peripheral surface of the body part; and a male screw that is engraved spirally in an outer peripheral surface of the cylindrical member and engaging with the female screw and that, when the cylindrical member is driven and revolved by the driving section, moves the cylindrical member in the center axis direction.

4. The electronic endoscope according to claim 1, wherein an optical axis of the objective lens is provided in a direction perpendicular to an axis of revolution of the lens holder.

5. The electronic endoscope according to claim 1, wherein the objective mirror reflects light entering through the objective lens, toward the body part along an optical path going along the center axis.

6. The electronic endoscope according to claim 1, further comprising:

a half mirror that is provided in a course of an optical path of light reflected from the objective mirror; and a light emitting body for emitting light for illumination, which is to be reflected by the half mirror and then reflected by the objective mirror, so as to illuminate a image-taking object through the objective lens.

7. The electronic endoscope according to claim 1, wherein a control section which performs image processing on an image signal obtained by image pick-up performed by the imaging device and an image memory which stores pick-up image data obtained by image processing performed by the control section are built in.

8. The electronic endoscope according to claim 1, wherein a battery accommodating part which accommodates a power battery for supplying electric power to the imaging device and the driving section is built in the body part.

* * * * *